(12) United States Patent
Guo et al.

(10) Patent No.: US 8,367,664 B2
(45) Date of Patent: Feb. 5, 2013

(54) SUBSTITUTED 3-(5-MEMBERED UNSATURATED HETEROCYCLYL-1, 3-DIHYDRO-INDOL-2-ONE'S AND DERIVATIVES THEREOF AS KINASE INHIBITORS

(75) Inventors: Xialing Guo, San Clemente, CA (US); Zhen Zhu, Foothill Ranch, CA (US); Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 1472 days.

(21) Appl. No.: 11/625,852

(22) Filed: Jan. 23, 2007

(65) Prior Publication Data

US 2007/0173501 A1   Jul. 26, 2007

Related U.S. Application Data

(60) Provisional application No. 60/761,660, filed on Jan. 24, 2006.

(51) Int. Cl.
*C07D 401/14* (2006.01)
*C07D 403/14* (2006.01)
*A61K 31/403* (2006.01)
*A61K 31/496* (2006.01)
*A61P 27/02* (2006.01)
*C07D 405/04* (2006.01)
*C07D 413/14* (2006.01)
*A61P 3/10* (2006.01)
*A61P 9/10* (2006.01)
*A61P 17/06* (2006.01)
*A61P 19/02* (2006.01)
*A61P 25/00* (2006.01)
*A61P 29/00* (2006.01)
*A61P 35/00* (2006.01)
*A61P 37/06* (2006.01)

(52) U.S. Cl. ........... 514/235.2; 514/253.09; 514/254.09; 514/323; 514/414; 544/144; 544/364; 544/373; 546/201; 548/466

(58) Field of Classification Search .................. None
See application file for complete search history.

(56) References Cited

U.S. PATENT DOCUMENTS

| 4,966,849 A | 10/1990 | Vallee et al. |
| 5,217,999 A | 6/1993 | Levitzki et al. |
| 5,302,606 A | 4/1994 | Spada et al. |
| 5,330,992 A | 7/1994 | Eissenstat |
| 5,792,783 A | 8/1998 | Tang et al. |
| 5,834,504 A | 11/1998 | Tang et al. |
| 5,883,113 A | 3/1999 | Tang et al. |
| 5,883,116 A | 3/1999 | Tang et al. |
| 5,886,020 A | 3/1999 | Tang et al. |
| 6,541,504 B1 | 4/2003 | Andrews et al. |
| 6,680,335 B2 * | 1/2004 | Tang .................... 514/414 |
| 6,747,025 B1 | 6/2004 | Andrews et al. |
| 6,765,012 B2 | 7/2004 | Andrews et al. |
| 7,005,444 B2 * | 2/2006 | Andrews et al. ............. 514/407 |
| 7,098,236 B2 | 8/2006 | Andrews et al. |
| 2008/0045526 A1 * | 2/2008 | Boral et al. ................. 514/232.8 |
| 2009/0099181 A1 * | 4/2009 | Wurster et al. ............ 514/235.5 |

FOREIGN PATENT DOCUMENTS

| GB | 829584 | * 3/1960 |
| WO | 91/15495 | 10/1991 |
| WO | 92/20642 | 11/1992 |
| WO | 92/21660 | 12/1992 |
| WO | 94/03427 | 2/1994 |
| WO | 94/10202 | 5/1994 |
| WO | 94/14808 | 7/1994 |
| WO | 02/29630 | 4/2002 |
| WO | WO 03/084951 | 10/2003 |
| WO | WO 2004/050621 | 6/2004 |

OTHER PUBLICATIONS

Higashiyama, K. et al., "Michael Reactions of 3-Acylmethyleneoxindoles with Active Methylene Compounds", Chemical & Pharmaceutical Bulletin, 33(2), 544-550, 1985.*
Grassmann et al., Chemical Abstracts, 28:44955, 1934.*
Plowman et al, 1994, DN&P 7(6): 334-339.
Bolen, 1993, Oncogen 8: 2025-2031.
Kendall & Thomas, 1994, Proc. Nat'l Acad. Sci 90: 10705-09.
Kim, et al, 1993 Nature 362: 841-844.
Jellinek, et al, Biochemistry 33: 10450-56, 1994.
Takano, et al, 1993, Mol. Bio. Cell 4:358A.
Kinsella, et al, 1992, Exp. Cell Res. 199: 56-62.
Wright, et al, 1992, J. Cellular Phys. 152: 448-57.
Mariani, et al, 1994, Proc. Am. Assoc. Cancer Res. 35: 2268.
Dutta, "Indigoid dyes. IV. 2, 1-Naphthothiophene-phenanthrenindigo", XP002439375-Abstract.
Pratesi, "The condensation products of isatin with pyrroles (pyrrole blues). II", XP002439376-Abstract.

\* cited by examiner

*Primary Examiner* — Fiona T Powers
(74) *Attorney, Agent, or Firm* — Krishna G. Banerjee; Joel German

(57) ABSTRACT

The present invention relates to organic molecules capable of modulating tyrosine kinase signal transduction in order to regulate, modulate and/or inhibit abnormal cell proliferation.

11 Claims, 6 Drawing Sheets

Scheme 1

Table 1

Table 2

Scheme 2

Table 3

Scheme 3

Scheme 4

Scheme 5

Scheme 6

Scheme 7

Table 7

Scheme 8

Table 7

Scheme 9

Table 8

Scheme 10

Table 12

Scheme 11

Table 12

SUBSTITUTED 3-(5-MEMBERED UNSATURATED HETEROCYCLYL-1, 3-DIHYDRO-INDOL-2-ONE'S AND DERIVATIVES THEREOF AS KINASE INHIBITORS

CROSS REFERENCE TO RELATED APPLICATIONS

This application claims priority to U.S. Provisional Application No. 60/761,660, filed Jan. 24, 2006, which is expressly incorporated herein by reference in its entirety.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci 90: 10705-09; Kim, et al, 1993, Nature 362: 841-844), RNA ligands (Jellinek, et al, Biochemistry 33: 10450-56); Takano, et al, 1993, Mol. Bio. Cell 4:358A; Kinsella, et al, 1992, Exp. Cell Res. 199: 56-62; Wright, et al, 1992, J. Cellular Phys. 152: 448-57) and tyrosine kinase inhibitors (PCT Application Nos. WO 94/03427; WO 92/21660; WO 91/15495; WO 94/14808; U.S. Pat. No. 5,330, 992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinylene-azaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

In addition, certain small compounds are disclosed in U.S. Pat. Nos. 5,792,783; 5,834,504; 5,883,113; 5,883,116 and 5,886,020 as useful for the treatment of diseases related to unregulated TKS transduction. See also U.S. patent application Ser. No. 10/256,381; WO 02/29630; U.S. Pat. No. 6,765,012, Ser. No. 10/886,213; U.S. Pat. Nos. 6,541,504 and 6,747,025. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

In one illustrative embodiment, the compounds of the present invention have the following general formulae:

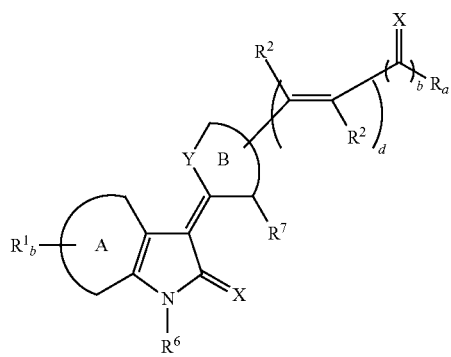

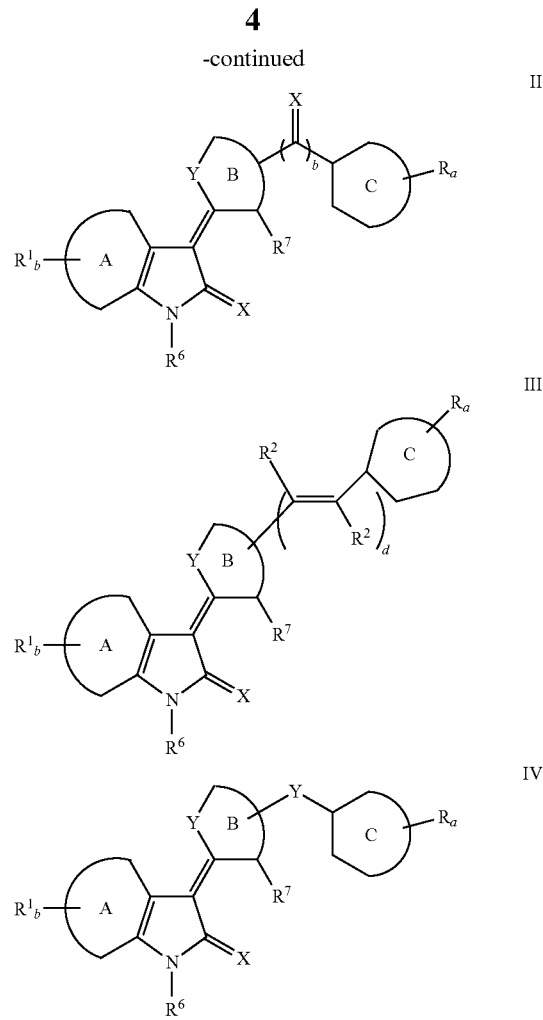

wherein

X is O or S;

Y is selected from the group consisting of O, S, $NR^3$ and $CR^3R^4$;

and wherein the ring system represented by A in formula V below, is a 5 or 6 membered aryl group, e.g. a carbocyclic aryl or a heterocyclic aryl

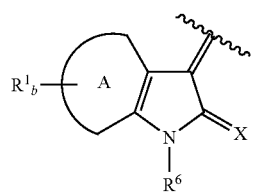

wherein said aryl group is selected from the group consisting of:

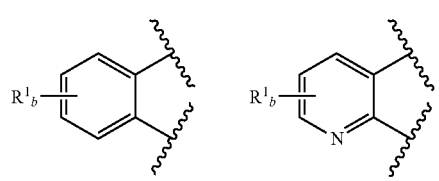

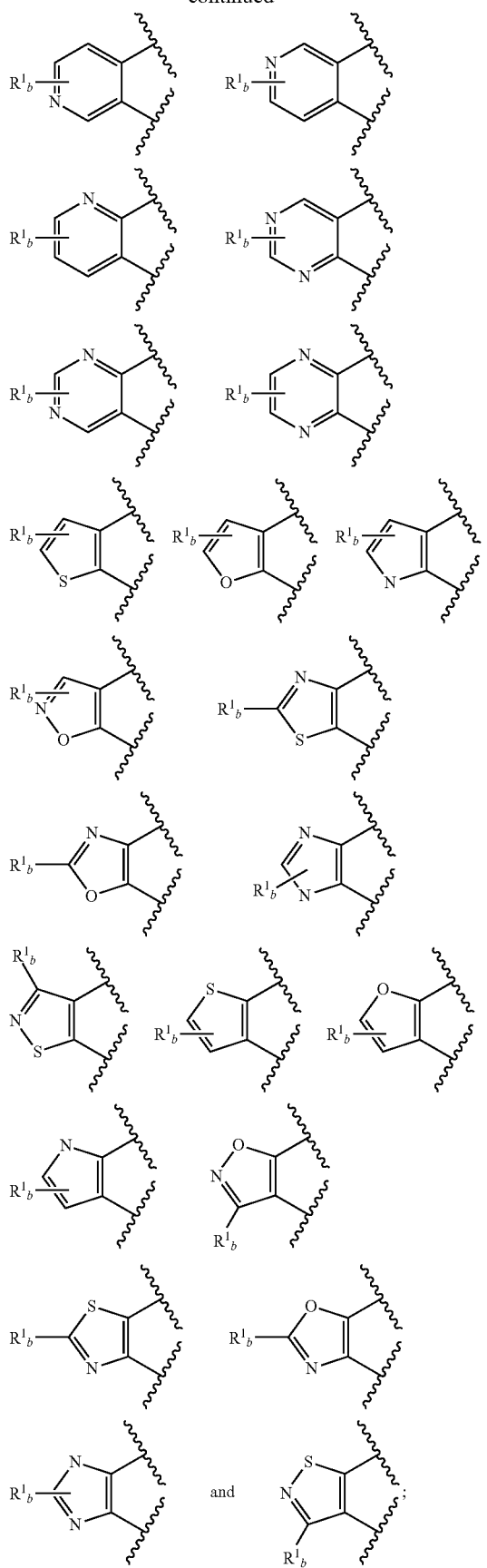
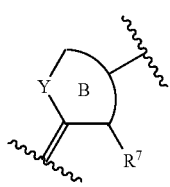
VI
and wherein the ring system represented by B in formula VI, above, is a five membered unsaturated heterocyclic ring wherein said unsaturated heterocyclic ring is selected from the group consisting of:
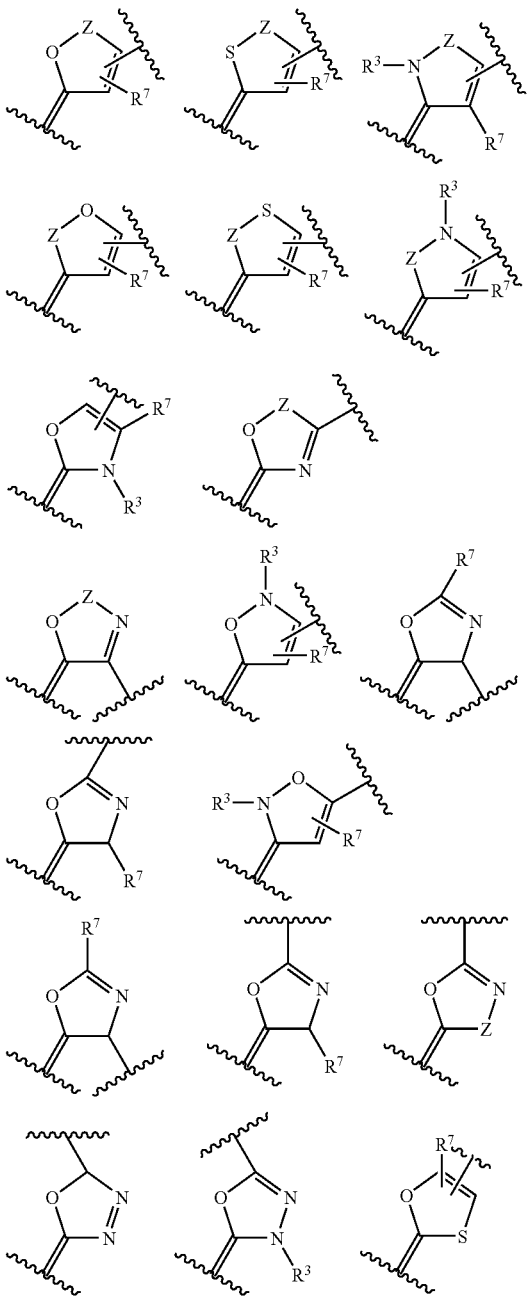

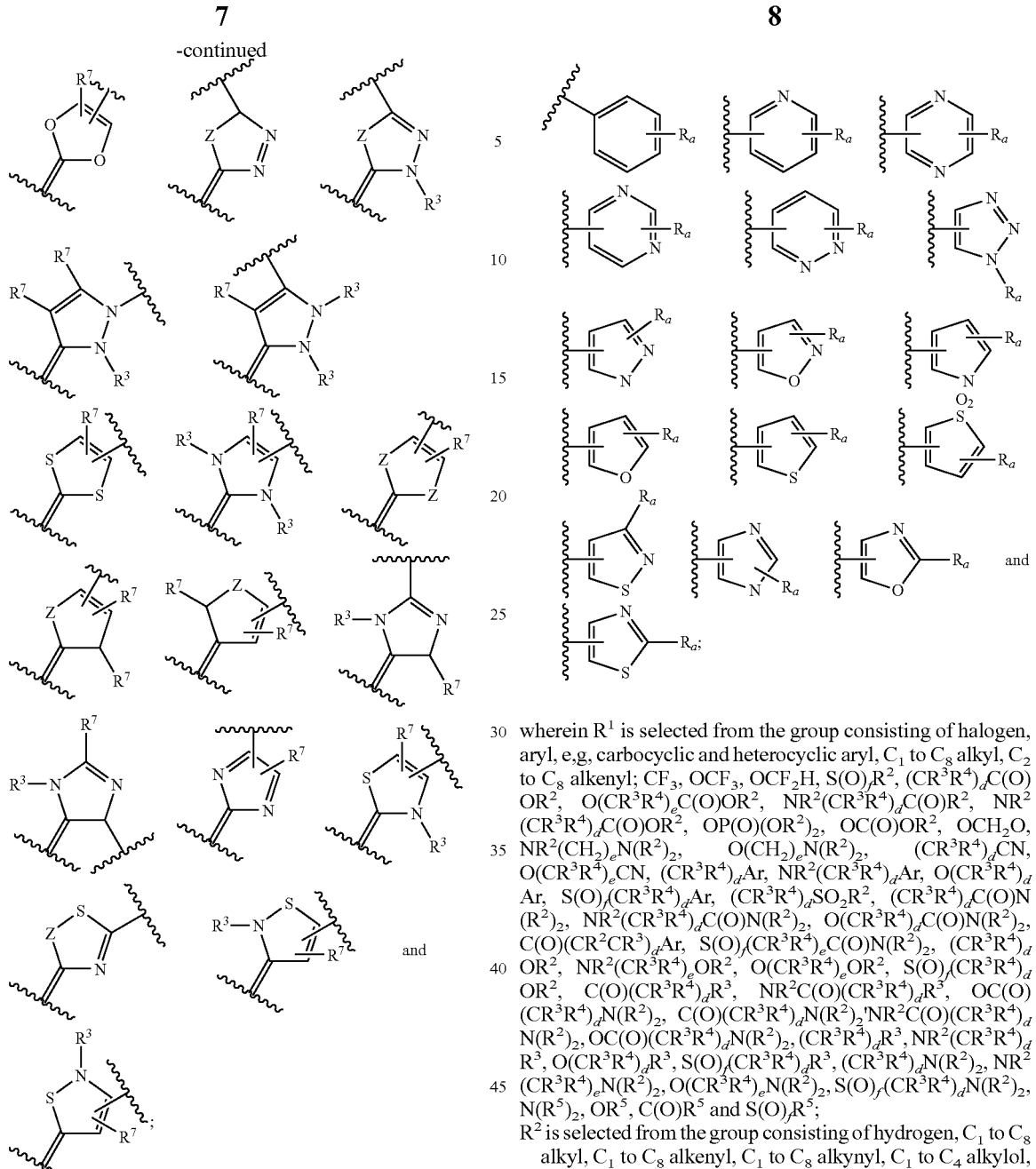

wherein Z is selected from the group consisting of $[C(R^2)_2]_c$, O, $NR^3$ and S;

VII

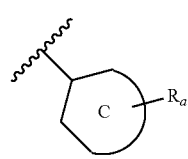

and wherein the ring system represented by C in formula VII, above, is a 5 or 6 membered aryl group e.g. a carbocyclic aryl or heterocyclic aryl, wherein said aryl group is selected from the group consisting of:

wherein $R^1$ is selected from the group consisting of halogen, aryl, e.g, carbocyclic and heterocyclic aryl, $C_1$ to $C_8$ alkyl, $C_2$ to $C_8$ alkenyl; $CF_3$, $OCF_3$, $OCF_2H$, $S(O)_fR^2$, $(CR^3R^4)_dC(O)OR^2$, $O(CR^3R^4)_eC(O)OR^2$, $NR^2(CR^3R^4)_dC(O)R^2$, $NR^2(CR^3R^4)_dC(O)OR^2$, $OP(O)(OR^2)_2$, $OC(O)OR^2$, $OCH_2O$, $NR^2(CH_2)_eN(R^2)_2$, $O(CH_2)_eN(R^2)_2$, $(CR^3R^4)_dCN$, $O(CR^3R^4)_eCN$, $(CR^3R^4)_dAr$, $NR^2(CR^3R^4)_dAr$, $O(CR^3R^4)_d$ $Ar$, $S(O)_f(CR^3R^4)_dAr$, $(CR^3R^4)_dSO_2R^2$, $(CR^3R^4)_dC(O)N(R^2)_2$, $NR^2(CR^3R^4)_dC(O)N(R^2)_2$, $O(CR^3R^4)_dC(O)N(R^2)_2$, $C(O)(CR^2CR^3)_dAr$, $S(O)_f(CR^3R^4)_eC(O)N(R^2)_2$, $(CR^3R^4)_dOR^2$, $NR^2(CR^3R^4)_eOR^2$, $O(CR^3R^4)_eOR^2$, $S(O)_f(CR^3R^4)_dOR^2$, $C(O)(CR^3R^4)_dR^3$, $NR^2C(O)(CR^3R^4)_dR^3$, $OC(O)(CR^3R^4)_dN(R^2)_2$, $C(O)(CR^3R^4)_dN(R^2)_2$, $NR^2C(O)(CR^3R^4)_dN(R^2)_2$, $OC(O)(CR^3R^4)_dN(R^2)_2$, $(CR^3R^4)_dR^3$, $NR^2(CR^3R^4)_dR^3$, $O(CR^3R^4)_dR^3$, $S(O)_f(CR^3R^4)_dR^3$, $(CR^3R^4)_dN(R^2)_2$, $NR^2(CR^3R^4)_eN(R^2)_2$, $O(CR^3R^4)_eN(R^2)_2$, $S(O)_f(CR^3R^4)_dN(R^2)_2$, $N(R^5)_2$, $OR^5$, $C(O)R^5$ and $S(O)_fR^5$;

$R^2$ is selected from the group consisting of hydrogen, $C_1$ to $C_8$ alkyl, $C_1$ to $C_8$ alkenyl, $C_1$ to $C_8$ alkynyl, $C_1$ to $C_4$ alkylol, lower alkylphenyl, phenyl, $(CR^3R^4)_dAr$, $(CR^3R^4)_dC(O)OR^6$, $(CR^3R^4)_dSO_2R^6$, $(CR^3R^4)_dOR^6$, $(CR^3R^4)_dOSO_2R^6$, $(CR^3R^4)_dP(O)(OR^6)_2$, $(CR^3R^4)_dR^6$, $(CR^3R^4)_eN(R^6)_2$ and $(CR^3R^4)_eNR^6C(O)N(R^6)_2$;

wherein $N(R^6)_2$ may form a 3-7 membered heterocyclic ring, for example, pyrrolidine, 3-fluoropyrrolidine, piperidine, 4-fluoropiperidine, N-methylpiperazine, morpholine, 2,6-dimethylmorpholine, thiomorpholine, and wherein said heterocyclic ring may be substituted with one or more of $R^3$; and $[C(R^2)_2]_c$ may form a 3-7 membered carbocyclic or heterocyclic ring;

R is selected from the group consisting of halogen, $C_1$ to $C_8$ alkyl, $C_2$ to $C_8$ conjugated alkenyl, $(CR^2=CR^2)_dCON(R^2)_2$, $CF_3$, $OCF_3$, $OCF_2H$, $(CR^3R^4)_dCN$, $NR^2(CR^3R^4)_eCN$, $O(CR^3R^4)_eCN$, $S(O)_fR^2$, $(CR^3R^4)_dC(O)OR^2$, $NR^2(CR^3R^4)_dC(O)OR^2$, $O(CR^3R^4)_dC(O)OR^2$, $S(O)_f(CR^3R^4)_dC(O)OR^2$, $(CR^3R^4)_dAr$, $NR^2(CR^3R^4)_dAr$, $O(CR^3R^4)_dAr$, $S(O)_f(CR^3R^4)_dAr$, $(CR^3R^4)_dSO_2R^2$, $NR^2(CR^3R^4)_dS(O)_f$ $R^2$, $O(CR^3R^4)_dS(O)_fR^2$, $S(O)_f(CR^3R^4)_eS(O)_fR^2$, $(CR^3R^4)_dC(O)N(R^2)_2$, $NR^2(CR^3R^4)_dC(O)N(R^2)_2$, $O(CR^3R^4)_dC(O)N(R^2)_2$, $S(O)_f(CR^3R^4)_eC(O)N(R^2)_2$, $(CR^3R^4)_dOR^2$, $NR^2(CR^3R^4)_eOR^2$, $O(CR^3R^4)_eOR^2$, $S(O)_f(CR^3R^4)_dOR^2$, $(CR^3R^4)_dOSO_2R^2$, $NR^2(CR^3R^4)_eOSO_2R^2$, $O(CR^3R^4)_eOSO_2R^2$, $S(O)_f(CR^3R^4)_eOSO_2R^2(CR^3R^4)_dP(O)(OR^2)_2$, $NR^2(CR^3R^4)_dP(O)(OR^2)_2O(CR^3R^4)_dP(O)(OR^2)_2$, $S(O)_f(CR^3R^4)_eP(O)(OR^2)_2$, $C(O)(CR^3R^4)_dR^3$, $NR^2C(O)(CR^3R^4)_dR^3$, $OC(O)(CR^3R^4)_dN(R^2)_2$, $C(O)(CR^3R^4)_dN(R^2)_2$, $NR^2C(O)(CR^3R^4)_dN(R^2)_2$, $OC(O)(CR^3R^4)_dN(R^2)_2$, $(CR^3R^4)_dR^3$, $NR^2(CR^3R^4)_dR^3$, $O(CR^3R^4)_dR^3$, $S(O)_f(CR^3R^4)_dR^3$, $HNC(O)R^2$, $HN-C(O)OR^2$, $(CR^3R^4)_dN(R^2)_2$, $NR^2(CR^3R^4)_eN(R^2)_2$, $O(CR^3R^4)_eN(R^2)_2$, $S(O)_f(CR^3R^4)_dN(R^2)_2$, $OP(O)(OR^2)_2$, $OC(O)OR^2$, $OCH_2O$, $HN-CH=CH$, $-N(COR^2)CH_2CH_2$, $HC=N-NH$, $N=CH-S$, $(CR^3R^4)_dC=C(CR^3R^4)_dR^2$, $(CR^3R^4)_dC=C(CR^3R^4)_dOR^2$, $(CR^3R^4)_dC=C(CR^3R^4)_dN(R^2)_2$, $(CR^3R^4)_dCC(CR^3R^4)_eR^2$, $(CR^3R^4)_dCC(CR^3R^4)_eOR^2$, $(CR^3R^4)_dCC(CR^3R^4)_dN(R^2)_2$, $(CR^3R^4)_dC(O)(CR^3R^4)_dR^2$, $(CR^3R^4)_dC(O)(CR^3R^4)_dOR^2$ and $(CR^3R^4)_dC(O)(CR^3R^4)_dN(R^2)_2$;

$R^3$ and $R^4$ may be selected from the group consisting of H, F, hydroxy, and $C_1$-$C_4$ alkyl or $CR^3R^4$ may represent a carbocyclic or heterocyclic ring of from 3 to 6 carbons or alternatively, $(CR^3R^4)_d$ and $(CR^3R^4)_e$ may form a 3-7 membered carbocyclic or heterocyclic ring, preferably $R^3$ and $R^4$ are H, F, $CH_3$ or hydroxy;

$R^5$ is Ar—$R^1{}_b$, wherein Ar is 5-7 membered carbocyclic aryl or 5-7 membered heterocyclic aryl;

$R^6$ is selected from the group consisting of hydrogen, $C_1$-$C_8$ alkyl, hydroxylmethyl and phenyl;

$R^7$ is selected from the group consisting of hydrogen, $C_1$-$C_8$ alkyl, $C_2$-$C_8$ alkenyl, $C_2$-$C_8$ alkynyl, $(R^2CCR^2)_aCN$ and aryl;

a is 0 or an integer of from 1 to 3;
b is 0 or an integer of from 1 to 2;
c is an integer of from 1 to 2;
d is 0 or an integer of from 1 to 5;
e is an integer of from 1 to 4;
f is 0 or an integer of from 1 to 2;
g is an integer of from 2 to 5, and further provided said alkyl or aryl radicals may be substituted with one or two halo, hydroxy, lower alkyloxy, lower alkyl amino or cycloalkylamino radicals wherein the cycloalkyl ring can include an enchained oxygen, sulfur or additional nitrogen atom and may be substituted with one or two halo or lower alkyl radicals; and pharmaceutically acceptable salts thereof.

BRIEF DESCRIPTION OF THE DRAWING FIGURES

Illustrative routes to compounds of the present invention are illustrated in Schemes 1 through 11 set forth in the Drawing Figures and are not intended to limit the scope of the invention.

DETAILED DESCRIPTION OF THE INVENTION

Figure 1:
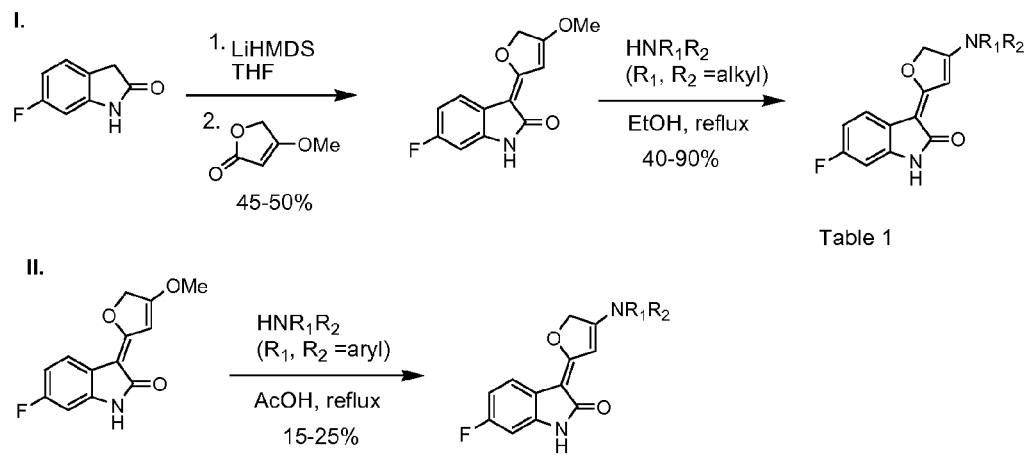
FIG. 1 shows methods for the preparation of compounds of Table 1, Table 2 and Table 3.
Figure 1:
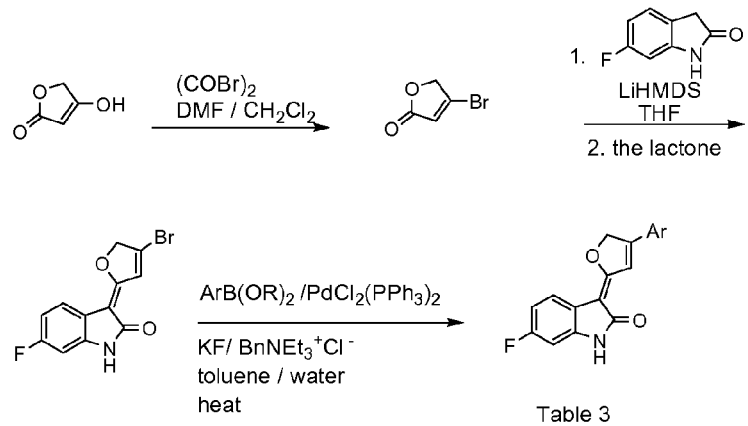
Figure 2:
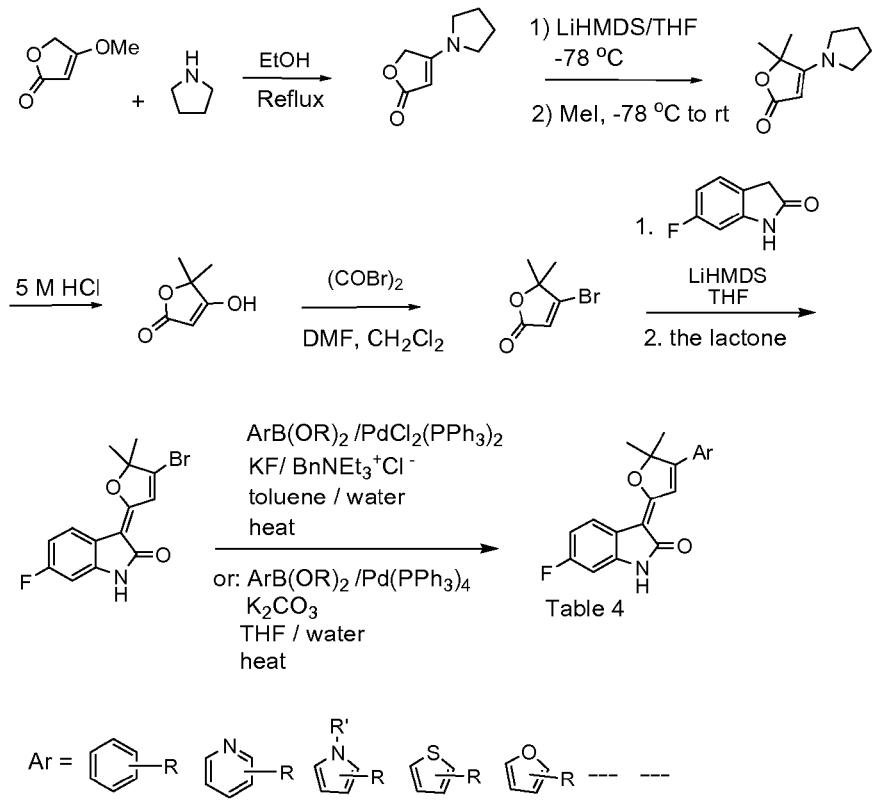
FIG. 2 shows methods for the preparation of compounds of Table 4 and Table 5.
Figure 2:
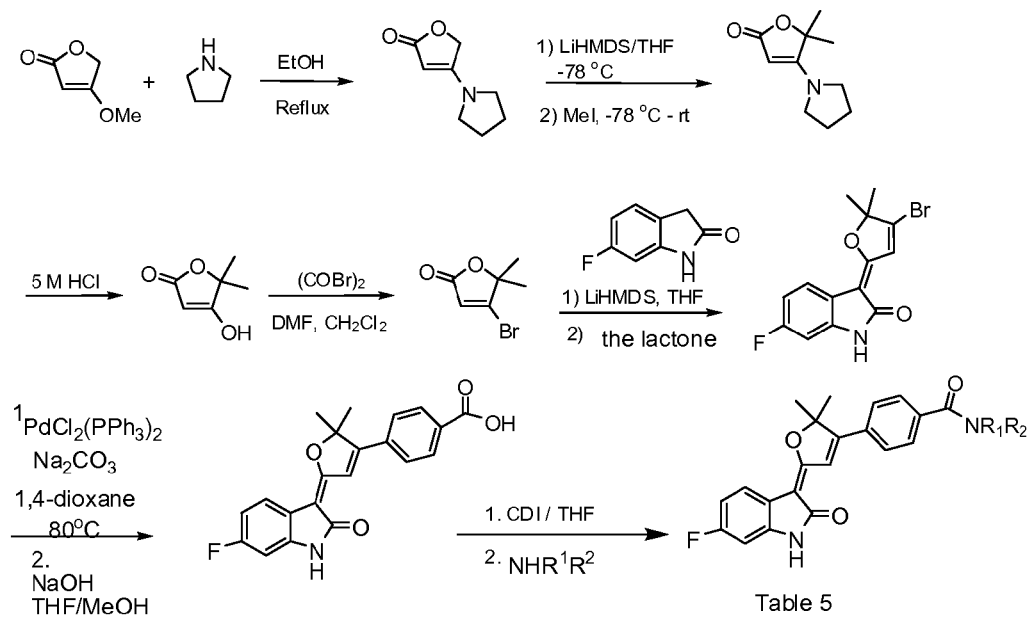

In particular, the compounds of the present invention may be selected from the group of compounds set forth in the Tables below.

TABLE 1

| | 3-[4-amino-5H-furan-(2E)-ylidene]-1,3-dihydro-indol-2-one derivatives | | |
|---|---|---|---|
| Example # | Chemical Structure | Chemical Name | FW |
| 1 | | 6-Fluoro-3-{4-[(2-methoxy-ethyl)-methyl-amino]-5H-furan-2-ylidene}-1,3-dihydro-indol-2-one | 304.319 |
| 2 | | 6-Fluoro-3-[4-(4-methyl-piperazin-1-yl)-5H-furan-2-ylidene]-1,3-dihydro-indol-2-one | 315.346 |

TABLE 1-continued

3-[4-amino-5H-furan-(2E)-ylidene]-1,3-dihydro-indol-2-one derivatives

| Example # | Chemical Structure | Chemical Name | FW |
|---|---|---|---|
| 3 | 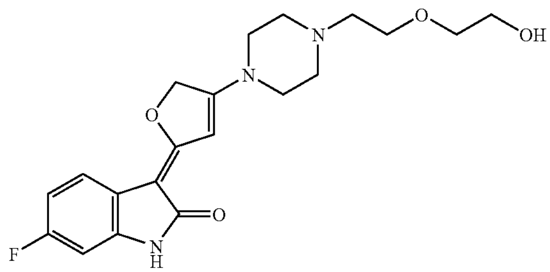 [SMILES: O=C1Nc2cc(F)ccc2/C1=C1/C=C(N2CCN(CCOCCO)CC2)CO1] | 6-Fluoro-3-(4-{4-[2-(2-hydroxy-ethoxy)-ethyl]-piperazin-1-yl}-5H-furan-2-ylidene)-1,3-dihydro-indol-2-one | 389.425 |
| 4 | 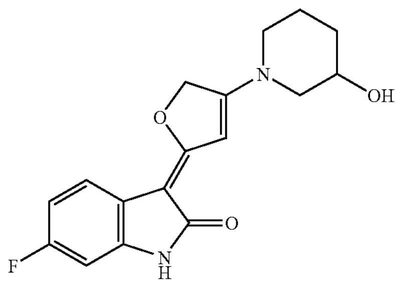 [SMILES: O=C1Nc2cc(F)ccc2/C1=C1/C=C(N2CCCC(O)C2)CO1] | 6-Fluoro-3-[4-(3-hydroxy-piperidin-1-yl)-5H-furan-2-ylidene]-1,3-dihydro-indol-2-one | 316.33 |
| 5 | 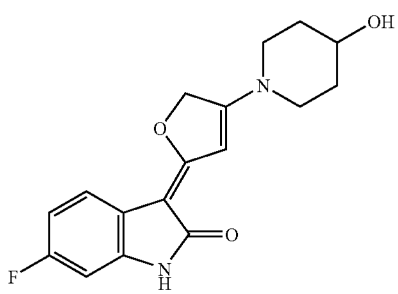 [SMILES: O=C1Nc2cc(F)ccc2/C1=C1/C=C(N2CCC(O)CC2)CO1] | 6-Fluoro-3-[4-(4-hydroxy-piperidin-1-yl)-5H-furan-2-ylidene]-1,3-dihydro-indol-2-one | 316.33 |
| 6 | 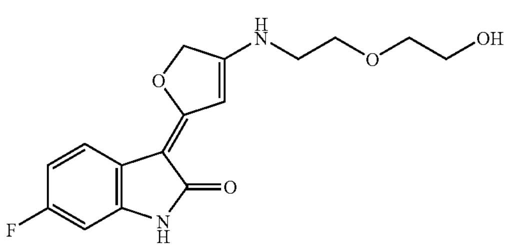 [SMILES: O=C1Nc2cc(F)ccc2/C1=C1/C=C(NCCOCCO)CO1] | 6-Fluoro-3-{4-[2-(2-hydroxy-ethoxy)-ethylamino]-5H-furan-2-ylidene}-1,3-dihydro-indol-2-one | 320.318 |
| 7 | 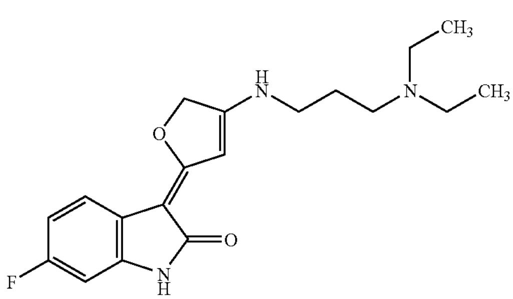 [SMILES: CCN(CC)CCCNC1=C/C(=C2\C(=O)Nc3cc(F)ccc32)OC1] | 3-[4-(3-Diethylamino-propylamino)-5H-furan-2-ylidene]-6-fluoro-1,3-dihydro-indol-2-one | 345.416 |

TABLE 1-continued

3-[4-amino-5H-furan-(2E)-ylidene]-1,3-dihydro-indol-2-one derivatives

| Example # | Chemical Structure | Chemical Name | FW |
|---|---|---|---|
| 8 | 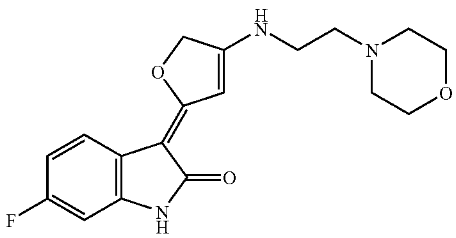 [SMILES: O=C1Nc2cc(F)ccc2/C1=C1/C=C(NCCN2CCOCC2)CO1] | 6-Fluoro-3-[4-(2-morpholin-4-yl-ethylamino)-5H-furan-2-ylidene]-1,3-dihydro-indol-2-one | 345.372 |
| 9 | 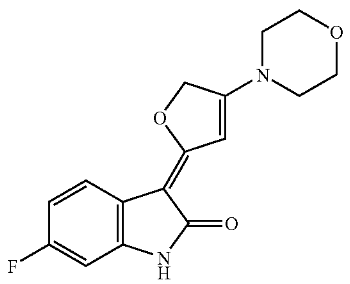 [SMILES: O=C1Nc2cc(F)ccc2/C1=C1/C=C(N2CCOCC2)CO1] | 6-Fluoro-3-(4-morpholin-4-yl-5H-furan-2-ylidene)-1,3-dihydro-indol-2-one | 302.303 |
| 10 | 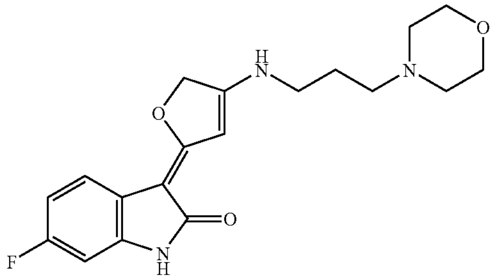 [SMILES: O=C1Nc2cc(F)ccc2/C1=C1/C=C(NCCCN2CCOCC2)CO1] | 6-Fluoro-3-[4-(3-morpholin-4-yl-propylamino)-5H-furan-2-ylidene]-1,3-dihydro-indol-2-one | 359.399 |

TABLE 2

3-[4-amino-5H-furan-(2E)-ylidene]-1,3-dihydro-indol-2-one derivatives

| Example # | Chemical Structure | Chemical Name | FW |
|---|---|---|---|
| 11 | 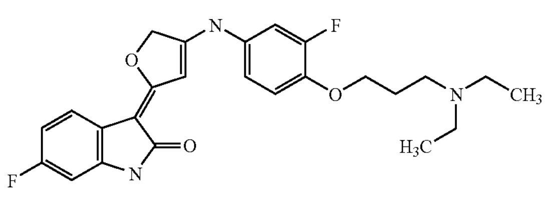 [SMILES: CCN(CC)CCCOc1ccc(NC2=C/C(=C3\C(=O)Nc4cc(F)ccc43)OC2)cc1F] | 3-{4-[4-(3-Diethylamino-propoxy)-3-fluoro-phenylamino]-5H-furan-2-ylidene}-6-fluoro-1,3-dihydro-indol-2-one | 455.502 |
| 12 | 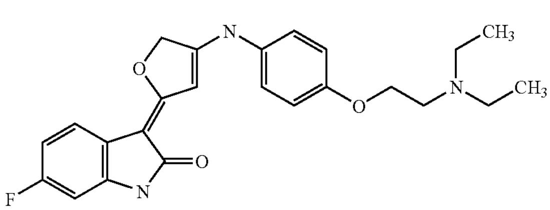 [SMILES: CCN(CC)CCOc1ccc(NC2=C/C(=C3\C(=O)Nc4cc(F)ccc43)OC2)cc1] | 3-{4-[4-(2-Diethylamino-ethoxy)-phenylamino]-5H-furan-2-ylidene}-6-fluoro-1,3-dihydro-indol-2-one | 423.485 |

TABLE 3

3-[5H-furan-(2E)-ylidene]-1,3-dihydro-indol-2-one derivatives

| Example # | Chemical Structure | Chemical Name | FW |
| --- | --- | --- | --- |
| 13 | 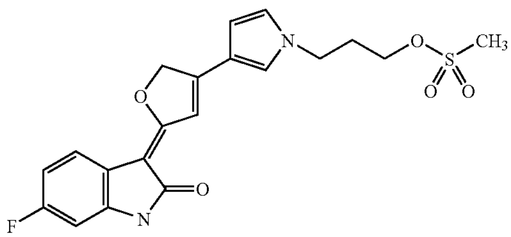 [SMILES: CS(=O)(=O)OCCCn1ccc(C2=C/C(=C3\C(=O)Nc4cc(F)ccc43)OC2)c1] | 3-{3-[(5E)-5-(6-fluoro-2-oxo-1,2-dihydro-3H-indol-3-ylidene)-2,5-dihydrofuran-3-yl]-1H-pyrrol-1-yl}propyl methanesulfonate | 418.443 |
| 14 | 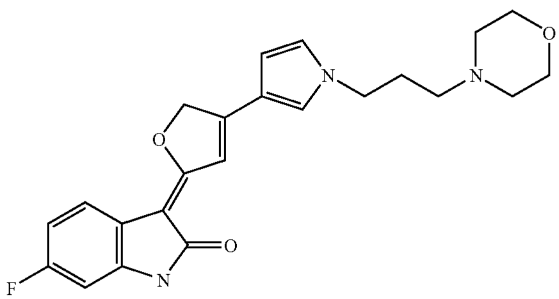 [SMILES: O=C1Nc2cc(F)ccc2/C1=C1/C=C(c2ccn(CCCN3CCOCC3)c2)CO1] | (3E)-6-fluoro-3-{4-[1-(3-morpholin-4-ylpropyl)-1H-pyrrol-3-yl]furan-2(5H)-ylidene}-1,3-dihydro-2H-indol-2-one | 409.459 |
| 15 | 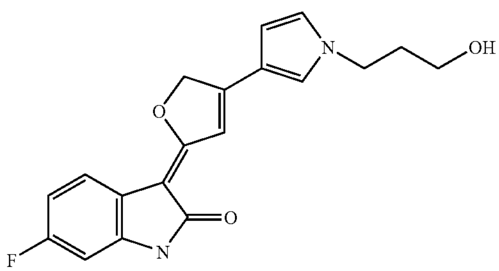 [SMILES: O=C1Nc2cc(F)ccc2/C1=C1/C=C(c2ccn(CCCO)c2)CO1] | (3E)-6-fluoro-3-{4-[1-(3-hydroxypropyl)-1H-pyrrol-3-yl]furan-2(5H)-ylidene}-1,3-dihydro-2H-indol-2-one | 340.352 |
| 16 | 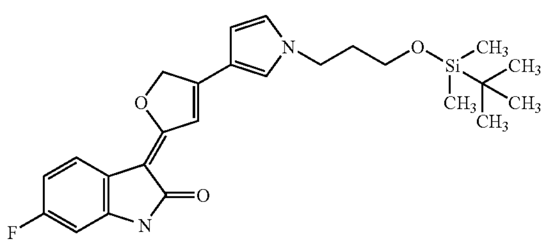 [SMILES: CC(C)(C)[Si](C)(C)OCCCn1ccc(C2=C/C(=C3\C(=O)Nc4cc(F)ccc43)OC2)c1] | (3E)-3-{4-[1-(3-{[tert-butyl(dimethyl)silyl]oxy}propyl)-1H-pyrrol-3-yl]furan-2(5H)-ylidene}-6-fluoro-1,3-dihydro-2H-indol-2-one | 454.615 |
| 17 | 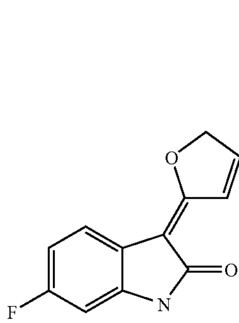 | (3E)-3-[4-(1-benzothien-3-yl)furan-2(5H)-ylidene]-6-fluoro-1,3-dihydro-2H-indol-2-one | 349.384 |

TABLE 3-continued

3-[5H-furan-(2E)-ylidene]-1,3-dihydro-indol-2-one derivatives

| Example # | Chemical Structure | Chemical Name | FW |
|---|---|---|---|
| 18 | 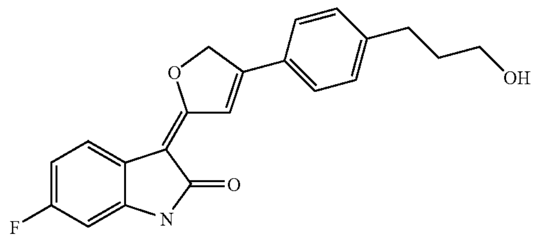 [SMILES: O=C1Nc2cc(F)ccc2/C1=C1/C=C(c2ccc(CCCO)cc2)CO1] | (3E)-6-fluoro-3-{4-[4-(3-hydroxypropyl)phenyl]furan-2(5H)-ylidene}-1,3-dihydro-2H-indol-2-one | 351.375 |
| 19 | 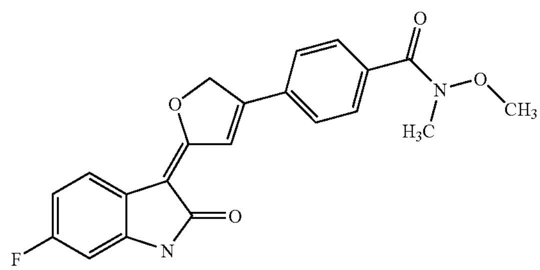 [SMILES: CON(C)C(=O)c1ccc(C2=C/C(=C3\C(=O)Nc4cc(F)ccc43)OC2)cc1] | 4-[(5E)-5-(6-fluoro-2-oxo-1,2-dihydro-3H-indol-3-ylidene)-2,5-dihydrofuran-3-yl]-N-methoxy-N-methylbenzamide | 380.373 |
| 20 | 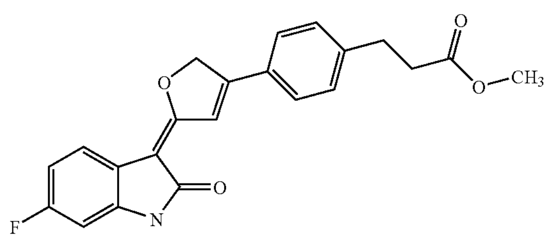 [SMILES: COC(=O)CCc1ccc(C2=C/C(=C3\C(=O)Nc4cc(F)ccc43)OC2)cc1] | methyl 3-{4-[(5E)-5-(6-fluoro-2-oxo-1,2-dihydro-3H-indol-3-ylidene)-2,5-dihydrofuran-3-yl]phenyl}propanoate | 379.385 |
| 21 | 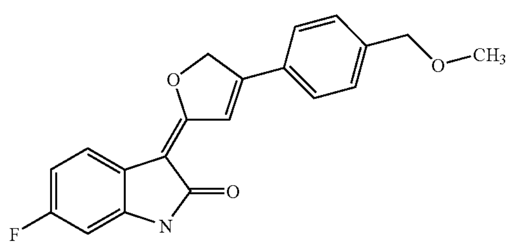 [SMILES: COCc1ccc(C2=C/C(=C3\C(=O)Nc4cc(F)ccc43)OC2)cc1] | (3E)-6-fluoro-3-{4-[4-(methoxymethyl)phenyl]furan-2(5H)-ylidene}-1,3-dihydro-2H-indol-2-one | 337.348 |
| 22 | 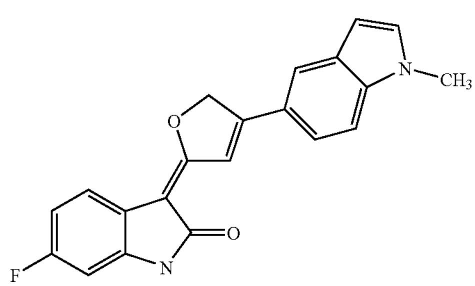 [SMILES: Cn1ccc2cc(C3=C/C(=C4\C(=O)Nc5cc(F)ccc54)OC3)ccc21] | (3E)-6-fluoro-3-[4-(1-methyl-1H-indol-5-yl)furan-2(5H)-ylidene]-1,3-dihydro-2H-indol-2-one | 346.359 |
| 23 | 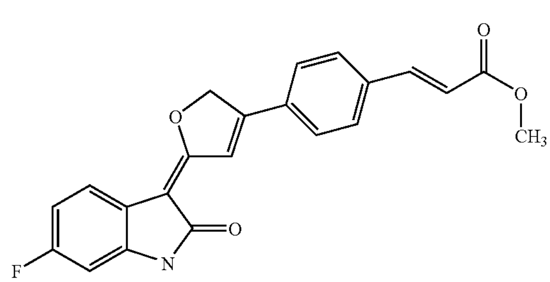 [SMILES: COC(=O)/C=C/c1ccc(C2=C/C(=C3\C(=O)Nc4cc(F)ccc43)OC2)cc1] | methyl (2E)-3-{4-[(5E)-5-(6-fluoro-2-oxo-1,2-dihydro-3H-indol-3-ylidene)-2,5-dihydrofuran-3-yl]phenyl}acrylate | 377.369 |

TABLE 3-continued

3-[5H-furan-(2E)-ylidene]-1,3-dihydro-indol-2-one derivatives

| Example # | Chemical Structure | Chemical Name | FW |
|---|---|---|---|
| 24 | 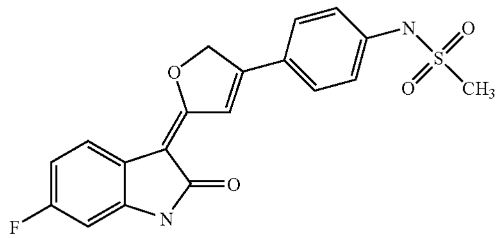 [SMILES: CS(=O)(=O)Nc1ccc(C2=C/C(=C3\C(=O)Nc4cc(F)ccc43)OC2)cc1] | N-{4-[(5E)-5-(6-fluoro-2-oxo-1,2-dihydro-3H-indol-3-ylidene)-2,5-dihydrofuran-3-yl]phenyl}methanesulfonamide | 386.401 |
| 25 | 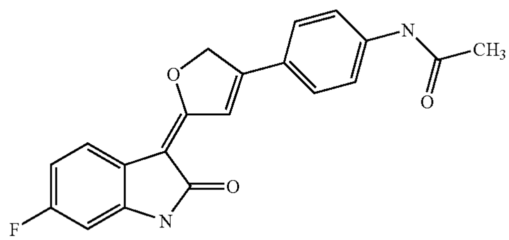 [SMILES: CC(=O)Nc1ccc(C2=C/C(=C3\C(=O)Nc4cc(F)ccc43)OC2)cc1] | N-{4-[(5E)-5-(6-fluoro-2-oxo-1,2-dihydro-3H-indol-3-ylidene)-2,5-dihydrofuran-3-yl]phenyl}acetamide | 350.348 |
| 26 | 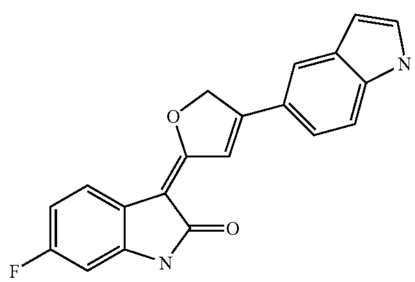 [SMILES: O=C1Nc2cc(F)ccc2/C1=C1/C=C(c2ccc3[nH]ccc3c2)CO1] | (3E)-6-fluoro-3-[4-(1H-indol-5-yl)furan-2(5H)-ylidene]-1,3-dihydro-2H-indol-2-one | 332.333 |
| 27 | 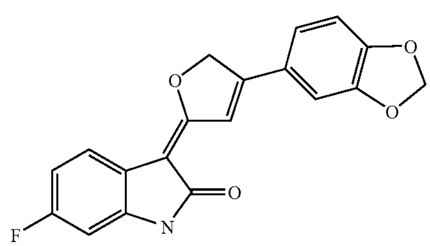 [SMILES: O=C1Nc2cc(F)ccc2/C1=C1/C=C(c2ccc3c(c2)OCO3)CO1] | (3E)-3-[4-(1,3-benzodioxol-5-yl)furan-2(5H)-ylidene]-6-fluoro-1,3-dihydro-2H-indol-2-one | 337.305 |
| 28 | 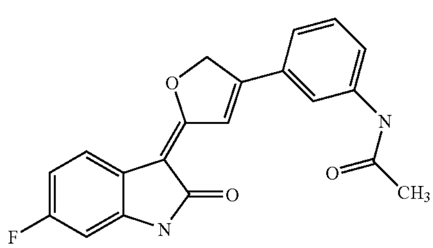 [SMILES: CC(=O)Nc1cccc(C2=C/C(=C3\C(=O)Nc4cc(F)ccc43)OC2)c1] | N-{3-[(5E)-5-(6-fluoro-2-oxo-1,2-dihydro-3H-indol-3-ylidene)-2,5-dihydrofuran-3-yl]phenyl}acetamide | 350.348 |
| 29 | 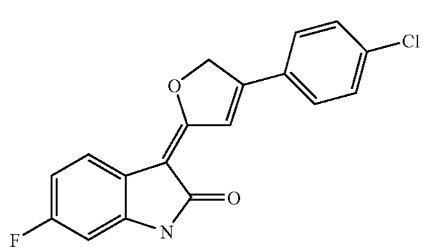 [SMILES: O=C1Nc2cc(F)ccc2/C1=C1/C=C(c2ccc(Cl)cc2)CO1] | (3E)-3-[4-(4-chlorophenyl)furan-2(5H)-ylidene]-6-fluoro-1,3-dihydro-2H-indol-2-one | 327.741 |

TABLE 3-continued

3-[5H-furan-(2E)-ylidene]-1,3-dihydro-indol-2-one derivatives

| Example # | Chemical Structure | Chemical Name | FW |
|---|---|---|---|
| 30 | 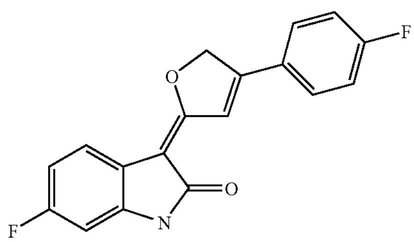 [SMILES: O=C1Nc2cc(F)ccc2/C1=C1/C=C(c2ccc(F)cc2)CO1] | (3E)-6-fluoro-3-[4-(4-fluorophenyl)furan-2(5H)-ylidene]-1,3-dihydro-2H-indol-2-one | 311.286 |
| 31 | 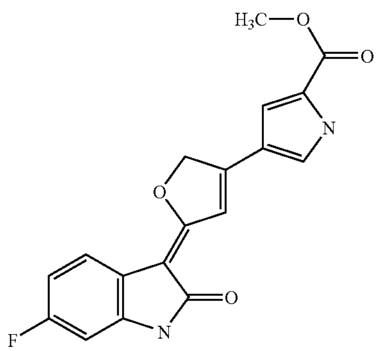 [SMILES: COC(=O)c1cc(C2=C/C(=C3\C(=O)Nc4cc(F)ccc43)OC2)c[nH]1] | methyl 4-[(5E)-5-(6-fluoro-2-oxo-1,2-dihydro-3H-indol-3-ylidene)-2,5-dihydrofuran-3-yl]-1H-pyrrole-2-carboxylate | 340.309 |
| 32 | 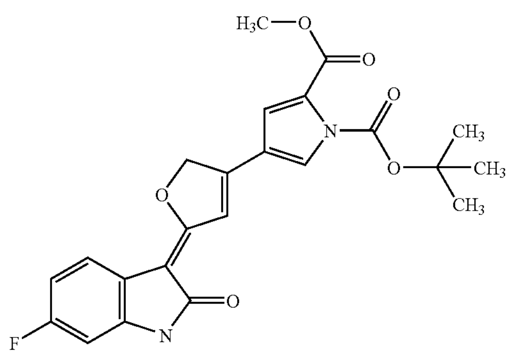 [SMILES: COC(=O)c1cc(C2=C/C(=C3\C(=O)Nc4cc(F)ccc43)OC2)cn1C(=O)OC(C)(C)C] | 1-tert-butyl 2-methyl 4-[(5E)-5-(6-fluoro-2-oxo-1,2-dihydro-3H-indol-3-ylidene)-2,5-dihydrofuran-3-yl]-1H-pyrrole-1,2-dicarboxylate | 440.425 |
| 33 | 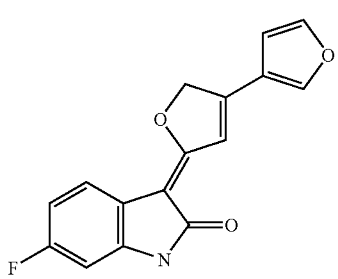 | (3E)-3-(3,3'-bifuran-5(2H)-ylidene)-6-fluoro-1,3-dihydro-2H-indol-2-one | 283.257 |
| 34 | 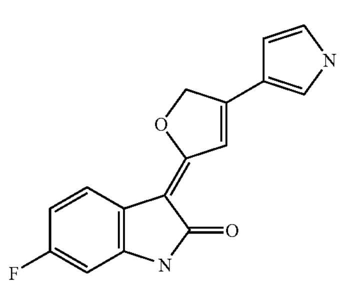 [SMILES: O=C1Nc2cc(F)ccc2/C1=C1/C=C(c2cc[nH]c2)CO1] | (3E)-6-fluoro-3-[4-(1H-pyrrol-3-yl)furan-2(5H)-ylidene]-1,3-dihydro-2H-indol-2-one | 282.273 |

TABLE 3-continued

3-[5H-furan-(2E)-ylidene]-1,3-dihydro-indol-2-one derivatives

| Example # | Chemical Structure | Chemical Name | FW |
|---|---|---|---|
| 35 | 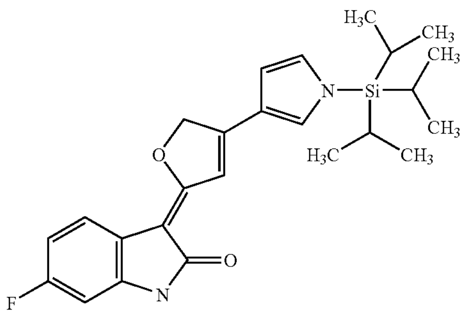 [SMILES: CC(C)[Si](C(C)C)(C(C)C)n1ccc(C2=C/C(=C3\C(=O)Nc4cc(F)ccc43)OC2)c1] | (3E)-6-fluoro-3-{4-[1-(triisopropylsilyl)-1H-pyrrol-3-yl]furan-2(5H)-ylidene}-1,3-dihydro-2H-indol-2-one | 438.616 |
| 36 | 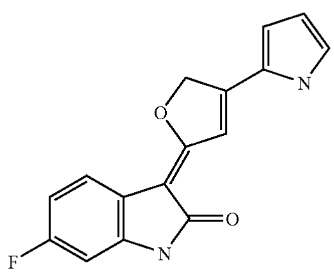 [SMILES: O=C1Nc2cc(F)ccc2/C1=C1/C=C(c2ccc[nH]2)CO1] | (3E)-6-fluoro-3-[4-(1H-pyrrol-2-yl)furan-2(5H)-ylidene]-1,3-dihydro-2H-indol-2-one | 282.273 |
| 37 | 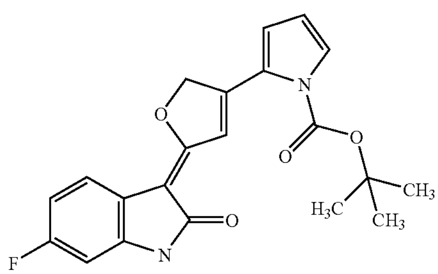 [SMILES: CC(C)(C)OC(=O)n1cccc1C1=C/C(=C2\C(=O)Nc3cc(F)ccc32)OC1] | tert-butyl 2-[(5E)-5-(6-fluoro-2-oxo-1,2-dihydro-3H-indol-3-ylidene)-2,5-dihydrofuran-3-yl]-1H-pyrrole-1-carboxylate | 382.389 |
| 38 | 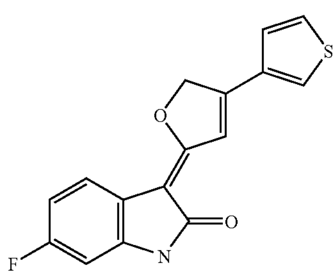 | (3E)-6-fluoro-3-[4-(3-thienyl)furan-2(5H)-ylidene]-1,3-dihydro-2H-indol-2-one | 299.324 |
| 39 | 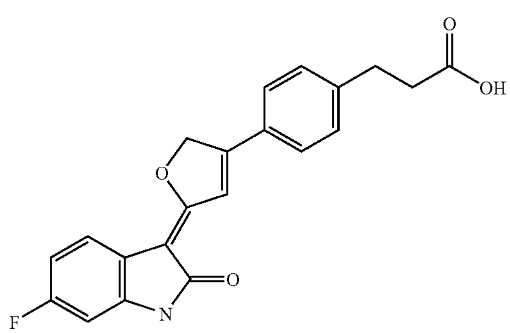 [SMILES: O=C(O)CCc1ccc(C2=C/C(=C3\C(=O)Nc4cc(F)ccc43)OC2)cc1] | 3-{4-[5-(6-Fluoro-2-oxo-1,2-dihydro-indol-3-ylidene)-2,5-dihydro-furan-3-yl]-phenyl}-propionic acid | 365.358 |

TABLE 3-continued

3-[5H-furan-(2E)-ylidene]-1,3-dihydro-indol-2-one derivatives

| Example # | Chemical Structure | Chemical Name | FW |
|---|---|---|---|
| 40 | 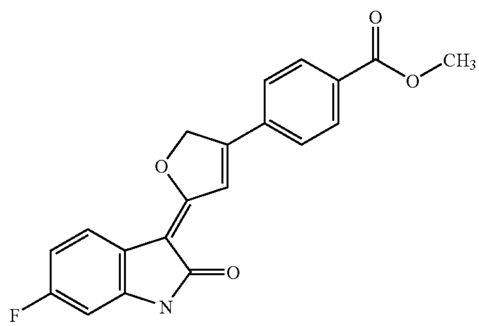 [SMILES: COC(=O)c1ccc(C2=C/C(=C3\C(=O)Nc4cc(F)ccc43)OC2)cc1] | 4-[5-(6-Fluoro-2-oxo-1,2-dihydro-indol-3-ylidene)-2,5-dihydro-furan-3-yl]-benzoic acid methyl ester | 351.332 |
| 41 | 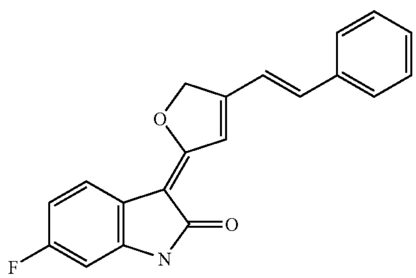 [SMILES: O=C1Nc2cc(F)ccc2/C1=C1C=C(/C=C/c2ccccc2)CO/1] | 6-Fluoro-3-(4-styryl-5H-furan-2-ylidene)-1,3-dihydro-indol-2-one | 319.334 |
| 42 | 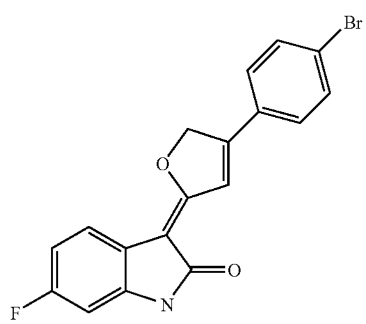 [SMILES: O=C1Nc2cc(F)ccc2/C1=C1/C=C(c2ccc(Br)cc2)CO1] | 3-[4-(4-Bromo-phenyl)-5H-furan-2-ylidene]-6-fluoro-1,3-dihydro-indol-2-one | 372.192 |
| 43 | 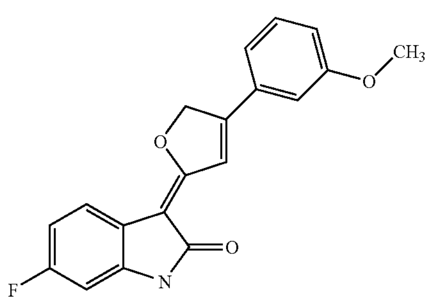 [SMILES: COc1cccc(C2=C/C(=C3\C(=O)Nc4cc(F)ccc43)OC2)c1] | 6-Fluoro-3-[4-(3-methoxy-phenyl)-5H-furan-2-ylidene]-1,3-dihydro-indol-2-one | 323.322 |
| 44 | 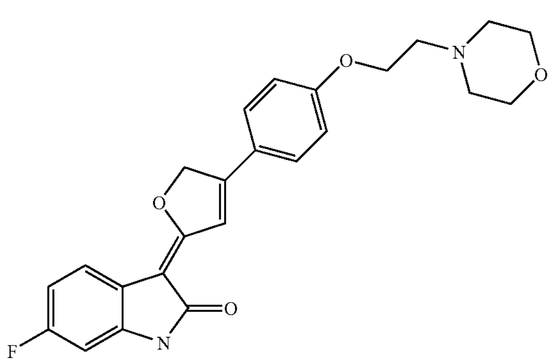 [SMILES: O=C1Nc2cc(F)ccc2/C1=C1/C=C(c2ccc(OCCN3CCOCC3)cc2)CO1] | 6-Fluoro-3-{4-[4-(2-morpholin-4-yl-ethoxy)-phenyl]-5H-furan-2-ylidene}-1,3-dihydro-indol-2-one | 422.454 |

TABLE 3-continued

3-[5H-furan-(2E)-ylidene]-1,3-dihydro-indol-2-one derivatives

| Example # | Chemical Structure | Chemical Name | FW |
|---|---|---|---|
| 45 | 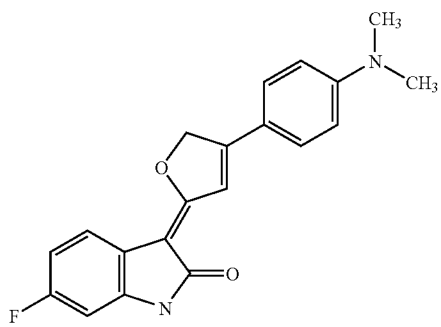 [SMILES: CN(C)c1ccc(C2=C/C(=C3\C(=O)Nc4cc(F)ccc43)OC2)cc1] | 3-[4-(4-Dimethylamino-phenyl)-5H-furan-2-ylidene]-6-fluoro-1,3-dihydro-indol-2-one | 336.364 |
| 46 | 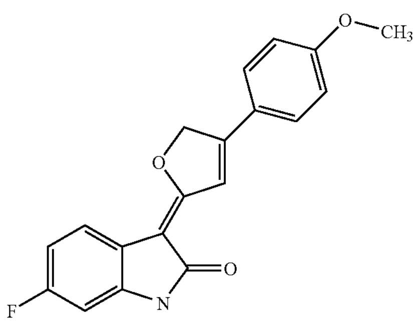 [SMILES: COc1ccc(C2=C/C(=C3\C(=O)Nc4cc(F)ccc43)OC2)cc1] | 6-Fluoro-3-[4-(4-methoxy-phenyl)-5H-furan-2-ylidene]-1,3-dihydro-indol-2-one | 323.322 |

TABLE 4

[5,5-dimethyl-5H-furan-(2E)-ylidene]-1,3-dihydro-indol-2-one derivatives

| Example # | Chemical Structure | Chemical Name | FW |
|---|---|---|---|
| 47 | 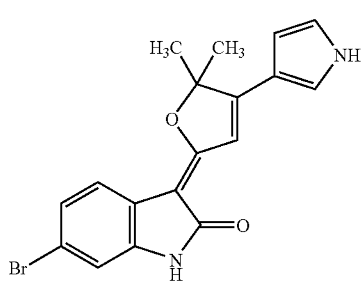 [SMILES: CC1(C)O/C(=C2/C(=O)Nc3cc(Br)ccc32)C=C1c1cc[nH]c1] | (3E)-6-bromo-3-[5,5-dimethyl-4-(1H-pyrrol-3-yl)furan-2(5H)-ylidene]-1,3-dihydro-2H-indol-2-one | 371.233 |
| 48 | 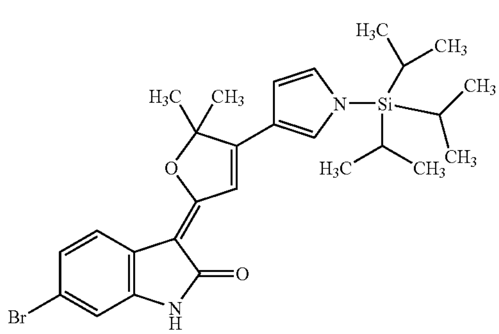 [SMILES: CC(C)[Si](C(C)C)(C(C)C)n1ccc(C2=C/C(=C3\C(=O)Nc4cc(Br)ccc43)OC2(C)C)c1] | (3E)-6-bromo-3-{5,5-dimethyl-4-[1-(triisopropylsilyl)-1H-pyrrol-3-yl]furan-2(5H)-ylidene}-1,3-dihydro-2H-indol-2-one | 527.576 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 49 | 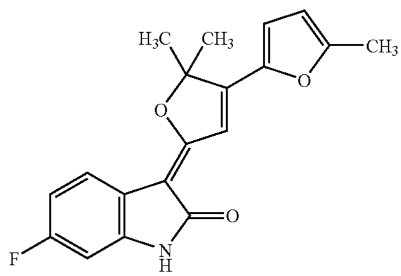 [SMILES: Cc1ccc(C2=C/C(=C3\C(=O)Nc4cc(F)ccc43)OC2(C)C)o1] | (3E)-6-fluoro-3-(2',2',5-trimethyl-2,3'-bifuran-5'(2'H)-ylidene)-1,3-dihydro-2H-indol-2-one | 325.337 |
| 50 | 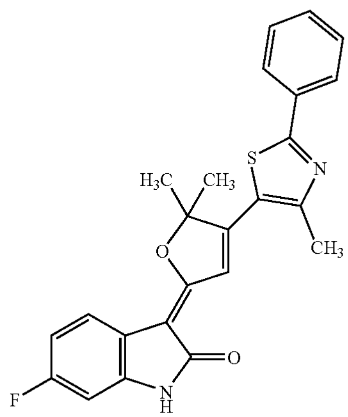 [SMILES: Cc1nc(-c2ccccc2)sc1C1=C/C(=C2\C(=O)Nc3cc(F)ccc32)OC1(C)C] | (3E)-3-[5,5-dimethyl-4-(4-methyl-2-phenyl-1,3-thiazol-5-yl)furan-2(5H)-ylidene]-6-fluoro-1,3-dihydro-2H-indol-2-one | 418.49 |
| 51 | 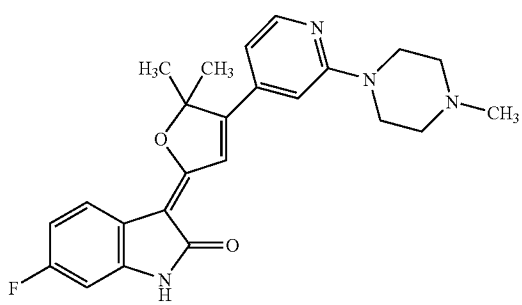 [SMILES: CN1CCN(c2cc(C3=C/C(=C4\C(=O)Nc5cc(F)ccc54)OC3(C)C)ccn2)CC1] | (3E)-3-{5,5-dimethyl-4-[2-(4-methylpiperazin-1-yl)pyridin-4-yl]furan-2(5H)-ylidene}-6-fluoro-1,3-dihydro-2H-indol-2-one | 420.486 |
| 52 | 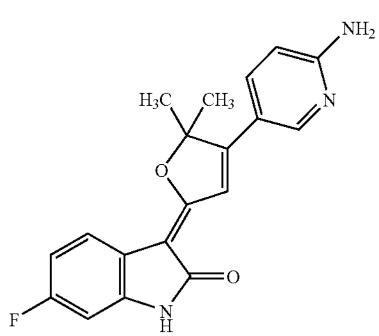 [SMILES: CC1(C)O/C(=C2/C(=O)Nc3cc(F)ccc32)C=C1c1ccc(N)nc1] | (3E)-3-[4-(6-aminopyridin-3-yl)-5,5-dimethylfuran-2(5H)-ylidene]-6-fluoro-1,3-dihydro-2H-indol-2-one | 337.352 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 53 | 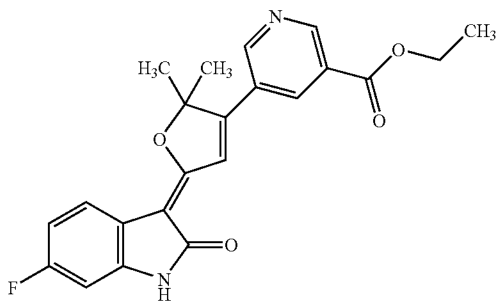 [SMILES: CCOC(=O)c1cncc(C2=C/C(=C3\C(=O)Nc4cc(F)ccc43)OC2(C)C)c1] | ethyl 5-[(5E)-5-(6-fluoro-2-oxo-1,2 dihydro-3H-indol-3-ylidene)-2,2-dimethyl-2,5-dihydrofuran-3-yl]nicotinate | 394.4 |
| 54 | 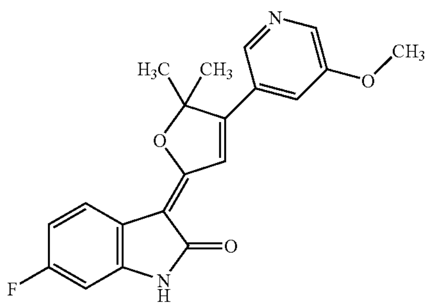 [SMILES: COc1cncc(C2=C/C(=C3\C(=O)Nc4cc(F)ccc43)OC2(C)C)c1] | (3E)-6-fluoro-3-[4-(5-methoxypyridin-3-yl)-5,5-dimethylfuran-2(5H)-ylidene]-1,3-dihydro-2H-indol-2-one | 352.363 |
| 55 | 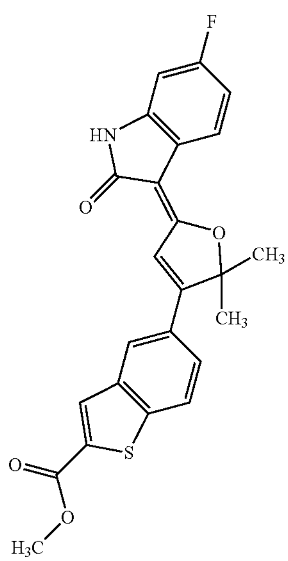 [SMILES: COC(=O)c1cc2cc(C3=C/C(=C4\C(=O)Nc5cc(F)ccc54)OC3(C)C)ccc2s1] | methyl 5-[(5E)-5-(6-fluoro-2-oxo-1,2-dihydro-3H-indol-3-ylidene)-2,2-dimethyl-2,5-dihydrofuran-3-yl]-1-benzothiophene-2-carboxylate | 435.473 |
| 56 | 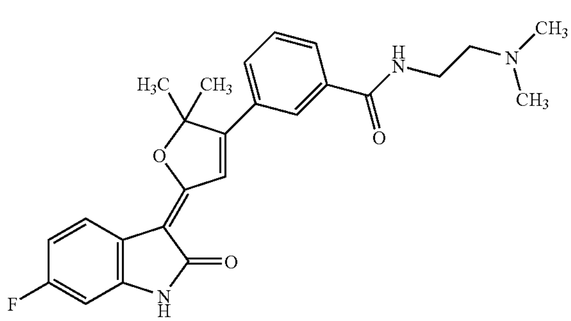 [SMILES: CN(C)CCNC(=O)c1cccc(C2=C/C(=C3\C(=O)Nc4cc(F)ccc43)OC2(C)C)c1] | N-[2-(dimethylamino)ethyl]-3-[(5E)-5-(6-fluoro-2-oxo-1,2-dihydro-3H-indol-3-ylidene)-2,2-dimethyl-2,5-dihydrofuran-3-yl]benzamide | 435.496 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 57 | 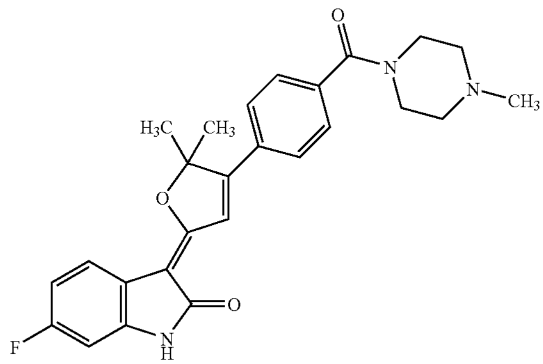 [SMILES: CN1CCN(C(=O)c2ccc(C3=C/C(=C4\C(=O)Nc5cc(F)ccc54)OC3(C)C)cc2)CC1] | (3E)-3-[5,5-dimethyl-4-{4-[(4-methylpiperazin-1-yl)carbonyl]phenyl}furan-2(5H)-ylidene]-6-fluoro-1,3-dihydro-2H-indol-2-one | 447.507 |
| 58 | 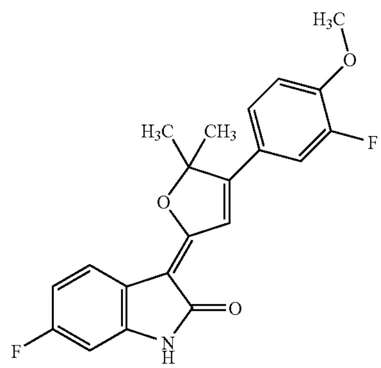 [SMILES: COc1ccc(C2=C/C(=C3\C(=O)Nc4cc(F)ccc43)OC2(C)C)cc1F] | (3E)-6-fluoro-3-[4-(3-fluoro-4-methoxyphenyl)-5,5-dimethylfuran 2(5H)-ylidene]-1,3-dihydro-2H-indol-2-one | 369.365 |
| 59 | 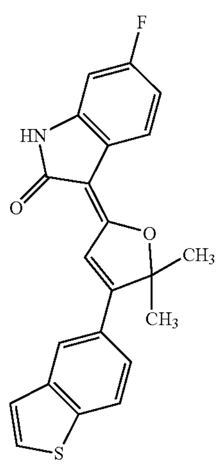 [SMILES: CC1(C)O/C(=C2/C(=O)Nc3cc(F)ccc32)C=C1c1ccc2sccc2c1] | (3E)-3-[4-(1-benzothien-5-yl)-5,5-dimethylfuran-2(5H)-ylidene]-6-fluoro-1,3-dihydro-2H-indol-2-one | 377.437 |
| 60 | 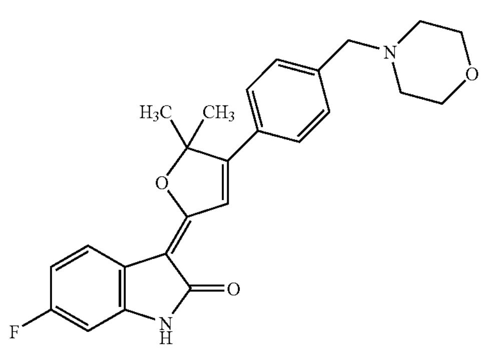 [SMILES: CC1(C)O/C(=C2/C(=O)Nc3cc(F)ccc32)C=C1c1ccc(CN2CCOCC2)cc1] | (3E)-3-{5,5-dimethyl-4-[4-(morpholin-4-ylmethyl)phenyl]furan-2(5H)-ylidene}-6-fluoro-1,3-dihydro-2H-indol-2-one | 420.482 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 61 | 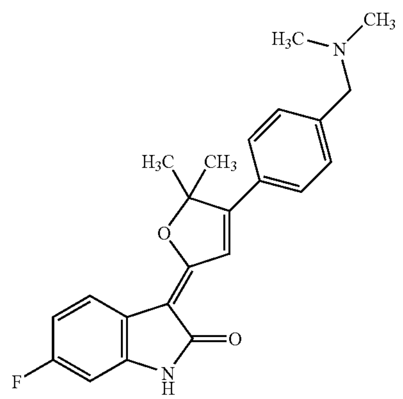 [SMILES: CN(C)Cc1ccc(C2=C/C(=C3\C(=O)Nc4cc(F)ccc43)OC2(C)C)cc1] | (3E)-3-[4-{4-[(dimethylamino)methyl]phenyl}-5,5-dimethylfuran-2(5H)-ylidene]-6-fluoro-1,3-dihydro-2H-indol-2-one | 378.445 |
| 62 | 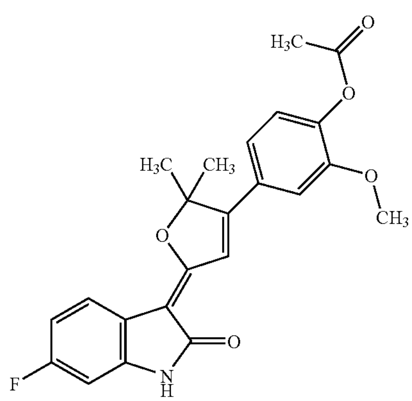 [SMILES: COc1cc(C2=C/C(=C3\C(=O)Nc4cc(F)ccc43)OC2(C)C)ccc1OC(C)=O] | 4-[(5E)-5-(6-fluoro-2-oxo-1,2-dihydro-3H-indol-3-ylidene)-2,2-dimethyl-2,5-dihydrofuran-3-yl]-2-methoxyphenyl acetate | 409.411 |
| 63 | 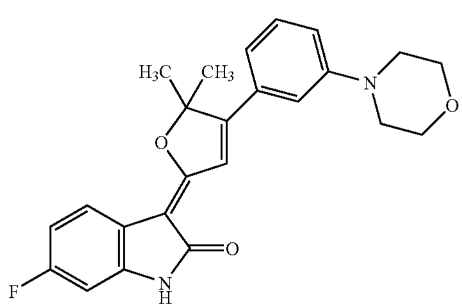 [SMILES: CC1(C)O/C(=C2/C(=O)Nc3cc(F)ccc32)C=C1c1cccc(N2CCOCC2)c1] | (3E)-3-[5,5-dimethyl-4-(3-morpholin-4-ylphenyl)furan-2(5H)-ylidene]-6-fluoro-1,3-dihydro-2H-indol-2-one | 406.455 |
| 64 | 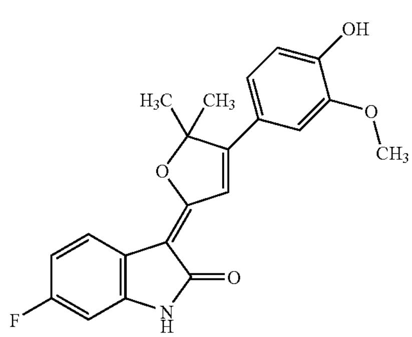 [SMILES: COc1cc(C2=C/C(=C3\C(=O)Nc4cc(F)ccc43)OC2(C)C)ccc1O] | (3E)-6-fluoro-3-[4-(4-hydroxy-3-methoxyphenyl)-5,5-dimethylfuran 2(5H)-ylidene]-1,3-dihydro-2H-indol-2-one | 367.374 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 65 | 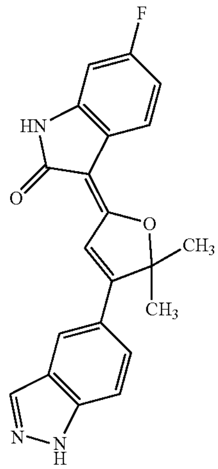 [SMILES: CC1(C)O/C(=C2/C(=O)Nc3cc(F)ccc32)C=C1c1ccc2[nH]ncc2c1] | (3E)-6-fluoro-3-[4-(1H-indazol-5-yl)-5,5-dmethylfuran-2(5H)-ylidene]-1,3-dihydro-2H-indol-2-one | 361.374 |
| 66 | 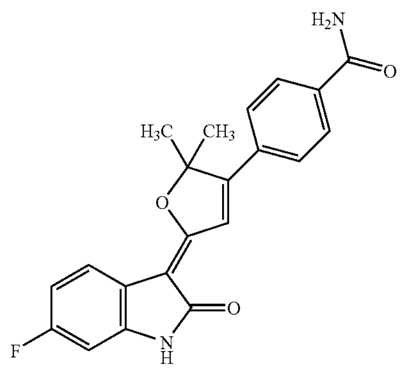 [SMILES: CC1(C)O/C(=C2/C(=O)Nc3cc(F)ccc32)C=C1c1ccc(C(N)=O)cc1] | 4-[(5E)-5-(6-fluoro-2-oxo-1,2-dihydro-3H-indol-3-ylidene)-2,2-dimethyl-2,5-dihydrofuran-3-yl]benzamide | 364.374 |
| 67 | 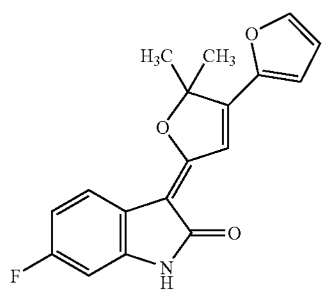 [SMILES: CC1(C)O/C(=C2/C(=O)Nc3cc(F)ccc32)C=C1c1ccco1] | (3E)-3-(2',2'-dimethyl-2,3'-bifuran-5'(2'H)-ylidene)-6-fluoro-1,3-dihydro-2H-indol-2-one | 311.311 |
| 68 | 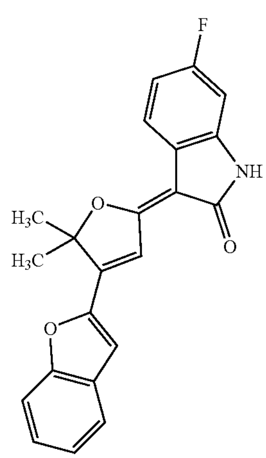 [SMILES: CC1(C)O/C(=C2/C(=O)Nc3cc(F)ccc32)C=C1c1cc2ccccc2o1] | (3E)-3-[4-(1-benzofuran-2-yl)-5,5-dimethylfuran-2(5H)-ylidene]-6-fluoro-1,3-dihydro-2H-indol-2-one | 361.37 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 69 | 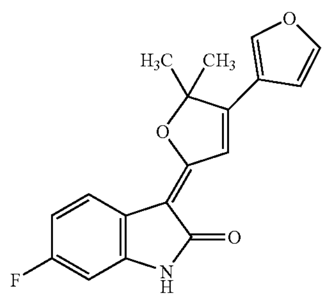 [SMILES: CC1(C)O/C(=C2/C(=O)Nc3cc(F)ccc32)C=C1c1ccoc1] | (3E)-3-(2,2-dimethyl-3,3'-bifuran-5(2H)-ylidene)-6-fluoro-1,3-dihydro-2H-indol-2-one | 311.311 |
| 70 | 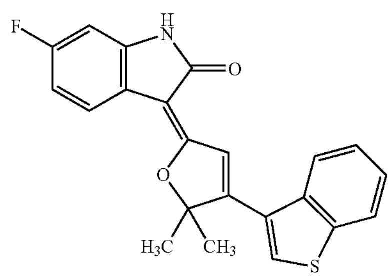 [SMILES: CC1(C)O/C(=C2/C(=O)Nc3cc(F)ccc32)C=C1c1csc2ccccc12] | (3E)-3-[4-(1-benzothien-3-yl)-5,5-dimethylfuran-2(5H)-ylidene]-6-fluoro-1,3-dihydro-2H-indol-2-one | 377.437 |
| 71 | 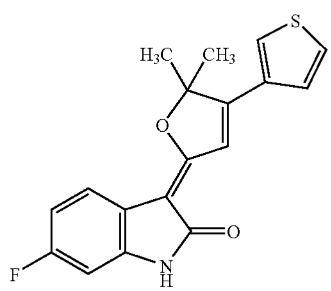 [SMILES: CC1(C)O/C(=C2/C(=O)Nc3cc(F)ccc32)C=C1c1ccsc1] | (3E)-3-[5,5-dimethyl-4-(3-thienyl)furan-2(5H)-ylidene]-6-fluoro-1,3-dihydro-2H-indol-2-one | 327.378 |
| 72 | 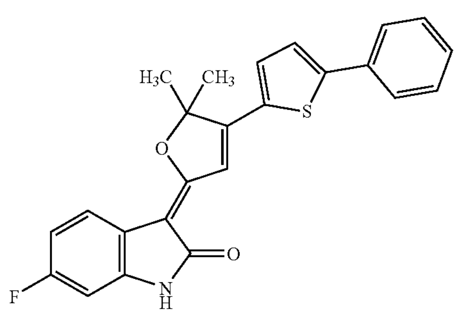 [SMILES: CC1(C)O/C(=C2/C(=O)Nc3cc(F)ccc32)C=C1c1ccc(-c2ccccc2)s1] | (3E)-3-[5,5-dimethyl-4-(5-phenyl-2-thienyl)furan-2(5H)-ylidene]-6-fluoro-1,3-dihydro-2H-indol-2-one | 403.475 |
| 73 | 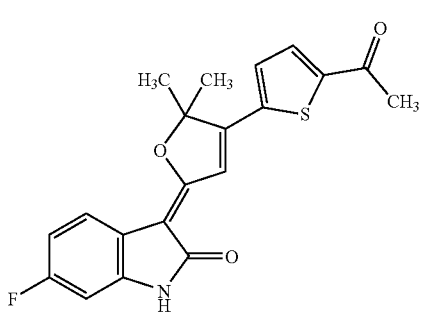 [SMILES: CC(=O)c1ccc(C2=C/C(=C3\C(=O)Nc4cc(F)ccc43)OC2(C)C)s1] | (3E)-3-[4-(5-acetyl-2-thienyl)-5,5-dimethylfuran-2(5H)-ylidene]-6-fluoro-1,3-dihydro-2H-indol-2-one | 369.414 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 74 | 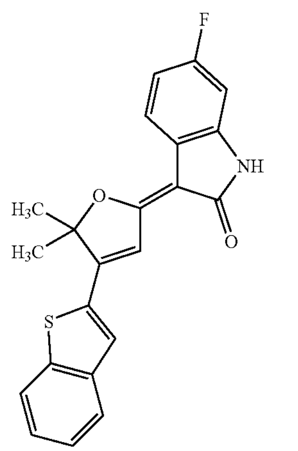 [SMILES: CC1(C)O/C(=C2/C(=O)Nc3cc(F)ccc32)C=C1c1cc2ccccc2s1] | (3E)-3-[4-(1-benzothien-2-yl)-5,5-dimethylfuran-2(5H)-ylidene]-6-fluoro-1,3-dihydro-2H-indol-2-one | 377.437 |
| 75 | 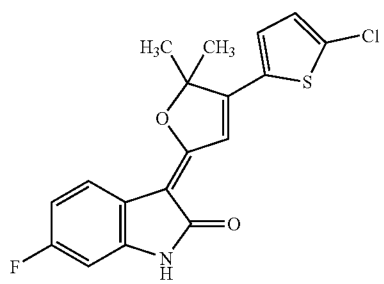 [SMILES: CC1(C)O/C(=C2/C(=O)Nc3cc(F)ccc32)C=C1c1ccc(Cl)s1] | (3E)-3-[4-(5-chloro-2-thienyl)-5,5-dimethylfuran-2(5H)-ylidene]-6-fluoro-1,3-dihydro-2H-indol-2-one | 361.823 |
| 76 | 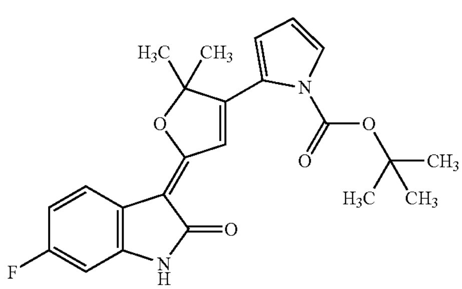 [SMILES: CC(C)(C)OC(=O)n1cccc1C1=C/C(=C2\C(=O)Nc3cc(F)ccc32)OC1(C)C] | tert-butyl 2-[(5E)-5-(6-fluoro-2-oxo-1,2-dihydro-3H-indol-3-ylidene)-2,2-dimethyl-2,5-dihydrofuran-3-yl]-1H-pyrrole-1-carboxylate | 410.443 |
| 77 | 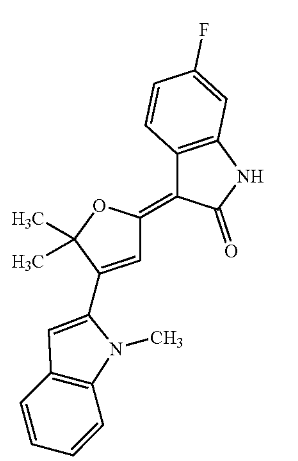 [SMILES: Cn1c(C2=C/C(=C3\C(=O)Nc4cc(F)ccc43)OC2(C)C)cc2ccccc21] | (3E)-3-[5,5-dimethyl-4-(1-methyl-1H-indol-2-yl)furan-2(5H)-ylidene]-6-fluoro-1,3-dihydro-2H-indol-2-one | 374.413 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 78 | 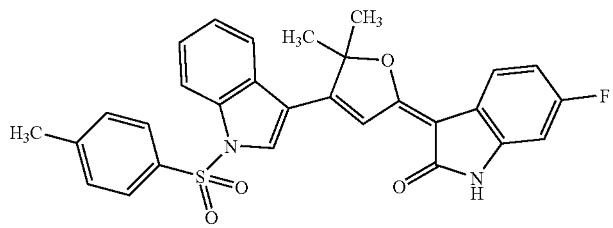 [SMILES: Cc1ccc(S(=O)(=O)n2cc(C3=C/C(=C4\C(=O)Nc5cc(F)ccc54)OC3(C)C)c3ccccc32)cc1] | (3E)-3-[5,5-dimethyl-4-{1-[(4-methylphenyl)sulfonyl]-1H-indol-3-yl}furan-2(5H)-ylidene]-6-fluoro-1,3-dihydro-2H-indol-2-one | 514.575 |
| 79 | 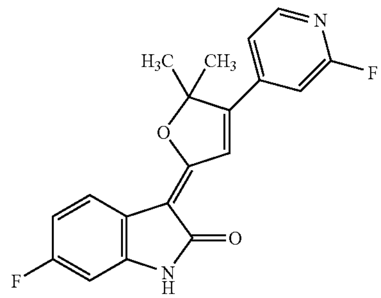 [SMILES: CC1(C)O/C(=C2/C(=O)Nc3cc(F)ccc32)C=C1c1ccnc(F)c1] | (3E)-6-fluoro-3-[4-(2-fluoropyridin-4-yl)-5,5-dimethylfuran-2(5H)-ylidene]-1,3-dihydro-2H-indol-2-one | 340.328 |
| 80 | 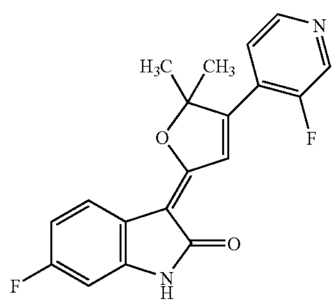 [SMILES: CC1(C)O/C(=C2/C(=O)Nc3cc(F)ccc32)C=C1c1ccncc1F] | (3E)-6-fluoro-3-[4-(3-fluoropyridin-4-yl)-5,5-dimethylfuran-2(5H)-ylidene]-1,3-dihydro-2H-indol-2-one | 340.328 |
| 81 | 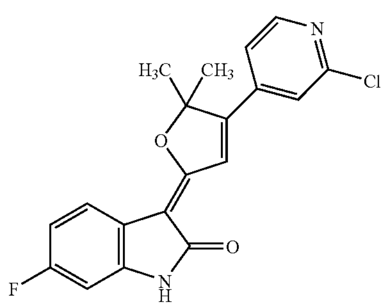 | (3E)-3-[4-(2-chloropyridin-4-yl)-5,5-dimethylfuran-2(5H)-ylidene]-6-fluoro-1,3-dihydro-2H-indol-2-one | 356.783 |
| 82 | 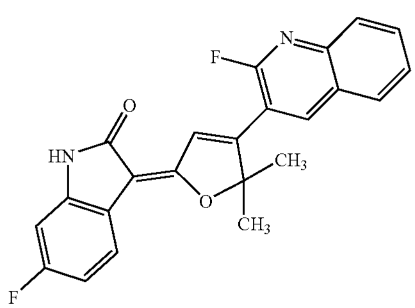 [SMILES: CC1(C)O/C(=C2/C(=O)Nc3cc(F)ccc32)C=C1c1cc2ccccc2nc1F] | (3E)-6-fluoro-3-[4-(2-fluoroquinolin-3-yl)-5,5-dimethylfuran-2(5H)-ylidene]-1,3-dihydro-2H-indol-2-one | 390.387 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 83 | 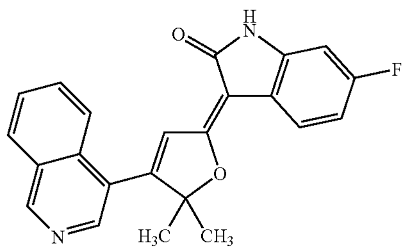 [SMILES: CC1(C)O/C(=C2/C(=O)Nc3cc(F)ccc32)C=C1c1cncc2ccccc12] | (3E)-6-fluoro-3-(4-isoquinolin-4-yl-5,5-dimethylfuran-2(5H)-ylidene)-1,3-dihydro-2H-indol-2-one | 372.397 |
| 84 | 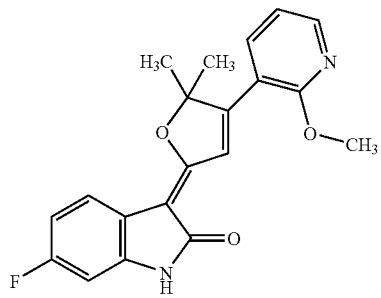 [SMILES: COc1ncccc1C1=C/C(=C2\C(=O)Nc3cc(F)ccc32)OC1(C)C] | (3E)-6-fluoro-3-[4-(2-methoxypyridin-3-yl)-5,5-dimethylfuran-2(5H)-ylidene]-1,3-dihydro-2H-indol-2-one | 352.363 |
| 85 | 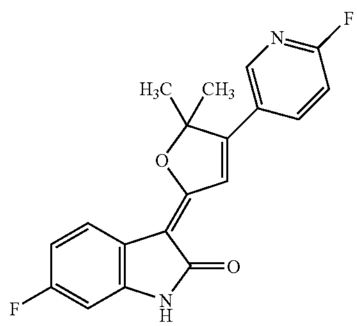 [SMILES: CC1(C)O/C(=C2/C(=O)Nc3cc(F)ccc32)C=C1c1ccc(F)nc1] | (3E)-6-fluoro-3-[4-(6-fluoropyridin-3-yl)-5,5-dimethylfuran-2(5H)-ylidene]-1,3-dihydro-2H-indol-2-one | 340.328 |
| 86 | 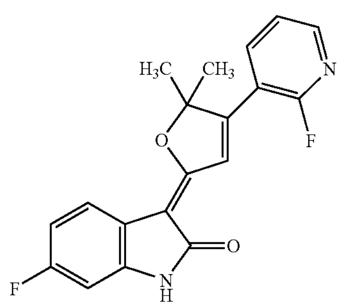 [SMILES: CC1(C)O/C(=C2/C(=O)Nc3cc(F)ccc32)C=C1c1cccnc1F] | (3E)-6-fluoro-3-[4-(2-fluoropyridin-3-yl)-5,5-dimethylfuran-2(5H)-ylidene]-1,3-dihydro-2H-indol-2-one | 340.328 |
| 87 | 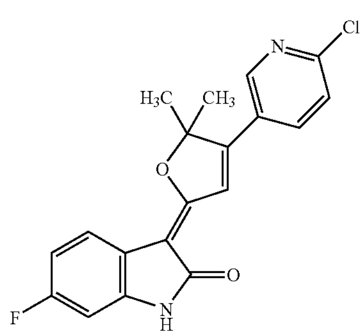 [SMILES: CC1(C)O/C(=C2/C(=O)Nc3cc(F)ccc32)C=C1c1ccc(Cl)nc1] | (3E)-3-[4-(6-chloropyridin-3-yl)-5,5-dimethylfuran-2(5H)-ylidene]-6-fluoro-1,3-dihydro-2H-indol-2-one | 356.783 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 88 | 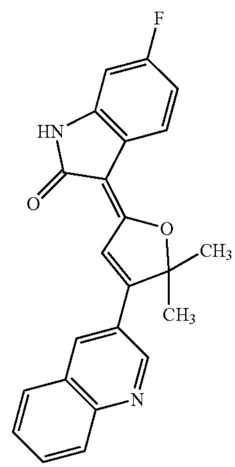 [SMILES: CC1(C)O/C(=C2/C(=O)Nc3cc(F)ccc32)C=C1c1cnc2ccccc2c1] | (3E)-3-(5,5-dimethyl-4-quinolin-3-ylfuran-2(5H)-ylidene)-6-fluoro-1,3-dihydro-2H-indol-2-one | 372.397 |
| 89 | 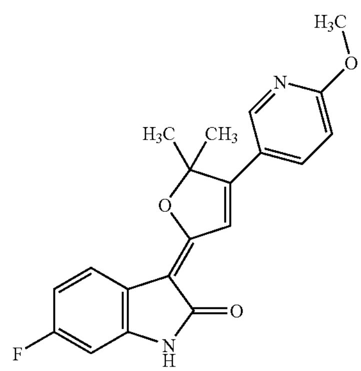 [SMILES: COc1ccc(C2=C/C(=C3\C(=O)Nc4cc(F)ccc43)OC2(C)C)cn1] | (3E)-6-fluoro-3-[4-(6-methoxypyridin-3-yl)-5,5-dimethylfuran-2(5H)-ylidene]-1,3-dihydro-2H-indol-2-one | 352.363 |
| 90 | 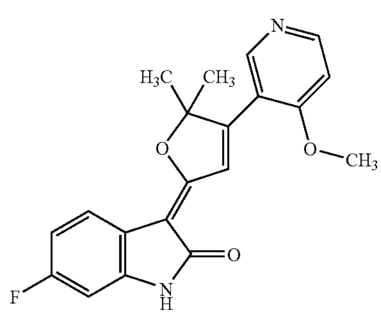 [SMILES: COc1ccncc1C1=C/C(=C2\C(=O)Nc3cc(F)ccc32)OC1(C)C] | (3E)-6-fluoro-3-[4-(4-methoxypyridin-3-yl)-5,5-dimethylfuran-2(5H)-ylidene]-1,3-dihydro-2H-indol-2-one | 352.363 |
| 91 | 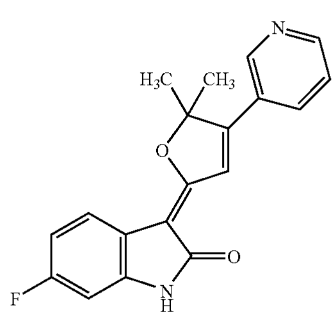 [SMILES: CC1(C)O/C(=C2/C(=O)Nc3cc(F)ccc32)C=C1c1cccnc1] | (3E)-3-(5,5-dimethyl-4-pyridin-3-ylfuran-2(5H)-ylidene)-6-fluoro-1,3-dihydro-2H-indol-2-one | 322.337 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 92 | 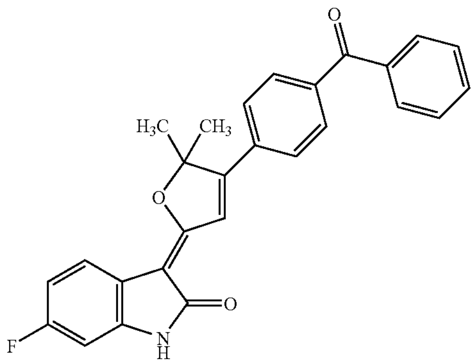 [SMILES: CC1(C)O/C(=C2/C(=O)Nc3cc(F)ccc32)C=C1c1ccc(C(=O)c2ccccc2)cc1] | (3E)-3-[4-(4-benzoylphenyl)-5,5-dimethylfuran-2(5H)-ylidene]-6-fluoro-1,3-dihydro-2H-indol-2-one | 425.457 |
| 93 | 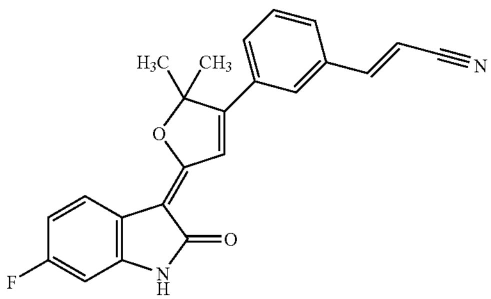 [SMILES: CC1(C)O/C(=C2/C(=O)Nc3cc(F)ccc32)C=C1c1cccc(/C=C/C#N)c1] | (2E)-3-{3-[(5E)-5-(6-fluoro-2-oxo-1,2-dihydro-3H-indol-3-ylidene)-2,2-dimethyl-2,5-dihydrofuran-3-yl]phenyl}acrylonitrile | 372.397 |
| 94 | 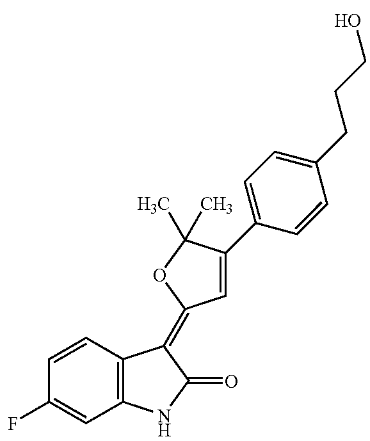 [SMILES: CC1(C)O/C(=C2/C(=O)Nc3cc(F)ccc32)C=C1c1ccc(CCCO)cc1] | (3E)-6-fluoro-3-{4-[4-(3-hydroxypropyl)phenyl]-5,5-dimethylfuran-2(5H)-ylidene}-1,3-dihydro-2H-indol-2-one | 379.429 |
| 95 | 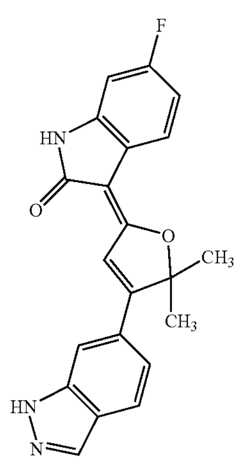 [SMILES: CC1(C)O/C(=C2/C(=O)Nc3cc(F)ccc32)C=C1c1ccc2cn[nH]c2c1] | (3E)-6-fluoro-3-[4-(1H-indazol-6-yl)-5,5-dimethylfuran-2(5H)-ylidene]-1,3-dihydro-2H-indol-2-one | 361.374 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 96 | 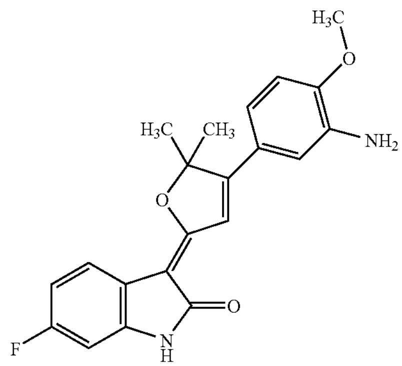 [SMILES: COc1ccc(C2=C/C(=C3\C(=O)Nc4cc(F)ccc43)OC2(C)C)cc1N] | (3E)-3-[4-(3-amino-4-methoxyphenyl)-5,5-dimethylfuran 2(5H)-ylidene]-6-fluoro-1,3-dihydro-2H-indol-2-one | 366.39 |
| 97 | 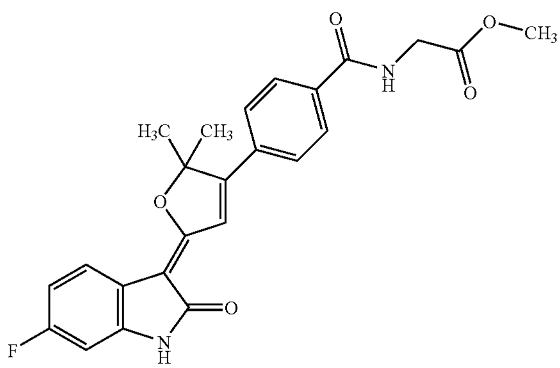 [SMILES: COC(=O)CNC(=O)c1ccc(C2=C/C(=C3\C(=O)Nc4cc(F)ccc43)OC2(C)C)cc1] | methyl ({4-[(5E)-5-(6-fluoro-2-oxo-1,2-dihydro-3H-indol-3-ylidene)-2,2-dimethyl-2,5-dihydrofuran-3-yl]benzoyl}amino)acetate | 436.437 |
| 98 | 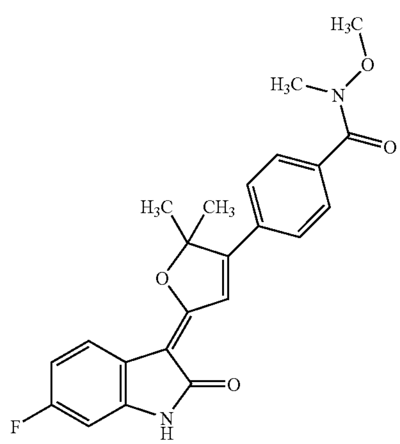 [SMILES: CON(C)C(=O)c1ccc(C2=C/C(=C3\C(=O)Nc4cc(F)ccc43)OC2(C)C)cc1] | 4-[(5E)-5-(6-fluoro-2-oxo-1,2-dihydro-3H-indol-3-ylidene)-2,2-dimethyl-2,5-dihydrofuran-3-yl]-N-methoxy-N-methylbenzamide | 408.427 |
| 99 | 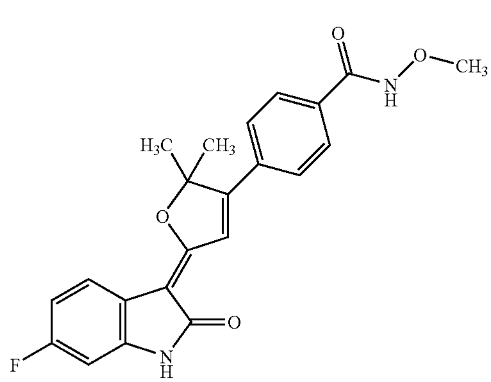 [SMILES: CONC(=O)c1ccc(C2=C/C(=C3\C(=O)Nc4cc(F)ccc43)OC2(C)C)cc1] | 4-[(5E)-5-(6-fluoro-2-oxo-1,2-dihydro-3H-indol-3-ylidene)-2,2-dimethyl-2,5-dihydrofuran-3-yl]-N-methoxybenzamide | 394.4 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 100 | 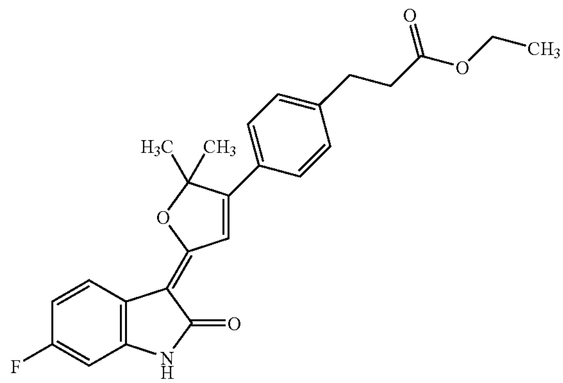 [SMILES: CCOC(=O)CCc1ccc(C2=C/C(=C3\C(=O)Nc4cc(F)ccc43)OC2(C)C)cc1] | ethyl 3-{4-[(5E)-5-(6-fluoro-2-oxo-1,2-dihydro-3H-indol-3-ylidene)-2,2-dimethyl-2,5-dihydrofuran-3-yl]phenyl}propanoate | 421.466 |
| 101 | 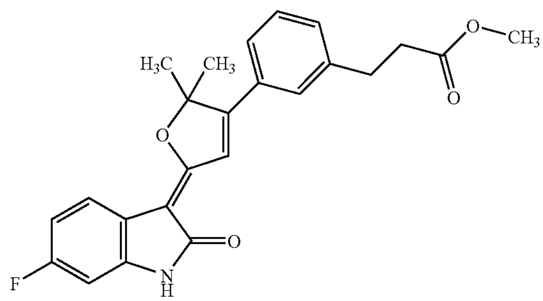 [SMILES: COC(=O)CCc1cccc(C2=C/C(=C3\C(=O)Nc4cc(F)ccc43)OC2(C)C)c1] | methyl 3-{3-[(5E)-5-(6-fluoro-2-oxo-1,2-dihydro-3H-indol-3-ylidene)-2,2-dimethyl-2,5-dihydrofuran-3-yl]phenyl}propanoate | 407.439 |
| 102 | 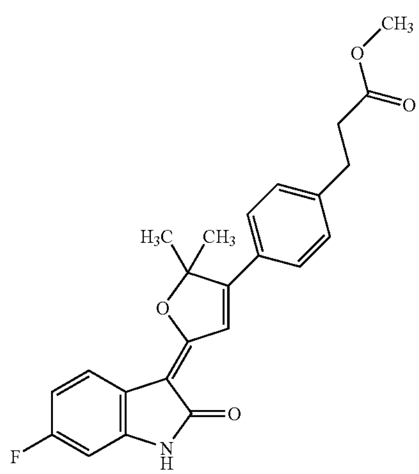 [SMILES: COC(=O)CCc1ccc(C2=C/C(=C3\C(=O)Nc4cc(F)ccc43)OC2(C)C)cc1] | methyl 3-{4-[(5E)-5-(6-fluoro-2-oxo-1,2-dihydro-3H-indol-3-ylidene)-2,2-dimethyl-2,5-dihydrofuran-3-yl]phenyl}propanoate | 407.439 |
| 103 | 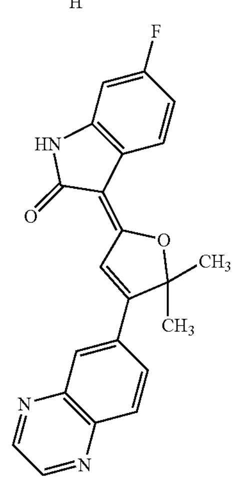 | (3E)-3-(5,5-dimethyl-4-quinoxalin-6-ylfuran-2(5H)-ylidene)-6-fluoro-1,3-dihydro-2H-indol-2-one | 373.385 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 104 | 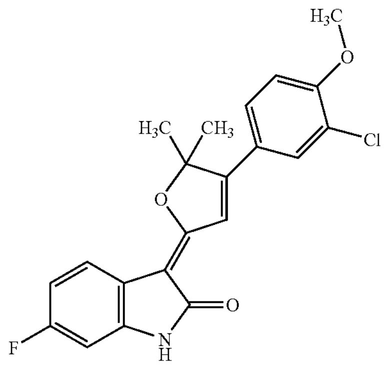 [SMILES: COc1ccc(C2=C/C(=C3\C(=O)Nc4cc(F)ccc43)OC2(C)C)cc1Cl] | (3E)-3-[4-(3-chloro-4-methoxyphenyl)-5,5-dimethylfuran 2(5H)-ylidene]-6-fluoro-1,3-dihydro-2H-indol-2-one | 385.82 |
| 105 | 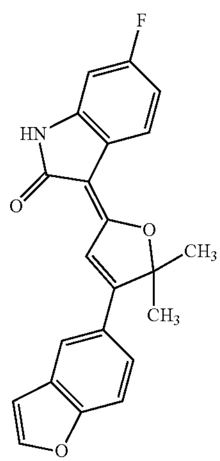 [SMILES: CC1(C)O/C(=C2/C(=O)Nc3cc(F)ccc32)C=C1c1ccc2occc2c1] | (3E)-3-[4-(1-benzofuran-5-yl)-5,5-dimethylfuran-2(5H)-ylidene]-6-fluoro-1,3-dihydro-2H-indol-2-one | 361.37 |
| 106 | 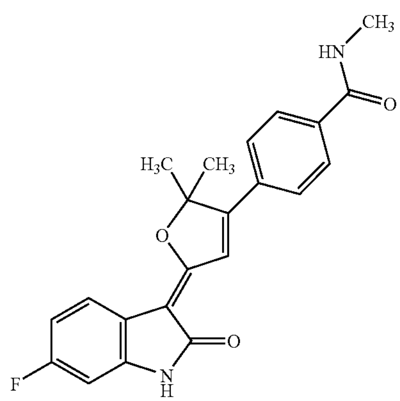 [SMILES: CNC(=O)c1ccc(C2=C/C(=C3\C(=O)Nc4cc(F)ccc43)OC2(C)C)cc1] | 4-[(5E)-5-(6-fluoro-2-oxo-1,2-dihydro-3H-indol-3-ylidene)-2,2-dimethyl-2,5-dihydrofuran-3-yl]-N-methylbenzamide | 378.401 |
| 107 | 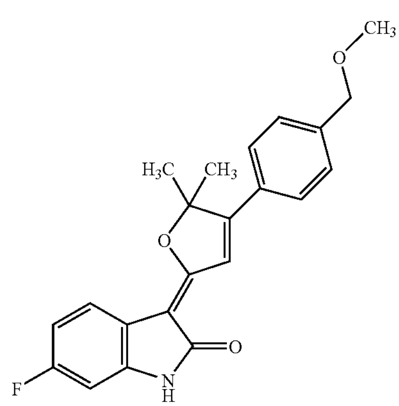 [SMILES: COCc1ccc(C2=C/C(=C3\C(=O)Nc4cc(F)ccc43)OC2(C)C)cc1] | (3E)-6-fluoro-3-{4-[4-(methoxymethyl)phenyl]-5,5-dimethylfuran-2(5H)-ylidene}-1,3-dihydro-2H-indol-2-one | 365.402 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 108 | 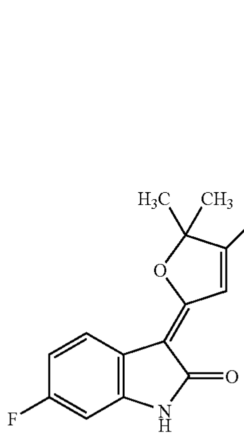 | methyl {4-[(5E)-5-(6-fluoro-2-oxo-1,2-dihydro-3H-indol-3-ylidene)-2,2-dimethyl-2,5-dihydrofuran-3-yl]phenyl}carbamate | 394.4 |
| 109 | 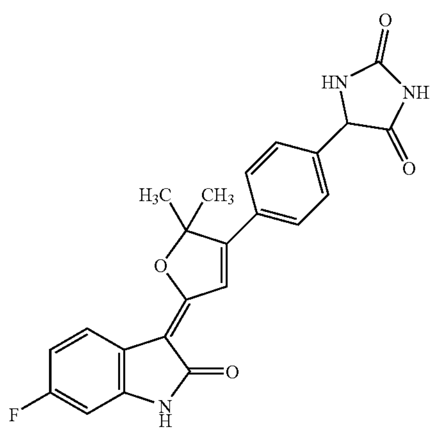 [SMILES: CC1(C)O/C(=C2/C(=O)Nc3cc(F)ccc32)C=C1c1ccc(C2NC(=O)NC2=O)cc1] | 5-{4-[(5E)-5-(6-fluoro-2-oxo-1,2-dihydro-3H-indol-3-ylidene)-2,2-dimethyl-2,5-dihydrofuran-3-yl]phenyl}imidazolidine-2,4-dione | 419.41 |
| 110 | 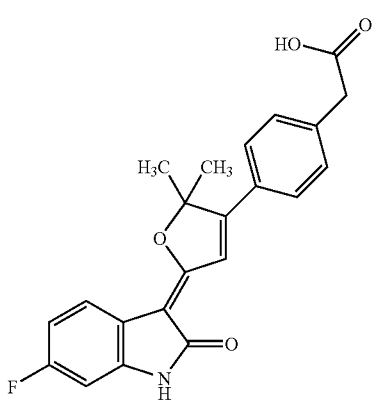 [SMILES: CC1(C)O/C(=C2/C(=O)Nc3cc(F)ccc32)C=C1c1ccc(CC(=O)O)cc1] | {4-[(5E)-5-(6-fluoro-2-oxo-1,2-dihydro-3H-indol-3-ylidene)-2,2-dimethyl-2,5-dihydrofuran-3-yl]phenyl}acetic acid | 379.385 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 111 | 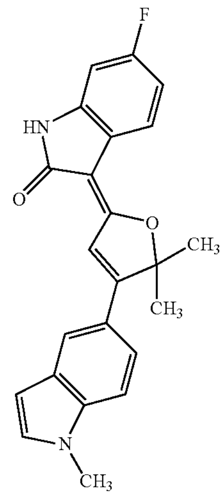 [SMILES: Cn1ccc2cc(C3=C/C(=C4\C(=O)Nc5cc(F)ccc54)OC3(C)C)ccc21] | (3E)-3-[5,5-dimethyl-4-(1-methyl-1H-indol-5-yl)furan-2(5H)-ylidene]-6-fluoro-1,3-dihydro-2H-indol-2-one | 374.413 |
| 112 | 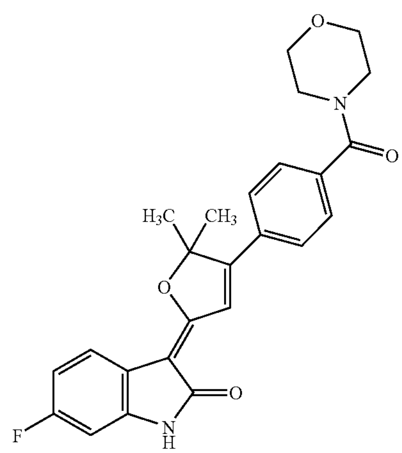 [SMILES: CC1(C)O/C(=C2/C(=O)Nc3cc(F)ccc32)C=C1c1ccc(C(=O)N2CCOCC2)cc1] | (3E)-3-{5,5-dimethyl-4-[4-(morpholin-4-ylcarbonyl)phenyl]furan-2(5H)-ylidene}-6-fluoro-1,3-dihydro-2H-indol-2-one | 434.465 |
| 113 | 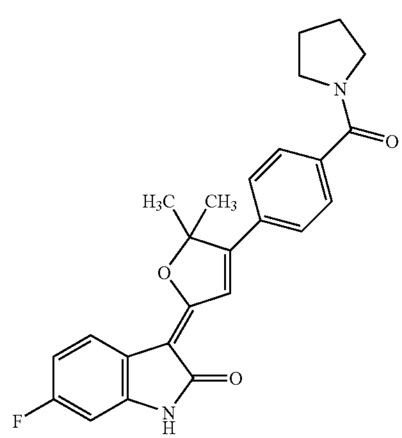 [SMILES: CC1(C)O/C(=C2/C(=O)Nc3cc(F)ccc32)C=C1c1ccc(C(=O)N2CCCC2)cc1] | (3E)-3-{5,5-dimethyl-4-[4-(pyrrolidin-1-ylcarbonyl)phenyl]furan-2(5H)-ylidene}-6-fluoro-1,3-dihydro-2H-indol-2-one | 418.466 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 114 | 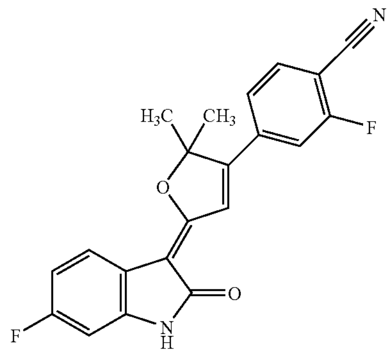 [SMILES: CC1(C)O/C(=C2/C(=O)Nc3cc(F)ccc32)C=C1c1ccc(C#N)c(F)c1] | 2-fluoro-4-[(5E)-5-(6-fluoro-2-oxo-1,2-dihydro-3H-indol-3-ylidene)-2,2-dimethyl-2,5-dihydrofuran-3-yl]benzonitrile | 364.35 |
| 115 | 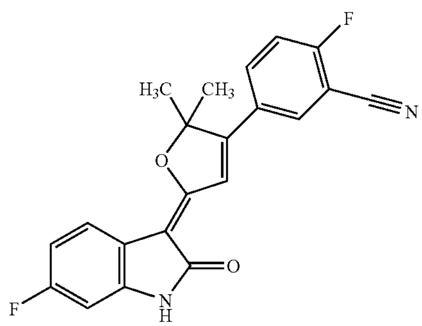 [SMILES: CC1(C)O/C(=C2/C(=O)Nc3cc(F)ccc32)C=C1c1ccc(F)c(C#N)c1] | 2-fluoro-5-[(5E)-5-(6-fluoro-2-oxo-1,2-dihydro-3H-indol-3-ylidene)-2,2-dimethyl-2,5-dihydrofuran-3-yl]benzonitrile | 364.35 |
| 116 | 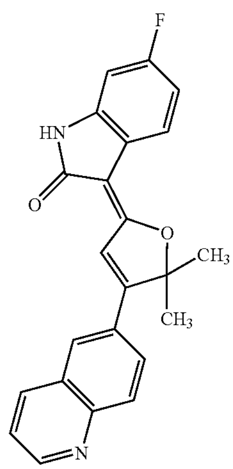 [SMILES: CC1(C)O/C(=C2/C(=O)Nc3cc(F)ccc32)C=C1c1ccc2ncccc2c1] | (3E)-3-(5,5-dimethyl-4-quinolin-6-ylfuran-2(5H)-ylidene)-6-fluoro-1,3-dihydro-2H-indol-2-one | 372.397 |
| 117 | 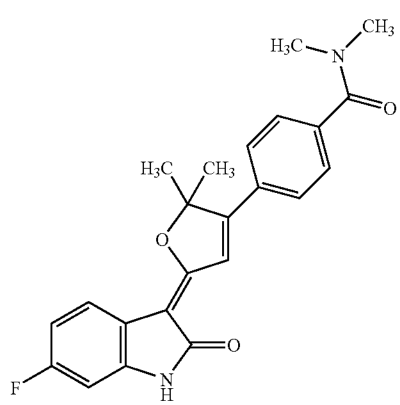 [SMILES: CN(C)C(=O)c1ccc(C2=C/C(=C3\C(=O)Nc4cc(F)ccc43)OC2(C)C)cc1] | 4-[(5E)-5-(6-fluoro-2-oxo-1,2-dihydro-3H-indol-3-ylidene)-2,2-dimethyl-2,5-dihydrofuran-3-yl]-N,N-dimethylbenzamide | 392.428 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 118 | 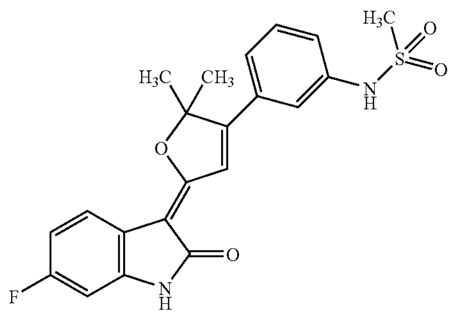 [SMILES: CC1(C)O/C(=C2/C(=O)Nc3cc(F)ccc32)C=C1c1cccc(NS(C)(=O)=O)c1] | N-{3-[(5E)-5-(6-fluoro-2-oxo-1,2-dihydro-3H-indol-3-ylidene)-2,2-dimethyl-2,5-dihydrofuran-3-yl]phenyl}methanesulfonamide | 414.455 |
| 119 | 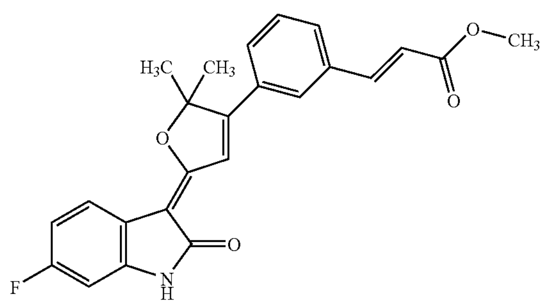 [SMILES: COC(=O)/C=C/c1cccc(C2=C/C(=C3\C(=O)Nc4cc(F)ccc43)OC2(C)C)c1] | methyl (2E)-3-{3-[(5E)-5-(6-fluoro-2-oxo-1,2-dihydro-3H-indol-3-ylidene)-2,2-dimethyl-2,5-dihydrofuran-3-yl]phenyl}acrylate | 405.423 |
| 120 | 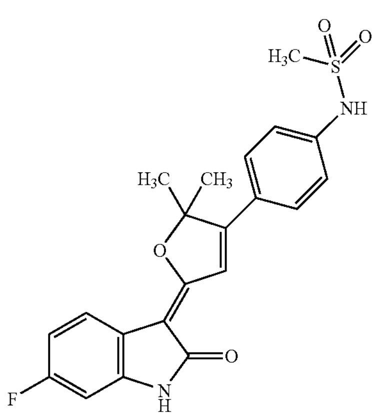 [SMILES: CC1(C)O/C(=C2/C(=O)Nc3cc(F)ccc32)C=C1c1ccc(NS(C)(=O)=O)cc1] | N-{4-[(5E)-5-(6-fluoro-2-oxo-1,2-dihydro-3H-indol-3-ylidene)-2,2-dimethyl-2,5-dihydrofuran-3-yl]phenyl}methanesulfonamide | 414.455 |
| 121 | 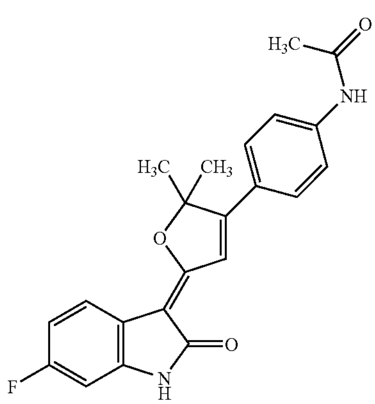 [SMILES: CC(=O)Nc1ccc(C2=C/C(=C3\C(=O)Nc4cc(F)ccc43)OC2(C)C)cc1] | N-{4-[(5E)-5-(6-fluoro-2-oxo-1,2-dihydro-3H-indol-3-ylidene)-2,2-dimethyl-2,5-dihydrofuran-3-yl]phenyl}acetamide | 378.401 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 122 | 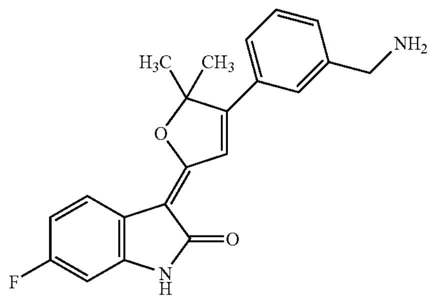 [SMILES: CC1(C)O/C(=C2/C(=O)Nc3cc(F)ccc32)C=C1c1cccc(CN)c1] | (3E)-3-{4-[3-(aminomethyl)phenyl] 5,5-dimethylfuran-2(5H)-ylidene}-6-fluoro-1,3-dihydro-2H-indol-2-one | 350.391 |
| 123 | 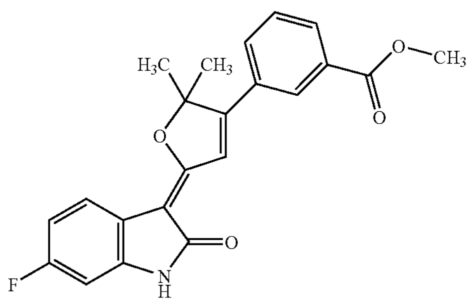 [SMILES: COC(=O)c1cccc(C2=C/C(=C3\C(=O)Nc4cc(F)ccc43)OC2(C)C)c1] | methyl 3-[(5E)-5-(6-fluoro-2-oxo-1,2-dihydro-3H-indol-3-ylidene)-2,2-dimethyl-2,5-dihydrofuran-3-yl]benzoate | 379.385 |
| 124 | 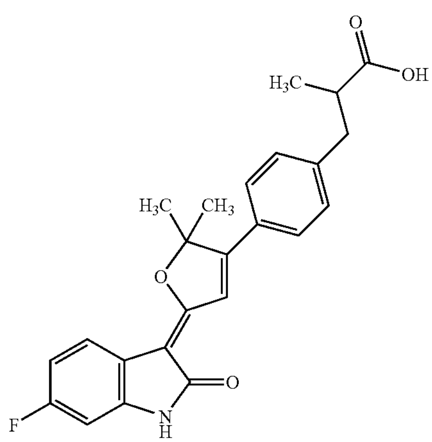 [SMILES: CC(Cc1ccc(C2=C/C(=C3\C(=O)Nc4cc(F)ccc43)OC2(C)C)cc1)C(=O)O] | 2-amino-3-{4-[(5E)-5-(6-fluoro-2-oxo-1,2-dihydro-3H-indol-3-ylidene)-2,2-dimethyl-2,5-dihydrofuran-3-yl]phenyl}propanoic acid | 408.427 |
| 125 | 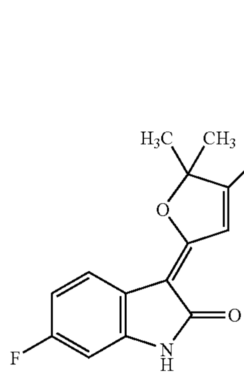 | (3E)-3-{4-[4-(aminomethyl)phenyl] 5,5-dimethylfuran-2(5H)-ylidene}-6-fluoro-1,3-dihydro-2H-indol-2-one | 350.391 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 126 | 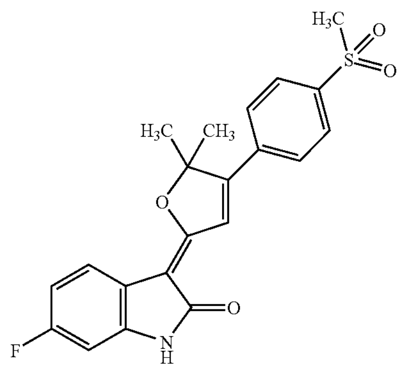 [SMILES: CC1(C)O/C(=C2/C(=O)Nc3cc(F)ccc32)C=C1c1ccc(S(C)(=O)=O)cc1] | (3E)-3-{5,5-dimethyl-4-[4-(methylsulfonyl)phenyl]furan-2(5H)-ylidene}-6-fluoro-1,3-dihydro-2H-indol-2-one | 399.44 |
| 127 | 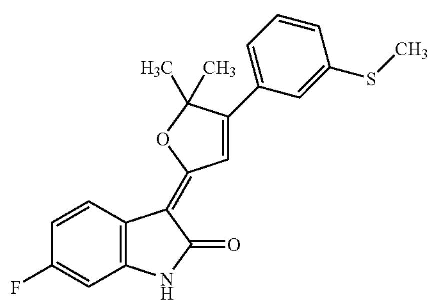 | (3E)-3-{5,5-dimethyl-4-[3-(methylthio)phenyl]furan-2(5H)-ylidene}-6-fluoro-1,3-dihydro-2H-indol-2-one | 367.442 |
| 128 | 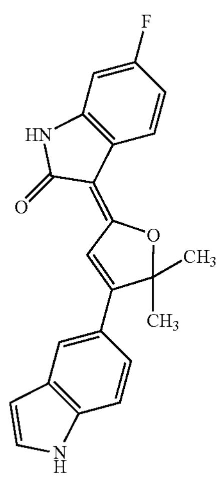 [SMILES: CC1(C)O/C(=C2/C(=O)Nc3cc(F)ccc32)C=C1c1ccc2[nH]ccc2c1] | (3E)-6-fluoro-3-[4-(1H-indol-5-yl)-5,5-dimethylfuran-2(5H)-ylidene]-1,3-dihydro-2H-indol-2-one | 360.386 |
| 129 | 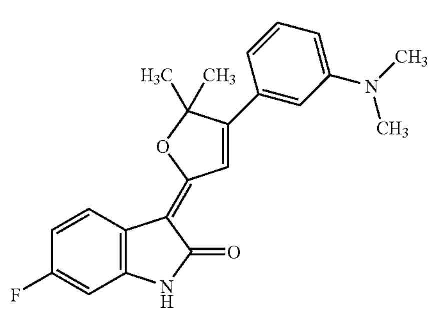 [SMILES: CN(C)c1cccc(C2=C/C(=C3\C(=O)Nc4cc(F)ccc43)OC2(C)C)c1] | (3E)-3-{4-[3-(dimethylamino)phenyl]-5,5-dimethylfuran-2(5H)-ylidene}-6-fluoro-1,3-dihydro-2H-indol-2-one | 364.418 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 130 | 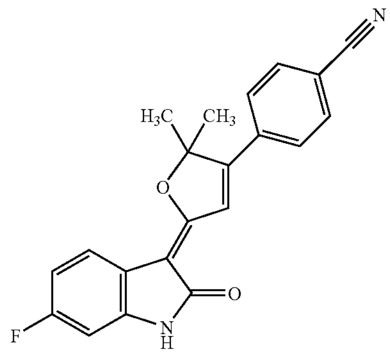 [SMILES: CC1(C)O/C(=C2/C(=O)Nc3cc(F)ccc32)C=C1c1ccc(C#N)cc1] | 4-[(5E)-5-(6-fluoro-2-oxo-1,2-dihydro-3H-indol-3-ylidene)-2,2-dimethyl-2,5-dihydrofuran-3-yl]benzonitrile | 346.359 |
| 131 | 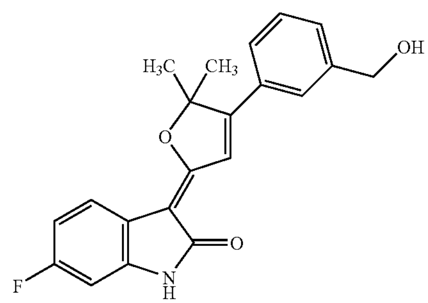 [SMILES: CC1(C)O/C(=C2/C(=O)Nc3cc(F)ccc32)C=C1c1cccc(CO)c1] | (3E)-6-fluoro-3-{4-[3-(hydroxymethyl)phenyl]-5,5-dimethylfuran-2(5H)-ylidene}1,3-dihydro-2H-indol-2-one | 351.375 |
| 132 | 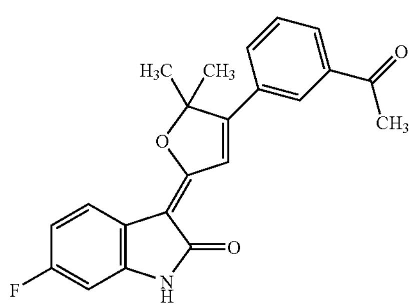 [SMILES: CC(=O)c1cccc(C2=C/C(=C3\C(=O)Nc4cc(F)ccc43)OC2(C)C)c1] | (3E)-3-[4-(3-acetylphenyl)-5,5-dimethylfuran-2(5H)-ylidene]-6-fluoro-1,3-dihydro-2H-indol-2-one | 363.386 |
| 133 | 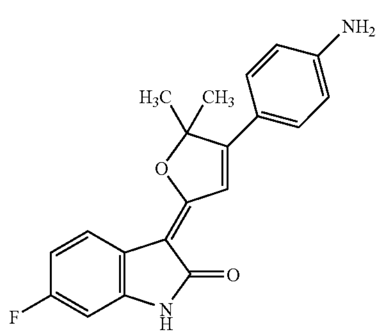 [SMILES: CC1(C)O/C(=C2/C(=O)Nc3cc(F)ccc32)C=C1c1ccc(N)cc1] | (3E)-3-[4-(4-aminophenyl)-5,5-dimethylfuran-2(5H)-ylidene]-6-fluoro-1,3-dihydro-2H-indol-2-one | 336.364 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 134 | 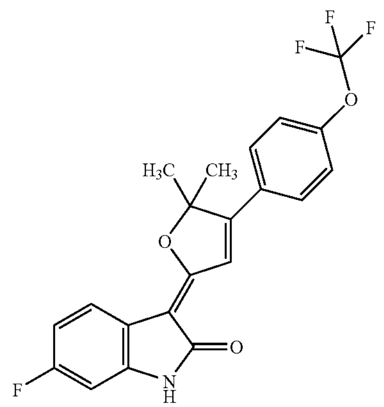 [SMILES: CC1(C)O/C(=C2/C(=O)Nc3cc(F)ccc32)C=C1c1ccc(OC(F)(F)F)cc1] | (3E)-3-{5,5-dimethyl-4-[4-(trifluoromethoxy)phenyl]furan-2(5H)-ylidene}-6-fluoro-1,3-dihydro-2H-indol-2-one | 405.345 |
| 135 | 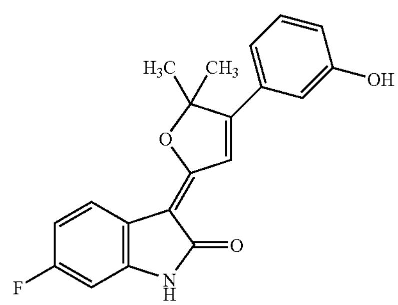 [SMILES: CC1(C)O/C(=C2/C(=O)Nc3cc(F)ccc32)C=C1c1cccc(O)c1] | (3E)-6-fluoro-3-[4-(3-hydroxyphenyl)-5,5-dimethylfuran-2(5H)-ylidene]-1,3-dihydro-2H-indol-2-one | 337.348 |
| 136 | 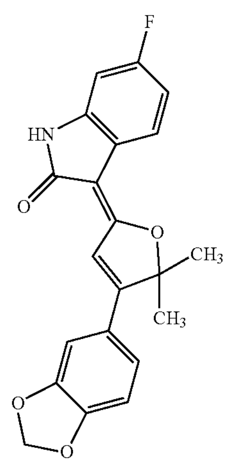 [SMILES: CC1(C)O/C(=C2/C(=O)Nc3cc(F)ccc32)C=C1c1ccc2c(c1)OCO2] | (3E)-3-[4-(1,3-benzodioxol-5-yl)-5,5-dimethylfuran-2(5H)-ylidene]-6-fluoro-1,3-dihydro-2H-indol-2-one | 365.358 |
| 137 | 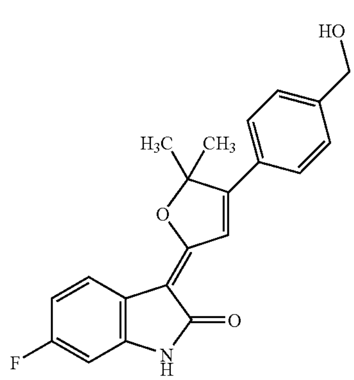 [SMILES: CC1(C)O/C(=C2/C(=O)Nc3cc(F)ccc32)C=C1c1ccc(CO)cc1] | (3E)-6-fluoro-3-{4-[4-(hydroxymethyl)phenyl]-5,5-dimethylfuran-2(5H)-ylidene}-1,3-dihydro-2H-indol-2-one | 351.375 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 138 | 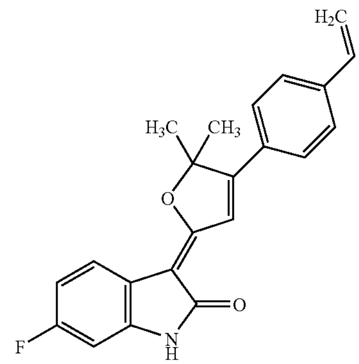 [SMILES: C=Cc1ccc(C2=C/C(=C3\C(=O)Nc4cc(F)ccc43)OC2(C)C)cc1] | (3E)-3-[5,5-dimethyl-4-(4-vinylphenyl)furan-2(5H)-ylidene]-6-fluoro-1,3-dihydro-2H-indol-2-one | 347.387 |
| 139 | 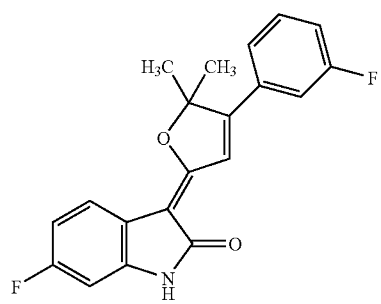 [SMILES: CC1(C)O/C(=C2/C(=O)Nc3cc(F)ccc32)C=C1c1cccc(F)c1] | (3E)-6-fluoro-3-[4-(3-fluorophenyl)5,5-dimethylfuran-2(5H)-ylidene]-1,3-dihydro-2H-indol-2-one | 339.34 |
| 140 | 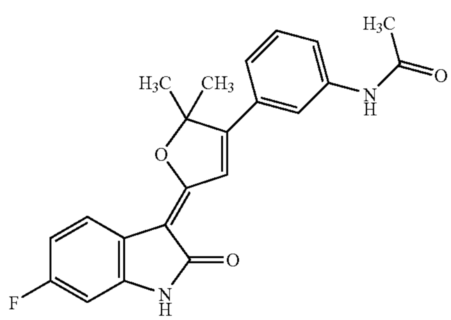 [SMILES: CC(=O)Nc1cccc(C2=C/C(=C3\C(=O)Nc4cc(F)ccc43)OC2(C)C)c1] | N-{3-[(5E)-5-(6-fluoro-2-oxo-1,2-dihydro-3H-indol-3-ylidene)-2,2-dimethyl-2,5-dihydrofuran-3-yl]phenyl}acetamide | 378.401 |
| 141 | 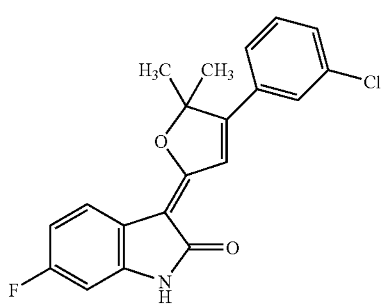 [SMILES: CC1(C)O/C(=C2/C(=O)Nc3cc(F)ccc32)C=C1c1cccc(Cl)c1] | (3E)-3-[4-(3-chlorophenyl)-5,5-dimethylfuran-2(5H)-ylidene]-6-fluoro-1,3-dihydro-2H-indol-2-one | 355.794 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 142 | 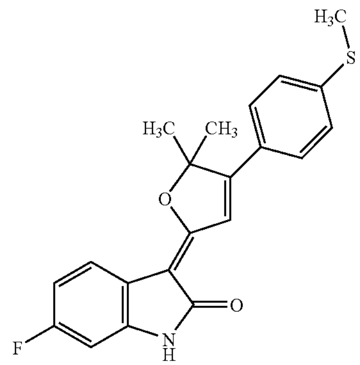 [SMILES: CSc1ccc(C2=C/C(=C3\C(=O)Nc4cc(F)ccc43)OC2(C)C)cc1] | (3E)-3-{5,5-dimethyl-4-[4-(methylthio)phenyl]furan-2(5H)-ylidene}-6-fluoro-1,3-dihydro-2H-indol-2-one | 367.442 |
| 143 | 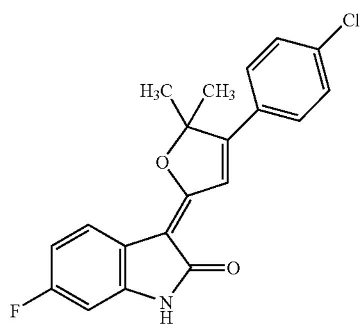 [SMILES: CC1(C)O/C(=C2/C(=O)Nc3cc(F)ccc32)C=C1c1ccc(Cl)cc1] | (3E)-3-[4-(4-chlorophenyl)-5,5-dimethylfuran-2(5H)-ylidene]-6-fluoro-1,3-dihydro-2H-indol-2-one | 355.794 |
| 144 | 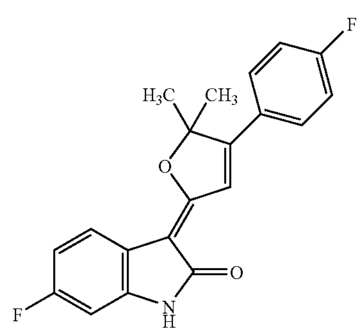 [SMILES: CC1(C)O/C(=C2/C(=O)Nc3cc(F)ccc32)C=C1c1ccc(F)cc1] | (3E)-6-fluoro-3-[4-(4-fluorophenyl) 5,5-dimethylfuran-2(5H)-ylidene]-1,3-dihydro-2H-indol-2-one | 339.34 |
| 145 | 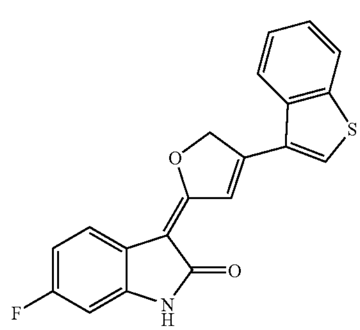 [SMILES: O=C1Nc2cc(F)ccc2/C1=C1/C=C(c2csc3ccccc23)CO1] | (3E)-3-[4-(1-benzothien-3-yl)furan-2(5H)-ylidene]-6-fluoro-1,3-dihydro-2H-indol-2-one | 349.384 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 146 | 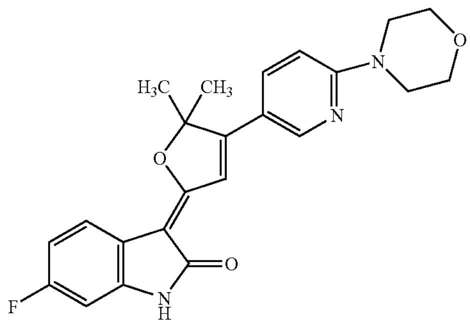 [SMILES: CC1(C)O/C(=C2/C(=O)Nc3cc(F)ccc32)C=C1c1ccc(N2CCOCC2)nc1] | 3-[5,5-Dimethyl-4-(6-morpholin-4-yl-pyridin-3-yl)-5H-furan-2-ylidene]-6-fluoro-1,3-dihydro-indol-2-one | 407.443 |
| 147 | 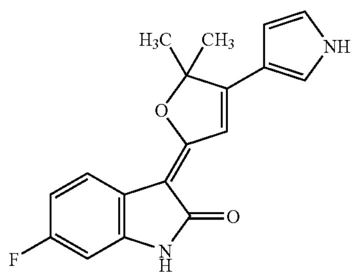 [SMILES: CC1(C)O/C(=C2/C(=O)Nc3cc(F)ccc32)C=C1c1cc[nH]c1] | (3E)-3-[5,5-dimethyl-4-(1H-pyrrol-3-yl)furan-2(5H)-ylidene]-6-fluoro-1,3-dihydro-2H-indol-2-one | 310.327 |
| 148 | 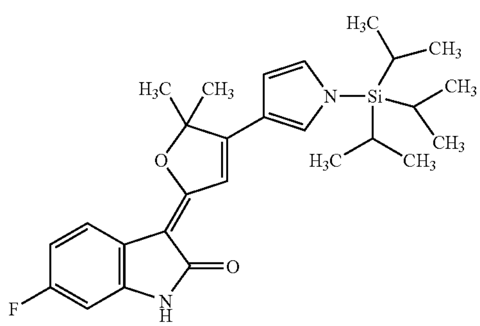 [SMILES: CC(C)[Si](C(C)C)(C(C)C)n1ccc(C2=C/C(=C3\C(=O)Nc4cc(F)ccc43)OC2(C)C)c1] | (3E)-3-{5,5-dimethyl-4-[1-(triisopropylsilyl)-1H-pyrrol-3-yl]furan-2(5H)-ylidene}-6-fluoro-1,3-dihydro-2H-indol-2-one | 466.669 |
| 149 | 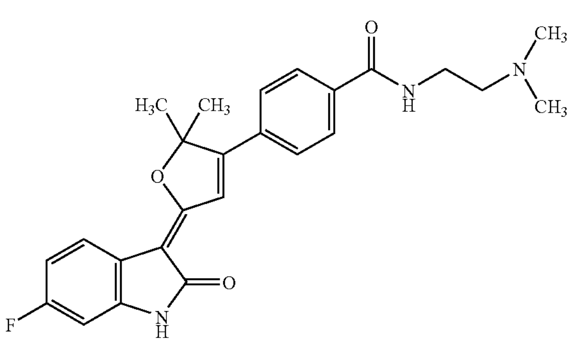 [SMILES: CN(C)CCNC(=O)c1ccc(C2=C/C(=C3\C(=O)Nc4cc(F)ccc43)OC2(C)C)cc1] | N-(2-Dimethylamino-ethyl)-4-[5-(6-fluoro-2-oxo-1,2-dihydro-indol-3-ylidene)-2,2-dimethyl-2,5-dihydro-furan-3-yl]-benzamide | 435.496 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 150 | 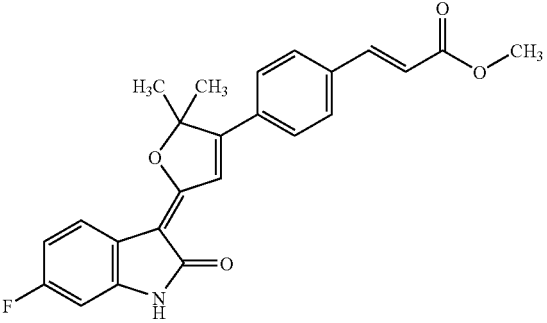 [SMILES: COC(=O)/C=C/c1ccc(C2=C/C(=C3\C(=O)Nc4cc(F)ccc43)OC2(C)C)cc1] | 3-{4-[5-(6-Fluoro-2-oxo-1,2-dihydro-indol-3-ylidene)-2,2-dimethyl-2,5-dihydro-furan-3-yl]-phenyl}-acrylic acid methyl ester | 405.423 |
| 151 | 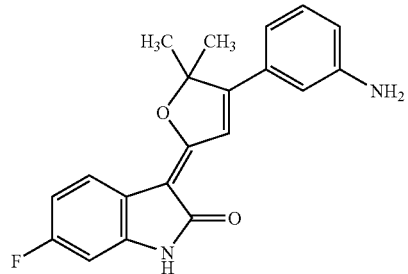 [SMILES: CC1(C)O/C(=C2/C(=O)Nc3cc(F)ccc32)C=C1c1cccc(N)c1] | 3-[4-(3-Amino-phenyl)-5,5-dimethyl-5H-furan-2-ylidene]-6-fluoro-1,3-dihydro-indol-2-one | 336.364 |
| 152 | 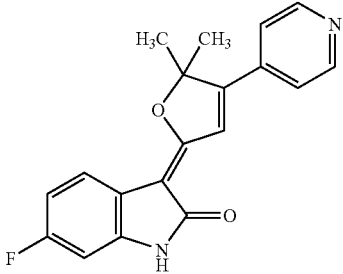 [SMILES: CC1(C)O/C(=C2/C(=O)Nc3cc(F)ccc32)C=C1c1ccncc1] | 3-(5,5-Dimethyl-4-pyridin-4-yl-5H-furan-2-ylidene)-6-fluoro-1,3-dihydro-indol-2-one | 322.337 |
| 153 | 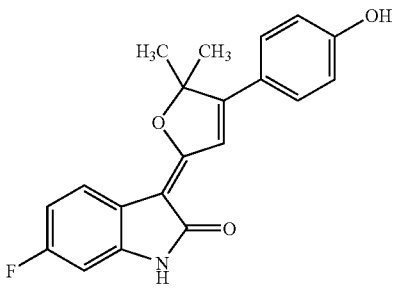 [SMILES: CC1(C)O/C(=C2/C(=O)Nc3cc(F)ccc32)C=C1c1ccc(O)cc1] | 6-Fluoro-3-[4-(4-hydroxy-phenyl)-5,5-dimethyl-5H-furan-2-ylidene]-1,3-dihydro-indol-2-one | 337.348 |
| 154 | 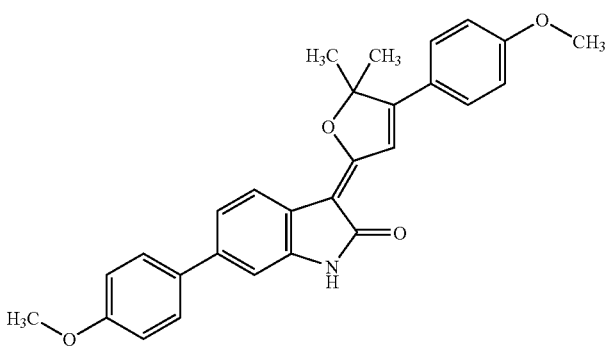 | (3E)-6-(4-methoxyphenyl)-3-[4-(4-methoxyphenyl)-5,5-dimethylfuran 2(5H)-ylidene]-1,3-dihydro-2H-indol-2-one | 439.509 |

TABLE 4-continued

[5,5-dimethyl-5H-furan-(2E)-ylidene]-1,3-dihydro-indol-2-one derivatives

| Example # | Chemical Structure | Chemical Name | FW |
|---|---|---|---|
| 155 | 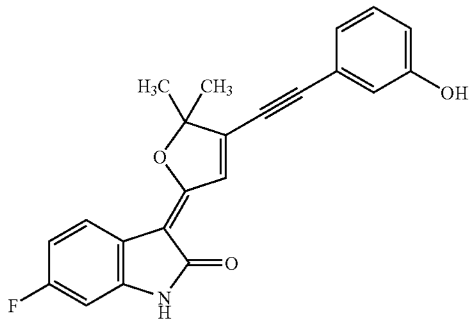 [SMILES: CC1(C)O/C(=C2/C(=O)Nc3cc(F)ccc32)C=C1C#Cc1cccc(O)c1] | (3E)-6-fluoro-3-{4-[(3-hydroxyphenyl)ethynyl]-5,5-dimethylfuran-2(5H)-ylidene}-1,3-dihydro-2H-indol-2-one | 361.37 |
| 156 | 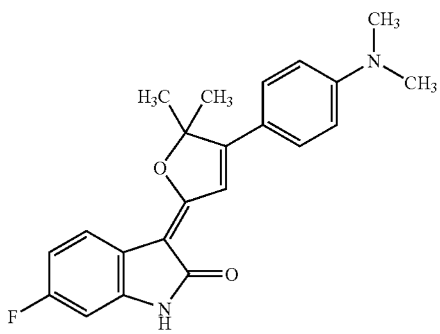 [SMILES: CN(C)c1ccc(C2=C/C(=C3\C(=O)Nc4cc(F)ccc43)OC2(C)C)cc1] | (3E)-3-{4-[4-(dimethylamino)phenyl]-5,5-dimethylfuran-2(5H)-ylidene}-6-fluoro-1,3-dihydro-2H-indol-2-one | 364.418 |
| 157 | 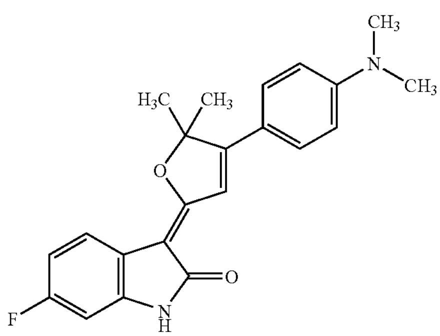 [SMILES: CN(C)c1ccc(C2=C/C(=C3\C(=O)Nc4cc(F)ccc43)OC2(C)C)cc1] | (3E)-3-{4-[4-(dimethylamino)phenyl]-5,5-dimethylfuran-2(5H)-ylidene}-6-fluoro-1,3-dihydro-2H-indol-2-one | 364.418 |
| 158 | 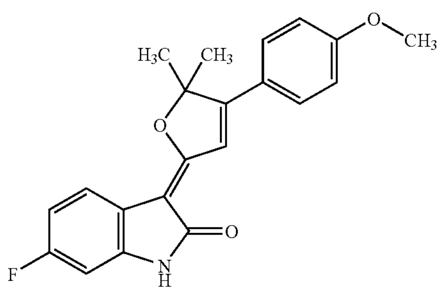 [SMILES: COc1ccc(C2=C/C(=C3\C(=O)Nc4cc(F)ccc43)OC2(C)C)cc1] | (3E)-6-fluoro-3-[4-(4-methoxyphenyl)-5,5-dimethylfuran 2(5H)-ylidene]-1,3-dihydro-2H-indol-2-one | 351.375 |

TABLE 5

[5,5-dimethyl-5H-furan-(2E)-ylidene]-1,3-dihydro-indol-2-one benzamide derivatives

| Example # | Chemical Structure | Chemical Name | FW |
|---|---|---|---|
| 159 | 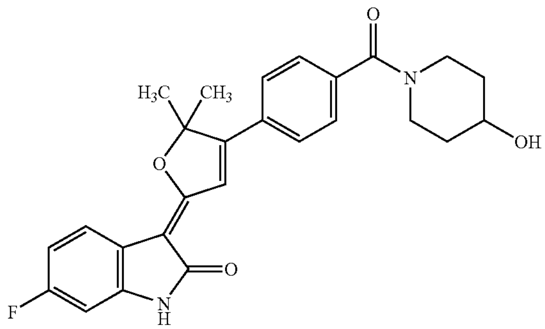 [SMILES: CC1(C)O/C(=C2/C(=O)Nc3cc(F)ccc32)C=C1c1ccc(C(=O)N2CCC(O)CC2)cc1] | (3E)-6-fluoro-3-[4-{4-[(4-hydroxypiperidin-1-yl)carbonyl]phenyl}-5,5-dimethylfuran-2(5H)-ylidene]-1,3-dihydro-2H-indol-2-one | 448.4915 |
| 160 | 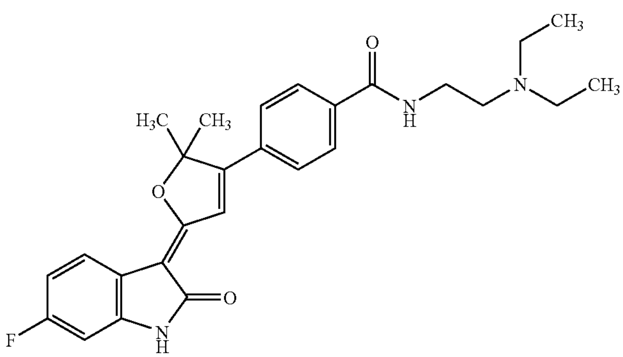 [SMILES: CCN(CC)CCNC(=O)c1ccc(C2=C/C(=C3\C(=O)Nc4cc(F)ccc43)OC2(C)C)cc1] | N-[2-(diethylamino)ethyl]-4-[(5E)-5-(6-fluoro-2-oxo-1,2-dihydro-3H-indol-3-ylidene)-2,2-dimethyl-2,5-dihydrofuran-3-yl]benzamide | 463.55 |
| 161 | 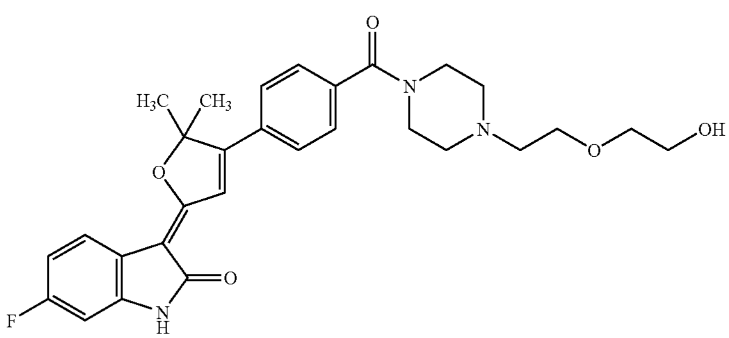 [SMILES: CC1(C)O/C(=C2/C(=O)Nc3cc(F)ccc32)C=C1c1ccc(C(=O)N2CCN(CCOCCO)CC2)cc1] | (3E)-6-fluoro-3-{4-[4-({4-[2-(2-hydroxyethoxy)ethyl]piperazin-1-yl}carbonyl)phenyl]-5,5-dimethylfuran-2(5H)-ylidene}-1,3-dihydro-2H-indol-2-one | 521.5858 |
| 162 | 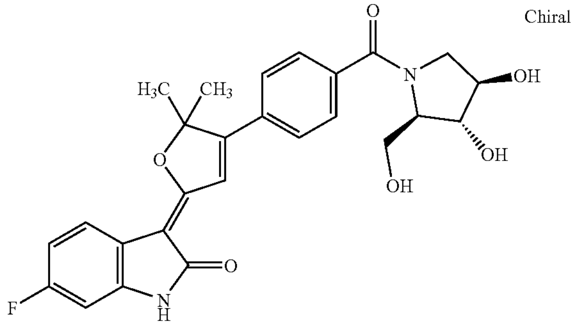 [SMILES: CC1(C)O/C(=C2/C(=O)Nc3cc(F)ccc32)C=C1c1ccc(C(=O)N2C[C@@H](O)[C@H](O)[C@H]2CO)cc1] | (3E)-3-[4-(4-{[(2R,3R,4R)-3,4-dihydroxy-2-(hydroxymethyl)pyrrolidin-1-yl]carbonyl}phenyl)-5,5-dimethylfuran-2(5H)-ylidene]-6-fluoro-1,3-dihydro-2H-indol-2-one | 480.4895 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 163 | 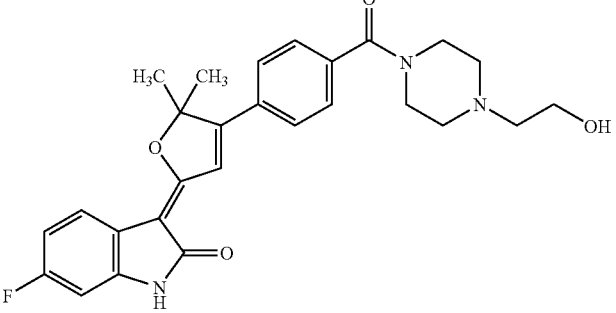 | (3E)-6-fluoro-3-[4-(4-{[4-(2-hydroxyethyl)piperazin-1-yl]carbonyl}phenyl)-5,5-dimethylfuran-2(5H)-ylidene]-1,3-dihydro-2H-indol-2-one | 477.5332 |
| 164 | 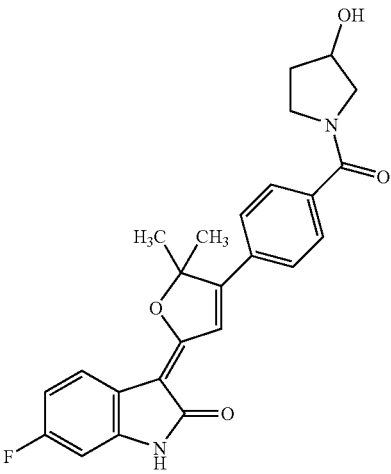 [SMILES: CC1(C)O/C(=C2/C(=O)Nc3cc(F)ccc32)C=C1c1ccc(C(=O)N2CCC(O)C2)cc1] | 6-Fluoro-3-[4-[4-(3-hydroxy-pyrrolidine-1-carbonyl)-phenyl]-5,5-dimethyl-5H-furan-(2E)-ylidene]-1,3-dihydro-indol-2-one | 434.4647 |
| 165 | 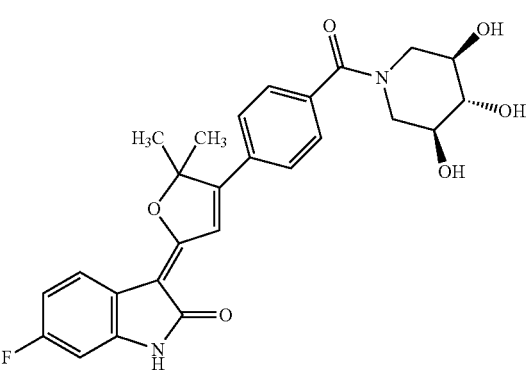 [SMILES: CC1(C)O/C(=C2/C(=O)Nc3cc(F)ccc32)C=C1c1ccc(C(=O)N2C[C@@H](O)[C@H](O)[C@@H](O)C2)cc1] | 3-[5,5-Dimethyl-4-[4-((3R,4R,5S)-3,4,5-trihydroxy-piperidine-1-carbonyl)-phenyl]-5H-furan-(2E)-ylidene]-6-fluoro-1,3-dihydro-indol-2-one | 480.4895 |
| 166 | 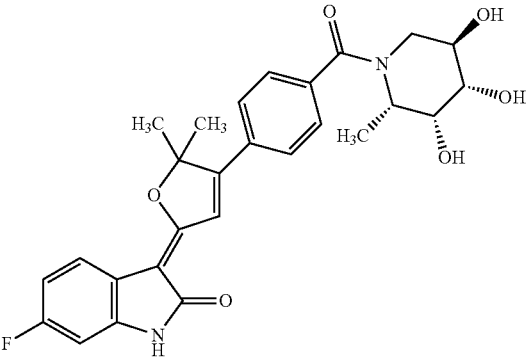 [SMILES: C[C@H]1[C@@H](O)[C@@H](O)[C@H](O)CN1C(=O)c1ccc(C2=C/C(=C3\C(=O)Nc4cc(F)ccc43)OC2(C)C)cc1] | 3-[5,5-Dimethyl-4-[4-((2S,3R,4S,5R)-3,4,5-trihydroxy-2-methyl-piperidine-1-carbonyl)-phenyl]-5H-furan-(2E)-ylidene]-6-fluoro-1,3-dihydro-indol-2-one | 494.5163 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 167 | 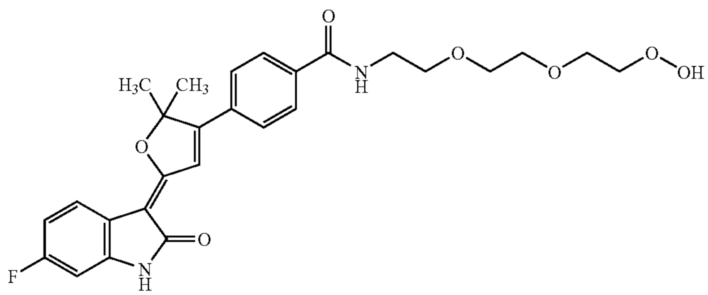 [SMILES: CC1(C)O/C(=C2/C(=O)Nc3cc(F)ccc32)C=C1c1ccc(C(=O)NCCOCCOCCOO)cc1] | 4-[(5E)-5-(6-fluoro-2-oxo-1,2-dihydro-3H-indol-3-ylidene)-2,2-dimethyl-2,5-dihydrofuran-3-yl]-N-(2-{2-[2-(2-hydroxyethoxy)ethoxy]ethoxy}ethyl)benzamide | 540.5847 |
| 168 | 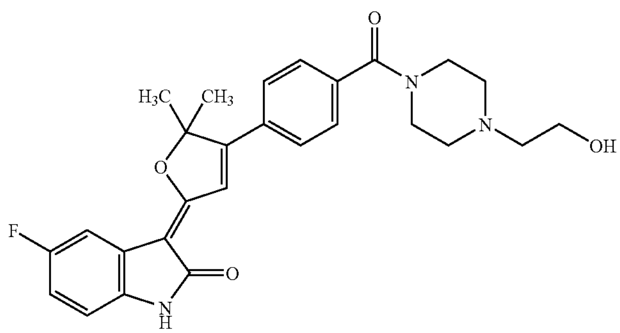 [SMILES: CC1(C)O/C(=C2/C(=O)Nc3ccc(F)cc32)C=C1c1ccc(C(=O)N2CCN(CCO)CC2)cc1] | (3E)-5-fluoro-3-[4-(4-{[4-(2-hydroxyethyl)piperazin-1-yl]carbonyl}phenyl)-5,5-dimethylfuran-2(5H)-ylidene]-1,3-dihydro-2H-indol-2-one | 477.5332 |
| 169 | 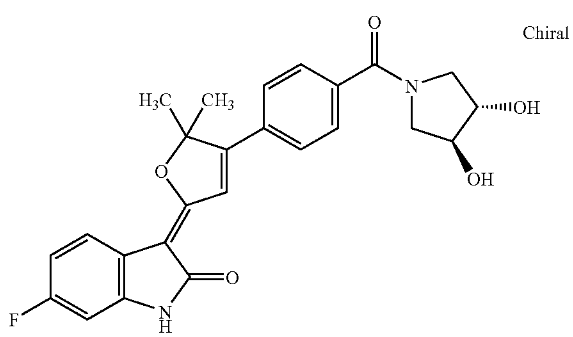 [SMILES: CC1(C)O/C(=C2/C(=O)Nc3cc(F)ccc32)C=C1c1ccc(C(=O)N2C[C@H](O)[C@@H](O)C2)cc1] | (3E)-3-[4-(4-{[(3S,4S)-3,4-dihydroxypyrrolidin-1-yl]carbonyl}phenyl)-5,5-dimethylfuran-2(5H)-ylidene]-6-fluoro-1,3-dihydro-2H-indol-2-one | 450.4637 |
| 170 | 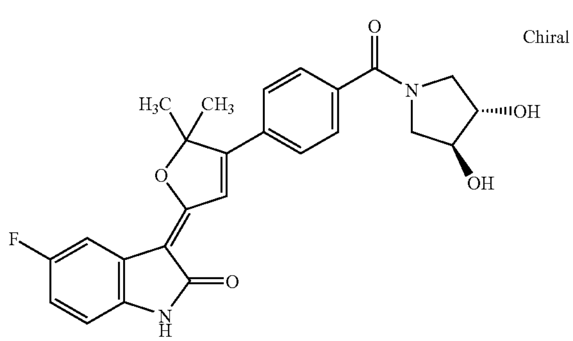 [SMILES: CC1(C)O/C(=C2/C(=O)Nc3ccc(F)cc32)C=C1c1ccc(C(=O)N2C[C@H](O)[C@@H](O)C2)cc1] | (3E)-3-[4-(4-{[(3S,4S)-3,4-dihydroxypyrrolidin-1-yl]carbonyl}phenyl)-5,5-dimethylfuran-2(5H)-ylidene]-5-fluoro-1,3-dihydro-2H-indol-2-one | 450.4637 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 171 | 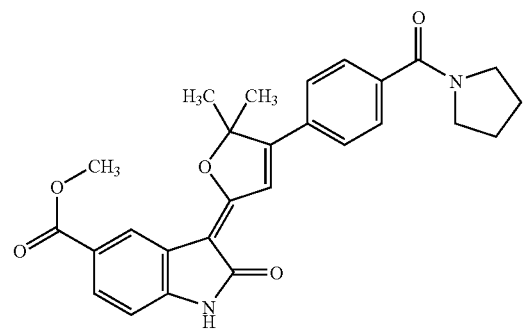 [SMILES: COC(=O)c1ccc2c(c1)/C(=C1/C=C(c3ccc(C(=O)N4CCCC4)cc3)C(C)(C)O1)C(=O)N2] | methyl (3E)-3-{5,5-dimethyl-4-[4-(pyrrolidin-1-ylcarbonyl)phenyl]furan-2(5H)-ylidene}-2-oxoindoline-5-carboxylate | 458.5114 |
| 172 | 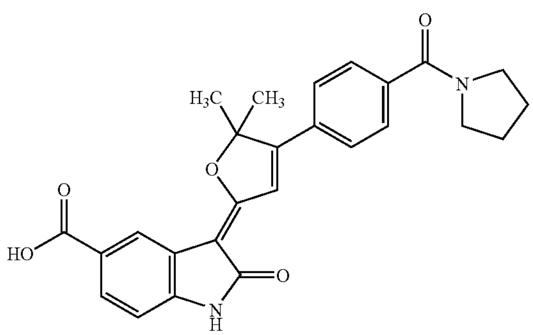 [SMILES: CC1(C)O/C(=C2/C(=O)Nc3ccc(C(=O)O)cc32)C=C1c1ccc(C(=O)N2CCCC2)cc1] | (3E)-3-{5,5-dimethyl-4-[4-(pyrrolidin-1-ylcarbonyl)phenyl]furan-2(5H)-ylidene}-2-oxoindoline-5-carboxylic acid | 444.4846 |
| 173 | 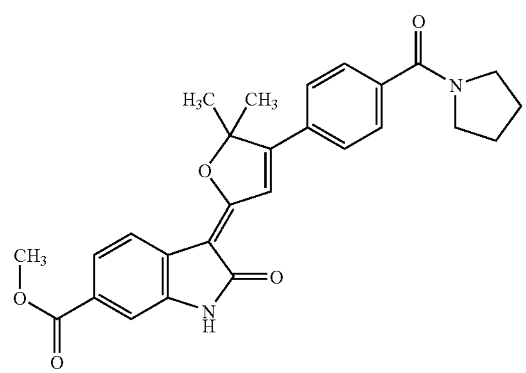 [SMILES: COC(=O)c1ccc2c(c1)NC(=O)/C2=C1\C=C(c2ccc(C(=O)N3CCCC3)cc2)C(C)(C)O1] | methyl (3E)-3-{5,5-dimethyl-4-[4-(pyrrolidin-1-ylcarbonyl)phenyl]furan-2(5H)-ylidene}-2-oxoindoline-6-carboxylate | 458.5114 |
| 174 | 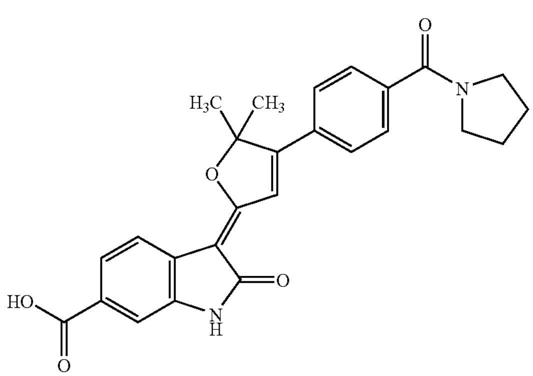 [SMILES: CC1(C)O/C(=C2/C(=O)Nc3cc(C(=O)O)ccc32)C=C1c1ccc(C(=O)N2CCCC2)cc1] | (3E)-3-{5,5-dimethyl-4-[4-(pyrrolidin-1-ylcarbonyl)phenyl]furan-2(5H)-ylidene}-2-oxoindoline-6-carboxylic acid | 444.4846 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 175 | 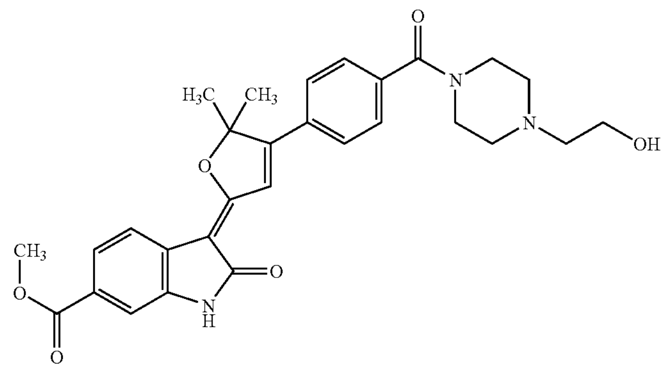 [SMILES: COC(=O)c1ccc2c(c1)NC(=O)/C2=C1\C=C(c2ccc(C(=O)N3CCN(CCO)CC3)cc2)C(C)(C)O1] | methyl (3E)-3-[4-(4-{[4-(2-hydroxyethyl)piperazin-1-yl]carbonyl}phenyl)-5,5-dimethylfuran-2(5H)-ylidene]-2-oxoindoline-6-carboxylate | 517.5789 |
| 176 | 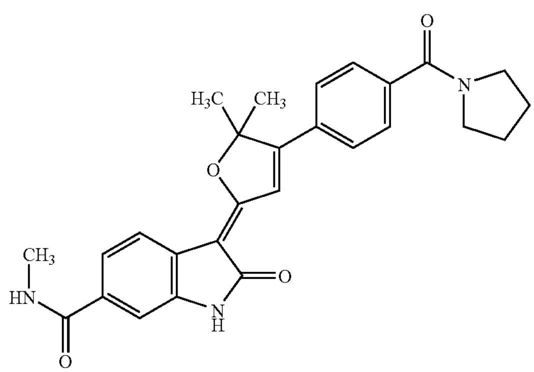 [SMILES: CNC(=O)c1ccc2c(c1)NC(=O)/C2=C1\C=C(c2ccc(C(=O)N3CCCC3)cc2)C(C)(C)O1] | (3E)-3-{5,5-dimethyl-4-[4-(pyrrolidin-1-ylcarbonyl)phenyl]furan-2(5H)-ylidene}-N-methyl-2-oxoindoline-6-carboxamide | 457.5273 |
| 177 | 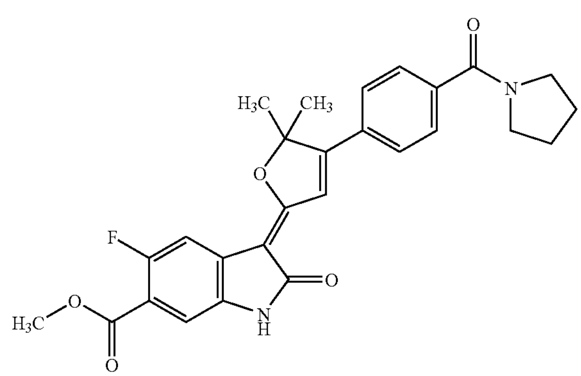 [SMILES: COC(=O)c1cc2c(cc1F)/C(=C1/C=C(c3ccc(C(=O)N4CCCC4)cc3)C(C)(C)O1)C(=O)N2] | methyl (3E)-3-{5,5-dimethyl-4-[4-(pyrrolidin-1-ylcarbonyl)phenyl]furan-2(5H)-ylidene}-5-fluoro-2-oxoindoline-6-carboxylate | 476.5015 |
| 178 | 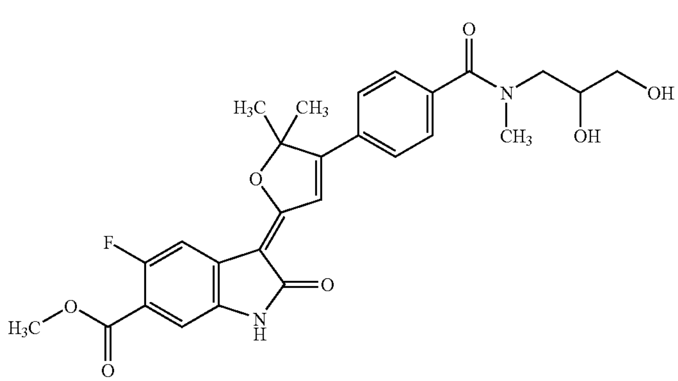 [SMILES: COC(=O)c1cc2c(cc1F)/C(=C1/C=C(c3ccc(C(=O)N(C)CC(O)CO)cc3)C(C)(C)O1)C(=O)N2] | methyl (3E)-3-[4-(4-{[(2,3-dihydroxypropyl)(methyl)amino]carbonyl}phenyl)-5,5-dimethylfuran-2(5H)-ylidene]-5-fluoro-2-oxoindoline-6-carboxylate | 510.5153 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 179 | 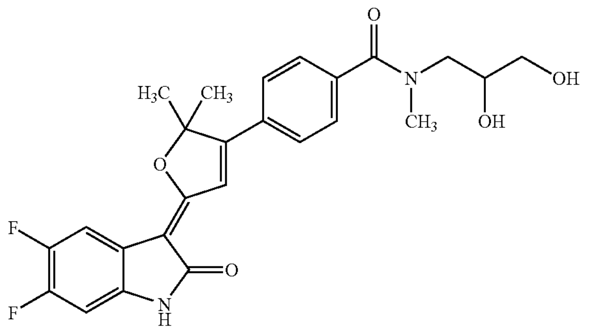 [SMILES: CN(CC(O)CO)C(=O)c1ccc(C2=C/C(=C3\C(=O)Nc4cc(F)c(F)cc43)OC2(C)C)cc1] | 4-[(5E)-5-(5,6-difluoro-2-oxo-1,2-dihydro-3H-indol-3-ylidene)-2,2-dimethyl-2,5-dihydrofuran-3-yl]-N-(2,3-dihydroxypropyl)-N-methylbenzamide | 470.47 |
| 180 | 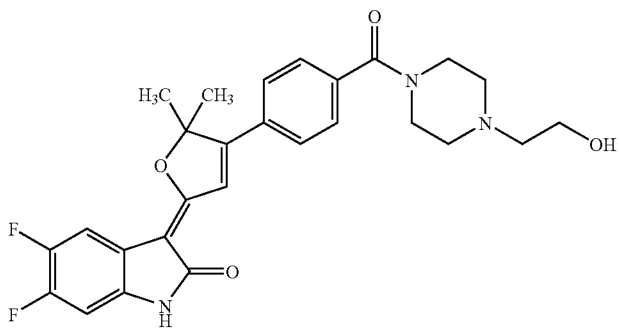 [SMILES: CC1(C)O/C(=C2/C(=O)Nc3cc(F)c(F)cc32)C=C1c1ccc(C(=O)N2CCN(CCO)CC2)cc1] | (3E)-5,6-difluoro-3-[4-(4-{[4-(2-hydroxyethyl)piperazin-1-yl]carbonyl}phenyl)-5,5-dimethylfuran-2(5H)-ylidene]-1,3-dihydro-2H-indol-2-one | 495.52 |
| 181 | Chiral | ethyl (2S)-2-({4-[(5E)-5-(6-fluoro-2-oxo-1,2-dihydro-3H-indol-3-ylidene)-2,2-dimethyl-2,5-dihydrofuran-3-yl]benzoyl}amino)-4-(methylthio)butanoate | 524.6101 |
| 182 | 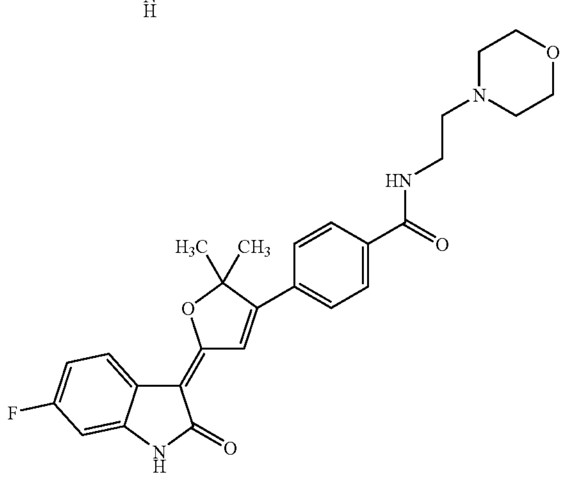 | 4-[(5E)-5-(6-fluoro-2-oxo-1,2-dihydro-3H-indol-3-ylidene)-2,2-dimethyl-2,5-dihydrofuran-3-yl]-N-(2-morpholin-4-ylethyl)benzamide | 477.5332 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 183 | 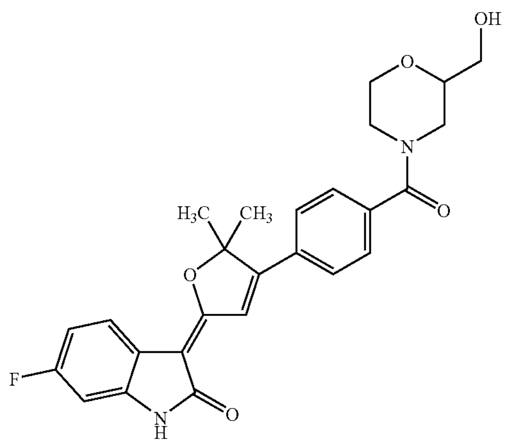 [SMILES: CC1(C)O/C(=C2/C(=O)Nc3cc(F)ccc32)C=C1c1ccc(C(=O)N2CCOC(CO)C2)cc1] | (3E)-6-fluoro-3-[4-(4-{[2-(hydroxymethyl)morpholin-4-yl]carbonyl}phenyl)-5,5-dimethylfuran-2(5H)-ylidene]-1,3-dihydro-2H-indol-2-one | 464.4905 |
| 184 | 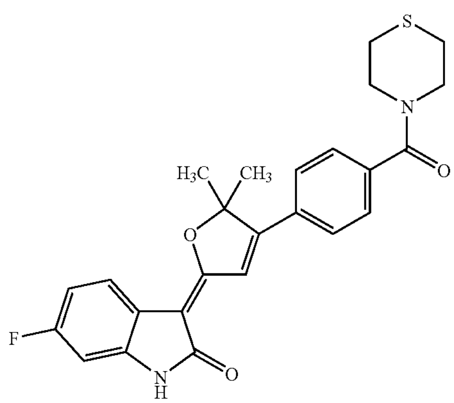 [SMILES: CC1(C)O/C(=C2/C(=O)Nc3cc(F)ccc32)C=C1c1ccc(C(=O)N2CCSCC2)cc1] | (3E)-3-{5,5-dimethyl-4-[4-(thiomorpholin-4-ylcarbonyl)phenyl]furan-2(5H)-ylidene}-6-fluoro-1,3-dihydro-2H-indol-2-one | 450.5317 |
| 185 | 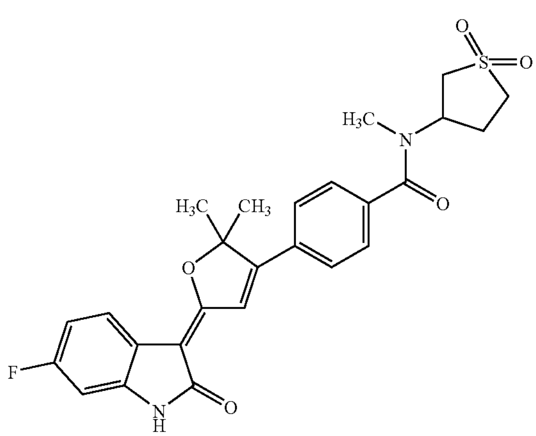 [SMILES: CN(C(=O)c1ccc(C2=C/C(=C3\C(=O)Nc4cc(F)ccc43)OC2(C)C)cc1)C1CCS(=O)(=O)C1] | N-(1,1-dioxidotetrahydro-3-thienyl)-4-[(5E)-5-(6-fluoro-2-oxo-1,2-dihydro-3H-indol-3-ylidene)-2,2-dimethyl-2,5-dihydrofuran-3-yl]-N-methylbenzamide | 496.5565 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 186 | 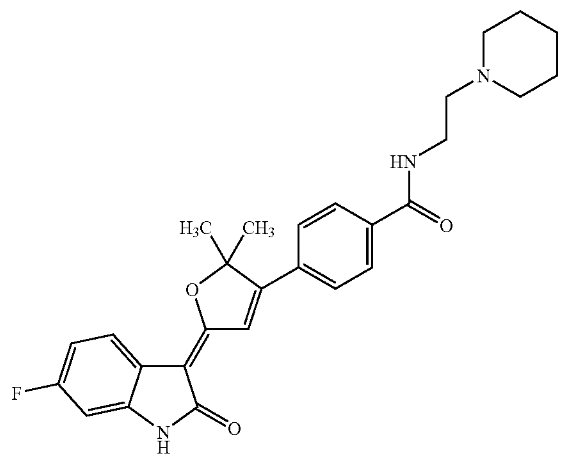 [SMILES: CC1(C)O/C(=C2/C(=O)Nc3cc(F)ccc32)C=C1c1ccc(C(=O)NCCN2CCCCC2)cc1] | 4-[(5E)-5-(6-fluoro-2-oxo-1,2-dihydro-3H-indol-3-ylidene)-2,2-dimethyl-2,5-dihydrofuran-3-yl]-N-(2-piperidin-1-ylethyl)benzamide | 475.561 |
| 187 | 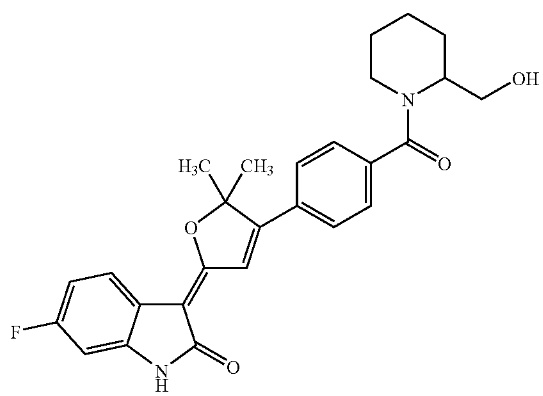 [SMILES: CC1(C)O/C(=C2/C(=O)Nc3cc(F)ccc32)C=C1c1ccc(C(=O)N2CCCCC2CO)cc1] | (3E)-6-fluoro-3-[4-(4-{[2-(hydroxymethyl)piperidin-1-yl]carbonyl}phenyl)-5,5-dimethylfuran-2(5H)-ylidene]-1,3-dihydro-2H-indol-2-one | 462.5183 |
| 188 | 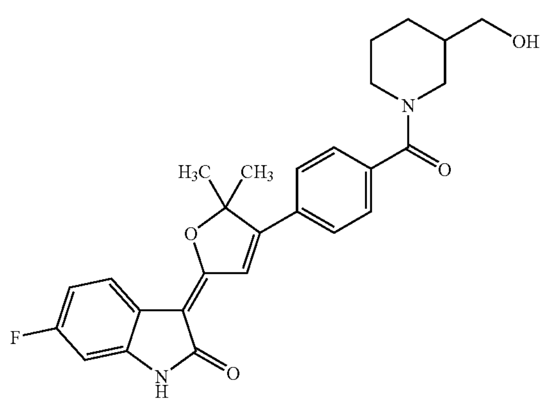 [SMILES: CC1(C)O/C(=C2/C(=O)Nc3cc(F)ccc32)C=C1c1ccc(C(=O)N2CCCC(CO)C2)cc1] | (3E)-6-fluoro-3-[4-(4-{[3-(hydroxymethyl)piperidin-1-yl]carbonyl}phenyl)-5,5-dimethylfuran-2(5H)-ylidene]-1,3-dihydro-2H-indol-2-one | 462.5183 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 189 | 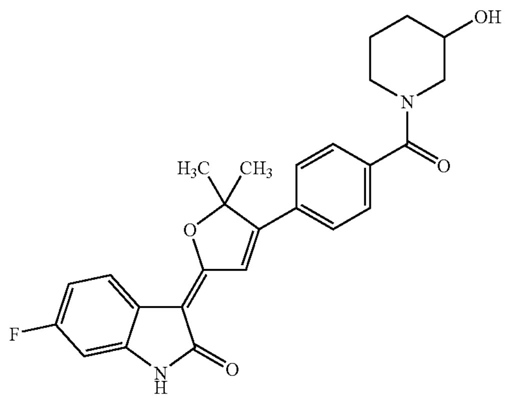 [SMILES: CC1(C)O/C(=C2/C(=O)Nc3cc(F)ccc32)C=C1c1ccc(C(=O)N2CCCC(O)C2)cc1] | (3E)-6-fluoro-3-[4-{4-[(3-hydroxypiperidin-1-yl)carbonyl]phenyl}-5,5-dimethylfuran-2(5H)-ylidene]-1,3-dihydro-2H-indol-2-one | 448.4915 |
| 190 | 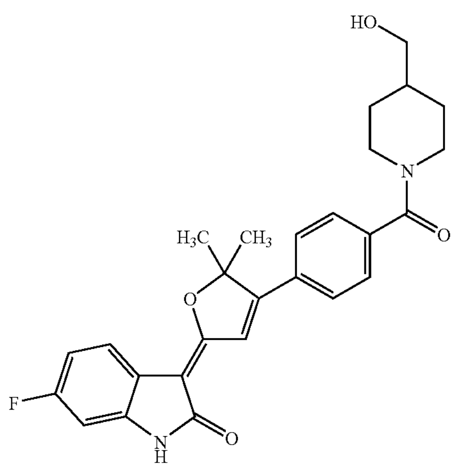 [SMILES: CC1(C)O/C(=C2/C(=O)Nc3cc(F)ccc32)C=C1c1ccc(C(=O)N2CCC(CO)CC2)cc1] | (3E)-6-fluoro-3-[4-(4-{[4-(hydroxymethyl)piperidin-1-yl]carbonyl}phenyl)-5,5-dimethylfuran-2(5H)-ylidene]-1,3-dihydro-2H-indol-2-one | 462.5183 |
| 191 | 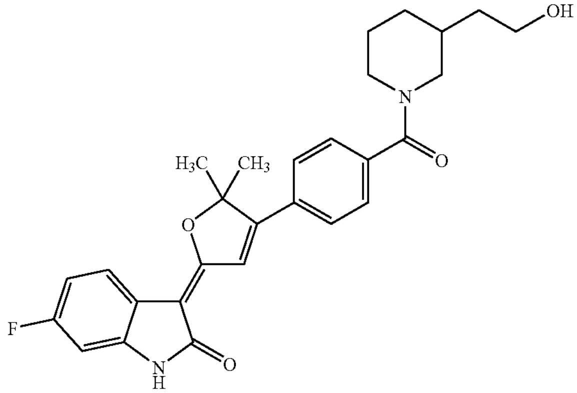 [SMILES: CC1(C)O/C(=C2/C(=O)Nc3cc(F)ccc32)C=C1c1ccc(C(=O)N2CCCC(CCO)C2)cc1] | (3E)-6-fluoro-3-[4-(4-{[3-(2-hydroxyethyl)piperidin-1-yl]carbonyl}phenyl)-5,5-dimethylfuran-2(5H)-ylidene]-1,3-dihydro-2H-indol-2-one | 476.5451 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 192 | 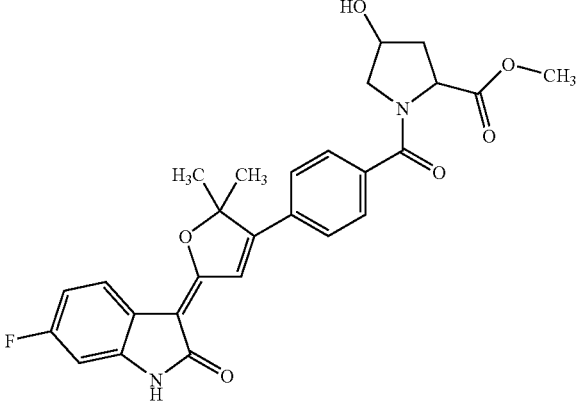 [SMILES: COC(=O)C1CC(O)CN1C(=O)c1ccc(C2=C/C(=C3\C(=O)Nc4cc(F)ccc43)OC2(C)C)cc1] | methyl 1-{4-[(5E)-5-(6-fluoro-2-oxo-1,2-dihydro-3H-indol-3-ylidene)-2,2-dimethyl-2,5-dihydrofuran-3-yl]benzoyl}-4-hydroxypyrrolidine-2-carboxylate | 492.5005 |
| 193 | 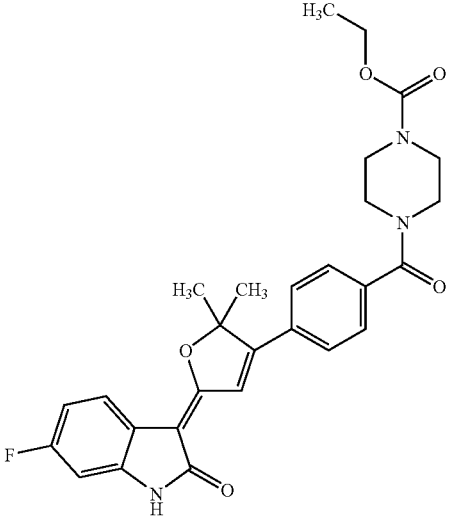 [SMILES: CCOC(=O)N1CCN(C(=O)c2ccc(C3=C/C(=C4\C(=O)Nc5cc(F)ccc54)OC3(C)C)cc2)CC1] | ethyl 4-{4-[(5E)-5-(6-fluoro-2-oxo-1,2-dihydro-3H-indol-3-ylidene)-2,2-dimethyl-2,5-dihydrofuran-3-yl]benzoyl} piperazine-1-carboxylate | 505.5432 |
| 194 | 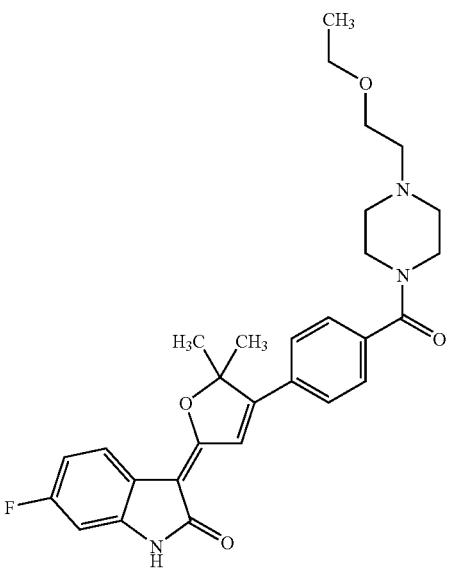 [SMILES: CCOCCN1CCN(C(=O)c2ccc(C3=C/C(=C4\C(=O)Nc5cc(F)ccc54)OC3(C)C)cc2)CC1] | (3E)-3-[4-(4-{[4-(2-ethoxyethyl) piperazin-1-yl]carbonyl}phenyl)-5,5-dimethylfuran-2(5H)-ylidene]-6-fluoro-1,3-dihydro-2H-indol-2-one | 505.5868 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 195 | 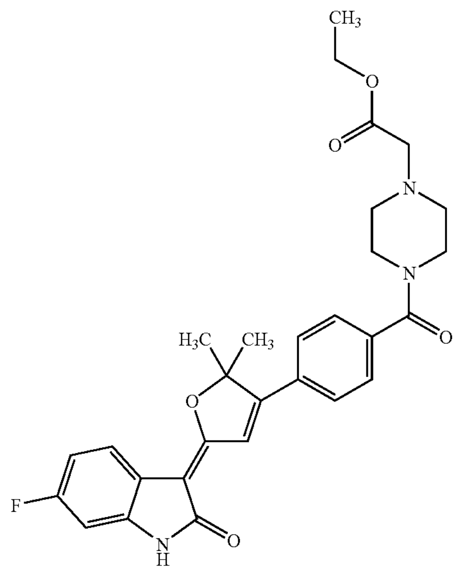 [SMILES: CCOC(=O)CN1CCN(C(=O)c2ccc(C3=C/C(=C4\C(=O)Nc5cc(F)ccc54)OC3(C)C)cc2)CC1] | ethyl (4-{4-[(5E)-5-(6-fluoro-2-oxo-1,2-dihydro-3H-indol-3-ylidene)-2,2-dimethyl-2,5-dihydrofuran-3-yl]benzoyl}piperazin-1-yl)acetate | 519.57 |
| 196 | 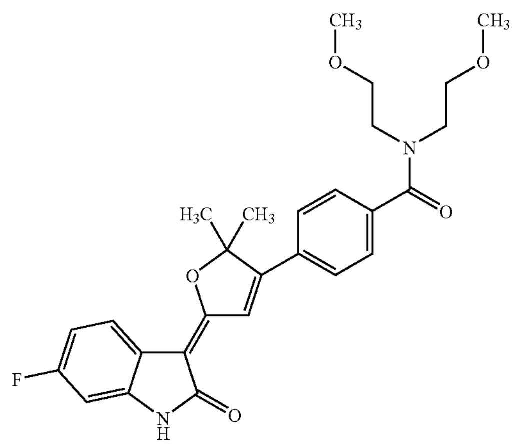 [SMILES: COCCN(CCOC)C(=O)c1ccc(C2=C/C(=C3\C(=O)Nc4cc(F)ccc43)OC2(C)C)cc1] | 4-[(5E)-5-(6-fluoro-2-oxo-1,2-dihydro-3H-indol-3-ylidene)-2,2-dimethyl-2,5-dihydrofuran-3-yl]-N,N-bis(2-methoxyethyl)benzamide | 480.5331 |
| 197 | 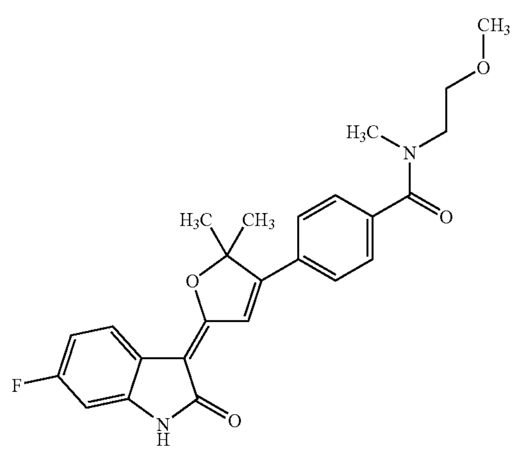 [SMILES: COCCN(C)C(=O)c1ccc(C2=C/C(=C3\C(=O)Nc4cc(F)ccc43)OC2(C)C)cc1] | 4-[(5E)-5-(6-fluoro-2-oxo-1,2-dihydro-3H-indol-3-ylidene)-2,2-dimethyl-2,5-dihydrofuran-3-yl]-N-(2-methoxyethyl)-N-methylbenzamide | 436.4805 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 198 | 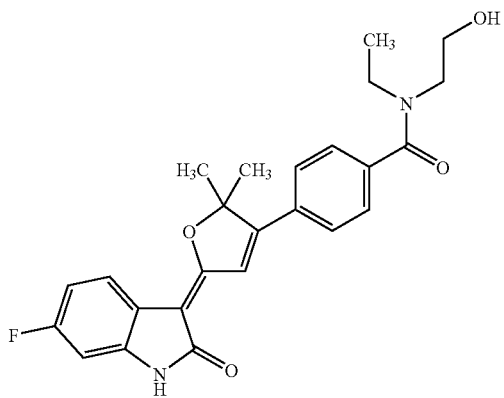 [SMILES: CCN(CCO)C(=O)c1ccc(C2=C/C(=C3\C(=O)Nc4cc(F)ccc43)OC2(C)C)cc1] | N-ethyl-4-[(5E)-5-(6-fluoro-2-oxo-1,2-dihydro-3H-indol-3-ylidene)-2,2-dimethyl-2,5-dihydrofuran-3-yl]-N-(2-hydroxyethyl)benzamide | 436.4805 |
| 199 | 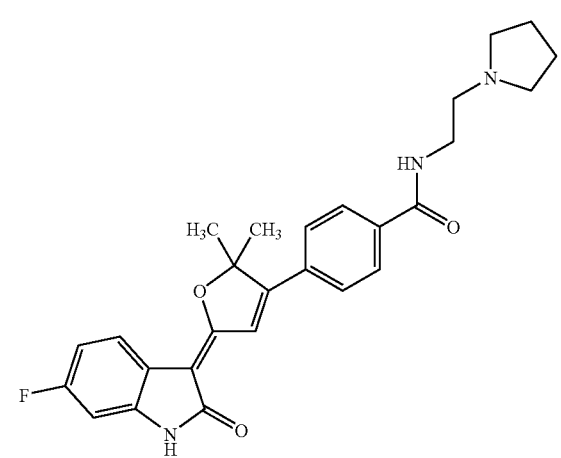 [SMILES: CC1(C)O/C(=C2/C(=O)Nc3cc(F)ccc32)C=C1c1ccc(C(=O)NCCN2CCCC2)cc1] | 4-[(5E)-5-(6-fluoro-2-oxo-1,2-dihydro-3H-indol-3-ylidene)-2,2-dimethyl-2,5-dihydrofuran-3-yl]-N-(2-pyrrolidin-1-ylethyl)benzamide | 461.5342 |
| 200 | 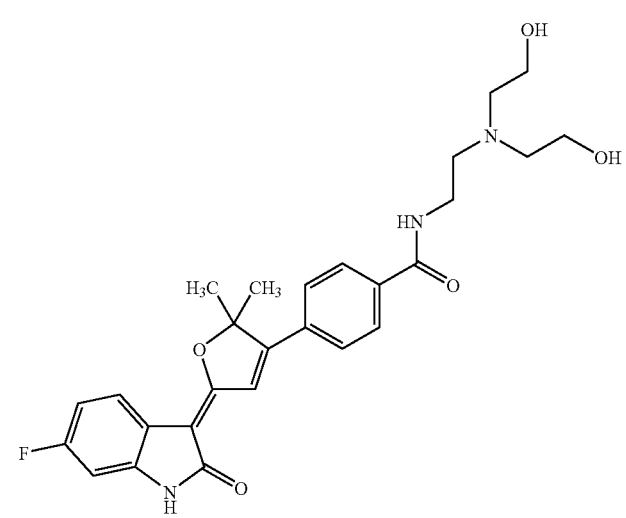 [SMILES: CC1(C)O/C(=C2/C(=O)Nc3cc(F)ccc32)C=C1c1ccc(C(=O)NCCN(CCO)CCO)cc1] | N-{2-[bis(2-hydroxyethyl)amino]ethyl}-4-[(5E)-5-(6-fluoro-2-oxo-1,2-dihydro-3H-indol-3-ylidene)-2,2-dimethyl-2,5-dihydrofuran-3-yl]benzamide | 495.548 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 201 | 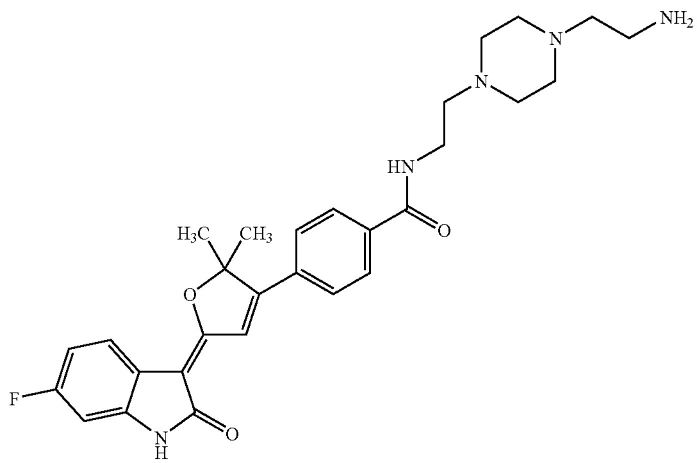 [SMILES: CC1(C)O/C(=C2/C(=O)Nc3cc(F)ccc32)C=C1c1ccc(C(=O)NCCN2CCN(CCN)CC2)cc1] | N-{2-[4-(2-aminoethyl)piperazin-1-yl]ethyl}-4-[(5E)-5-(6-fluoro-2-oxo-1,2-dihydro-3H-indol-3-ylidene)-2,2-dimethyl-2,5-dihydrofuran-3-yl]benzamide | 519.6176 |
| 202 | 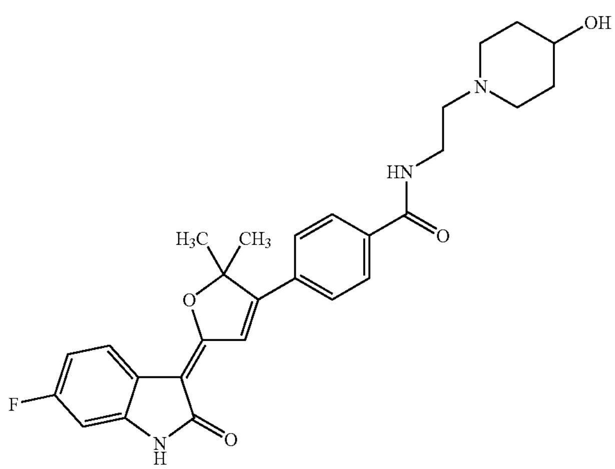 [SMILES: CC1(C)O/C(=C2/C(=O)Nc3cc(F)ccc32)C=C1c1ccc(C(=O)NCCN2CCC(O)CC2)cc1] | 4-[(5E)-5-(6-fluoro-2-oxo-1,2-dihydro-3H-indol-3-ylidene)-2,2-dimethyl-2,5-dihydrofuran-3-yl]-N-[2-(4-hydroxypiperidin-1-yl)ethyl]benzamide | 491.56 |
| 203 | 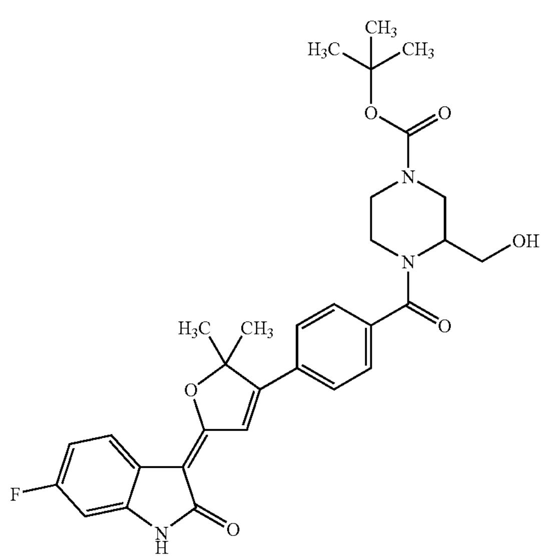 [SMILES: CC(C)(C)OC(=O)N1CCN(C(=O)c2ccc(C3=C/C(=C4\C(=O)Nc5cc(F)ccc54)OC3(C)C)cc2)C(CO)C1] | tert-butyl 4-{4-[(5E)-5-(6-fluoro-2-oxo-1,2-dihydro-3H-indol-3-ylidene)-2,2-dimethyl-2,5-dihydrofuran-3-yl]benzoyl}-3-(hydroxymethyl)piperazine-1-carboxylate | 563.6226 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 204 | 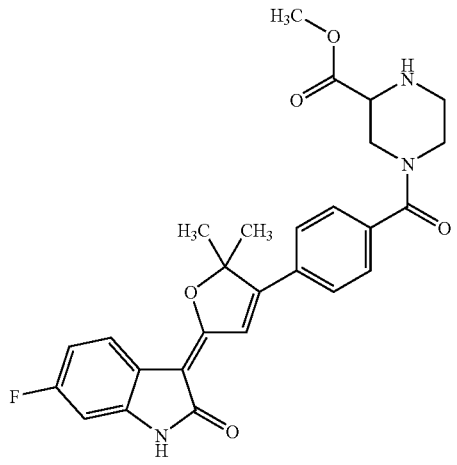 [SMILES: COC(=O)C1CN(C(=O)c2ccc(C3=C/C(=C4\C(=O)Nc5cc(F)ccc54)OC3(C)C)cc2)CCN1] | methyl 4-{4-[(5E)-5-(6-fluoro-2-oxo-1,2-dihydro-3H-indol-3-ylidene)-2,2-dimethyl-2,5-dihydrofuran-3-yl]benzoyl}piperazine-2-carboxylate | 491.5164 |
| 205 | 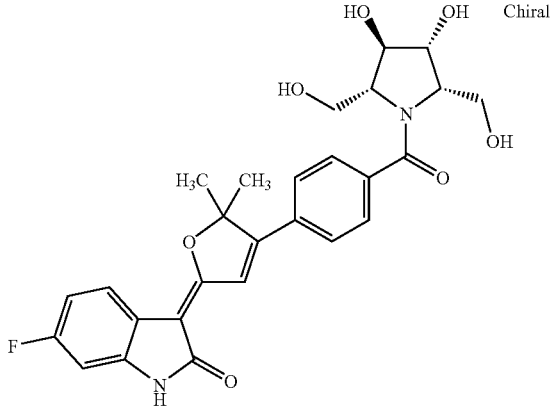 [SMILES: CC1(C)O/C(=C2/C(=O)Nc3cc(F)ccc32)C=C1c1ccc(C(=O)N2[C@H](CO)[C@@H](O)[C@H](O)[C@@H]2CO)cc1] | (3E)-3-[4-(4-{[(2R,3R,4R,5S)-3,4-dihydroxy-2,5-bis(hydroxymethyl)pyrrolidin-1-yl]carbonyl}phenyl)-5,5-dimethylfuran-2(5H)-ylidene]-6-fluoro-1,3-dihydro-2H-indol-2-one | 510.5153 |
| 206 | 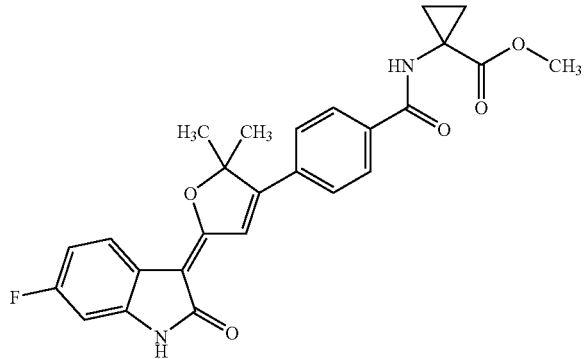 [SMILES: COC(=O)C1(NC(=O)c2ccc(C3=C/C(=C4\C(=O)Nc5cc(F)ccc54)OC3(C)C)cc2)CC1] | methyl 1-({4-[(5E)-5-(6-fluoro-2-oxo-1,2-dihydro-3H-indol-3-ylidene)-2,2-dimethyl-2,5-dihydrofuran-3-yl]benzoyl}amino)cyclopropanecarboxylate | 462.4747 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 207 | 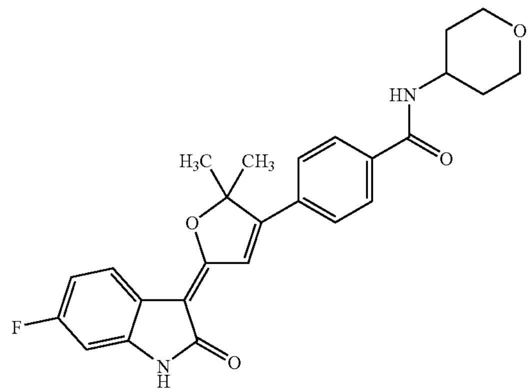 [SMILES: CC1(C)O/C(=C2/C(=O)Nc3cc(F)ccc32)C=C1c1ccc(C(=O)NC2CCOCC2)cc1] | 4-[(5E)-5-(6-fluoro-2-oxo-1,2-dihydro-3H-indol-3-ylidene)-2,2-dimethyl-2,5-dihydrofuran-3-yl]-N-(tetrahydro-2H-pyran-4-yl)benzamide | 448.4915 |
| 208 | 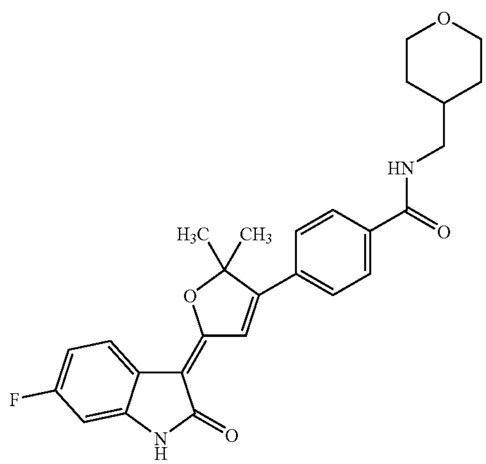 [SMILES: CC1(C)O/C(=C2/C(=O)Nc3cc(F)ccc32)C=C1c1ccc(C(=O)NCC2CCOCC2)cc1] | 4-[(5E)-5-(6-fluoro-2-oxo-1,2-dihydro-3H-indol-3-ylidene)-2,2-dimethyl-2,5-dihydrofuran-3-yl]-N-(tetrahydro-2H-pyran-4-ylmethyl)benzamide | 462.5183 |
| 209 | 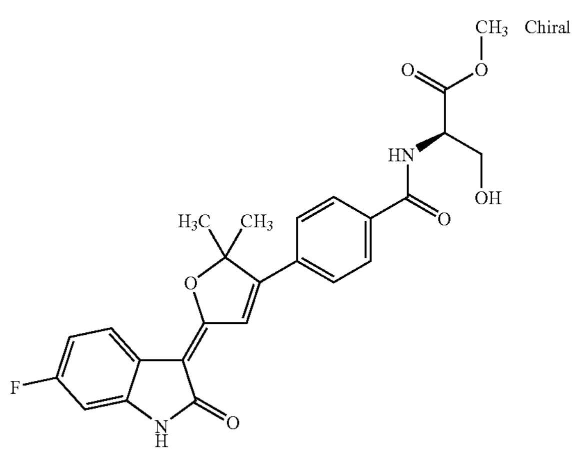 [SMILES: COC(=O)[C@@H](CO)NC(=O)c1ccc(C2=C/C(=C3\C(=O)Nc4cc(F)ccc43)OC2(C)C)cc1] | methyl (2R)-2-({4-[(5E)-5-(6-fluoro-2-oxo-1,2-dihydro-3H-indol-3-ylidene)-2,2-dimethyl-2,5-dihydrofuran-3-yl]benzoyl}amino)-3-hydroxypropanoate | 466.4627 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 210 | 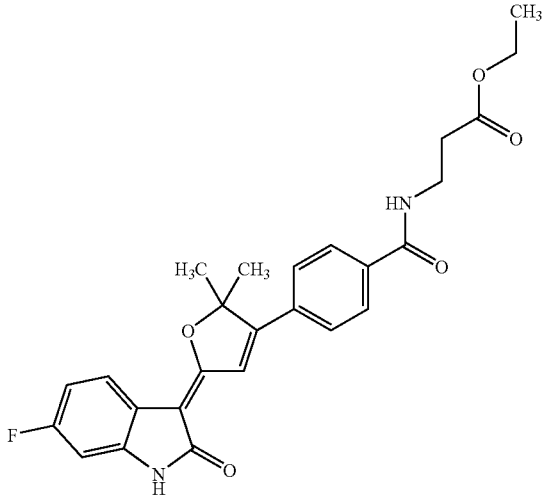 [SMILES: CCOC(=O)CCNC(=O)c1ccc(C2=C/C(=C3\C(=O)Nc4cc(F)ccc43)OC2(C)C)cc1] | ethyl 3-({4-[(5E)-5-(6-fluoro-2-oxo-1,2-dihydro-3H-indol-3-ylidene)-2,2-dimethyl-2,5-dihydrofuran-3-yl]benzoyl}amino)propanoate | 464.4905 |
| 211 | 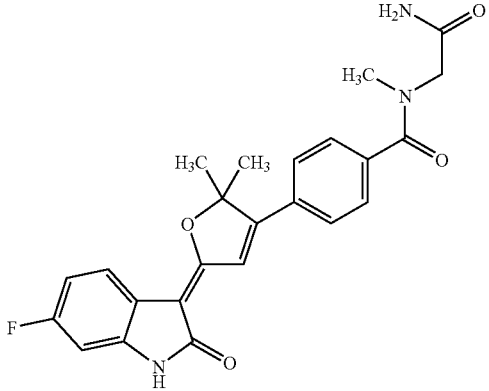 [SMILES: CN(CC(N)=O)C(=O)c1ccc(C2=C/C(=C3\C(=O)Nc4cc(F)ccc43)OC2(C)C)cc1] | N-(2-amino-2-oxoethyl)-4-[(5E)-5-(6-fluoro-2-oxo-1,2-dihydro-3H-indol-3-ylidene)-2,2-dimethyl-2,5-dihydrofuran-3-yl]-N-methylbenzamide | 435.4528 |
| 212 | 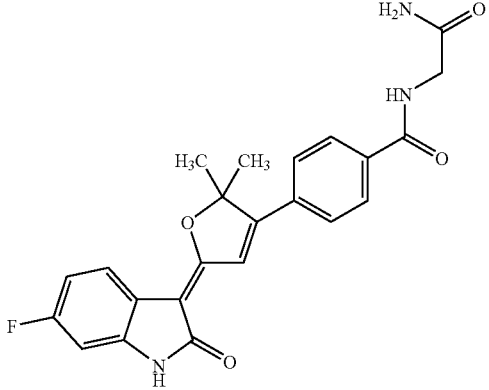 [SMILES: CC1(C)O/C(=C2/C(=O)Nc3cc(F)ccc32)C=C1c1ccc(C(=O)NCC(N)=O)cc1] | N-(2-amino-2-oxoethyl)-4-[(5E)-5-(6-fluoro-2-oxo-1,2-dihydro-3H-indol-3-ylidene)-2,2-dimethyl-2,5-dihydrofuran-3-yl]benzamide | 421.426 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 213 | 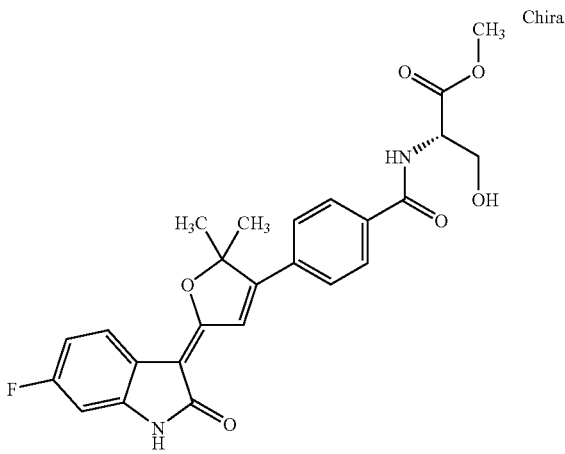 [SMILES: COC(=O)[C@H](CO)NC(=O)c1ccc(C2=C/C(=C3\C(=O)Nc4cc(F)ccc43)OC2(C)C)cc1] | methyl (2S)-2-({4-[(5E)-5-(6-fluoro-2-oxo-1,2-dihydro-3H-indol-3-ylidene)-2,2-dimethyl-2,5-dihydrofuran-3-yl]benzoyl}amino)-3-hydroxypropanoate | 466.4627 |
| 214 | 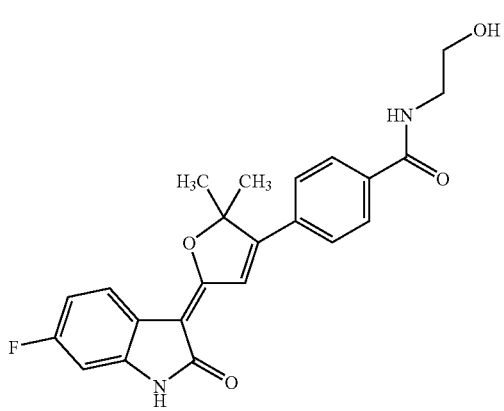 [SMILES: CC1(C)O/C(=C2/C(=O)Nc3cc(F)ccc32)C=C1c1ccc(C(=O)NCCO)cc1] | 4-[(5E)-5-(6-fluoro-2-oxo-1,2-dihydro-3H-indol-3-ylidene)-2,2-dimethyl-2,5-dihydrofuran-3-yl]-N-(2-hydroxyethyl)benzamide | 408.4269 |
| 215 | 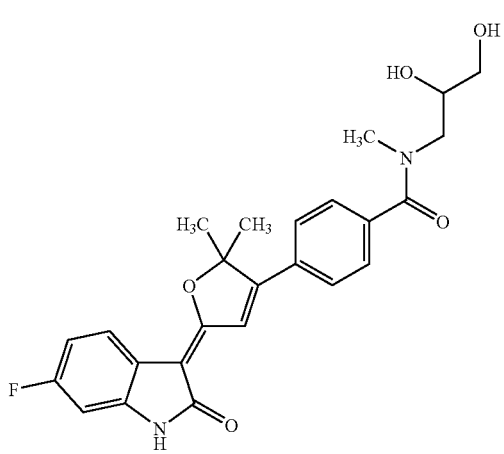 [SMILES: CN(CC(O)CO)C(=O)c1ccc(C2=C/C(=C3\C(=O)Nc4cc(F)ccc43)OC2(C)C)cc1] | N-(2,3-dihydroxypropyl)-4-[(5E)-5-(6-fluoro-2-oxo-1,2-dihydro-3H-indol-3-ylidene)-2,2-dimethyl-2,5-dihydrofuran-3-yl]-N-methylbenzamide | 452.4795 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 216 | 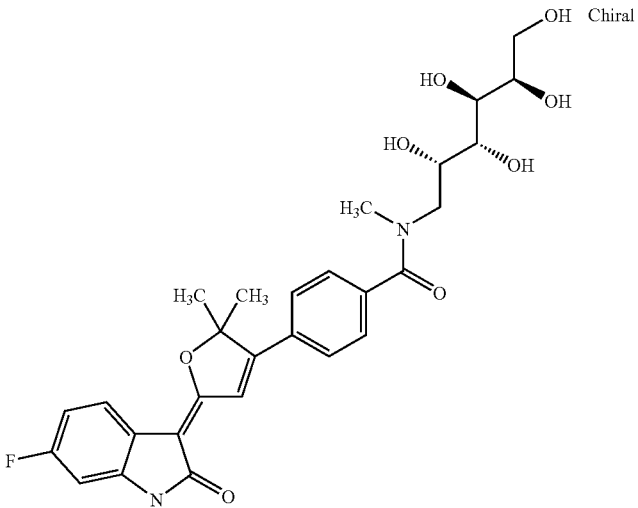 Chiral | 4-[(5E)-5-(6-fluoro-2-oxo-1,2-dihydro-3H-indol-3-ylidene)-2,2-dimethyl-2,5-dihydrofuran-3-yl]-N-(2-methyl-N-[(2S,3R,4S,5R)-2,3,4,5,6-pentahydroxyhexyl]benzamide | 542.5569 |
| 217 | 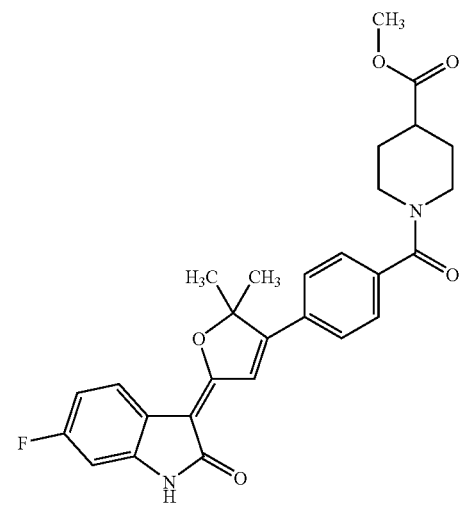 [SMILES: COC(=O)C1CCN(C(=O)c2ccc(C3=C/C(=C4\C(=O)Nc5cc(F)ccc54)OC3(C)C)cc2)CC1] | methyl 1-{4-[(5E)-5-(6-fluoro-2-oxo-1,2-dihydro-3H-indol-3-ylidene)-2,2-dimethyl-2,5-dihydrofuran-3-yl]benzoyl} piperidine-4-carboxylate | 490.5283 |
| 218 | 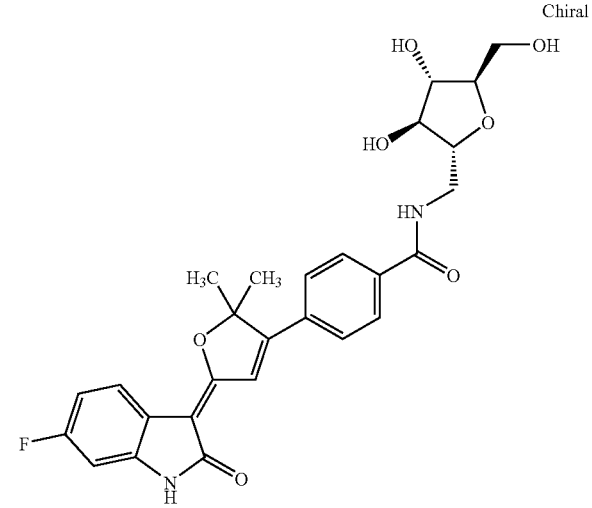 [SMILES: CC1(C)O/C(=C2/C(=O)Nc3cc(F)ccc32)C=C1c1ccc(C(=O)NC[C@H]2O[C@H](CO)[C@@H](O)[C@@H]2O)cc1] Chiral | N-{[(2R,3S,4S,5R)-3,4-dihydroxy-5-(hydroxymethyl)tetrahydrofuran-2-yl]methyl}-4-[(5E)-5-(6-fluoro-2-oxo-1,2-dihydro-3H-indol-3-ylidene)-2,2-dimethyl-2,5-dihydrofuran-3-yl]benzamide | 510.5153 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 219 | 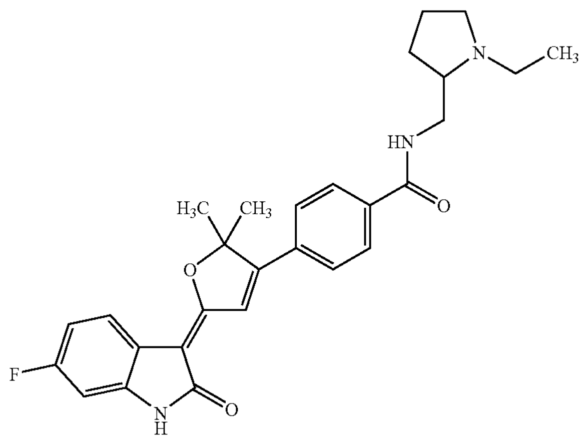 [SMILES: CCN1CCCC1CNC(=O)c1ccc(C2=C/C(=C3\C(=O)Nc4cc(F)ccc43)OC2(C)C)cc1] | N-[(1-ethylpyrrolidin-2-yl)methyl]-4-[(5E)-5-(6-fluoro-2-oxo-1,2-dihydro-3H-indol-3-ylidene)-2,2-dimethyl-2,5-dihydrofuran-3-yl]benzamide | 475.561 |
| 220 | 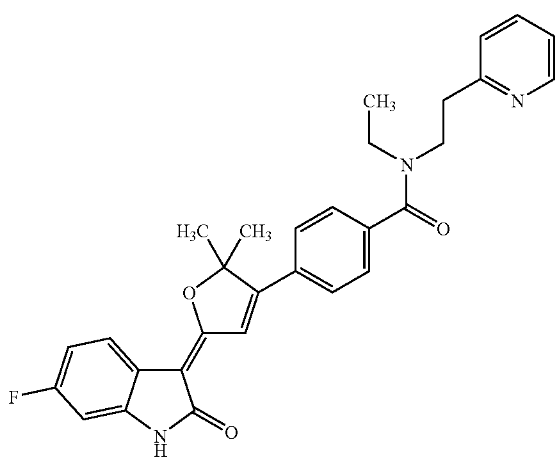 [SMILES: CCN(CCc1ccccn1)C(=O)c1ccc(C2=C/C(=C3\C(=O)Nc4cc(F)ccc43)OC2(C)C)cc1] | N-ethyl-4-[(5E)-5-(6-fluoro-2-oxo-1,2-dihydro-3H-indol-3-ylidene)-2,2-dimethyl-2,5-dihydrofuran-3-yl]-N-(2-pyridin-2-ylethyl)benzamide | 497.5672 |
| 221 | 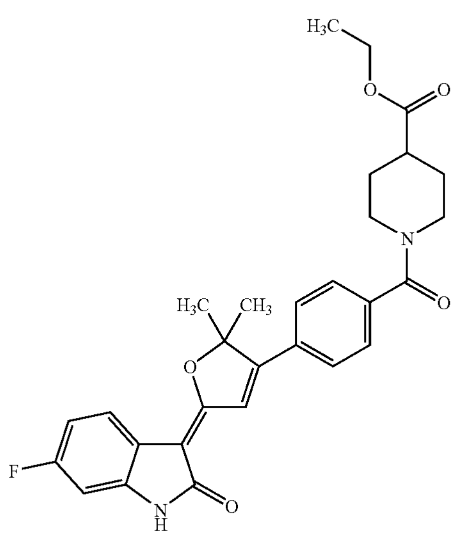 | ethyl 1-{4-[(5E)-5-(6-fluoro-2-oxo-1,2-dihydro-3H-indol-3-ylidene)-2,2-dimethyl-2,5-dihydrofuran-3-yl]benzoyl}piperidine-4-carboxylate | 504.5551 |

TABLE 5-continued

[5,5-dimethyl-5H-furan-(2E)-ylidene]-1,3-dihydro-indol-2-one benzamide derivatives

| Example # | Chemical Structure | Chemical Name | FW |
|---|---|---|---|
| 222 | 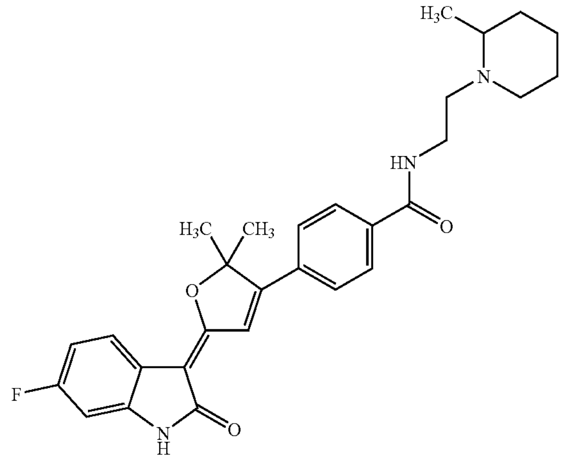 [SMILES: CC1CCCCN1CCNC(=O)c1ccc(C2=C/C(=C3\C(=O)Nc4cc(F)ccc43)OC2(C)C)cc1] | 4-[(5E)-5-(6-fluoro-2-oxo-1,2-dihydro-3H-indol-3-ylidene)-2,2-dimethyl-2,5-dihydrofuran-3-yl]-N-[2-(2-methylpiperidin-1-yl)ethyl]benzamide | 489.5878 |

TABLE 6

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 223 | 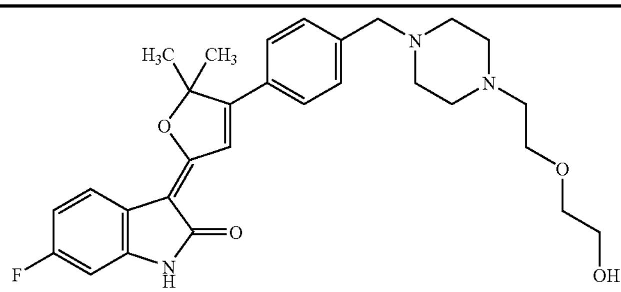 | (3E)-6-fluoro-3-{4-[4-({4-[2-(2-hydroxyethoxy)ethyl]piperazin-1-yl}methyl)phenyl]-5,5-dimethylfuran-2(5H)-ylidene}-1,3-dihydro-2H-indol-2-one | 507.6026 |
| 224 | 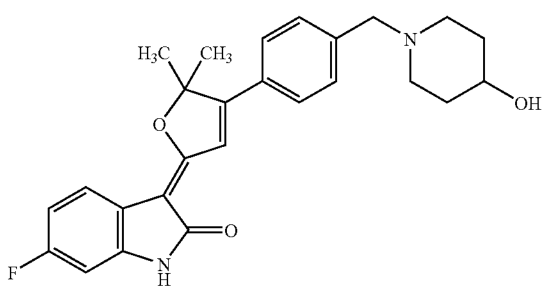 [SMILES: CC1(C)O/C(=C2/C(=O)Nc3cc(F)ccc32)C=C1c1ccc(CN2CCC(O)CC2)cc1] | (3E)-6-fluoro-3-[4-{4-[(4-hydroxypiperidin-1-yl)methyl]phenyl}-5,5-dimethylfuran-2(5H)-ylidene]-1,3-dihydro-2H-indol-2-one | 434.5083 |
| 225 | 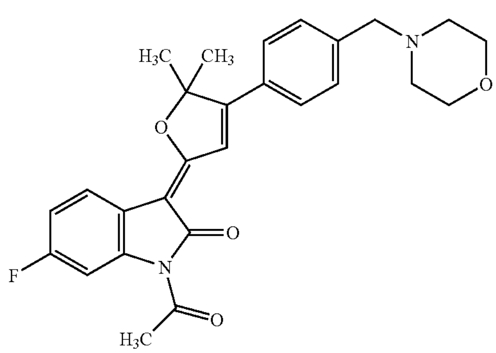 [SMILES: CC(=O)N1C(=O)/C(=C2\C=C(c3ccc(CN4CCOCC4)cc3)C(C)(C)O2)c2ccc(F)cc21] | (3E)-1-acetyl-3-{5,5-dimethyl-4-[4-(morpholin-4-ylmethyl)phenyl]furan-2(5H)-ylidene}-6-fluoro-1,3-dihydro-2H-indol-2-one | 462.5183 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 226 | 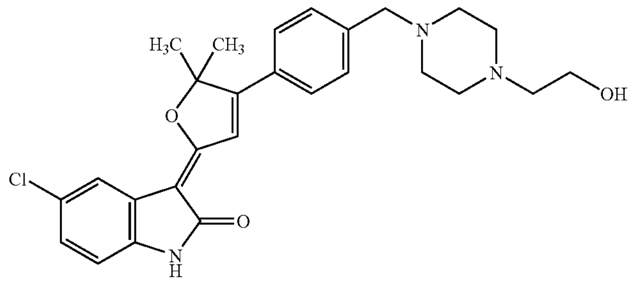 [SMILES: CC1(C)O/C(=C2/C(=O)Nc3ccc(Cl)cc32)C=C1c1ccc(CN2CCN(CCO)CC2)cc1] | (3E)-5-chloro-3-[4-(4-{[4-(2-hydroxyethyl)piperazin-1-yl]methyl}phenyl)-5,5-dimethylfuran-2(5H)-ylidene]-1,3-dihydro-2H-indol-2-one | 480.005 |
| 227 | 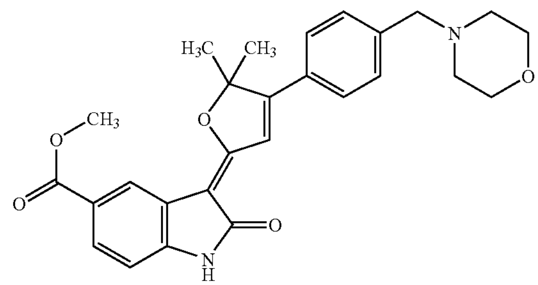 [SMILES: COC(=O)c1ccc2c(c1)/C(=C1/C=C(c3ccc(CN4CCOCC4)cc3)C(C)(C)O1)C(=O)N2] | methyl (3E)-3-{5,5-dimethyl-4-[4-(morpholin-4-ylmethyl)phenyl]furan-2(5H)-ylidene}-2-oxoindoline-5-carboxylate | 460.5272 |
| 228 | 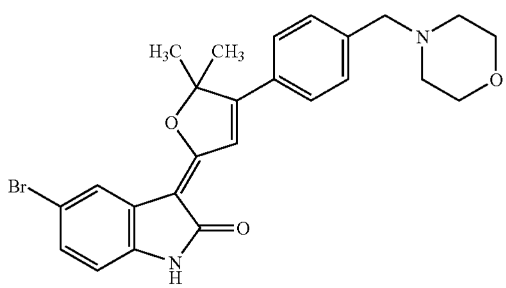 [SMILES: CC1(C)O/C(=C2/C(=O)Nc3ccc(Br)cc32)C=C1c1ccc(CN2CCOCC2)cc1] | (3E)-5-bromo-3-{5,5-dimethyl-4-[4-(morpholin-4-ylmethyl)phenyl]furan-2(5H)-ylidene}-1,3-dihydro-2H-indol-2-one | 481.3875 |
| 229 | 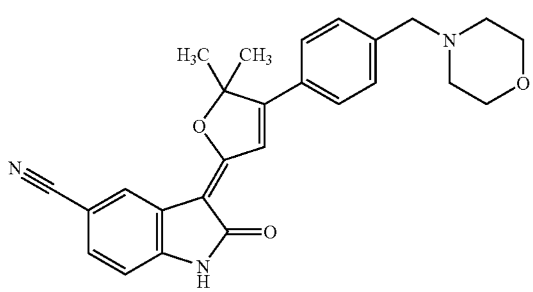 [SMILES: CC1(C)O/C(=C2/C(=O)Nc3ccc(C#N)cc32)C=C1c1ccc(CN2CCOCC2)cc1] | (3E)-3-{5,5-dimethyl-4-[4-(morpholin-4-ylmethyl)phenyl]furan-2(5H)-ylidene}-2-oxoindoline-5-carbonitrile | 427.5015 |
| 230 | 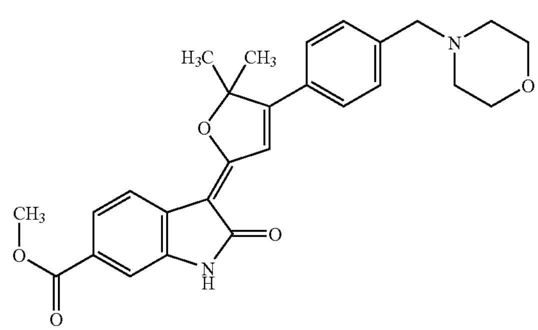 [SMILES: COC(=O)c1ccc2c(c1)NC(=O)/C2=C1\C=C(c2ccc(CN3CCOCC3)cc2)C(C)(C)O1] | methyl (3E)-3-{5,5-dimethyl-4-[4-(morpholin-4-ylmethyl)phenyl]furan-2(5H)-ylidene}-2-oxoindoline-6-carboxylate | 460.5272 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 231 | 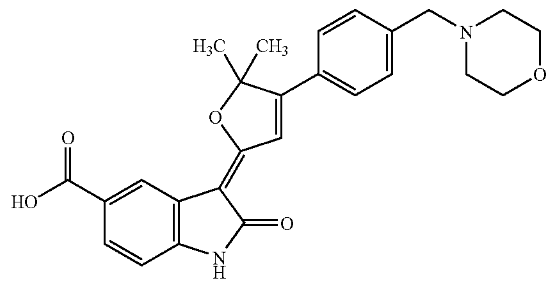 [SMILES: CC1(C)O/C(=C2/C(=O)Nc3ccc(C(=O)O)cc32)C=C1c1ccc(CN2CCOCC2)cc1] | (3E)-3-{5,5-dimethyl-4-[4-(morpholin-4-ylmethyl)phenyl]furan-2(5H)-ylidene}-2-oxoindoline-5-carboxylic acid | 446.5004 |
| 232 | 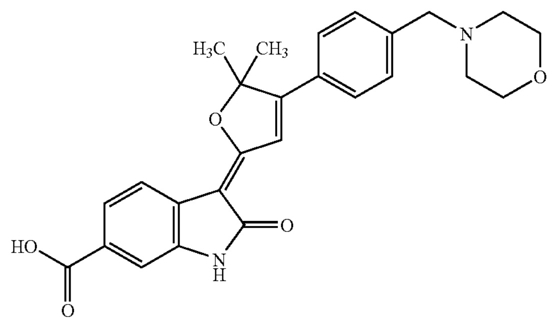 [SMILES: CC1(C)O/C(=C2/C(=O)Nc3cc(C(=O)O)ccc32)C=C1c1ccc(CN2CCOCC2)cc1] | (3E)-3-{5,5-dimethyl-4-[4-(morpholin-4-ylmethyl)phenyl]furan-2(5H)-ylidene}-2-oxoindoline-6-carboxylic acid | 446.5004 |
| 233 | 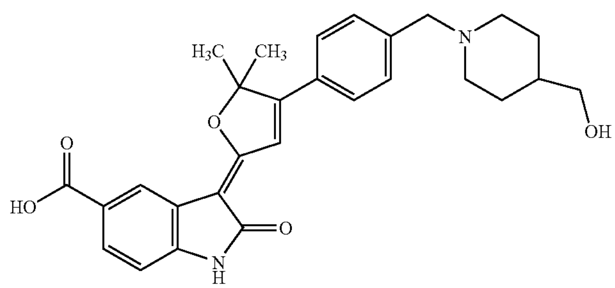 [SMILES: CC1(C)O/C(=C2/C(=O)Nc3ccc(C(=O)O)cc32)C=C1c1ccc(CN2CCC(CO)CC2)cc1] | (3E)-3-[4-(4-{[4-(hydroxymethyl)piperidin-1-yl]methyl}phenyl)-5,5-dimethylfuran-2(5H)-ylidene]-2-oxoindoline-5-carboxylic acid | 474.554 |
| 234 | 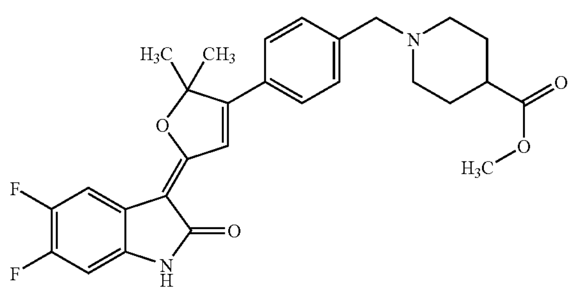 [SMILES: COC(=O)C1CCN(Cc2ccc(C3=C/C(=C4\C(=O)Nc5cc(F)c(F)cc54)OC3(C)C)cc2)CC1] | methyl 1-{4-[(5E)-5-(5,6-difluoro-2-oxo-1,2-dihydro-3H-indol-3-ylidene)-2,2-dimethyl-2,5-dihydrofuran-3-yl]benzyl}piperidine-4-carboxylate | 494.54 |
| 235 | 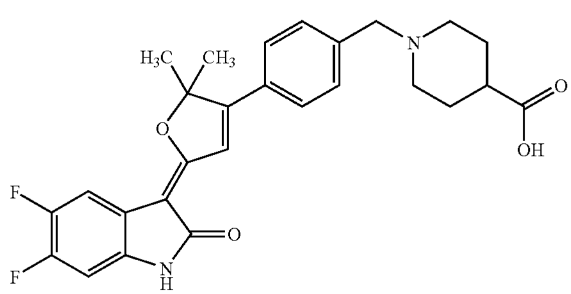 [SMILES: CC1(C)O/C(=C2/C(=O)Nc3cc(F)c(F)cc32)C=C1c1ccc(CN2CCC(C(=O)O)CC2)cc1] | 1-{4-[(5E)-5-(5,6-difluoro-2-oxo-1,2-dihydro-3H-indol-3-ylidene)-2,2-dimethyl-2,5-dihydrofuran-3-yl]benzyl}piperidine-4-carboxylic acid | 480.51 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 236 | Chiral | ethyl (2S)-2-({4-[(5E)-5-(6-fluoro-2-oxo-1,2-dihydro-3H-indol-3-ylidene)-2,2-dimethyl-2,5-dihydrofuran-3-yl]benzyl}amino)-4-(methylthio)butanoate | 510.6269 |
| 237 | 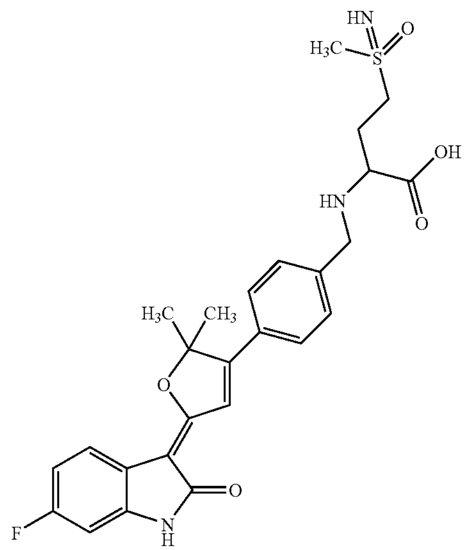 [SMILES: CC1(C)O/C(=C2/C(=O)Nc3cc(F)ccc32)C=C1c1ccc(CNC(CCS(C)(=N)=O)C(=O)O)cc1] | 2-({4-[(5E)-5-(6-fluoro-2-oxo-1,2-dihydro-3H-indol-3-ylidene)-2,2-dimethyl-2,5-dihydrofuran-3-yl]benzyl}amino)-4-(S-methylsulfonimidoyl)butanoic acid | 513.5872 |
| 238 | 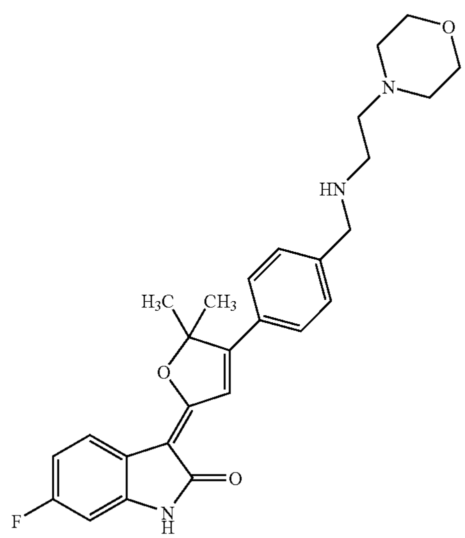 [SMILES: CC1(C)O/C(=C2/C(=O)Nc3cc(F)ccc32)C=C1c1ccc(CNCCN2CCOCC2)cc1] | (3E)-3-[5,5-dimethyl-4-(4-{[(2-morpholin-4-ylethyl)amino]methyl}phenyl)furan-2(5H)-ylidene]-6-fluoro-1,3-dihydro-2H-indol-2-one | 463.55 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 239 | 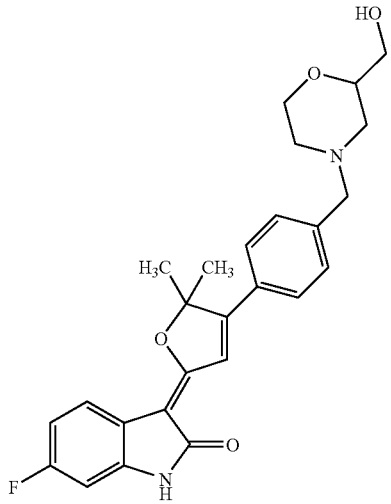 [SMILES: CC1(C)O/C(=C2/C(=O)Nc3cc(F)ccc32)C=C1c1ccc(CN2CCOC(CO)C2)cc1] | (3E)-6-fluoro-3-[4-(4-{[2-(hydroxymethyl)morpholin-4-yl]methyl}phenyl)-5,5-dimethylfuran-2(5H)-ylidene]-1,3-dihydro-2H-indol-2-one | 450.5073 |
| 240 | 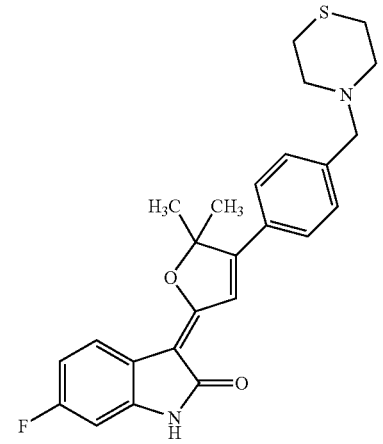 [SMILES: CC1(C)O/C(=C2/C(=O)Nc3cc(F)ccc32)C=C1c1ccc(CN2CCSCC2)cc1] | (3E)-3-{5,5-dimethyl-4-[4-(thiomorpholin-4-ylmethyl)phenyl]furan-2(5H)-ylidene}-6-fluoro-1,3-dihydro-2H-indol-2-one | 436.5485 |
| 241 | 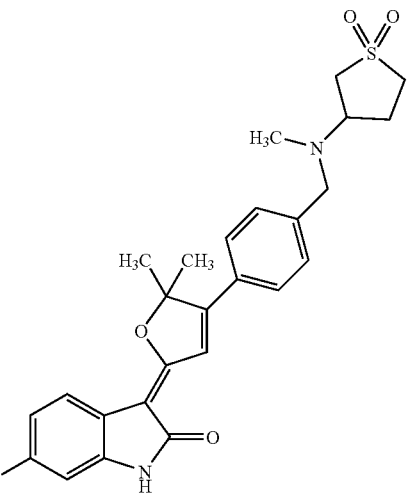 | (3E)-3-[4-(4-{[(1,1-dioxidotetrahydro-3-thienyl)(methyl)amino]methyl}phenyl)-5,5-dimethylfuran-2(5H)-ylidene]-6-fluoro-1,3-dihydro-2H-indol-2-one | 482.5733 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 242 | 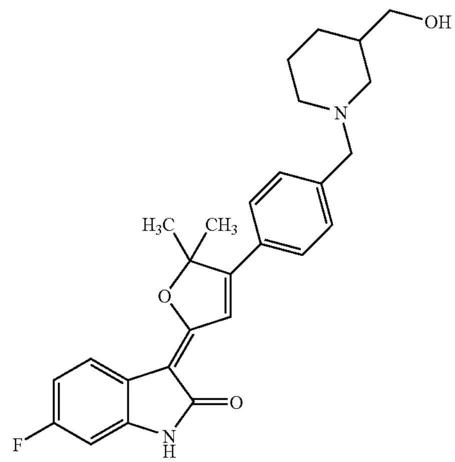 [SMILES: CC1(C)O/C(=C2/C(=O)Nc3cc(F)ccc32)C=C1c1ccc(CN2CCCC(CO)C2)cc1] | (3E)-6-fluoro-3-[4-(4-{[3-(hydroxymethyl)piperidin-1-yl]methyl}phenyl)-5,5-dimethylfuran-2(5H)-ylidene]-1,3-dihydro-2H-indol-2-one | 448.5351 |
| 243 | 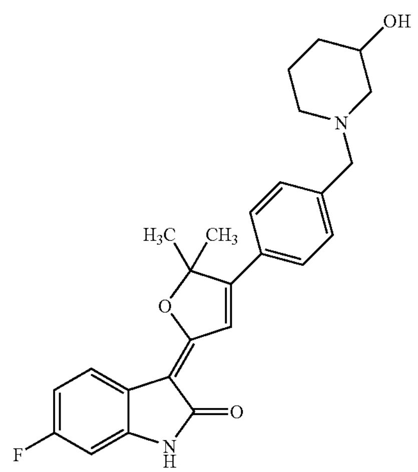 [SMILES: CC1(C)O/C(=C2/C(=O)Nc3cc(F)ccc32)C=C1c1ccc(CN2CCCC(O)C2)cc1] | (3E)-6-fluoro-3-[4-{4-[(3-hydroxypiperidin-1-yl)methyl]phenyl}-5,5-dimethylfuran-2(5H)-ylidene]-1,3-dihydro-2H-indol-2-one | 434.5083 |
| 244 | 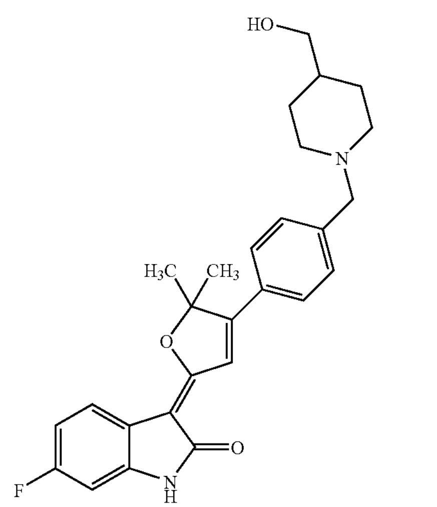 [SMILES: CC1(C)O/C(=C2/C(=O)Nc3cc(F)ccc32)C=C1c1ccc(CN2CCC(CO)CC2)cc1] | (3E)-6-fluoro-3-[4-(4-{[4-(hydroxymethyl)piperidin-1-yl]methyl}phenyl)-5,5-dimethylfuran-2(5H)-ylidene]-1,3-dihydro-2H-indol-2-one | 448.5351 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 245 | 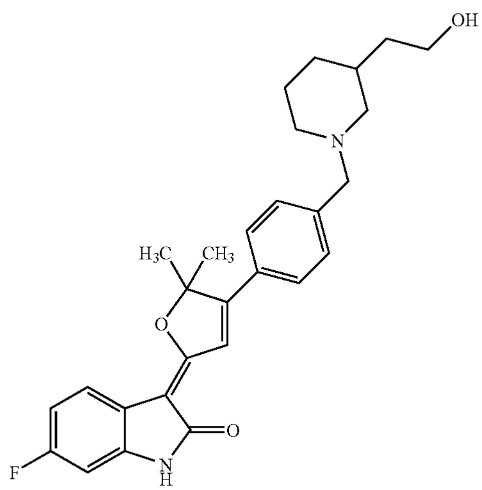 [SMILES: CC1(C)O/C(=C2/C(=O)Nc3cc(F)ccc32)C=C1c1ccc(CN2CCCC(CCO)C2)cc1] | (3E)-6-fluoro-3-[4-(4-{[3-(2-hydroxyethyl)piperidin-1-yl]methyl}phenyl)-5,5-dimethylfuran-2(5H)-ylidene]-1,3-dihydro-2H-indol-2-one | 462.5619 |
| 246 | 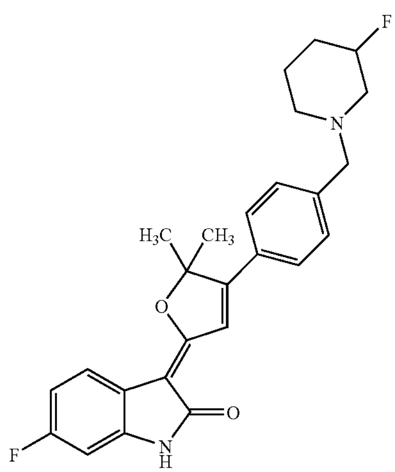 [SMILES: CC1(C)O/C(=C2/C(=O)Nc3cc(F)ccc32)C=C1c1ccc(CN2CCCC(F)C2)cc1] | (3E)-6-fluoro-3-[4-{4-[(3-fluoropiperidin-1-yl)methyl]phenyl}-5,5-dimethylfuran-2(5H)-ylidene]-1,3-dihydro-2H-indol-2-one | 436.4994 |
| 247 | 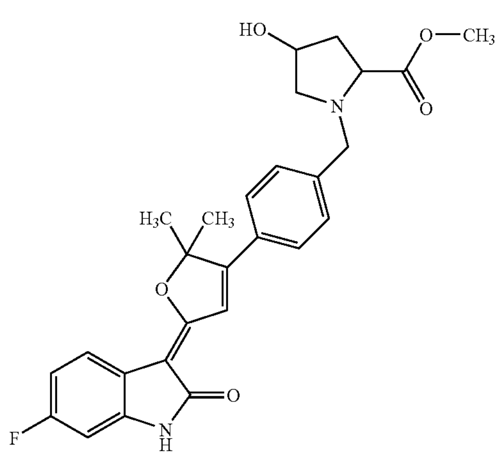 [SMILES: COC(=O)C1CC(O)CN1Cc1ccc(C2=C/C(=C3\C(=O)Nc4cc(F)ccc43)OC2(C)C)cc1] | methyl 1-{4-[(5E)-5-(6-fluoro-2-oxo-1,2-dihydro-3H-indol-3-ylidene)-2,2-dimethyl-2,5-dihydrofuran-3-yl]benzyl}-4-hydroxypyrrolidine-2-carboxylate | 478.5173 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 248 | 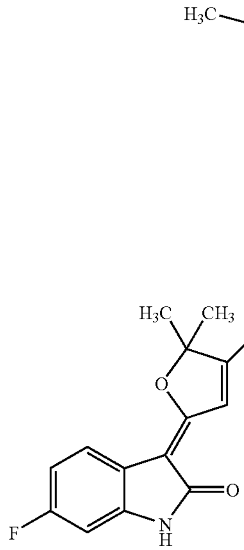 | ethyl 4-{4-[(5E)-5-(6-fluoro-2-oxo-1,2-dihydro-3H-indol-3-ylidene)-2,2-dimethyl-2,5-dihdrofuran-3-yl]benzyl} piperazine-1-carboxylate | 491.56 |
| 249 | 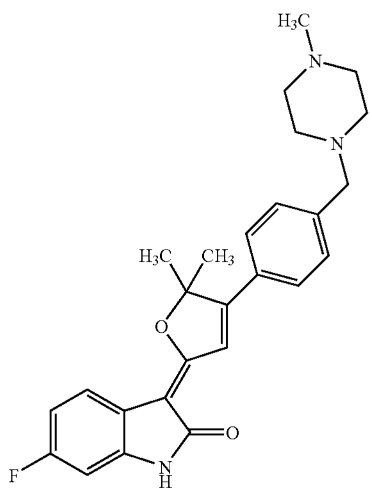 [SMILES: CN1CCN(Cc2ccc(C3=C/C(=C4\C(=O)Nc5cc(F)ccc54)OC3(C)C)cc2)CC1] | (3E)-3-[5,5-dimethyl-4-{4-[(4-methylpiperazin-1-yl)methyl] phenyl}furan-2(5H)-ylidene]-6-fluoro-1,3-dihydro-2H-indol-2-one | 433.5242 |
| 250 | 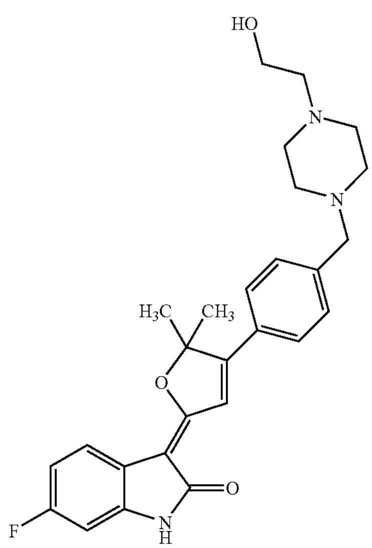 [SMILES: CC1(C)O/C(=C2/C(=O)Nc3cc(F)ccc32)C=C1c1ccc(CN2CCN(CCO)CC2)cc1] | (3E)-6-fluoro-3-[4-(4-{[4-(2-hydroxyethyl)piperazin-1-yl] methyl}phenyl)-5,5-dimethylfuran-2(5H)-ylidene]-1,3-dihydro-2H-indol-2-one | 463.55 |

TABLE 6-continued
[5,5-dimethyl-5H-furan-(2E)-ylidene]-1,3-dihydro-indol-2-one benzylmethyl amine derivatives
| Example # | Chemical Structure | Chemical Name | FW |
|---|---|---|---|
| 251 | 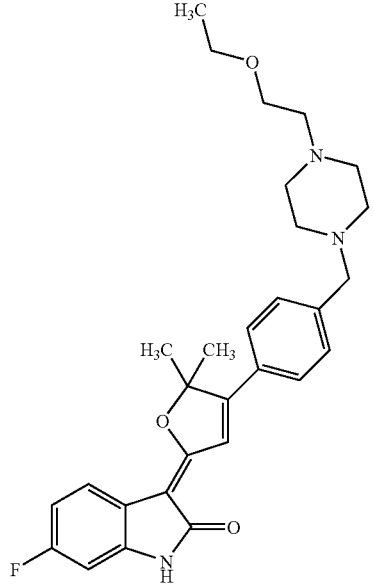 [SMILES: CCOCCN1CCN(Cc2ccc(C3=C/C(=C4\C(=O)Nc5cc(F)ccc54)OC3(C)C)cc2)CC1] | (3E)-3-[4-(4-{[4-(2-ethoxyethyl)piperazin-1-yl]methyl}phenyl)-5,5-dimethylfuran-2(5H)-ylidene]-6-fluoro-1,3-dihydro-2H-indol-2-one | 491.6036 |
| 252 | 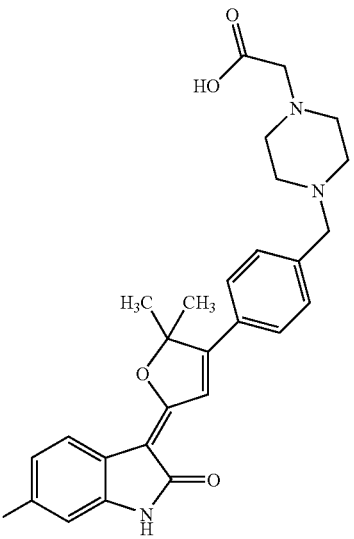 | (4-{4-[(5E)-5-(6-fluoro-2-oxo-1,2-dihydro-3H-indol-3-ylidene)-2,2-dimethyl-2,5-dihydrofuran-3-yl]benzyl}piperazin-1-yl)acetic acid | 477.5332 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 253 | 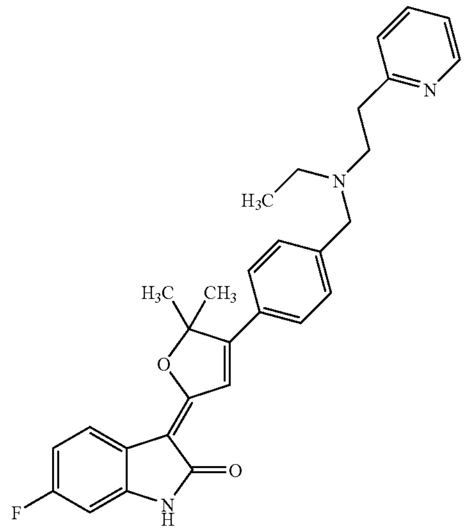 [SMILES: CCN(CCc1ccccn1)Cc1ccc(C2=C/C(=C3\C(=O)Nc4cc(F)ccc43)OC2(C)C)cc1] | (3E)-3-[4-(4-{[ethyl(2-pyridin-2-ylethyl)amino]methyl}phenyl)-5,5-dimethylfuran-2(5H)-ylidene]-6-fluoro-1,3-dihydro-2H-indol-2-one | 483.584 |
| 254 | 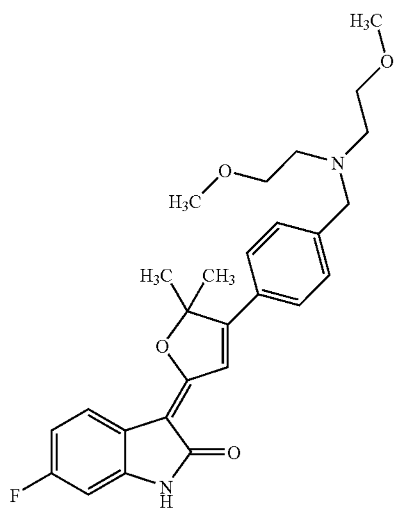 [SMILES: COCCN(CCOC)Cc1ccc(C2=C/C(=C3\C(=O)Nc4cc(F)ccc43)OC2(C)C)cc1] | (3E)-3-[4-(4-{[bis(2-methoxyethyl)amino]methyl}phenyl)-5,5-dimethylfuran-2(5H)-ylidene]-6-fluoro-1,3-dihydro-2H-indol-2-one | 466.5499 |
| 255 | 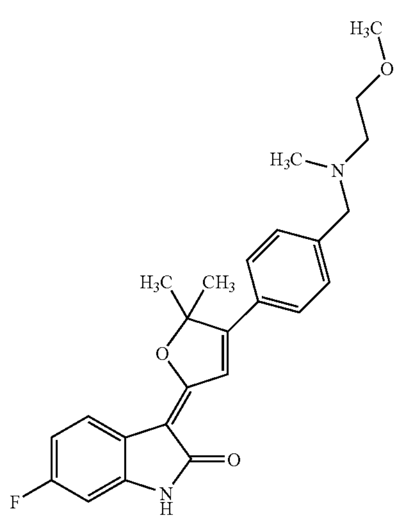 [SMILES: COCCN(C)Cc1ccc(C2=C/C(=C3\C(=O)Nc4cc(F)ccc43)OC2(C)C)cc1] | (3E)-6-fluoro-3-[4-(4-{[(2-methoxyethyl)(methyl)amino]methyl}phenyl)-5,5-dimethylfuran-2(5H)-ylidene]-1,3-dihydro-2H-indol-2-one | 422.4973 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 256 | 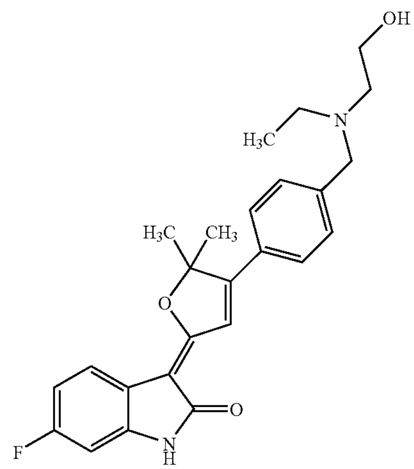 [SMILES: CCN(CCO)Cc1ccc(C2=C/C(=C3\C(=O)Nc4cc(F)ccc43)OC2(C)C)cc1] | (3E)-3-[4-(4-{[ethyl(2-hydroxyethyl)amino]methyl}phenyl)-5,5-dimethylfuran-2(5H)-ylidene]-6-fluoro-1,3-dihydro-2H-indol-2-one | 422.4973 |
| 257 | 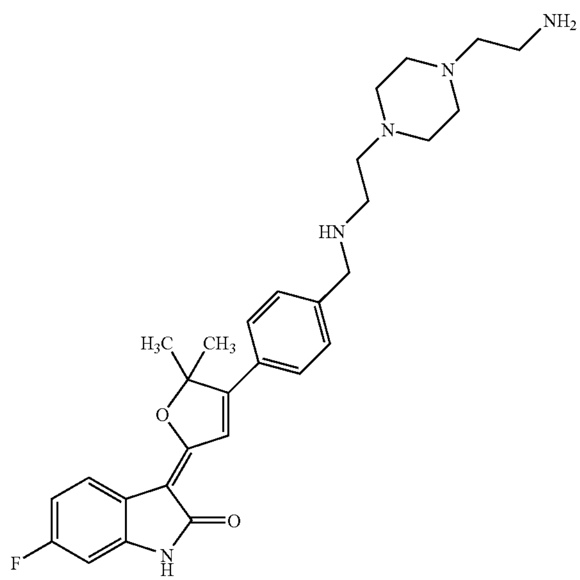 [SMILES: CC1(C)O/C(=C2/C(=O)Nc3cc(F)ccc32)C=C1c1ccc(CNCCN2CCN(CCN)CC2)cc1] | (3E)-3-[4-{4-[({2-[4-(2-aminoethyl)piperazin-1-yl]ethyl}amino)methyl]phenyl}-5,5-dimethylfuran-2(5H)-ylidene]-6-fluoro-1,3-dihydro-2H-indol-2-one | 505.6344 |
| 258 | 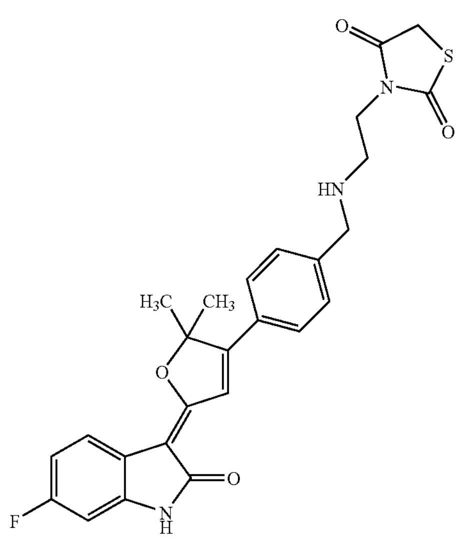 [SMILES: CC1(C)O/C(=C2/C(=O)Nc3cc(F)ccc32)C=C1c1ccc(CNCCN2C(=O)CSC2=O)cc1] | 3-[2-({4-[(5E)-5-(6-fluoro-2-oxo-1,2-dihydro-3H-indol-3-ylidene)-2,2-dimethyl-2,5-dihydrofuran-3-yl]benzyl}amino)ethyl]-1,3-thiazolidine-2,4-dione | 493.5566 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 259 | 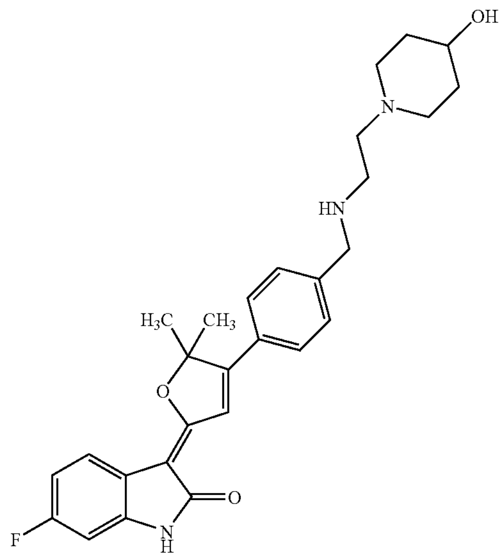 [SMILES: CC1(C)O/C(=C2/C(=O)Nc3cc(F)ccc32)C=C1c1ccc(CNCCN2CCC(O)CC2)cc1] | (3E)-6-fluoro-3-{4-[4-({[2-(4-hydroxypiperidin-1-yl)ethyl]amino}methyl)phenyl]-5,5-dimethylfuran-2(5H)-ylidene}-1,3-dihydro-2H-indol-2-one | 477.5768 |
| 260 | 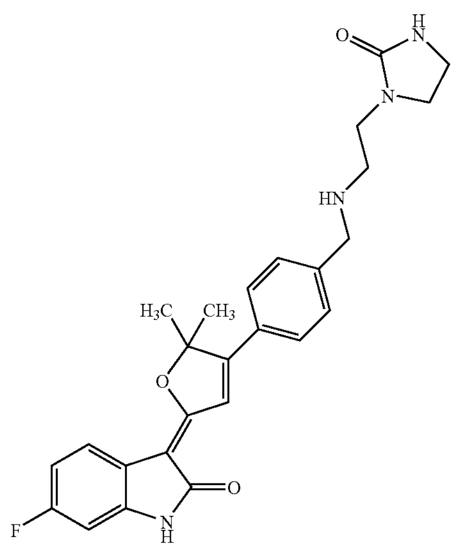 [SMILES: CC1(C)O/C(=C2/C(=O)Nc3cc(F)ccc32)C=C1c1ccc(CNCCN2CCNC2=O)cc1] | (3E)-3-{5,5-dimethyl-4-[4-({[2-(2-oxoimidazolidin-1-yl)ethyl]amino}methyl)phenyl]furan-2(5H)-ylidene}-6-fluoro-1,3-dihydro-2H-indol-2-one | 462.5223 |
| 261 | 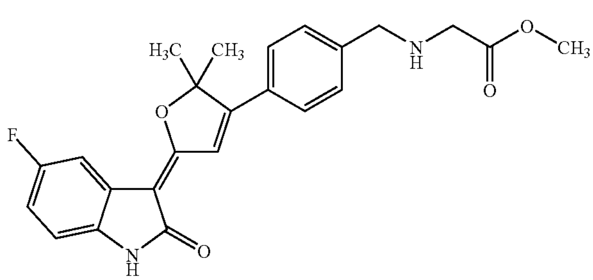 [SMILES: COC(=O)CNCc1ccc(C2=C/C(=C3\C(=O)Nc4ccc(F)cc43)OC2(C)C)cc1] | methyl ({4-[(5E)-5-(5-fluoro-2-oxo-1,2-dihydro-3H-indol-3-ylidene)-2,2-dimethyl-2,5-dihydrofuran-3-yl]benzyl}amino)acetate | 422.4537 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 262 | 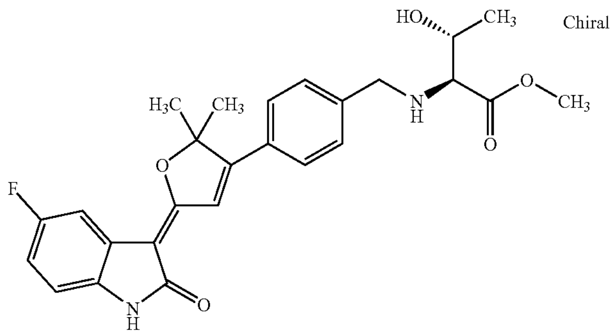 [SMILES: COC(=O)[C@@H](NCc1ccc(C2=C/C(=C3\C(=O)Nc4ccc(F)cc43)OC2(C)C)cc1)[C@@H](C)O] | methyl (2S,3R)-2-({4-[(5E)-5-(5-fluoro-2-oxo-1,2-dihydro-3H-indol-3-ylidene)-2,2-dimethyl-2,5-dihydrofuran-3-yl]benzyl}amino)-3-hydroxybutanoate | 466.5063 |
| 263 | 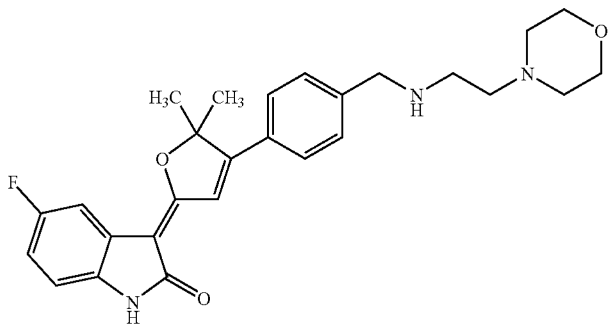 [SMILES: CC1(C)O/C(=C2/C(=O)Nc3ccc(F)cc32)C=C1c1ccc(CNCCN2CCOCC2)cc1] | (3E)-3-[5,5-dimethyl-4-(4-{[(2-morpholin-4-ylethyl)amino]methyl}phenyl)furan-2(5H)-ylidene]-5-fluoro-1,3-dihydro-2H-indol-2-one | 463.55 |
| 264 | 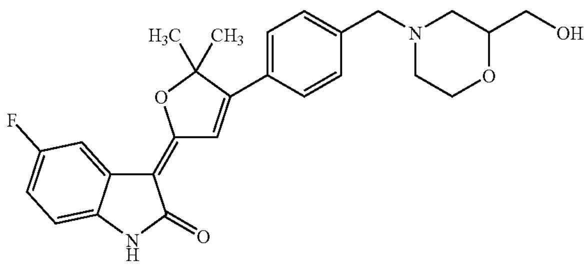 [SMILES: CC1(C)O/C(=C2/C(=O)Nc3ccc(F)cc32)C=C1c1ccc(CN2CCOC(CO)C2)cc1] | (3E)-5-fluoro-3-[4-(4-{[2-(hydroxymethyl)morpholin-4-yl]methyl}phenyl)-5,5-dimethylfuran-2(5H)-ylidene]-1,3-dihydro-2H-indol-2-one | 450.5073 |
| 265 | 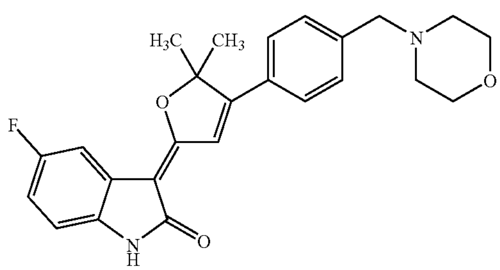 [SMILES: CC1(C)O/C(=C2/C(=O)Nc3ccc(F)cc32)C=C1c1ccc(CN2CCOCC2)cc1] | (3E)-3-{5,5-dimethyl-4-[4-(morpholin-4-ylmethyl)phenyl]furan-2(5H)-ylidene}-5-fluoro-1,3-dihydro-2H-indol-2-one | 420.4815 |
| 266 | 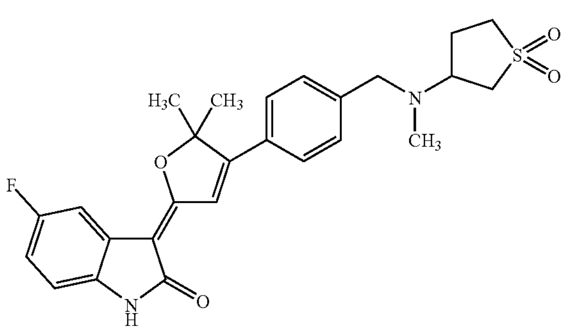 [SMILES: CN(Cc1ccc(C2=C/C(=C3\C(=O)Nc4ccc(F)cc43)OC2(C)C)cc1)C1CCS(=O)(=O)C1] | (3E)-3-[4-(4-{[(1,1-dioxidotetrahydro-3-thienyl)(methyl)amino]methyl}phenyl)-5,5-dimethylfuran-2(5H)-ylidene]-5-fluoro-1,3-dihydro-2H-indol-2-one | 482.5733 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 267 | 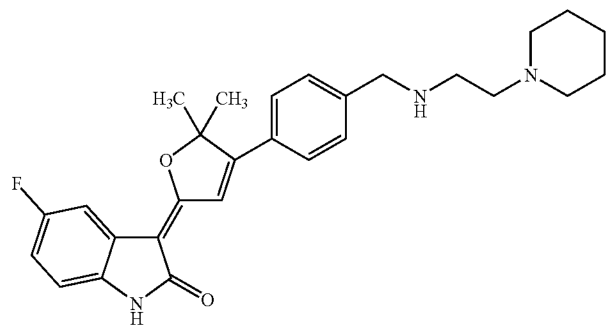 [SMILES: CC1(C)O/C(=C2/C(=O)Nc3ccc(F)cc32)C=C1c1ccc(CNCCN2CCCCC2)cc1] | (3E)-3-[5,5-dimethyl-4-(4-{[(2-piperidin-1-ylethyl)amino]methyl}phenyl)furan-2(5H)-ylidene]-5-fluoro-1,3-dihydro-2H-indol-2-one | 461.5778 |
| 268 | 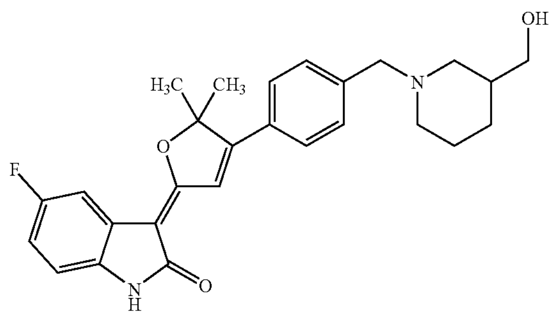 [SMILES: CC1(C)O/C(=C2/C(=O)Nc3ccc(F)cc32)C=C1c1ccc(CN2CCCC(CO)C2)cc1] | (3E)-5-fluoro-3-[4-(4-{[3-(hydroxymethyl)piperidin-1-yl]methyl}phenyl)-5,5-dimethylfuran-2(5H)-ylidene]-1,3-dihydro-2H-indol-2-one | 448.5351 |
| 269 | 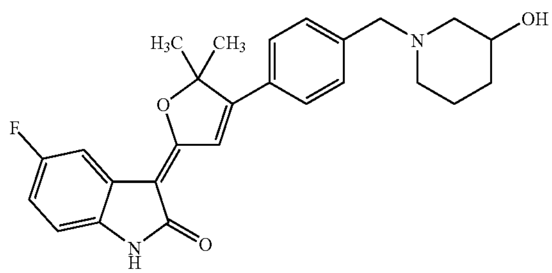 [SMILES: CC1(C)O/C(=C2/C(=O)Nc3ccc(F)cc32)C=C1c1ccc(CN2CCCC(O)C2)cc1] | (3E)-5-fluoro-3-[4-{4-[(3-hydroxypiperidin-1-yl)methyl]phenyl}-5,5-dimethylfuran-2(5H)-ylidene]-1,3-dihydro-2H-indol-2-one | 434.5083 |
| 270 | 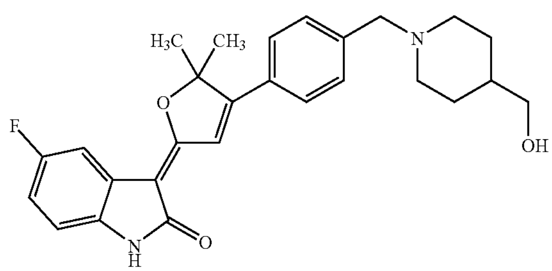 [SMILES: CC1(C)O/C(=C2/C(=O)Nc3ccc(F)cc32)C=C1c1ccc(CN2CCC(CO)CC2)cc1] | (3E)-5-fluoro-3-[4-(4-{[4-(hydroxymethyl)piperidin-1-yl]methyl}phenyl)-5,5-dimethylfuran-2(5H)-ylidene]-1,3-dihydro-2H-indol-2-one | 448.5351 |
| 271 | 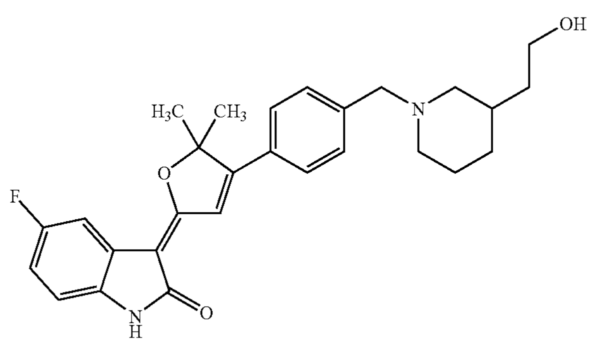 [SMILES: CC1(C)O/C(=C2/C(=O)Nc3ccc(F)cc32)C=C1c1ccc(CN2CCCC(CCO)C2)cc1] | (3E)-5-fluoro-3-[4-(4-{[3-(2-hydroxyethyl)piperidin-1-yl]methyl}phenyl)-5,5-dimethylfuran-2(5H)-ylidene]-1,3-dihydro-2H-indol-2-one | 462.5619 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 272 | Chiral | methyl (2S,4R)-1-{4-[(5E)-5-(5-fluoro-2-oxo-1,2-dihydro-3H-indol-3-ylidene)-2,2-dimethyl-2,5-dihydrofuran-3-yl]benzyl}-4-hydroxypyrrolidine-2-carboxylate | 478.5173 |
| 273 | 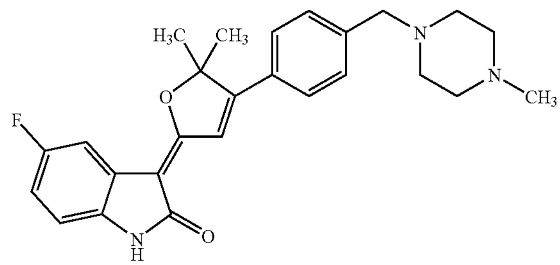 [SMILES: CN1CCN(Cc2ccc(C3=C/C(=C4\C(=O)Nc5ccc(F)cc54)OC3(C)C)cc2)CC1] | (3E)-3-[55-dimethyl-4-{4-[(4-methylpiperazin-1-yl)methyl]phenyl}furan-2(5H)-ylidene]-5-fluoro-1,3-dihydro-2H-indol-2-one | 433.5242 |
| 274 | 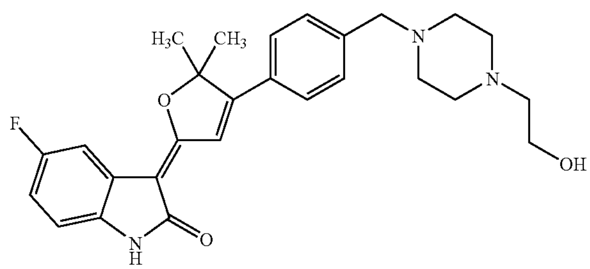 [SMILES: CC1(C)O/C(=C2/C(=O)Nc3ccc(F)cc32)C=C1c1ccc(CN2CCN(CCO)CC2)cc1] | (3E)-5-fluoro-3-[4-(4-{[4-(2-hydroxyethyl)piperazin-1-yl]methyl}phenyl)-5,5-dimethylfuran-2(5H)-ylidene]-1,3-dihydro-2H-indol-2-one | 463.55 |
| 275 | 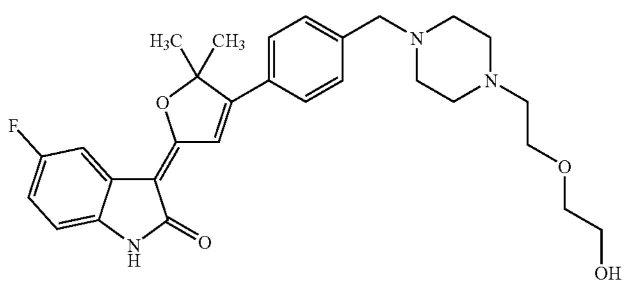 [SMILES: CC1(C)O/C(=C2/C(=O)Nc3ccc(F)cc32)C=C1c1ccc(CN2CCN(CCOCCO)CC2)cc1] | (3E)-5-fluoro-3-{4-[4-({4-[2-(2-hydroxyethoxy)ethyl]piperazin-1-yl}methyl)phenyl]-5,5-dimethylfuran-2(5H)-ylidene}-1,3-dihydro-2H-indol-2-one | 507.6026 |
| 276 | 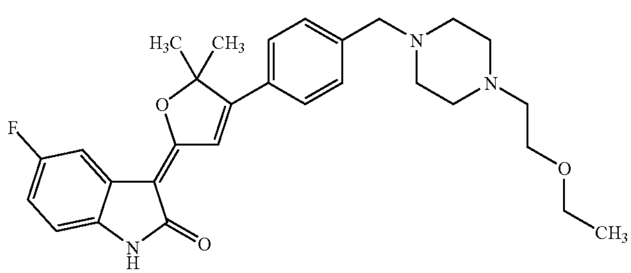 [SMILES: CCOCCN1CCN(Cc2ccc(C3=C/C(=C4\C(=O)Nc5ccc(F)cc54)OC3(C)C)cc2)CC1] | (3E)-3-[4-(4-{[4-(2-ethoxyethyl)piperazin-1-yl]methyl}phenyl)-5,5-dimethylfuran-2(5H)-ylidene]-5-fluoro-1,3-dihydro-2H-indol-2-one | 491.6036 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 277 | 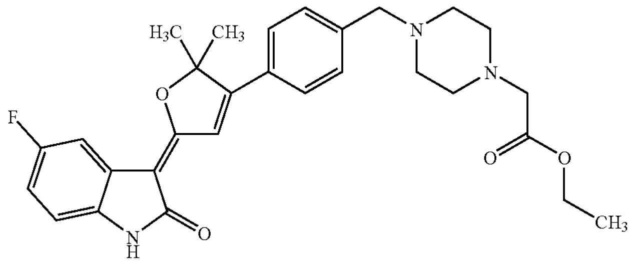 [SMILES: CCOC(=O)CN1CCN(Cc2ccc(C3=C/C(=C4\C(=O)Nc5ccc(F)cc54)OC3(C)C)cc2)CC1] | ethyl (4-{4-[(5E)-5-(5-fluoro-2-oxo-1,2-dihydro-3H-indol-3-ylidene)-2,2-dimethyl-2,5-dihydrofuran-3-yl]benzyl}piperazin-1-yl)acetate | 505.5868 |
| 278 | 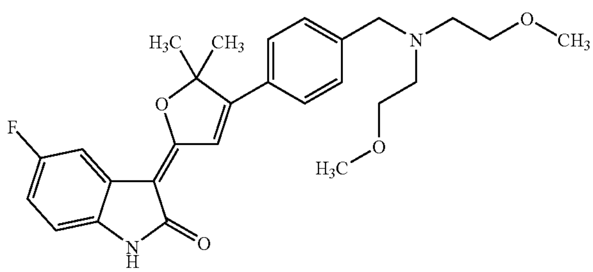 [SMILES: COCCN(CCOC)Cc1ccc(C2=C/C(=C3\C(=O)Nc4ccc(F)cc43)OC2(C)C)cc1] | (3E)-3-[4-(4-{[bis(2-methoxyethyl)amino]methyl}phenyl)-5,5-dimethylfuran-2(5H)-ylidene]-5-fluoro-1,3-dihydro-2H-indol-2-one | 466.5499 |
| 279 | 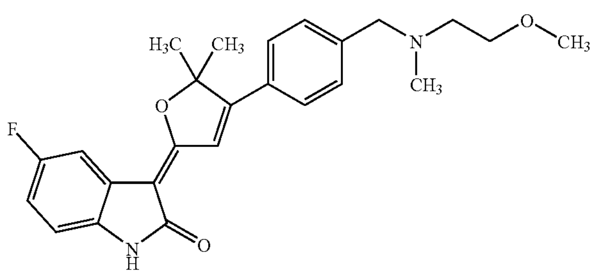 [SMILES: COCCN(C)Cc1ccc(C2=C/C(=C3\C(=O)Nc4ccc(F)cc43)OC2(C)C)cc1] | (3E)-5-fluoro-3-[4-(4-{[(2-methoxyethyl)(methyl)amino]methyl}phenyl)-5,5-dimethylfuran-2(5H)-ylidene]-1,3-dihydro-2H-indol-2-one | 422.4973 |
| 280 | 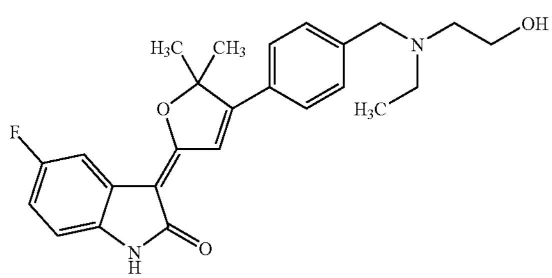 [SMILES: CCN(CCO)Cc1ccc(C2=C/C(=C3\C(=O)Nc4ccc(F)cc43)OC2(C)C)cc1] | (3E)-3-[4-(4-{[ethyl(2-hydroxyethyl)amino]methyl}phenyl)-5,5-dimethylfuran-2(5H)-ylidene]-5-fluoro-1,3-dihydro-2H-indol-2-one | 422.4973 |
| 281 | 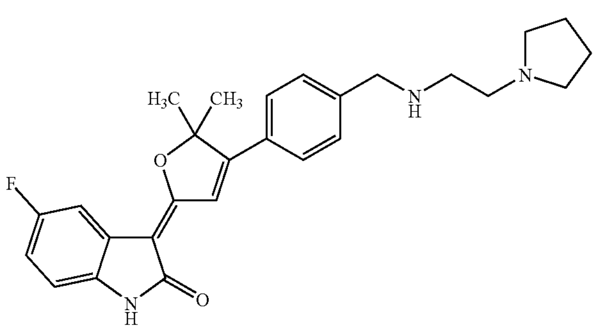 [SMILES: CC1(C)O/C(=C2/C(=O)Nc3ccc(F)cc32)C=C1c1ccc(CNCCN2CCCC2)cc1] | (3E)-3-[5,5-dimethyl-4-(4-{[(2-pyrrolidin-1-ylethyl)amino]methyl}phenyl)furan-2(5H)-ylidene]-5-fluoro-1,3-dihydro-2H-indol-2-one | 447.551 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 282 | 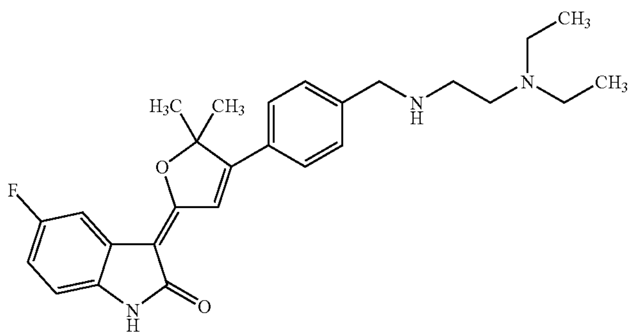 [SMILES: CCN(CC)CCNCc1ccc(C2=C/C(=C3\C(=O)Nc4ccc(F)cc43)OC2(C)C)cc1] | (3E)-3-{4-[4-({[2-(diethylamino)ethyl]amino}methyl)phenyl]-5,5-dimethylfuran-2(5H)-ylidene}-5-fluoro-1,3-dihydro-2H-indol-2-one | 449.5668 |
| 283 | 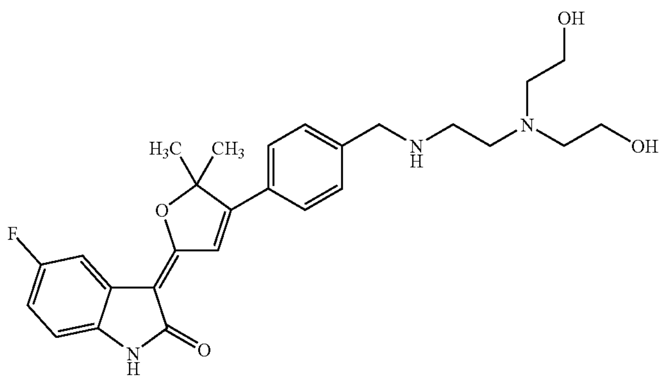 [SMILES: CC1(C)O/C(=C2/C(=O)Nc3ccc(F)cc32)C=C1c1ccc(CNCCN(CCO)CCO)cc1] | (3E)-3-[4-{4-[({2-[bis(2-hydroxyethyl)amino]ethyl}amino)methyl]phenyl}-5,5-dimethylfuran-2(5H)-ylidene]-5-fluoro-1,3-dihydro-2H-indol-2-one | 481.5648 |
| 284 | 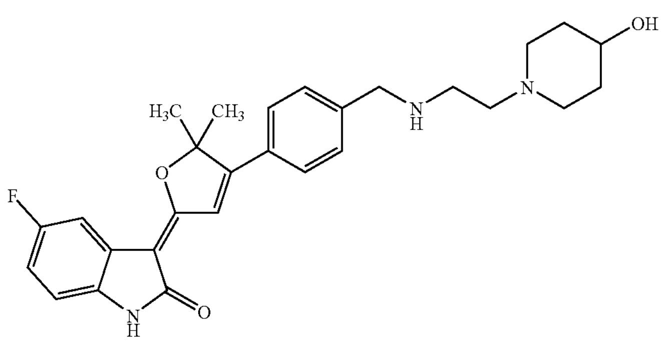 [SMILES: CC1(C)O/C(=C2/C(=O)Nc3ccc(F)cc32)C=C1c1ccc(CNCCN2CCC(O)CC2)cc1] | (3E)-5-fluoro-3-{4-[4-({[2-(4-hydroxypiperidin-1-yl)ethyl]amino}methyl)phenyl]-5,5-dimethylfuran-2(5H)-ylidene}-1,3-dihydro-2H-indol-2-one | 477.5768 |
| 285 | 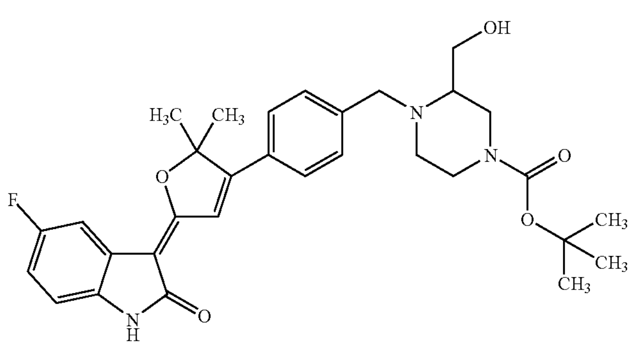 [SMILES: CC(C)(C)OC(=O)N1CCN(Cc2ccc(C3=C/C(=C4\C(=O)Nc5ccc(F)cc54)OC3(C)C)cc2)C(CO)C1] | tert-butyl 4-{4-[(5E)-5-(5-fluoro-2-oxo-1,2-dihydro-3H-indol-3-ylidene)-2,2-dimethyl-2,5-dihydrofuran-3-yl]benzyl}-3-(hydroxymethyl)piperazine-1-carboxylate | 549.6394 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 286 | 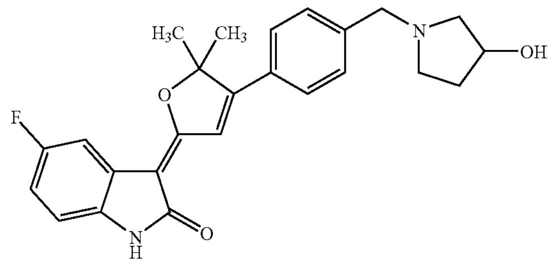 [SMILES: CC1(C)O/C(=C2/C(=O)Nc3ccc(F)cc32)C=C1c1ccc(CN2CCC(O)C2)cc1] | (3E)-5-fluoro-3-[4-{4-[(3-hydroxypyrrolidin-1-yl)methyl]phenyl}-5,5-dimethylfuran-2(5H)-ylidene]-1,3-dihydro-2H-indol-2-one | 420.4815 |
| 287 | Chiral | (3E)-3-[4-(4-{[(2R,3R,4R,5S)-3,4-dihydroxy-2,5-bis(hydroxymethyl)pyrrolidin-1-yl]methyl}phenyl)-5,5-dimethylfuran-2(5H)-ylidene]-5-fluoro-1,3-dihydro-2H-indol-2-one | 496.5321 |
| 288 | 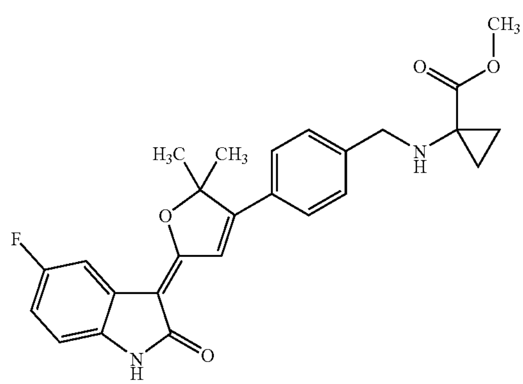 [SMILES: COC(=O)C1(NCc2ccc(C3=C/C(=C4\C(=O)Nc5ccc(F)cc54)OC3(C)C)cc2)CC1] | methyl 1-({4-[(5E)-5-(5-fluoro-2-oxo-1,2-dihydro-3H-indol-3-ylidene)-2,2-dimethyl-2,5-dihydrofuran-3-yl]benzyl}amino)cyclopropanecarboxylate | 448.4915 |
| 289 | 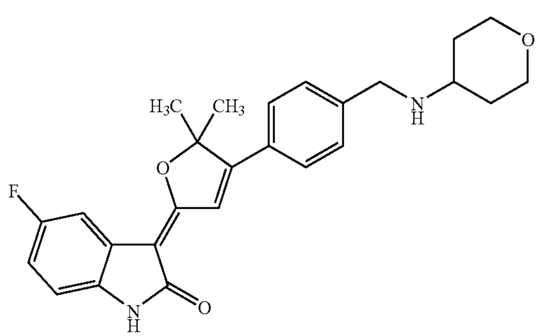 [SMILES: CC1(C)O/C(=C2/C(=O)Nc3ccc(F)cc32)C=C1c1ccc(CNC2CCOCC2)cc1] | (3E)-3-[5,5-dimethyl-4-{4-[(tetrahydro-2H-pyran-4-ylamino)methyl]phenyl}furan-2(5H)-ylidene]-5-fluoro-1,3-dihydro-2H-indol-2-one | 434.5083 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 290 | 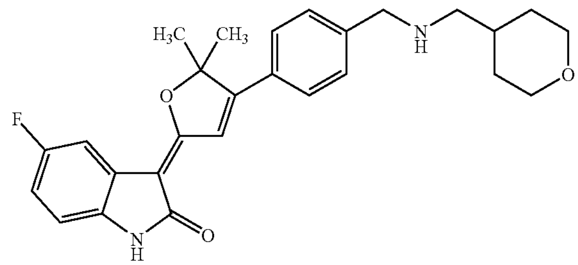 [SMILES: CC1(C)O/C(=C2/C(=O)Nc3ccc(F)cc32)C=C1c1ccc(CNCC2CCOCC2)cc1] | (3E)-3-[5,5-dimethyl-4-(4-{[(tetrahydro-2H-pyran-4-ylmethyl)amino]methyl}phenyl)furan-2(5H)-ylidene]-5-fluoro-1,3-dihydro-2H-indol-2-one | 448.5351 |
| 291 | 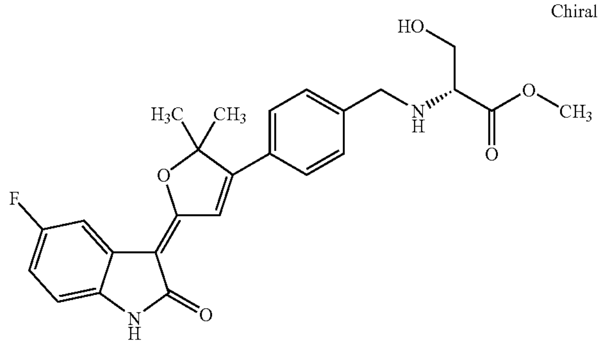 [SMILES: COC(=O)[C@@H](CO)NCc1ccc(C2=C/C(=C3\C(=O)Nc4ccc(F)cc43)OC2(C)C)cc1] | methyl (2R)-2-({4-[(5E)-5-(5-fluoro-2-oxo-1,2-dihydro-3H-indol-3-ylidene)-2,2-dimethyl-2,5-dihydrofuran-3-yl]benzyl}amino)-3-hydroxypropanoate | 452.4795 |
| 292 | 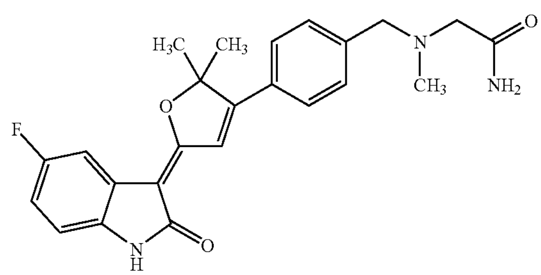 [SMILES: CN(CC(N)=O)Cc1ccc(C2=C/C(=C3\C(=O)Nc4ccc(F)cc43)OC2(C)C)cc1] | 2-[{4-[(5E)-5-(5-fluoro-2-oxo-1,2-dihydro-3H-indol-3-ylidene)-2,2-dimethyl-2,5-dihydrofuran-3-yl]benzyl}(methyl)amino]acetamide | 421.4696 |
| 293 | 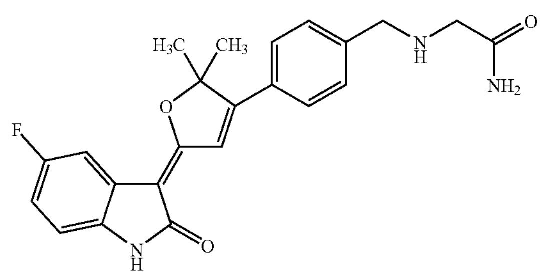 [SMILES: CC1(C)O/C(=C2/C(=O)Nc3ccc(F)cc32)C=C1c1ccc(CNCC(N)=O)cc1] | 2-({4-[(5E)-5-(5-fluoro-2-oxo-1,2-dihydro-3H-indol-3-ylidene)-2,2-dimethyl-2,5-dihydrofuran-3-yl]benzyl}amino)acetamide | 407.4428 |
| 294 | 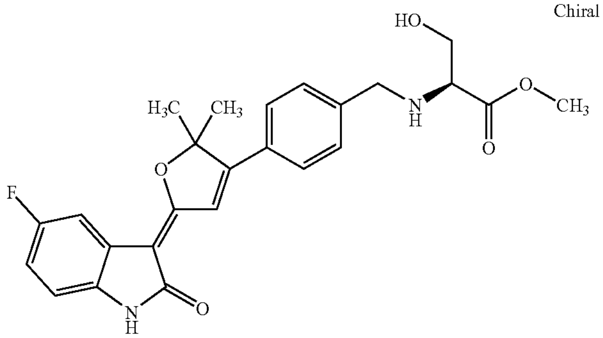 [SMILES: COC(=O)[C@H](CO)NCc1ccc(C2=C/C(=C3\C(=O)Nc4ccc(F)cc43)OC2(C)C)cc1] | methyl (2S)-2-({4-[(5E)-5-(5-fluoro-2-oxo-1,2-dihydro-3H-indol-3-ylidene)-2,2-dimethyl-2,5-dihydrofuran-3-yl]benzyl}amino)-3-hydroxypropanoate | 452.4795 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 295 | 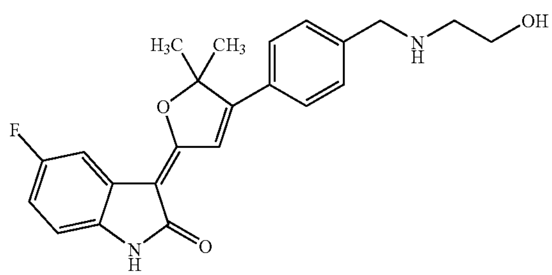 [SMILES: CC1(C)O/C(=C2/C(=O)Nc3ccc(F)cc32)C=C1c1ccc(CNCCO)cc1] | (3E)-5-fluoro-3-[4-(4-{[(2-hydroxyethyl)amino]methyl}phenyl)-5,5-dimethylfuran-2(5H)-ylidene]-1,3-dihydro-2H-indol-2-one | 394.4437 |
| 296 | 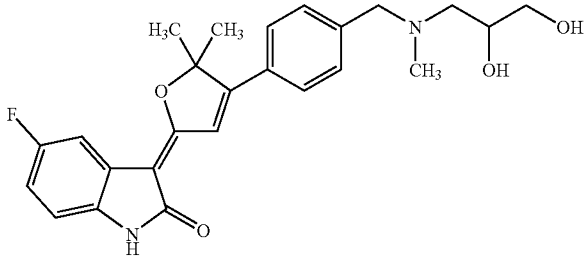 [SMILES: CN(Cc1ccc(C2=C/C(=C3\C(=O)Nc4ccc(F)cc43)OC2(C)C)cc1)CC(O)CO] | (3E)-3-[4-(4-{[(2,3-dihydroxypropyl)(methyl)amino]methyl}phenyl)-5,5-dimethylfuran-2(5H)-ylidene]-5-fluoro-1,3-dihydro-2H-indol-2-one | 438.4963 |
| 297 | Chiral | (3E)-3-{5,5-dimethyl-4-[4-({methyl[(2S,3R,4S,5R)-2,3,4,5,6-pentahydroxyhexyl]amino}methyl)phenyl]furan-2(5H)-ylidene}-5-fluoro-1,3-dihydro-2H-indol-2-one | 528.5737 |
| 298 | Chiral | (3E)-3-[4-{4-[({[(2R,3S,4S,5R)-3,4-dihydroxy-5-(hydroxymethyl)tetrahydrofuran-2-yl]methyl}amino)methyl]phenyl}-5,5-dimethylfuran-2(5H)-ylidene]-5-fluoro-1,3-dihydro-2H-indol-2-one | 496.5321 |
| 299 | 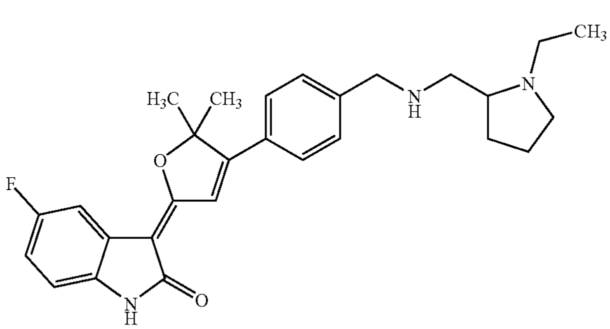 [SMILES: CCN1CCCC1CNCc1ccc(C2=C/C(=C3\C(=O)Nc4ccc(F)cc43)OC2(C)C)cc1] | (3E)-3-{4-[4-({[(1-ethylpyrrolidin-2-yl)methyl]amino}methyl)phenyl]-5,5-dimethylfuran-2(5H)-ylidene}-5-fluoro-1,3-dihydro-2H-indol-2-one | 461.5778 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 300 | 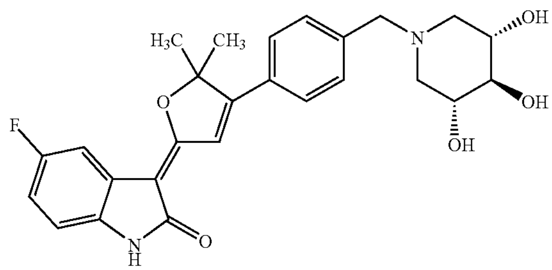 [SMILES: CC1(C)O/C(=C2/C(=O)Nc3ccc(F)cc32)C=C1c1ccc(CN2C[C@@H](O)[C@H](O)[C@@H](O)C2)cc1] | rel-(3E)-3-[5,5-dimethyl-4-(4-{[(3R,4r,5S)-3,4,5-trihydroxypiperidin-1-yl]methyl}phenyl)furan-2(5H)-ylidene]-5-fluoro-1,3-dihydro-2H-indol-2-one | 466.5063 |
| 301 | 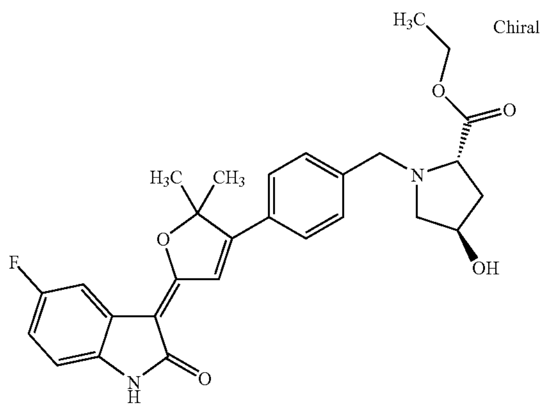 [SMILES: CCOC(=O)[C@@H]1C[C@@H](O)CN1Cc1ccc(C2=C/C(=C3\C(=O)Nc4ccc(F)cc43)OC2(C)C)cc1] | ethyl (2S,4R)-1-{4-[(5E)-5-(5-fluoro-2-oxo-1,2-dihydro-3H-indol-3-ylidene)-2,2-dimethyl-2,5-dihydrofuran-3-yl]benzyl}-4-hydroxypyrrolidine-2-carboxylate | 492.5441 |
| 302 | 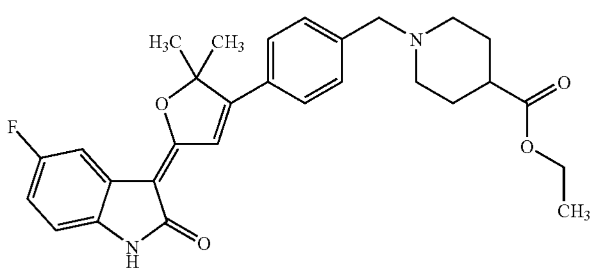 [SMILES: CCOC(=O)C1CCN(Cc2ccc(C3=C/C(=C4\C(=O)Nc5ccc(F)cc54)OC3(C)C)cc2)CC1] | ethyl 1-{4-[(5E)-5-(5-fluoro-2-oxo-1,2-dihydro-3H-indol-3-ylidene)-2,2-dimethyl-2,5-dihydrofuran-3-yl]benzyl}piperidine-4-carboxylate | 490.5719 |
| 303 | 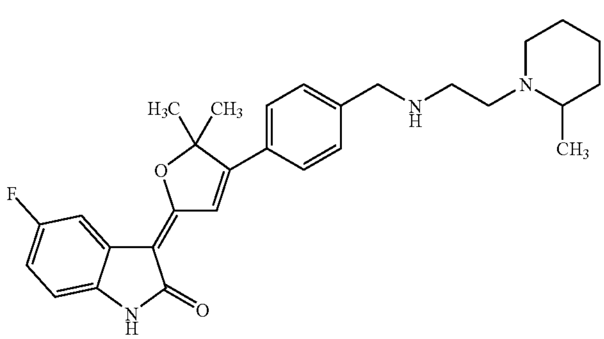 [SMILES: CC1CCCCN1CCNCc1ccc(C2=C/C(=C3\C(=O)Nc4ccc(F)cc43)OC2(C)C)cc1] | (3E)-3-{5,5-dimethyl-4-[4-({[2-(2-methylpiperidin-1-yl)ethyl]amino}methyl)phenyl]furan-2(5H)-ylidene}-5-fluoro-1,3-dihydro-2H-indol-2-one | 475.6046 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 304 | 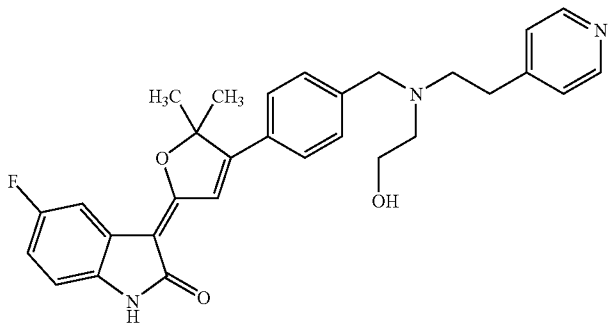 [SMILES: CC1(C)O/C(=C2/C(=O)Nc3ccc(F)cc32)C=C1c1ccc(CN(CCO)CCc2ccncc2)cc1] | (3E)-5-fluoro-3-[4-(4-{[(2-hydroxyethyl)(2-pyridin-4-ylethyl)amino]methyl}phenyl)-5,5-dimethylfuran-2(5H)-ylidene]-1,3-dihydro-2H-indol-2-one | 499.583 |
| 305 | 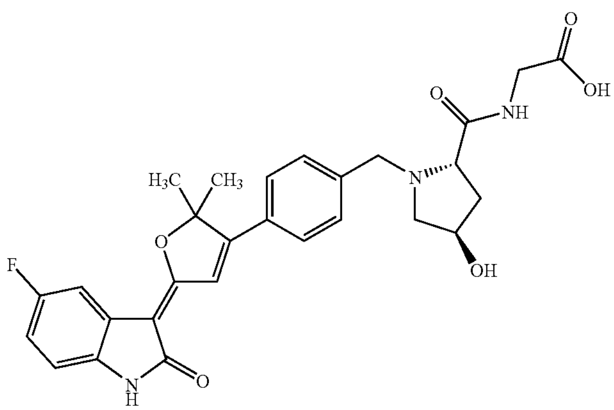 | (({[(2S,4R)-1-{4-[(5E)-5-(5-fluoro-2-oxo-1,2-dihydro-3H-indol-3-ylidene)-2,2-dimethyl-2,5-dihydrofuran-3-yl]benzyl}-4-hydroxypyrrolidin-2-yl]carbonyl}amino)acetic acid | 521.5422 |
| 306 | 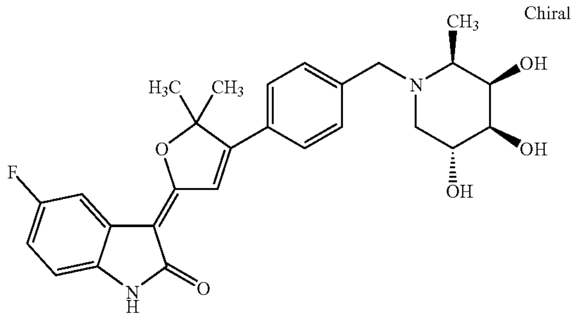 [SMILES: C[C@H]1[C@@H](O)[C@@H](O)[C@H](O)CN1Cc1ccc(C2=C/C(=C3\C(=O)Nc4ccc(F)cc43)OC2(C)C)cc1] | (3E)-3-[5,5-dimethyl-4-(4-{[(2S,3R,4S,5R)-3,4,5-trihydroxy-2-methylpiperidin-1-yl]methyl}phenyl)furan-2(5H)-ylidene]-5-fluoro-1,3-dihydro-2H-indol-2-one | 480.5331 |
| 307 | 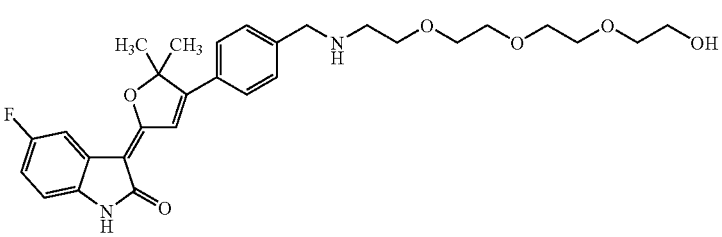 [SMILES: CC1(C)O/C(=C2/C(=O)Nc3ccc(F)cc32)C=C1c1ccc(CNCCOCCOCCOCCO)cc1] | (3E)-5-fluoro-3-{4-[4-(13-hydroxy-5,8,11-trioxa-2-azatridec-1-yl)phenyl]-5,5-dimethylfuran-2(5H)-ylidene}-1,3-dihydro-2H-indol-2-one | 526.6015 |
| 308 | 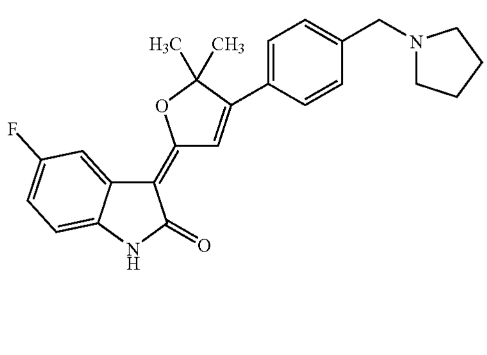 [SMILES: CC1(C)O/C(=C2/C(=O)Nc3ccc(F)cc32)C=C1c1ccc(CN2CCCC2)cc1] | (3E)-3-{5,5-dimethyl-4-[4-(pyrrolidin-1-ylmethyl)phenyl]furan-2(5H)-ylidene}-5-fluoro-1,3-dihydro-2H-indol-2-one | 404.4825 |

TABLE 6-continued

[5,5-dimethyl-5H-furan-(2E)-ylidene]-1,3-dihydro-indol-2-one benzylmethyl amine derivatives

| Example # | Chemical Structure | Chemical Name | FW |
|---|---|---|---|
| 309 | 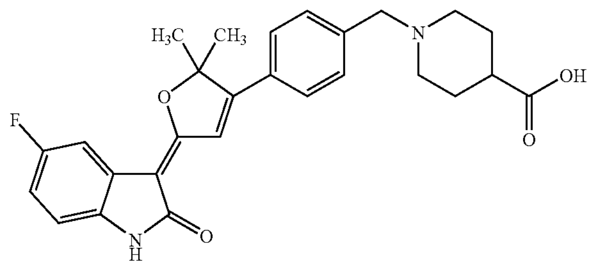 [SMILES: CC1(C)O/C(=C2/C(=O)Nc3ccc(F)cc32)C=C1c1ccc(CN2CCC(C(=O)O)CC2)cc1] | 1-{4-[(5E)-5-(5-fluoro-2-oxo-1,2-dihydro-3H-indol-3-ylidene)-2,2-dimethyl-2,5-dihydrofuran-3-yl]benzyl}piperidine-4-carboxylic acid | 462.5183 |
| 310 | 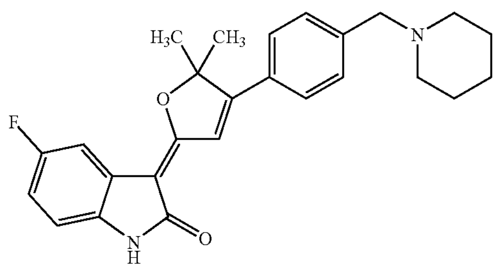 [SMILES: CC1(C)O/C(=C2/C(=O)Nc3ccc(F)cc32)C=C1c1ccc(CN2CCCCC2)cc1] | (3E)-3-{5,5-dimethyl-4-[4-(piperidin-1-ylmethyl)phenyl]furan-2(5H)-ylidene}-5-fluoro-1,3-dihydro-2H-indol-2-one | 418.5093 |

TABLE 7

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 311 | 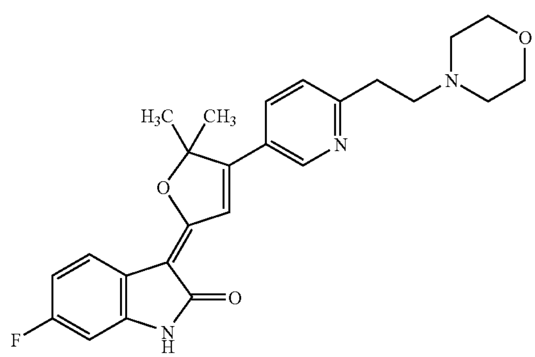 [SMILES: CC1(C)O/C(=C2/C(=O)Nc3cc(F)ccc32)C=C1c1ccc(CCN2CCOCC2)nc1] | (3E)-3-{5,5-dimethyl-4-[6-(2-morpholin-4-ylethyl)pyridin-3-yl]furan-2(5H)-ylidene}-6-fluoro-1,3-dihydro-2H-indol-2-one | 435.4964 |
| 312 | 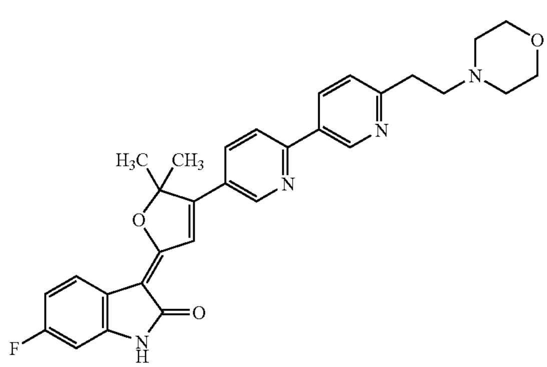 [SMILES: CC1(C)O/C(=C2/C(=O)Nc3cc(F)ccc32)C=C1c1ccc(-c2ccc(CCN3CCOCC3)nc2)nc1] | (3E)-3-{5,5-dimethyl-4-[6-(2-morpholin-4-ylethyl)-2,3'-bipyridin-5-yl]furan-2(5H)-ylidene}-6-fluoro-1,3-dihydro-2H-indol-2-one | 512.5821 |

TABLE 7-continued
[5,5-dimethyl-5H-furan-(2E)-ylidene]-1,3-dihydro-indol-2-one pyridin-3-yl derivatives
| Example # | Chemical Structure | Chemical Name | FW |
|---|---|---|---|
| 313 | 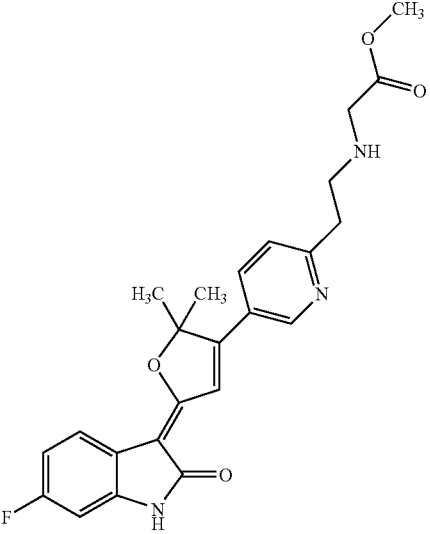 [SMILES: COC(=O)CNCCc1ccc(C2=C/C(=C3\C(=O)Nc4cc(F)ccc43)OC2(C)C)cn1] | methyl [(2-{5-[(5E)-5-(6-fluoro-2-oxo-1,2-dihydro-3H-indol-3-ylidene)-2,2-dimethyl-2,5-dihydrofuran-3-yl]pyridin-2-yl}ethyl)amino]acetate | 437.4686 |
| 314 | 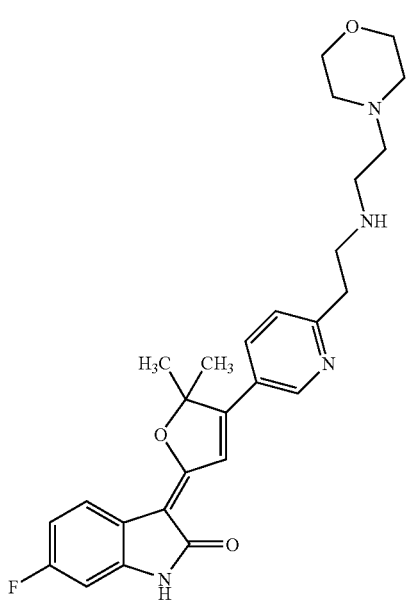 [SMILES: CC1(C)O/C(=C2/C(=O)Nc3cc(F)ccc32)C=C1c1ccc(CCNCCN2CCOCC2)nc1] | (3E)-3-[5,5-dimethyl-4-(6-{2-[(2-morpholin-4-ylethyl)amino]ethyl}pyridin-3-yl)furan-2(5H)-ylidene]-6-fluoro-1,3-dihydro-2H-indol-2-one | 478.5649 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 315 | 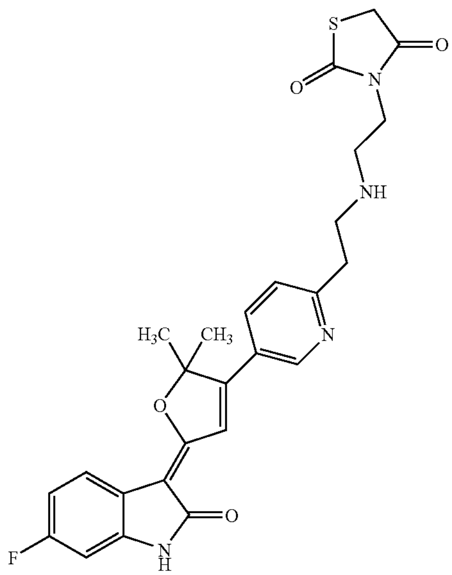 [SMILES: CC1(C)O/C(=C2/C(=O)Nc3cc(F)ccc32)C=C1c1ccc(CCNCCN2C(=O)CSC2=O)nc1] | 3-{2-[(2-{5-[(5E)-5-(6-fluoro-2-oxo-1,2-dihydro-3H-indol-3-ylidene)-2,2-dimethyl-2,5-dihydrofuran-3-yl]pyridin-2-yl}ethyl)amino]ethyl}-1,3-thiazolidine-2,4-dione | 508.5715 |
| 316 | 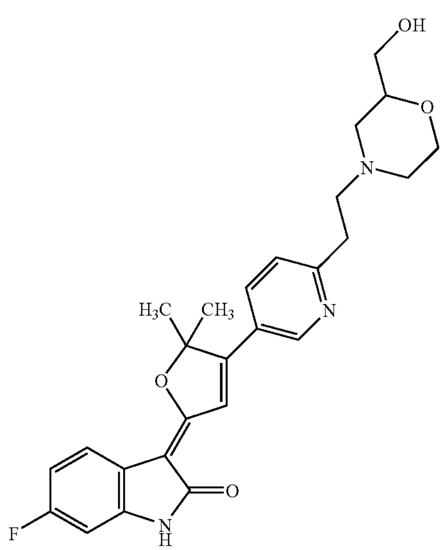 [SMILES: CC1(C)O/C(=C2/C(=O)Nc3cc(F)ccc32)C=C1c1ccc(CCN2CCOC(CO)C2)nc1] | (3E)-6-fluoro-3-[4-(6-{2-[2-(hydroxymethyl)morpholin-4-yl]ethyl}pyridin-3-yl)-5,5-dimethylfuran-2(5H)-ylidene]-1,3-dihydro-2H-indol-2-one | 465.5222 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 317 | 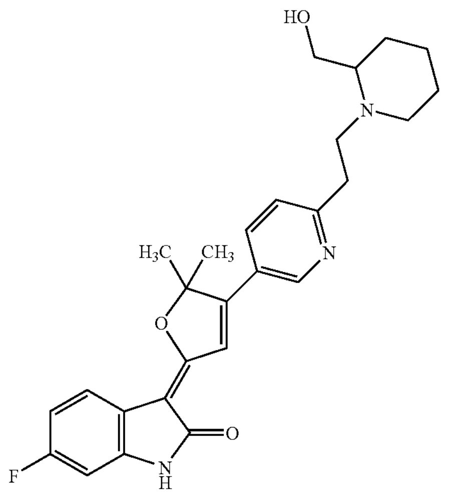 [SMILES: CC1(C)O/C(=C2/C(=O)Nc3cc(F)ccc32)C=C1c1ccc(CCN2CCCCC2CO)nc1] | (3E)-6-fluoro-3-[4-(6-{2-[2-(hydroxymethyl)piperidin-1-yl]ethyl}pyridin-3-yl)-5,5-dimethylfuran-2(5H)-ylidene]-1,3-dihydro-2H-indol-2-one | 463.55 |
| 318 | 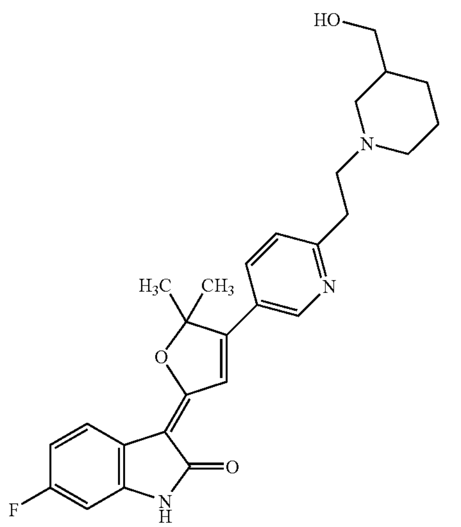 [SMILES: CC1(C)O/C(=C2/C(=O)Nc3cc(F)ccc32)C=C1c1ccc(CCN2CCCC(CO)C2)nc1] | (3E)-6-fluoro-3-[4-(6-{2-[3-(hydroxymethyl)piperidin-1-yl]ethyl}pyridin-3-yl)-5,5-dimethylfuran-2(5H)-ylidene]-1,3-dihydro-2H-indol-2-one | 463.55 |
| 319 | 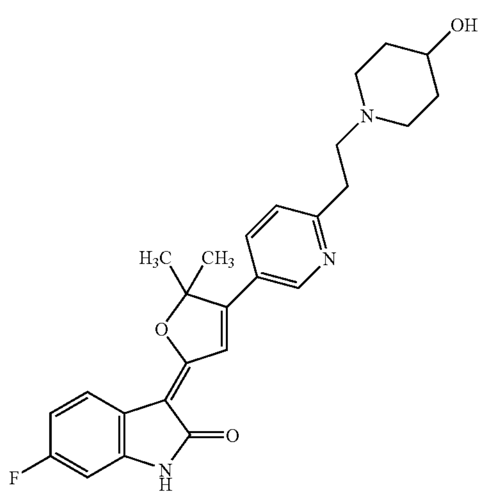 [SMILES: CC1(C)O/C(=C2/C(=O)Nc3cc(F)ccc32)C=C1c1ccc(CCN2CCC(O)CC2)nc1] | (3E)-6-fluoro-3-[4-{6-[2-(4-hydroxypiperidin-1-yl)ethyl]pyridin-3-yl}-5,5-dimethylfuran-2(5H)-ylidene]-1,3-dihydro-2H-indol-2-one | 449.5232 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 320 | 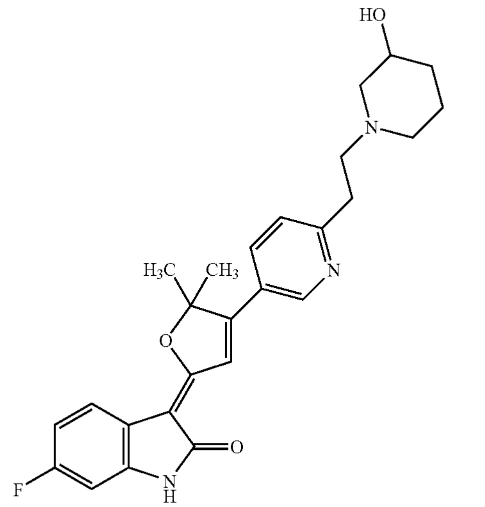 [SMILES: CC1(C)O/C(=C2/C(=O)Nc3cc(F)ccc32)C=C1c1ccc(CCN2CCCC(O)C2)nc1] | (3E)-6-fluoro-3-[4-{6-[2-(3-hydroxypiperidin-1-yl)ethyl]pyridin-3-yl}-5,5-dimethylfuran-2(5H)-ylidene]-1,3-dihydro-2H-indol-2-one | 449.5232 |
| 321 | 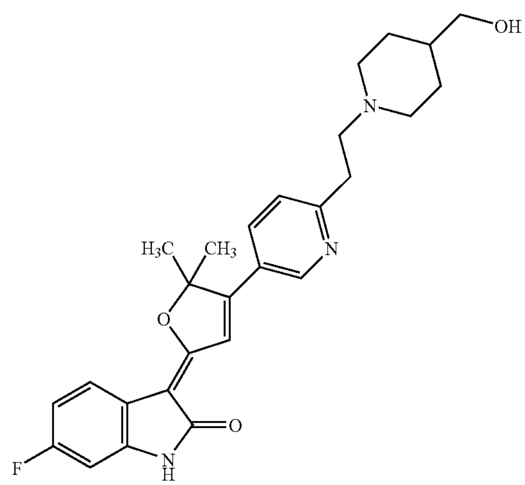 [SMILES: CC1(C)O/C(=C2/C(=O)Nc3cc(F)ccc32)C=C1c1ccc(CCN2CCC(CO)CC2)nc1] | (3E)-6-fluoro-3-[4-(6-{2-[4-(hydroxymethyl)piperidin-1-yl]ethyl}pyridin-3-yl)-5,5-dimethylfuran-2(5H)-ylidene]-1,3-dihydro-2H-indol-2-one | 463.55 |
| 322 | 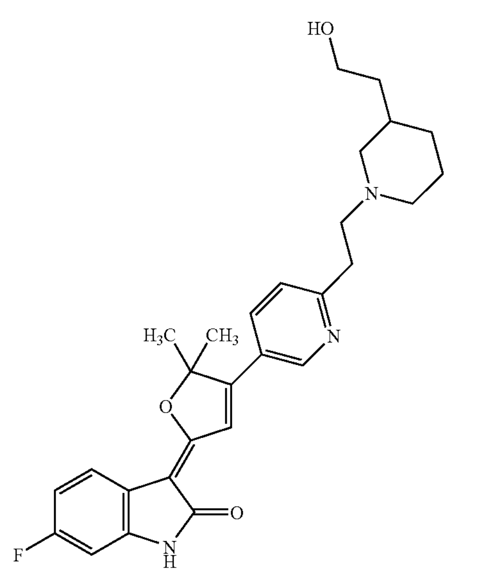 [SMILES: CC1(C)O/C(=C2/C(=O)Nc3cc(F)ccc32)C=C1c1ccc(CCN2CCCC(CCO)C2)nc1] | (3E)-6-fluoro-3-[4-(6-{2-[3-(2-hydroxyethyl)piperidin-1-yl]ethyl}pyridin-3-yl)-5,5-dimethylfuran-2(5H)-ylidene]-1,3-dihydro-2H-indol-2-one | 477.5768 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 323 | 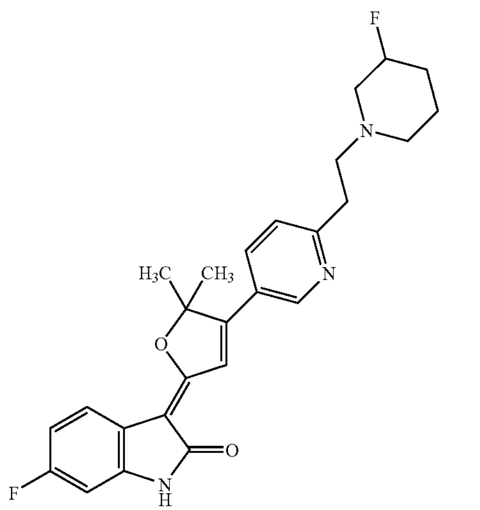 [SMILES: CC1(C)O/C(=C2/C(=O)Nc3cc(F)ccc32)C=C1c1ccc(CCN2CCCC(F)C2)nc1] | (3E)-6-fluoro-3-[4-{6-[2-(3-fluoropiperidin-1-yl)ethyl]pyridin-3-yl}-5,5-dimethylfuran-2(5H)-ylidene]-1,3-dihydro-2H-indol-2-one | 451.5143 |
| 324 | 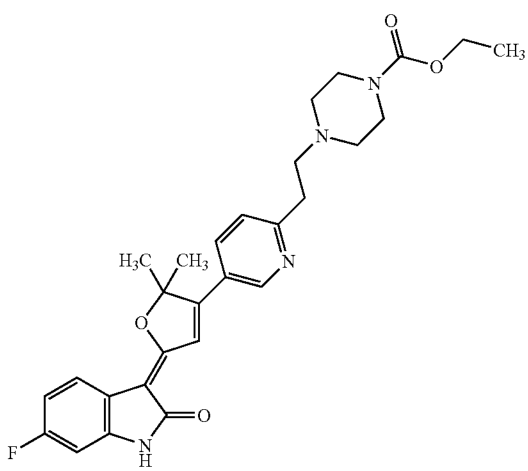 [SMILES: CCOC(=O)N1CCN(CCc2ccc(C3=C/C(=C4\C(=O)Nc5cc(F)ccc54)OC3(C)C)cn2)CC1] | ethyl 4-(2-{5-[(5E)-5-(6-fluoro-2-oxo-1,2-dihydro-3H-indol-3-ylidene)-2,2-dimethyl-2,5-dihydrofuran-3-yl]pyridin-2-yl}ethyl)piperazine-1-carboxylate | 506.5749 |
| 325 | 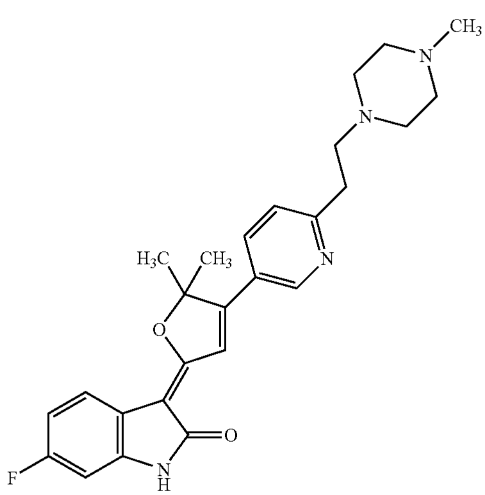 [SMILES: CN1CCN(CCc2ccc(C3=C/C(=C4\C(=O)Nc5cc(F)ccc54)OC3(C)C)cn2)CC1] | (3E)-3-[5,5-dimethyl-4-{6-[2-(4-methylpiperazin-1-yl)ethyl]pyridin-3-yl}furan-2(5H)-ylidene]-6-fluoro-1,3-dihydro-2H-indol-2-one | 448.5391 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 326 | 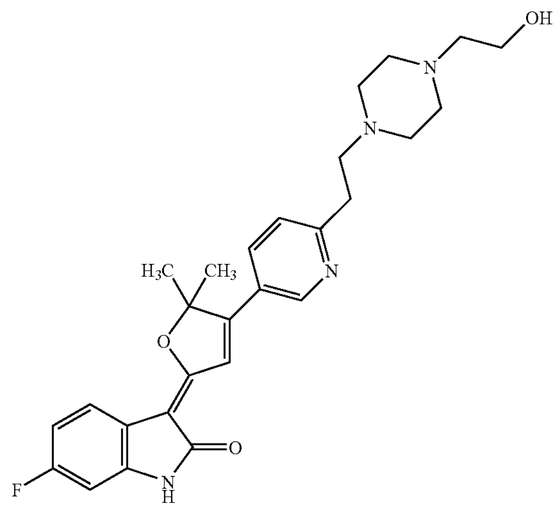 [SMILES: CC1(C)O/C(=C2/C(=O)Nc3cc(F)ccc32)C=C1c1ccc(CCN2CCN(CCO)CC2)nc1] | (3E)-6-fluoro-3-[4-(6-{2-[4-(2-hydroxyethyl)piperazin-1-yl]ethyl}pyridin-3-yl)-5,5-dimethylfuran-2(5H)-ylidene]-1,3-dihydro-2H-indol-2-one | 478.5649 |
| 327 | 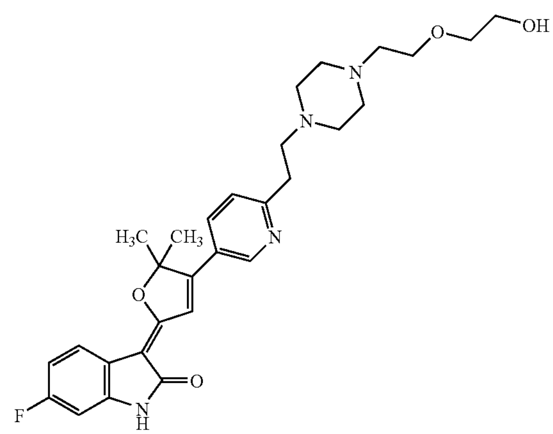 [SMILES: CC1(C)O/C(=C2/C(=O)Nc3cc(F)ccc32)C=C1c1ccc(CCN2CCN(CCOCCO)CC2)nc1] | (3E)-6-fluoro-3-{4-[6-(2-{4-[2-(2-hydroxyethoxy)ethyl]piperazin-1-yl}ethyl)pyridin-3-yl]-5,5-dimethylfuran-2(5H)-ylidene}-1,3-dihydro-2H-indol-2-one | 522.6175 |
| 328 | 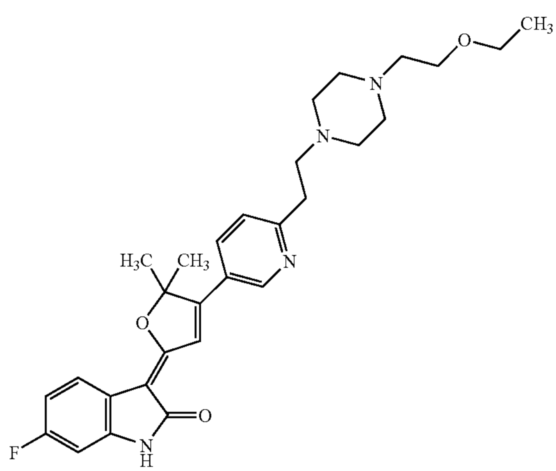 [SMILES: CCOCCN1CCN(CCc2ccc(C3=C/C(=C4\C(=O)Nc5cc(F)ccc54)OC3(C)C)cn2)CC1] | (3E)-3-[4-(6-{2-[4-(2-ethoxyethyl)piperazin-1-yl]ethyl}pyridin-3-yl)-5,5-dimethylfuran-2(5H)-ylidene]-6-fluoro-1,3-dihydro-2H-indol-2-one | 506.6185 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 329 | 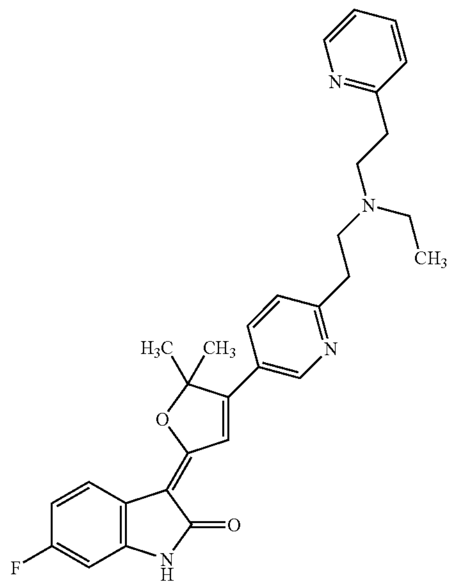 [SMILES: CCN(CCc1ccccn1)CCc1ccc(C2=C/C(=C3\C(=O)Nc4cc(F)ccc43)OC2(C)C)cn1] | (3E)-3-[4-(6-{2-[ethyl(2-pyridin-2-ylethyl)amino]ethyl}pyridin-3-yl)-5,5-dimethylfuran-2(5H)-ylidene]-6-fluoro-1,3-dihydro-2H-indol-2-one | 498.5989 |
| 330 | 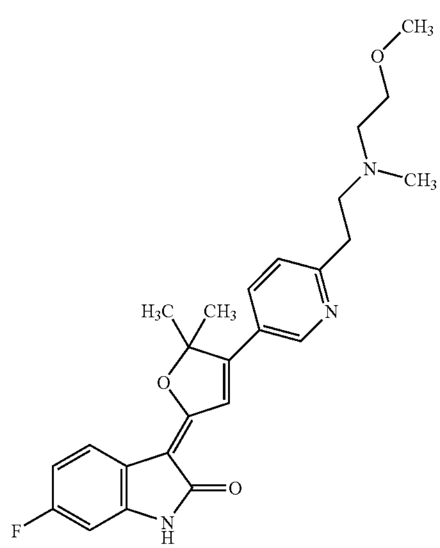 [SMILES: COCCN(C)CCc1ccc(C2=C/C(=C3\C(=O)Nc4cc(F)ccc43)OC2(C)C)cn1] | (3E)-6-fluoro-3-[4-(6-{2-[(2-methoxyethyl)(methyl)amino]ethyl}pyridin-3-yl)-5,5-dimethylfuran-2(5H)-ylidene]-1,3-dihydro-2H-indol-2-one | 437.5122 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 331 | 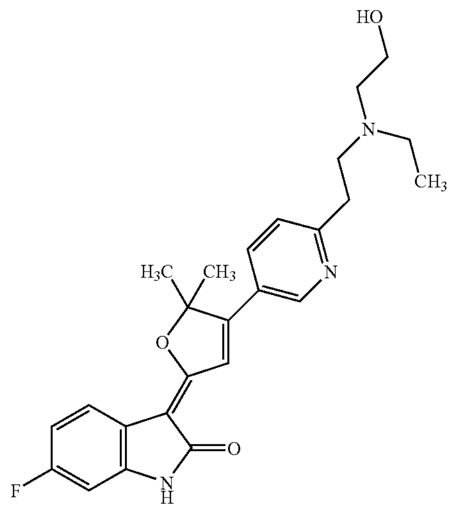 [SMILES: CCN(CCO)CCc1ccc(C2=C/C(=C3\C(=O)Nc4cc(F)ccc43)OC2(C)C)cn1] | (3E)-3-[4-(6-{2-[ethyl(2-hydroxyethyl)amino]ethyl}pyridin-3-yl)-5,5-dimethylfuran-2(5H)-ylidene]-6-fluoro-1,3-dihydro-2H-indol-2-one | 437.5122 |
| 332 | 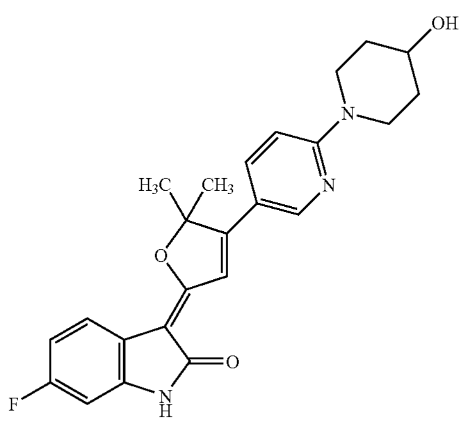 [SMILES: CC1(C)O/C(=C2/C(=O)Nc3cc(F)ccc32)C=C1c1ccc(N2CCC(O)CC2)nc1] | (3E)-6-fluoro-3-{4-[6-(4-hydroxypiperidin-1-yl)pyridin-3-yl]-5,5-dimethylfuran-2(5H)-ylidene}-1,3-dihydro-2H-indol-2-one | 421.4696 |
| 333 | 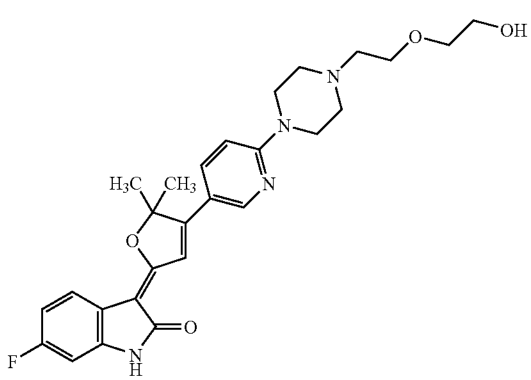 [SMILES: CC1(C)O/C(=C2/C(=O)Nc3cc(F)ccc32)C=C1c1ccc(N2CCN(CCOCCO)CC2)nc1] | (3E)-6-fluoro-3-[4-(6-{4-[2-(2-hydroxyethoxy)ethyl]piperazin-1-yl}pyridin-3-yl)-5,5-dimethylfuran-2(5H)-ylidene]-1,3-dihydro-2H-indol-2-one | 494.5639 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 334 | 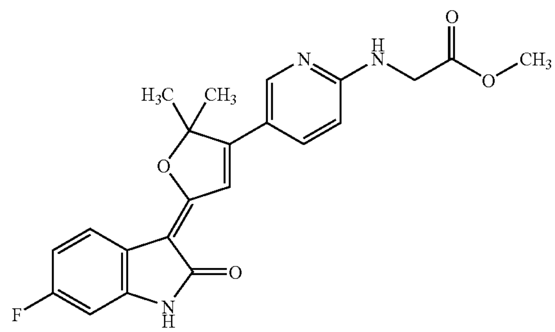 [SMILES: COC(=O)CNc1ccc(C2=C/C(=C3\C(=O)Nc4cc(F)ccc43)OC2(C)C)cn1] | methyl ({5-[(5E)-5-(6-fluoro-2-oxo-1,2-dihydro-3H-indol-3-ylidene)-2,2-dimethyl-2,5-dihydrofuran-3-yl]pyridin-2-yl}amino)acetate | 409.415 |
| 335 | Chiral | methyl (2S,3R)-2-({5-[(5E)-5-(6-fluoro-2-oxo-1,2-dihydro-3H-indol-3-ylidene)-2,2-dimethyl-2,5-dihydrofuran-3-yl]pyridin-2-yl}amino)-3-hydroxybutanoate | 453.4676 |
| 336 | Chiral | ethyl (2S)-2-({5-[(5E)-5-(6-fluoro-2-oxo-1,2-dihydro-3H-indol-3-ylidene)-2,2-dimethyl-2,5-dihydrofuran-3-yl]pyridin-2-yl}amino)-4-(methylthio)butanoate | 497.5882 |
| 337 | Chiral | (2S)-2-({5-[(5E)-5-(6-fluoro-2-oxo-1,2-dihydro-3H-indol-3-ylidene)-2,2-dimethyl-2,5-dihydrofuran-3-yl]pyridin-2-yl}amino)-3-(1,3-thiazol-4-yl)propanoic acid | 492.5289 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 338 | 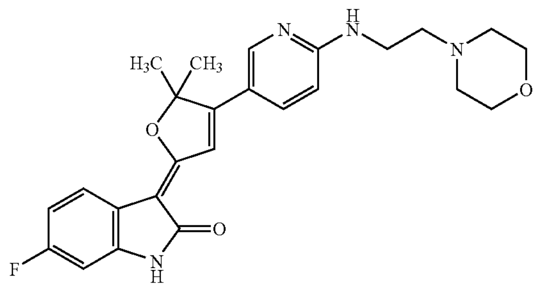 [SMILES: CC1(C)O/C(=C2/C(=O)Nc3cc(F)ccc32)C=C1c1ccc(NCCN2CCOCC2)nc1] | (3E)-3-[5,5-dimethyl-4-{6-[(2-morpholin-4-ylethyl)amino]pyridin-3-yl}furan-2(5H)-ylidene]-6-fluoro-1,3-dihydro-2H-indol-2-one | 450.5113 |
| 339 | 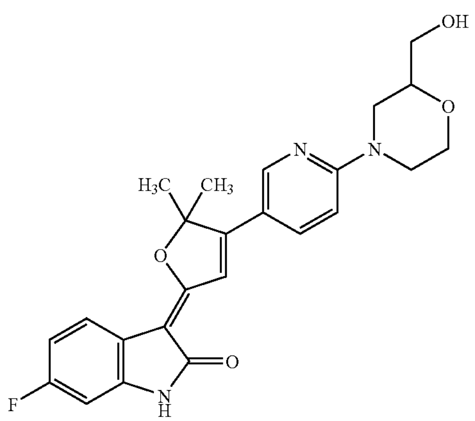 [SMILES: CC1(C)O/C(=C2/C(=O)Nc3cc(F)ccc32)C=C1c1ccc(N2CCOC(CO)C2)nc1] | (3E)-6-fluoro-3-[4-{6-[2-(hydroxymethyl)morpholin-4-yl]pyridin-3-yl}-5,5-dimethylfuran-2(5H)-ylidene]-1,3-dihydro-2H-indol-2-one | 437.4686 |
| 340 | 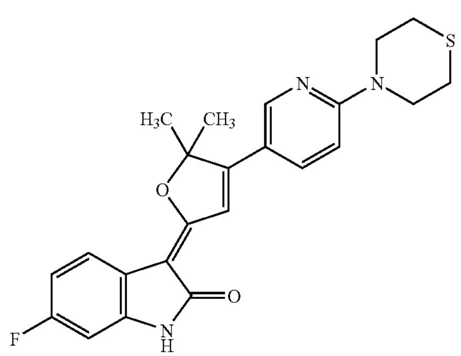 [SMILES: CC1(C)O/C(=C2/C(=O)Nc3cc(F)ccc32)C=C1c1ccc(N2CCSCC2)nc1] | (3E)-3-[5,5-dimethyl-4-(6-thiomorpholin-4-ylpyridin-3-yl)furan-2(5H)-ylidene]-6-fluoro-1,3-dihydro-2H-indol-2-one | 423.5098 |
| 341 | 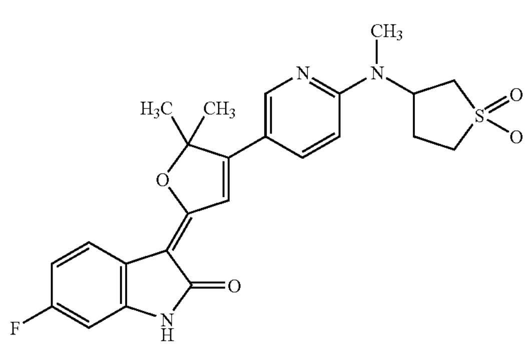 | (3E)-3-[4-{6-[(1,1-dioxidotetrahydro-3-thienyl)(methyl)amino]pyridin-3-yl}-5,5-dimethylfuran-2(5H)-ylidene]-6-fluoro-1,3-dihydro-2H-indol-2-one | 469.5346 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 342 | 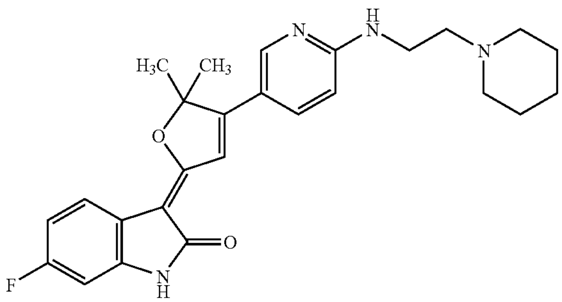 [SMILES: CC1(C)O/C(=C2/C(=O)Nc3cc(F)ccc32)C=C1c1ccc(NCCN2CCCCC2)nc1] | (3E)-3-[5,5-dimethyl-4-{6-[(2-piperidin-1-ylethyl)amino]pyridin-3-yl}furan-2(5H)-ylidene]-6-fluoro-1,3-dihydro-2H-indol-2-one | 448.5391 |
| 343 | 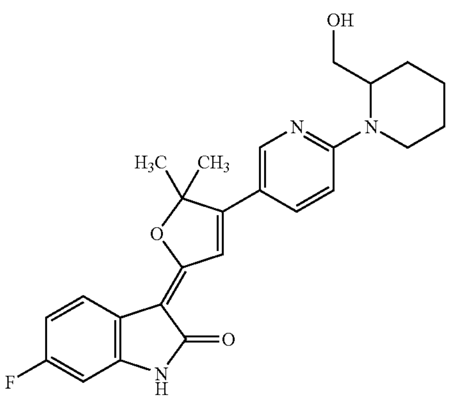 [SMILES: CC1(C)O/C(=C2/C(=O)Nc3cc(F)ccc32)C=C1c1ccc(N2CCCCC2CO)nc1] | (3E)-6-fluoro-3-[4-{6-[2-(hydroxymethyl)piperidin-1-yl]pyridin-3-yl}-5,5-dimethylfuran-2(5H)-ylidene]-1,3-dihydro-2H-indol-2-one | 435.4964 |
| 344 | 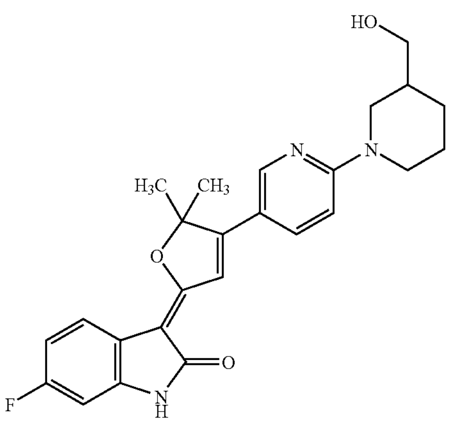 [SMILES: CC1(C)O/C(=C2/C(=O)Nc3cc(F)ccc32)C=C1c1ccc(N2CCCC(CO)C2)nc1] | (3E)-6-fluoro-3-[4-{6-[3-(hydroxymethyl)piperidin-1-yl]pyridin-3-yl}-5,5-dimethylfuran-2(5H)-ylidene]-1,3-dihydro-2H-indol-2-one | 435.4964 |
| 345 | 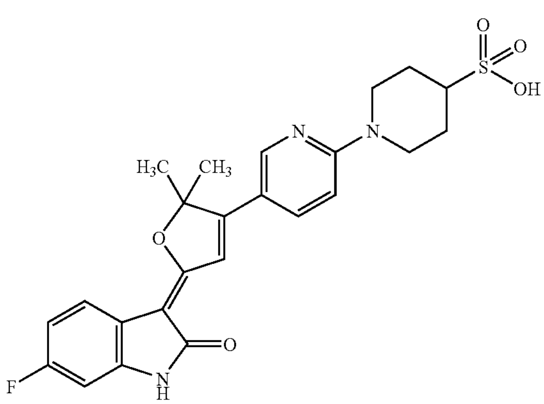 [SMILES: CC1(C)O/C(=C2/C(=O)Nc3cc(F)ccc32)C=C1c1ccc(N2CCC(S(=O)(=O)O)CC2)nc1] | 1-{5-[(5E)-5-(6-fluoro-2-oxo-1,2-dihydro-3H-indol-3-ylidene)-2,2-dimethyl-2,5-dihydrofuran-3-yl]pyridin-2-yl}piperidine-4-sulfonic acid | 485.5336 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 346 | 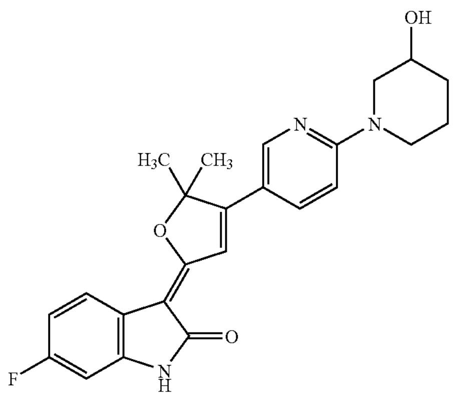 [SMILES: CC1(C)O/C(=C2/C(=O)Nc3cc(F)ccc32)C=C1c1ccc(N2CCCC(O)C2)nc1] | (3E)-6-fluoro-3-{4-[6-(3-hydroxypiperidin-1-yl)pyridin-3-yl]-5,5-dimethylfuran-2(5H)-ylidene}-1,3-dihydro-2H-indol-2-one | 421.4696 |
| 347 | 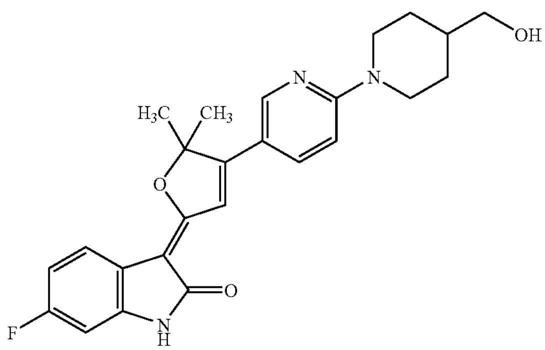 [SMILES: CC1(C)O/C(=C2/C(=O)Nc3cc(F)ccc32)C=C1c1ccc(N2CCC(CO)CC2)nc1] | (3E)-6-fluoro-3-[4-{6-[4-(hydroxymethyl)piperidin-1-yl]pyridin-3-yl}-5,5-dimethylfuran-2(5H)-ylidene]-1,3-dihydro-2H-indol-2-one | 435.4964 |
| 348 | 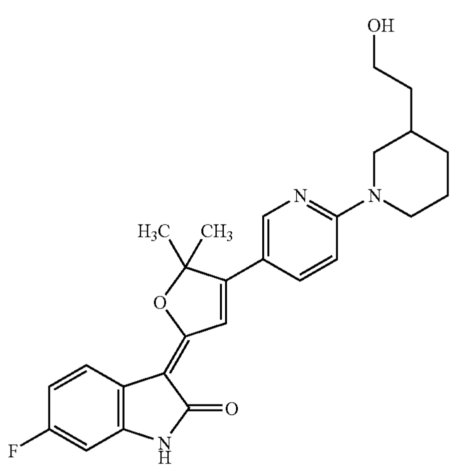 [SMILES: CC1(C)O/C(=C2/C(=O)Nc3cc(F)ccc32)C=C1c1ccc(N2CCCC(CCO)C2)nc1] | (3E)-6-fluoro-3-[4-{6-[3-(2-hydroxyethyl)piperidin-1-yl]pyridin-3-yl}-5,5-dimethylfuran-2(5H)-ylidene]-1,3-dihydro-2H-indol-2-one | 449.5232 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 349 | 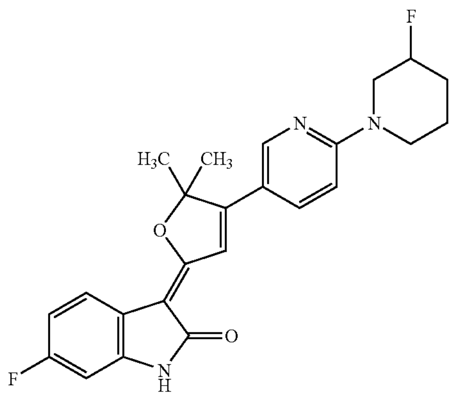 [SMILES: CC1(C)O/C(=C2/C(=O)Nc3cc(F)ccc32)C=C1c1ccc(N2CCCC(F)C2)nc1] | (3E)-6-fluoro-3-{4-[6-(3-fluoropiperidin-1-yl)pyridin-3-yl]-5,5-dimethylfuran-2(5H)-ylidene}-1,3-dihydro-2H-indol-2-one | 423.4607 |
| 350 | 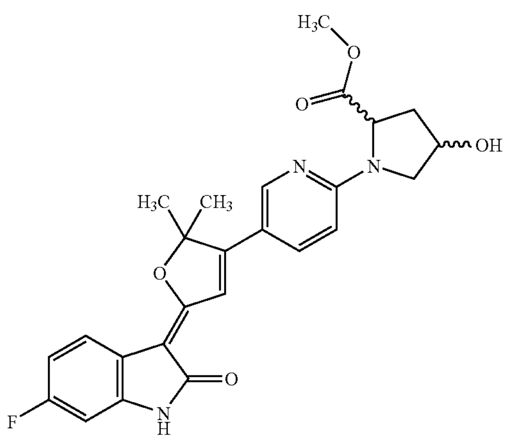 [SMILES: COC(=O)C1CC(O)CN1c1ccc(C2=C/C(=C3\C(=O)Nc4cc(F)ccc43)OC2(C)C)cn1] | methyl 1-{5-[(5E)-5-(6-fluoro-2-oxo-1,2-dihydro-3H-indol-3-ylidene)-2,2-dimethyl-2,5-dihydrofuran-3-yl]pyridin-2-yl}-4-hydroxypyrrolidine-2-carboxylate | 465.4786 |
| 351 | 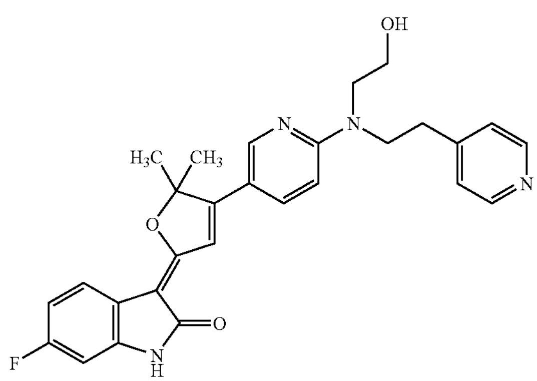 [SMILES: CC1(C)O/C(=C2/C(=O)Nc3cc(F)ccc32)C=C1c1ccc(N(CCO)CCc2ccncc2)nc1] | (3E)-6-fluoro-3-[4-{6-[(2-hydroxyethyl)(2-pyridin-4-ylethyl)amino]pyridin-3-yl}-5,5-dimethylfuran-2(5H)-ylidene]-1,3-dihydro-2H-indol-2-one | 486.5443 |
| 352 | 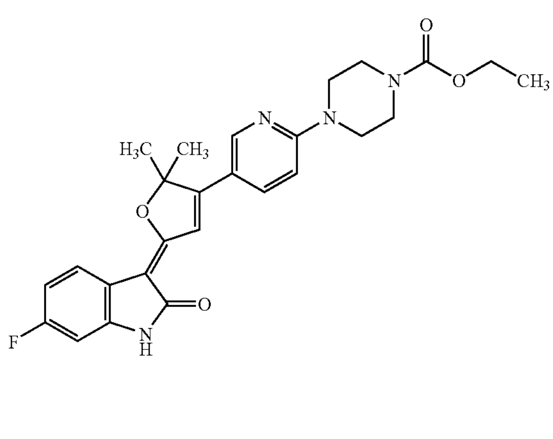 [SMILES: CCOC(=O)N1CCN(c2ccc(C3=C/C(=C4\C(=O)Nc5cc(F)ccc54)OC3(C)C)cn2)CC1] | ethyl 4-{5-[(5E)-5-(6-fluoro-2-oxo-1,2-dhydro-3H-indol-3-ylidene)-2,2-dimethyl-2,5-dihydrofuran-3-yl]pyridin-2-yl}piperazine-1-carboxylate | 478.5213 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 353 | 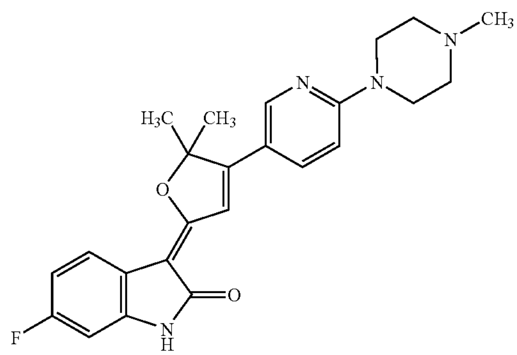 [SMILES: CN1CCN(c2ccc(C3=C/C(=C4\C(=O)Nc5cc(F)ccc54)OC3(C)C)cn2)CC1] | (3E)-3-{5,5-dimethyl-4-[6-(4-methylpiperazin-1-yl)pyridin-3-yl]furan-2(5H)-ylidene}-6-fluoro-1,3-dihydro-2H-indol-2-one | 420.4855 |
| 354 | 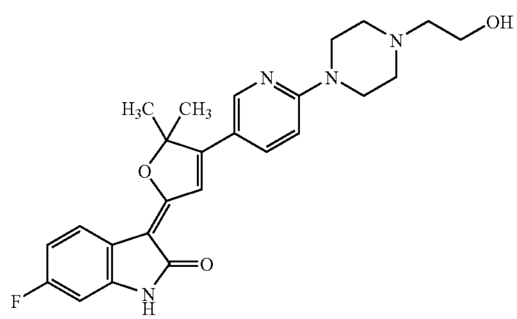 [SMILES: CC1(C)O/C(=C2/C(=O)Nc3cc(F)ccc32)C=C1c1ccc(N2CCN(CCO)CC2)nc1] | (3E)-6-fluoro-3-[4-{6-[4-(2-hydroxyethyl)piperazin-1-yl]pyridin-3-yl}-5,5-dimethylfuran-2(5H)-ylidene]-1,3-dihydro-2H-indol-2-one | 450.5113 |
| 355 | 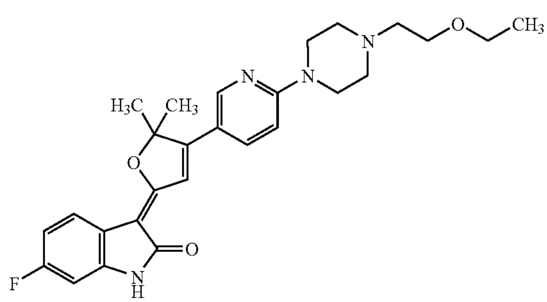 [SMILES: CCOCCN1CCN(c2ccc(C3=C/C(=C4\C(=O)Nc5cc(F)ccc54)OC3(C)C)cn2)CC1] | (3E)-3-[4-{6-[4-(2-ethoxyethyl)piperazin-1-yl]pyridin-3-yl}-5,5-dimethylfuran-2(5H)-ylidene]-6-fluoro-1,3-dihydro-2H-indol-2-one | 478.5649 |
| 356 | 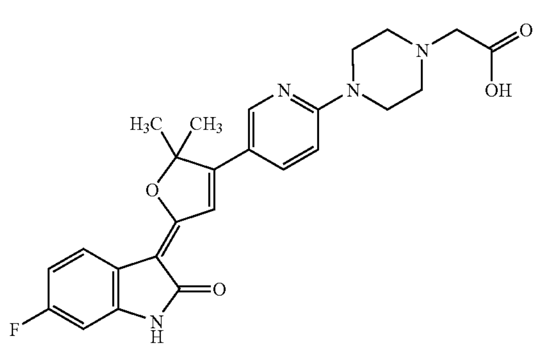 [SMILES: CC1(C)O/C(=C2/C(=O)Nc3cc(F)ccc32)C=C1c1ccc(N2CCN(CC(=O)O)CC2)nc1] | (4-{5-[(5E)-5-(6-fluoro-2-oxo-1,2-dihydro-3H-indol-3-ylidene)-2,2-dimethyl-2,5-dihydrofuran-3-yl]pyridin-2-yl}piperazin-1-yl)acetic acid | 464.4945 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 357 | 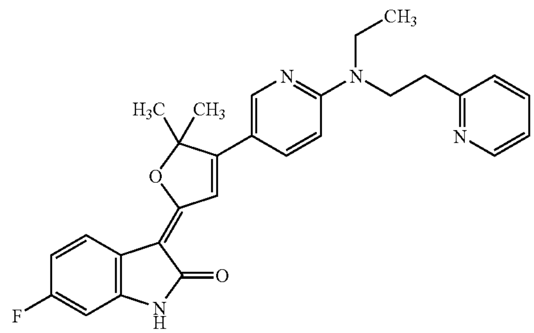 [SMILES: CCN(CCc1ccccn1)c1ccc(C2=C/C(=C3\C(=O)Nc4cc(F)ccc43)OC2(C)C)cn1] | (3E)-3-[4-{6-[ethyl(2-pyridin-2-ylethyl)amino]pyridin-3-yl}-5,5-dimethylfuran-2(5H)-ylidene]-6-fluoro-1,3-dihydro-2H-indol-2-one | 470.5453 |
| 358 | 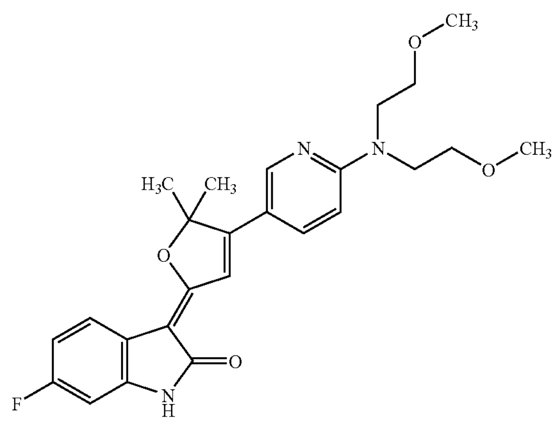 [SMILES: COCCN(CCOC)c1ccc(C2=C/C(=C3\C(=O)Nc4cc(F)ccc43)OC2(C)C)cn1] | (3E)-3-[4-{6-[bis(2-methoxyethyl)amino]pyridin-3-yl}-5,5-dimethylfuran-2(5H)-ylidene]-6-fluoro-1,3-dihydro-2H-indol-2-one | 453.5112 |
| 359 | 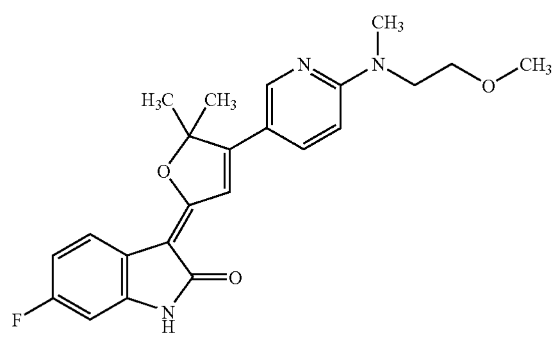 [SMILES: COCCN(C)c1ccc(C2=C/C(=C3\C(=O)Nc4cc(F)ccc43)OC2(C)C)cn1] | (3E)-6-fluoro-3-[4-{6-[(2-methoxyethyl)(methyl)amino]pyridin-3-yl}-5,5-dimethylfuran-2(5H)-ylidene]-1,3-dihydro-2H-indol-2-one | 409.4586 |
| 360 | 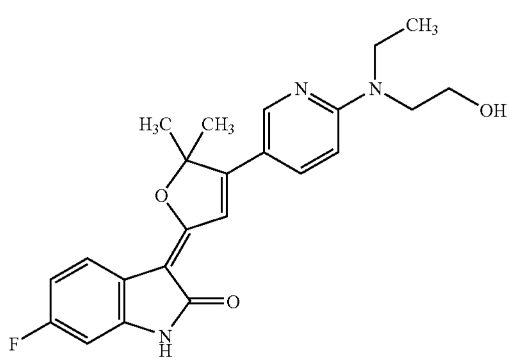 [SMILES: CCN(CCO)c1ccc(C2=C/C(=C3\C(=O)Nc4cc(F)ccc43)OC2(C)C)cn1] | (3E)-3-[4-{6-ethyl(2-hydroxyethyl)amino]pyridin-3-yl}-5,5-dimethylfuran-2(5H)-ylidene]-6-fluoro-1,3-dihydro-2H-indol-2-one | 409.4586 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 361 | 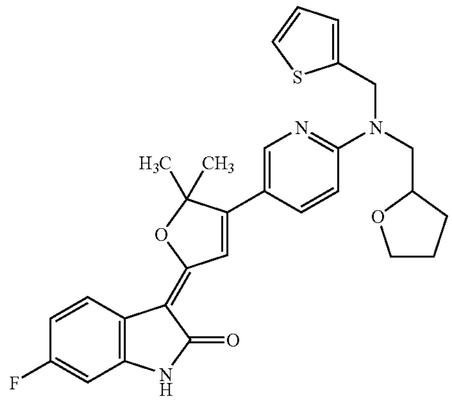 [SMILES: CC1(C)O/C(=C2/C(=O)Nc3cc(F)ccc32)C=C1c1ccc(N(Cc2cccs2)CC2CCCO2)nc1] | (3E)-3-[5,5-dimethyl-4-{6-[(tetrahydrofuran-2-ylmethyl)(2-thienylmethyl)amino]pyridin-3-yl}furan-2(5H)-ylidene]-6-fluoro-1,3-dihydro-2H-indol-2-one | 517.6222 |
| 362 | 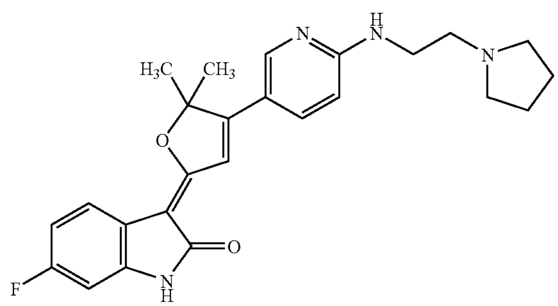 [SMILES: CC1(C)O/C(=C2/C(=O)Nc3cc(F)ccc32)C=C1c1ccc(NCCN2CCCC2)nc1] | (3E)-3-[5,5-dimethyl-4-{6-[(2-pyrrolidin-1-ylethyl)amino]pyridin-3-yl}furan-2(5H)-ylidene]-6-fluoro-1,3-dihydro-2H-indol-2-one | 434.5123 |
| 363 | 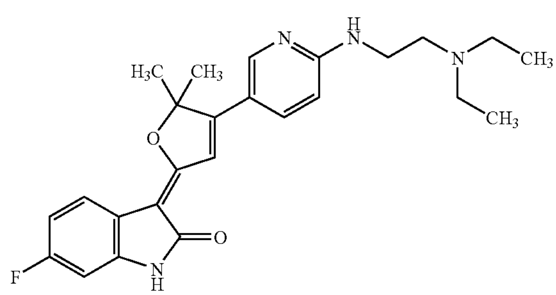 [SMILES: CCN(CC)CCNc1ccc(C2=C/C(=C3\C(=O)Nc4cc(F)ccc43)OC2(C)C)cn1] | (3E)-3-[4-(6-{[2-(diethylamino)ethyl]amino}pyridin-3-yl)-5,5-dimethylfuran-2(5H)-ylidene]-6-fluoro-1,3-dihydro-2H-indol-2-one | 436.5281 |
| 364 | 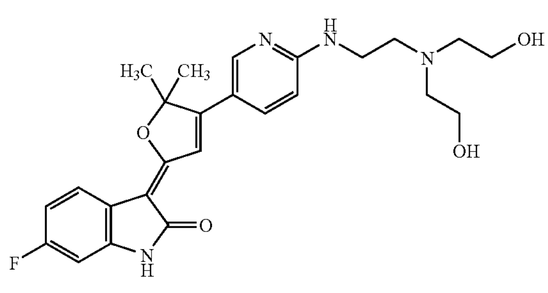 [SMILES: CC1(C)O/C(=C2/C(=O)Nc3cc(F)ccc32)C=C1c1ccc(NCCN(CCO)CCO)nc1] | (3E)-3-{4-[6-({2-[bis(2-hydroxyethyl)amino]ethyl}amino)pyridin-3-yl]-5,5-dimethylfuran-2(5H)-ylidene}-6-fluoro-1,3-dihydro-2H-indol-2-one | 468.5261 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 365 | 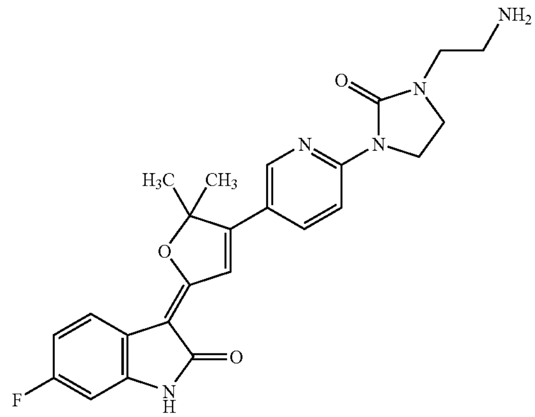 [SMILES: CC1(C)O/C(=C2/C(=O)Nc3cc(F)ccc32)C=C1c1ccc(N2CCN(CCN)C2=O)nc1] | (3E)-3-[4-{6-[3-(2-aminoethyl)-2-oxoimidazolidin-1-yl]pyridin-3-yl}-5,5-dimethylfuran-2(5H)-ylidene]-6-fluoro-1,3-dihydro-2H-indol-2-one | 449.4836 |
| 366 | 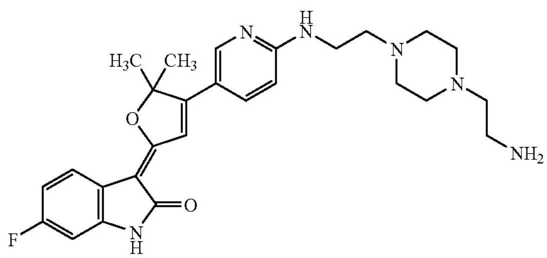 [SMILES: CC1(C)O/C(=C2/C(=O)Nc3cc(F)ccc32)C=C1c1ccc(NCCN2CCN(CCN)CC2)nc1] | (3E)-3-{4-[6-({2-[4-(2-aminoethyl)piperazin-1-yl]ethyl}amino)pyridin-3-yl]-5,5-dimethylfuran-(5H)-ylidene}-6-fluoro-1,3-dihydro-2H-indol-2-one | 492.5957 |
| 367 | 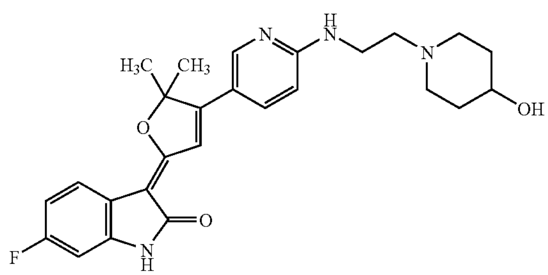 [SMILES: CC1(C)O/C(=C2/C(=O)Nc3cc(F)ccc32)C=C1c1ccc(NCCN2CCC(O)CC2)nc1] | (3E)-6-fluoro-3-[4-(6-{[2-(4-hydroxypiperidin-1-yl)ethyl]amino}pyridin-3-yl)-5,5-dimethylfuran-2(5H)-ylidene]-1,3-dihydro-2H-indol-2-one | 464.5381 |
| 368 | 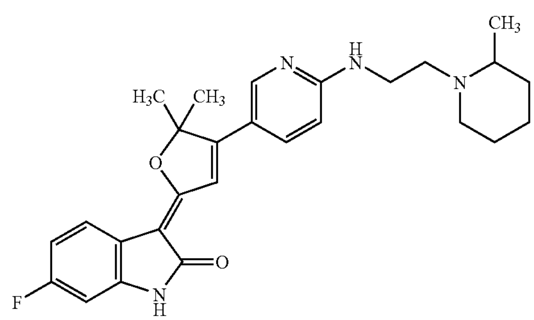 [SMILES: CC1CCCCN1CCNc1ccc(C2=C/C(=C3\C(=O)Nc4cc(F)ccc43)OC2(C)C)cn1] | (3E)-3-[5,5-dimethyl-4-(6-{[2-(2-methylpiperidin-1-yl)ethyl]amino}pyridin-3-yl)furan-2(5H)-ylidene]-6-fluoro-1,3-dihydro-2H-indol-2-one | 462.5659 |
| 369 | 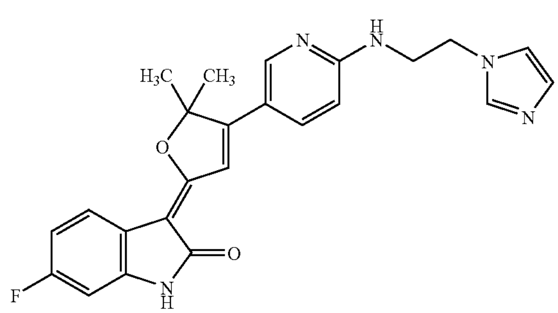 [SMILES: CC1(C)O/C(=C2/C(=O)Nc3cc(F)ccc32)C=C1c1ccc(NCCn2ccnc2)nc1] | (3E)-6-fluoro-3-[4-(6-{[2-(1H-imidazol-1-yl)ethyl]amino}pyridin-3-yl)-5,5-dimethylfuran-2(5H)-ylidene]-1,3-dihydro-2H-indol-2-one | 431.4688 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 370 | 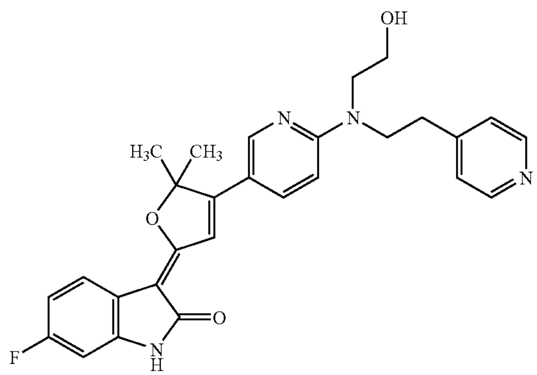 [SMILES: CC1(C)O/C(=C2/C(=O)Nc3cc(F)ccc32)C=C1c1ccc(N(CCO)CCc2ccncc2)nc1] | 6-Fluoro-3-[4-{6-[(2-hydroxy-ethyl)-(2-pyridin-4-yl-ethyl)-amino]-pyridin-3-yl}-5,5-dimethyl-5H-furan-(2E)-ylidene]-1,3-dihydro-indol-2-one | 486.5443 |
| 371 | 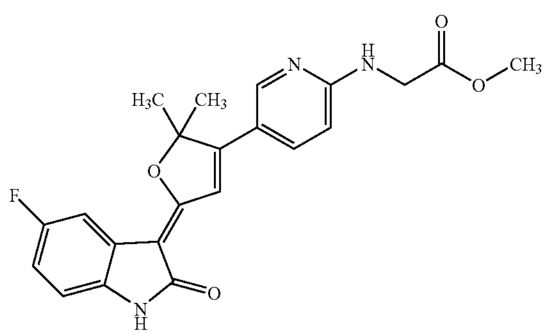 [SMILES: COC(=O)CNc1ccc(C2=C/C(=C3\C(=O)Nc4ccc(F)cc43)OC2(C)C)cn1] | methyl ({5-[(5E)-5-(5-fluoro-2-oxo-1,2-dihydro 3H-indol-3-ylidene)-2,2-dimethyl-2,5-dihydrofuran-3-yl]pyridin-2-yl}amino)acetate | 409.415 |
| 372 | 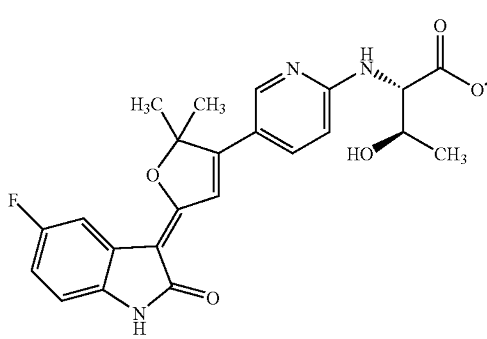 | methyl (2S,3R)-2-({5-[(5E)-5-(5-fluoro-2-oxo-1,2-dihydro-3H-indol-3-ylidene)-2,2-dimethyl-2,5-dihydrofuran-3-yl]pyridin-2-yl}amino)-3-hydroxybutanoate | 453.4676 |
| 373 | 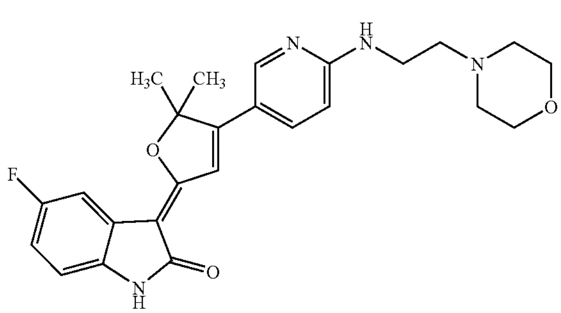 [SMILES: CC1(C)O/C(=C2/C(=O)Nc3ccc(F)cc32)C=C1c1ccc(NCCN2CCOCC2)nc1] | (3E)-3-[5,5-dimethyl-4-{6-[(2-morpholin-4-ylethyl)amino]pyridin-3-yl}furan-2(5H)-ylidene]-5-fluoro-1,3-dihydro-2H-indol-2-one | 450.5113 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 374 | 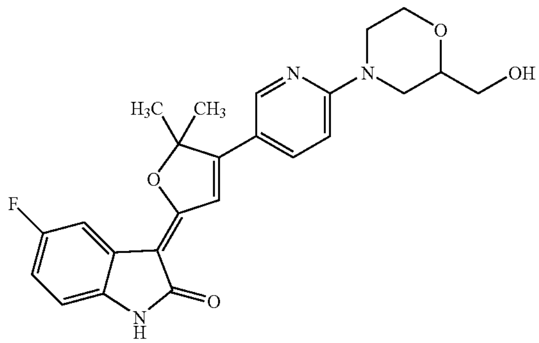 [SMILES: CC1(C)O/C(=C2/C(=O)Nc3ccc(F)cc32)C=C1c1ccc(N2CCOC(CO)C2)nc1] | (3E)-5-fluoro-3-[4-{6-[2-(hydroxymethyl)morpholin-4-yl]pyridin-3-yl}-5,5-dimethylfuran-2(5H)-ylidene]-1,3-dihydro-2H-indol-2-one | 437.4686 |
| 375 | 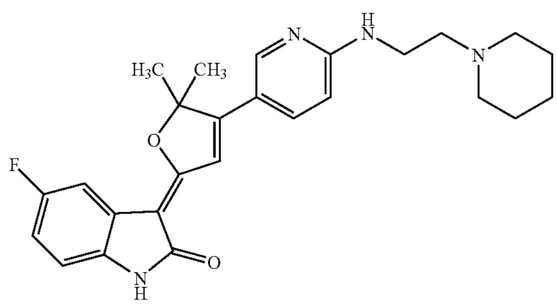 [SMILES: CC1(C)O/C(=C2/C(=O)Nc3ccc(F)cc32)C=C1c1ccc(NCCN2CCCCC2)nc1] | (3E)-3-[5,5-dimethyl-4-{6-[(2-piperidin-1-ylethyl)amino]pyridin-3-yl}furan-2(5H)-ylidene]-5-fluoro-1,3-dihydro-2H-indol-2-one | 448.5391 |
| 376 | 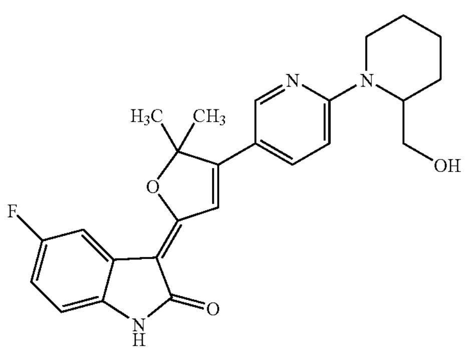 [SMILES: CC1(C)O/C(=C2/C(=O)Nc3ccc(F)cc32)C=C1c1ccc(N2CCCCC2CO)nc1] | (3E)-5-fluoro-3-[4-{6-[2-(hydroxymethyl)piperidin-1-yl]pyridin-3-yl}-5,5-dimethylfuran-2(5H)-ylidene]-1,3-dihydro-2H-indol-2-one | 435.4964 |
| 377 | 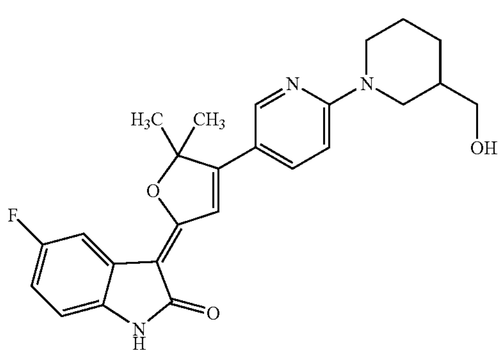 [SMILES: CC1(C)O/C(=C2/C(=O)Nc3ccc(F)cc32)C=C1c1ccc(N2CCCC(CO)C2)nc1] | (3E)-5-fluoro-3-[4-{6-[3-(hydroxymethyl)piperidin-1-yl]pyridin-3-yl}-5,5-dimethylfuran-2(5H)-ylidene]-1,3-dihydro-2H-indol-2-one | 435.4964 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 378 | 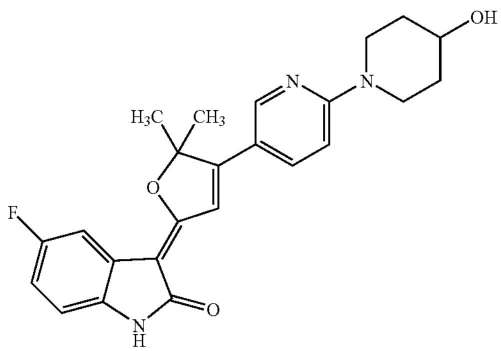 [SMILES: CC1(C)O/C(=C2/C(=O)Nc3ccc(F)cc32)C=C1c1ccc(N2CCC(O)CC2)nc1] | (3E)-5-fluoro-3-{4-[6-(4-hydroxypiperidin-1-yl)pyridin-3-yl]-5,5-dimethylfuran-2(5H)-ylidene}-1,3-dihydro-2H-indol-2-one | 421.4696 |
| 379 | 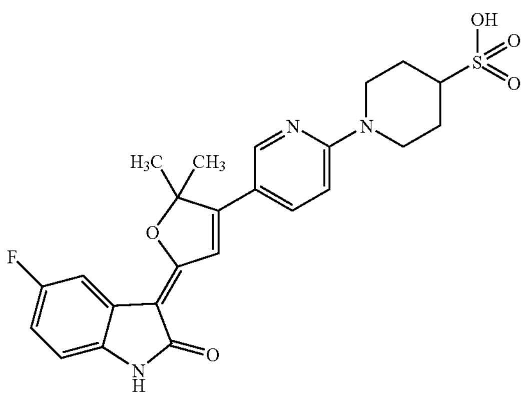 [SMILES: CC1(C)O/C(=C2/C(=O)Nc3ccc(F)cc32)C=C1c1ccc(N2CCC(S(=O)(=O)O)CC2)nc1] | 1-{5-[(5E)-5-(5-fluoro-2-oxo-1,2-dihydro-3H-indol-3-ylidene)-2,2-dimethyl-2,5-dihydrofuran-3-yl]pyridin-2-yl}piperidine-4-sulfonic acid | 485.5336 |
| 380 | 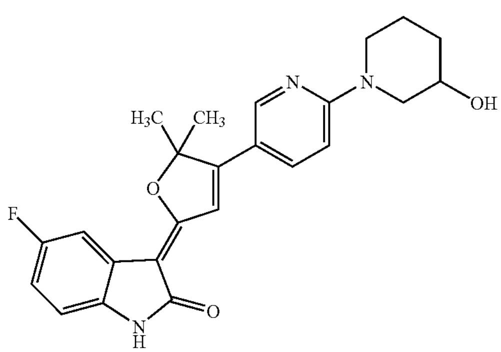 [SMILES: CC1(C)O/C(=C2/C(=O)Nc3ccc(F)cc32)C=C1c1ccc(N2CCCC(O)C2)nc1] | (3E)-5-fluoro-3-{4-[6-(3-hydroxypiperidin-1-yl)pyridin-3-yl]-5,5-dimethylfuran-2(5H)-ylidene}-1,3-dihydro-2H-indol-2-one | 421.4696 |
| 381 | 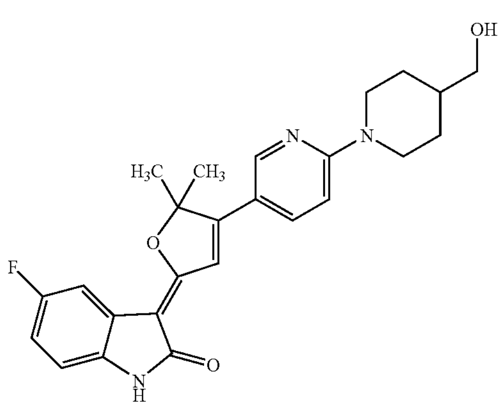 [SMILES: CC1(C)O/C(=C2/C(=O)Nc3ccc(F)cc32)C=C1c1ccc(N2CCC(CO)CC2)nc1] | (3E)-5-fluoro-3-[4-{6-[4-(hydroxymethyl)piperidin-1-yl]pyridin-3-yl}-5,5-dimethylfuran-2(5H)-ylidene]-1,3-dihydro-2H-indol-2-one | 435.4964 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 382 | 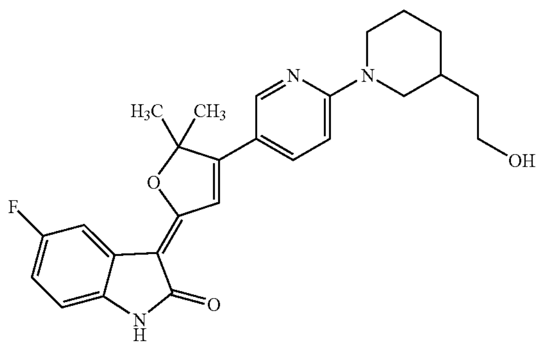 [SMILES: CC1(C)O/C(=C2/C(=O)Nc3ccc(F)cc32)C=C1c1ccc(N2CCCC(CCO)C2)nc1] | (3E)-5-fluoro-3-[4-{6-[3-(2-hydroxyethyl)piperidin-1-yl]pyridin-3-yl}-5,5-dimethylfuran-2(5H)-ylidene]-1,3-dihydro-2H-indol-2-one | 449.5232 |
| 383 | 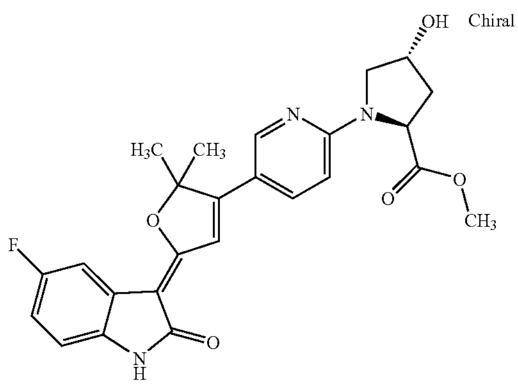 [SMILES: COC(=O)[C@@H]1C[C@@H](O)CN1c1ccc(C2=C/C(=C3\C(=O)Nc4ccc(F)cc43)OC2(C)C)cn1] | methyl (2S,4R)-1-{5-[(5E)-5-(5-fluoro-2-oxo-1,2-dihydro-3H-indol-3-ylidene)-2,2-dimethyl-2,5-dihydrofuran-3-yl]pyridin-2-yl}-4-hydroxypyrrolidine-2-carboxylate | 465.4786 |
| 384 | 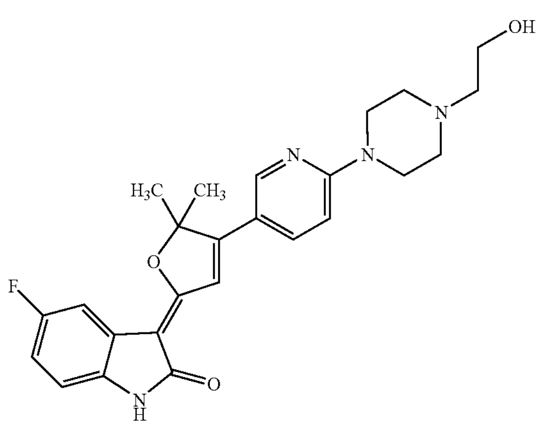 [SMILES: CC1(C)O/C(=C2/C(=O)Nc3ccc(F)cc32)C=C1c1ccc(N2CCN(CCO)CC2)nc1] | (3E)-5-fluoro-3-[4-{6-[4-(2-hydroxyethyl)piperazin-1-yl]pyridin-3-yl}-5,5-dimethylfuran-2(5H)-ylidene]-1,3-dihydro-2H-indol-2-one | 450.5113 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 385 | 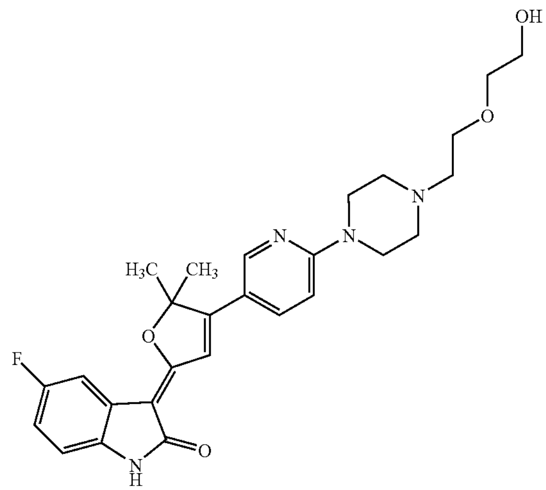 [SMILES: CC1(C)O/C(=C2/C(=O)Nc3ccc(F)cc32)C=C1c1ccc(N2CCN(CCOCCO)CC2)nc1] | (3E)-5-fluoro-3-[4-(6-{4-[2-(2-hydroxyethoxy)ethyl]piperazin-1-yl}pyridin-3-yl)-5,5-dimethylfuran-2(5H)-ylidene]-1,3-dihydro-2H-indol-2-one | 494.5639 |
| 386 | 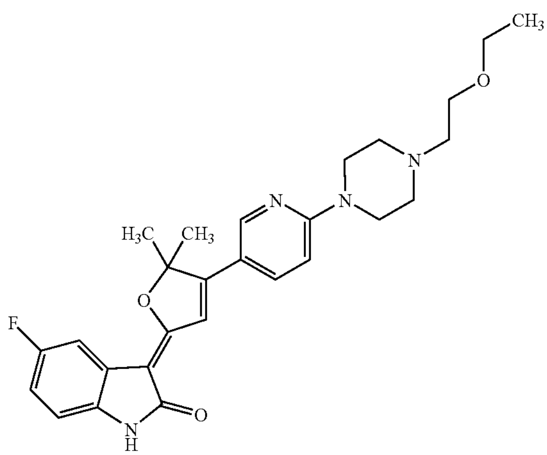 [SMILES: CCOCCN1CCN(c2ccc(C3=C/C(=C4\C(=O)Nc5ccc(F)cc54)OC3(C)C)cn2)CC1] | (3E)-3-[4-{6-[4-(2-ethoxyethyl)piperazin-1-yl]pyridin-3-yl}-5,5-dimethylfuran-2(5H)-ylidene]-5-fluoro-1,3-dihydro-2H-indol-2-one | 478.5649 |
| 387 | 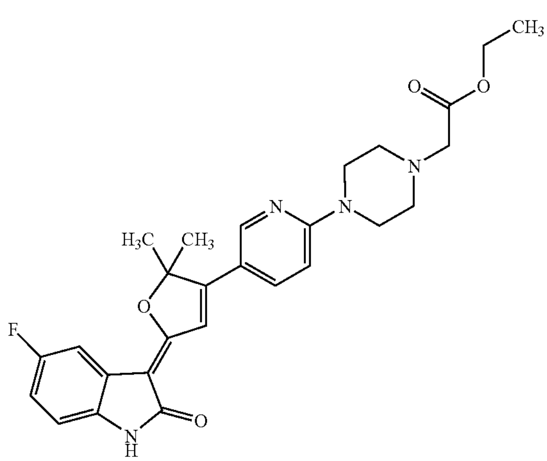 [SMILES: CCOC(=O)CN1CCN(c2ccc(C3=C/C(=C4\C(=O)Nc5ccc(F)cc54)OC3(C)C)cn2)CC1] | ethyl (4-{5-[(5E)-5-(5-fluoro-2-oxo-1,2-dihydro-3H-indol-3-ylidene)-2,2-dimethyl-2,5-dihydrofuran-3-yl]pyridin-2-yl}piperazin-1-yl)acetate | 492.5481 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 388 | 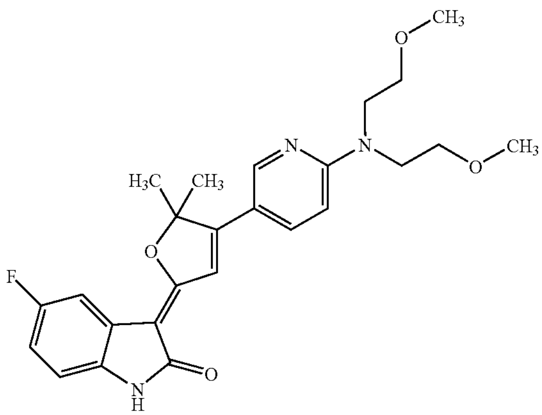 [SMILES: COCCN(CCOC)c1ccc(C2=C/C(=C3\C(=O)Nc4ccc(F)cc43)OC2(C)C)cn1] | (3E)-3-[4-{6-[bis(2-methoxyethyl)amino]pyridin-3-yl}-5,5-dimethylfuran-2(5H)-ylidene]-5-fluoro-1,3-dihydro-2H-indol-2-one | 453.5112 |
| 389 | 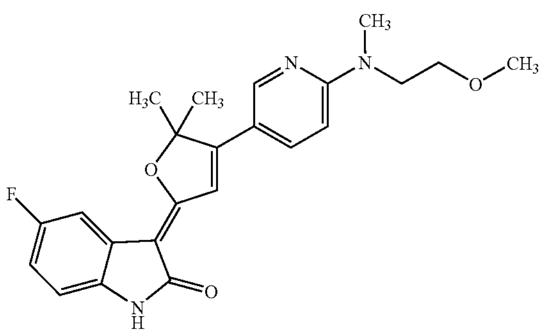 [SMILES: COCCN(C)c1ccc(C2=C/C(=C3\C(=O)Nc4ccc(F)cc43)OC2(C)C)cn1] | (3E)-5-fluoro-3-[4-{6-[(2-methoxyethyl)(methyl)amino]pyridin-3-yl}-5,5-dimethylfuran-2(5H)-ylidene]-1,3-dihydro-2H-indol-2-one | 409.4586 |
| 390 | 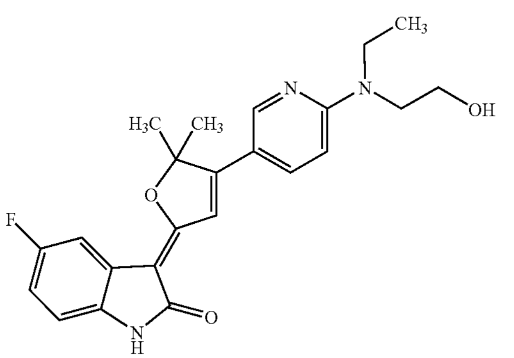 [SMILES: CCN(CCO)c1ccc(C2=C/C(=C3\C(=O)Nc4ccc(F)cc43)OC2(C)C)cn1] | (3E)-3-[4-{6-[ethyl(2-hydroxyethyl)amino]pyridin-3-yl}-5,5-dimethylfuran-2(5H)-ylidene]-5-fluoro-1,3-dihydro-2H-indol-2-one | 409.4586 |
| 391 | 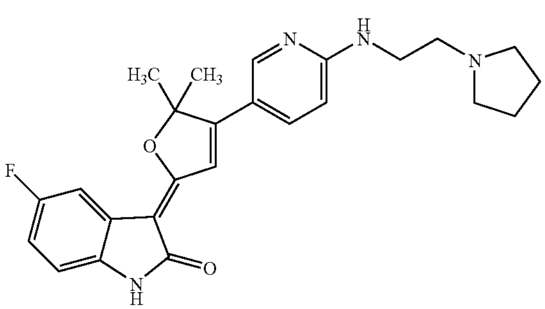 [SMILES: CC1(C)O/C(=C2/C(=O)Nc3ccc(F)cc32)C=C1c1ccc(NCCN2CCCC2)nc1] | (3E)-3-[5,5-dimethyl-4-{6-[(2-pyrrolidin-1-ylethyl)amino]pyridin-3-yl}furan-2(5H)-ylidene]-5-fluoro-1,3-dihydro-2H-indol-2-one | 434.5123 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 392 | 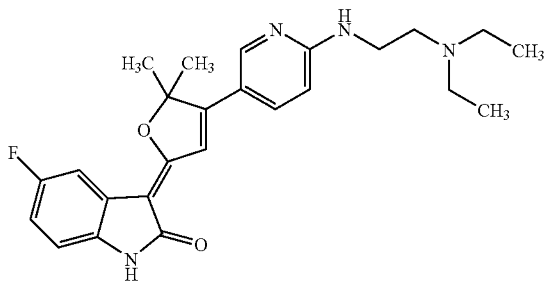 [SMILES: CCN(CC)CCNc1ccc(C2=C/C(=C3\C(=O)Nc4ccc(F)cc43)OC2(C)C)cn1] | (3E)-3-[4-(6-{[2-(diethylamino)ethyl]amino}pyridin-3-yl)-5,5-dimethylfuran-2(5H)-ylidene]-5-fluoro-1,3-dihydro-2H-indol-2-one | 436.5281 |
| 393 | 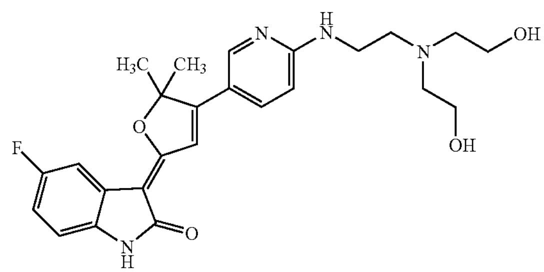 [SMILES: CC1(C)O/C(=C2/C(=O)Nc3ccc(F)cc32)C=C1c1ccc(NCCN(CCO)CCO)nc1] | (3E)-3-{4-[6-({2-[bis(2-hydroxyethyl)amino]ethyl}amino)pyridin-3-yl]-5,5-dimethylfuran-2(5H)-ylidene}-5-fluoro-1,3-dihydro-2H-indol-2-one | 468.5261 |
| 394 | 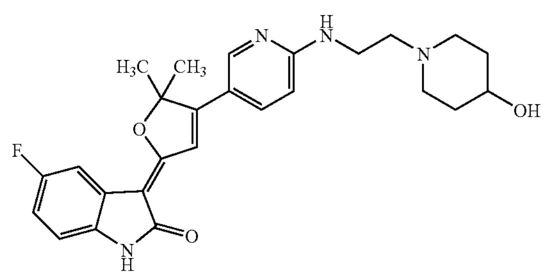 [SMILES: CC1(C)O/C(=C2/C(=O)Nc3ccc(F)cc32)C=C1c1ccc(NCCN2CCC(O)CC2)nc1] | (3E)-5-fluoro-3-[4-(6-{[2-(4-hydroxypiperidin-1-yl)ethyl]amino}pyridin-3-yl)-5,5-dimethylfuran-2(5H)-ylidene]-1,3-dihydro-2H-indol-2-one | 464.5381 |
| 395 | 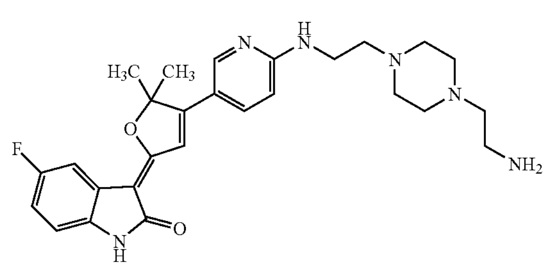 [SMILES: CC1(C)O/C(=C2/C(=O)Nc3ccc(F)cc32)C=C1c1ccc(NCCN2CCN(CCN)CC2)nc1] | (3E)-3-{4-[6-({2-[4-(2-aminoethyl)piperazin-1-yl]ethyl}amino)pyridin-3-yl]-5,5-dimethylfuran-2(5H)-ylidene}-5-fluoro-1,3-dihydro-2H-indol-2-one | 492.5957 |
| 396 | 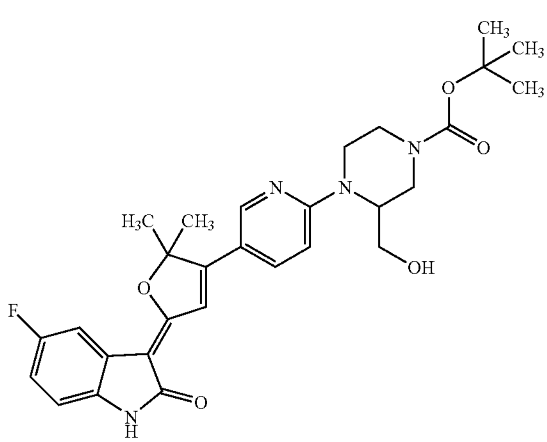 [SMILES: CC(C)(C)OC(=O)N1CCN(c2ccc(C3=C/C(=C4\C(=O)Nc5ccc(F)cc54)OC3(C)C)cn2)C(CO)C1] | tert-butyl 4-{5-[(5E)-5-(5-fluoro-2-oxo-1,2-dihydro-3H-indol-3-ylidene)-2,2-dimethyl-2,5-dihydrofuran-3-yl]pyridin-2-yl}-3-(hydroxymethyl)piperazine-1-carboxylate | 536.6007 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 397 | 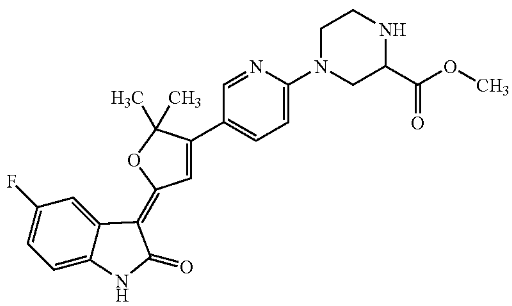 [SMILES: COC(=O)C1CN(c2ccc(C3=C/C(=C4\C(=O)Nc5ccc(F)cc54)OC3(C)C)cn2)CCN1] | methyl 4-{5-[(5E)-5-(5-fluoro-2-oxo-1,2-dihydro-3H-indol-3-ylidene)-2,2-dimethyl-2,5-dihydrofuran-3-yl]pyridin-2-yl}piperazine-2-carboxylate | 464.4945 |
| 398 | 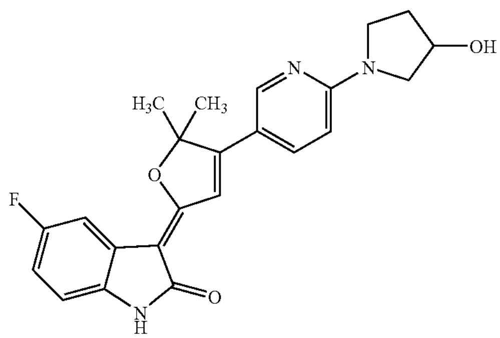 [SMILES: CC1(C)O/C(=C2/C(=O)Nc3ccc(F)cc32)C=C1c1ccc(N2CCC(O)C2)nc1] | (3E)-5-fluoro-3-{4-[6-(3-hydroxypyrrolidin-1-yl)pyridin-3-yl]-5,5-dimethylfuran-2(5H)-ylidene}-1,3-dihydro-2H-indol-2-one | 407.4428 |
| 399 | 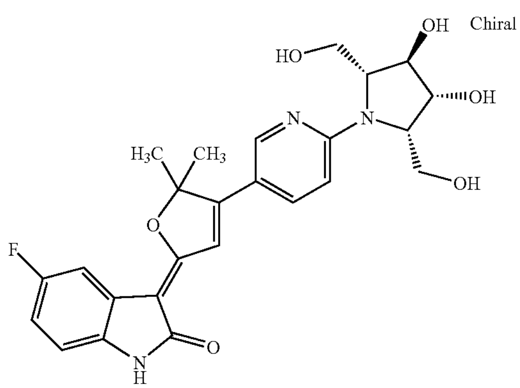 [SMILES: CC1(C)O/C(=C2/C(=O)Nc3ccc(F)cc32)C=C1c1ccc(N2[C@H](CO)[C@@H](O)[C@H](O)[C@@H]2CO)nc1] | (3E)-3-[4-{6-[(2R,3R,4R,5S)-3,4-dihydroxy-2,5-bis(hydroxymethyl)pyrrolidin-1-yl]pyridin-3-yl}-5,5-dimethylfuran-2(5H)-ylidene]-5-fluoro-1,3-dihydro-2H-indol-2-one | 483.4934 |
| 400 | 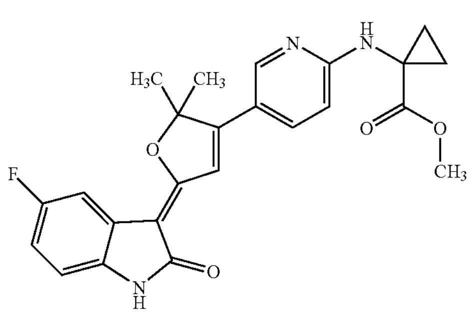 [SMILES: COC(=O)C1(Nc2ccc(C3=C/C(=C4\C(=O)Nc5ccc(F)cc54)OC3(C)C)cn2)CC1] | methyl 1-({5-[(5E)-5-(5-fluoro-2-oxo-1,2-dihydro-3H-indol-3-ylidene)-2,2-dimethyl-2,5-dihydrofuran-3-yl]pyridin-2-yl}amino)cyclopropanecarboxylate | 435.4528 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 401 | 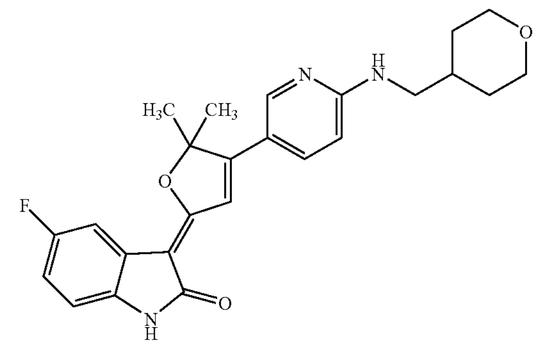 [SMILES: CC1(C)O/C(=C2/C(=O)Nc3ccc(F)cc32)C=C1c1ccc(NCC2CCOCC2)nc1] | (3E)-3-[5,5-dimethyl-4-{6-[(tetrahydro-2H-pyran-4-ylmethyl)amino]pyridin-3-yl}furan-2(5H)-ylidene]-5-fluoro-1,3-dihydro-2H-indol-2-one | 435.4964 |
| 402 | Chiral | methyl (2R)-2-({5-[(5E)-5-(5-fluoro-2-oxo-1,2-dihydro-3H-indol-3-ylidene)-2,2-dimethyl-2,5-dihydrofuran-3-yl]pyridin-2-yl}amino)-3-hydroxypropanoate | 439.4408 |
| 403 | 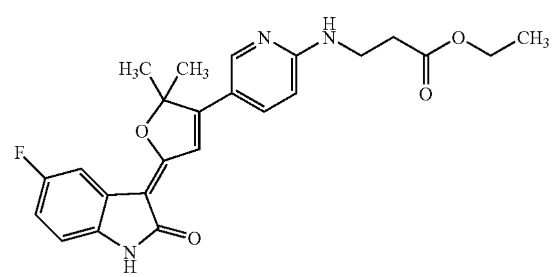 [SMILES: CCOC(=O)CCNc1ccc(C2=C/C(=C3\C(=O)Nc4ccc(F)cc43)OC2(C)C)cn1] | ethyl 3-({5-[(5E)-5-(5-fluoro-2-oxo-1,2-dihydro-3H-indol-3-ylidene)-2,2-dimethyl-2,5-dihydrofuran-3-yl]pyridin-2-yl}amino)propanoate | 437.4686 |
| 404 | 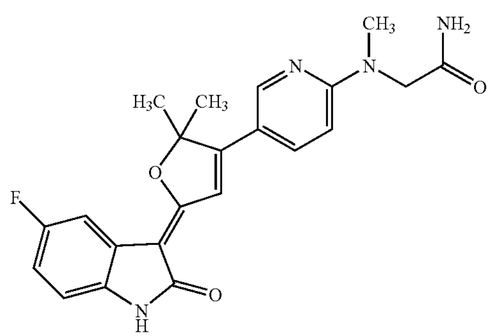 [SMILES: CN(CC(N)=O)c1ccc(C2=C/C(=C3\C(=O)Nc4ccc(F)cc43)OC2(C)C)cn1] | 2-[{5-[(5E)-5-(5-fluoro-2-oxo-1,2-dihydro-3H-indol-3-ylidene)-2,2-dimethyl-2,5-dihydrofuran-3-yl]pyridin-2-yl}(methyl)amino]acetamide | 408.4309 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 405 | 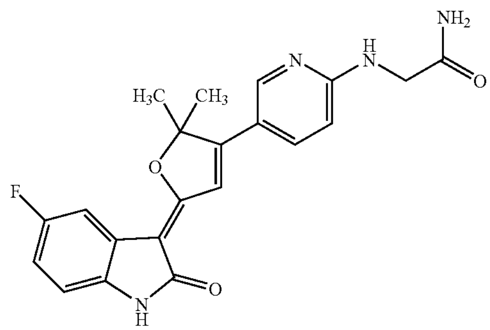 [SMILES: CC1(C)O/C(=C2/C(=O)Nc3ccc(F)cc32)C=C1c1ccc(NCC(N)=O)nc1] | 2-({5-[(5E)-5-(5-fluoro-2-oxo-1,2-dihydro-3H-indol-3-ylidene)-2,2-dimethyl-2,5-dihydrofuran-3-yl]pyridin-2-yl}amino)acetamide | 394.4041 |
| 406 | Chiral | methyl (2S)-2-({5-[(5E)-5-(5-fluoro-2-oxo-1,2-dihydro-3H-indol-3-ylidene)-2,2-dimethyl-2,5-dihydrofuran-3-yl]pyridin-2-yl}amino)-3-hydroxypropanoate | 439.4408 |
| 407 | 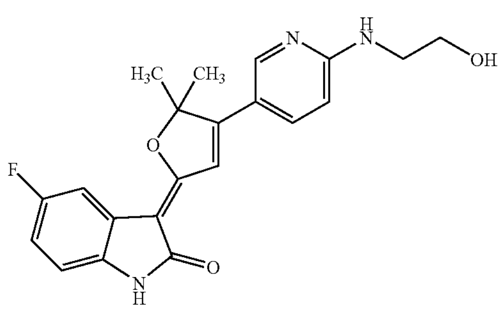 [SMILES: CC1(C)O/C(=C2/C(=O)Nc3ccc(F)cc32)C=C1c1ccc(NCCO)nc1] | (3E)-5-fluoro-3-[4-{6-[(2-hydroxyethyl)amino]pyridin-3-yl}-5,5-dimethylfuran-2(5H)-ylidene]-1,3-dihydro-2H-indol-2-one | 381.405 |
| 408 | 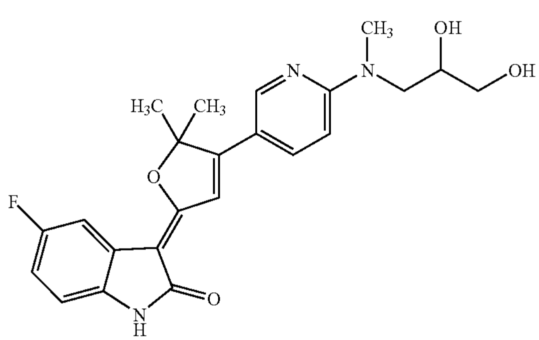 [SMILES: CN(CC(O)CO)c1ccc(C2=C/C(=C3\C(=O)Nc4ccc(F)cc43)OC2(C)C)cn1] | (3E)-3-[4-{6-[(2,3-dihydroxypropyl)(methyl)amino]pyridin-3-yl}-5,5-dimethylfuran-2(5H)-ylidene]-5-fluoro-1,3-dihydro-2H-indol-2-one | 425.4576 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 409 | 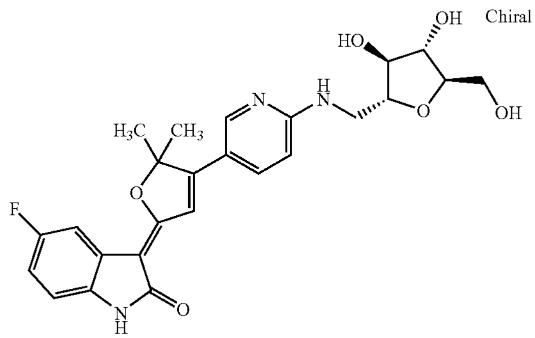 [SMILES: CC1(C)O/C(=C2/C(=O)Nc3ccc(F)cc32)C=C1c1ccc(NC[C@H]2O[C@H](CO)[C@@H](O)[C@@H]2O)nc1] | (3E)-3-{4-[6-({[(2R,3S,4S,5R)-3,4-dihydroxy-5-(hydroxymethyl)tetrahydrofuran-2-yl]methyl}amino)pyridin-3-yl]-5,5-dimethylfuran-2(5H)-ylidene}-5-fluoro-1,3-dihydro-2H-indol-2-one | 483.4934 |
| 410 | 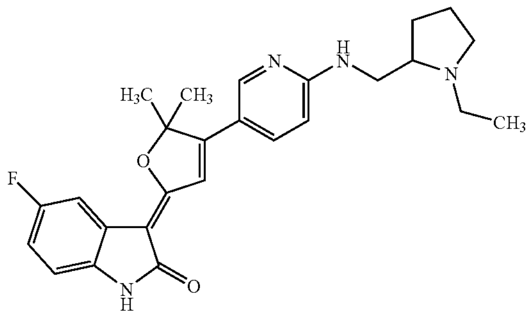 [SMILES: CCN1CCCC1CNc1ccc(C2=C/C(=C3\C(=O)Nc4ccc(F)cc43)OC2(C)C)cn1] | (3E)-3-[4-(6-{[(1-ethylpyrrolidin-2-yl)methyl]amino}pyridin-3-yl)-5,5-dimethylfuran-2(5H)-ylidene]-5-fluoro-1,3-dihydro-2H-indol-2-one | 448.5391 |
| 411 | 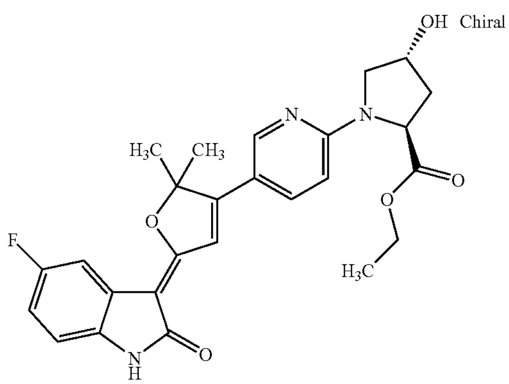 [SMILES: CCOC(=O)[C@@H]1C[C@@H](O)CN1c1ccc(C2=C/C(=C3\C(=O)Nc4ccc(F)cc43)OC2(C)C)cn1] | ethyl (2S,4R)-1-{5-[(5E)-5-(5-fluoro-2-oxo-1,2-dihydro-3H-indol-3-ylidene)-2,2-dimethyl-2,5-dihydrofuran-3-yl]pyridin-2-yl}-4-hydroxypyrrolidine-2-carboxylate | 479.5054 |
| 412 | 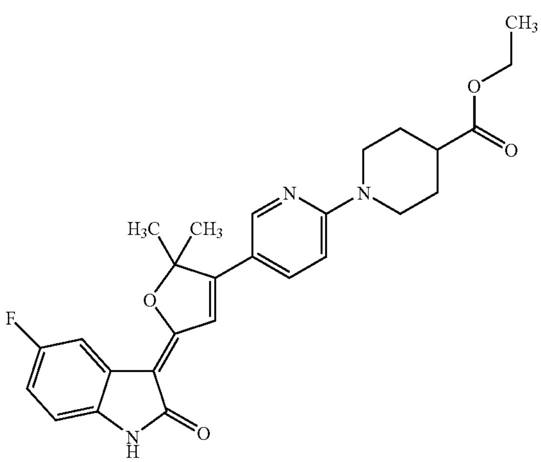 [SMILES: CCOC(=O)C1CCN(c2ccc(C3=C/C(=C4\C(=O)Nc5ccc(F)cc54)OC3(C)C)cn2)CC1] | ethyl 1-{5-[(5E)-5-(5-fluoro-2-oxo-1,2-dihydro-3H-indol-3-ylidene)-2,2-dimethyl-2,5-dihydrofuran-3-yl]pyridin-2-yl}piperidine-4-carboxylate | 477.5332 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 413 | 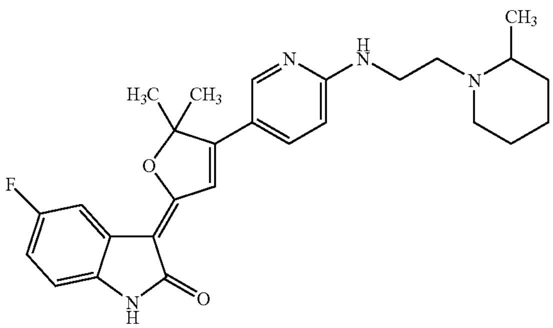 [SMILES: CC1CCCCN1CCNc1ccc(C2=C/C(=C3\C(=O)Nc4ccc(F)cc43)OC2(C)C)cn1] | (3E)-3-[5,5-dimethyl-4-(6-{[2-(2-methylpiperidin-1-yl)ethyl]amino}pyridin-3-yl)furan-2(5H)-ylidene]-5-fluoro-1,3-dihydro-2H-indol-2-one | 462.5659 |
| 414 | Chiral | ({[(2S,4R)-1-{5-[(5E)-5-(5-fluoro-2-oxo-1,2-dihydro-3H-indol-3-ylidene)-2,2-dimethyl-2,5-dihydrofuran-3-yl]pyridin-2-yl}-4-hydroxypyrrolidin-2-yl]carbonyl}amino)acetic acid | 508.5035 |
| 415 | 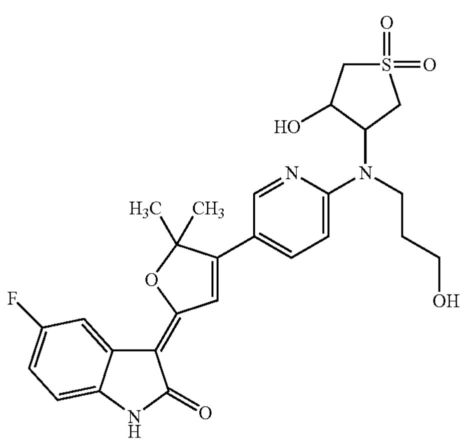 [SMILES: CC1(C)O/C(=C2/C(=O)Nc3ccc(F)cc32)C=C1c1ccc(N(CCCO)C2CS(=O)(=O)CC2O)nc1] | (3E)-5-fluoro-3-[4-{6-[(4-hydroxy-1,1-dioxidotetrahydro-3-thienyl)(3-hydroxypropyl)amino]pyridin-3-yl}-5,5-dimethylfuran-2(5H)-ylidene]-1,3-dihydro-2H-indol-2-one | 529.5862 |
| 416 | Chiral | (3E)-3-[5,5-dimethyl-4-(6-{[(2S)-pyrrolidin-2-ylmethyl]amino}pyridin-3-yl)furan-2(5H)-ylidene]-5-fluoro-1,3-dihydro-2H-indol-2-one | 420.4855 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 417 | 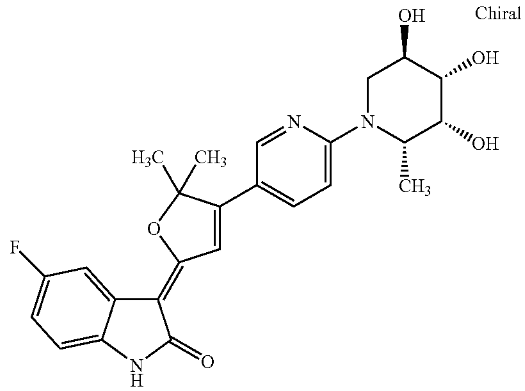 [SMILES: C[C@H]1[C@@H](O)[C@@H](O)[C@H](O)CN1c1ccc(C2=C/C(=C3\C(=O)Nc4ccc(F)cc43)OC2(C)C)cn1] | (3E)-3-[5,5-dimethyl-4-{6-[(2S,3R,4S,5R)-3,4,5-trihydroxy-2-methylpiperidin-1-yl]pyridin-3-yl}furan-2(5H)-ylidene]-5-fluoro-1,3-dihydro-2H-indol-2-one | 467.4944 |
| 418 | 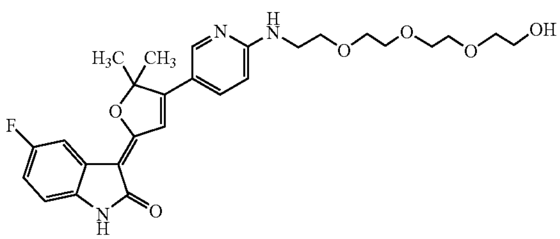 [SMILES: CC1(C)O/C(=C2/C(=O)Nc3ccc(F)cc32)C=C1c1ccc(NCCOCCOCCOCCO)nc1] | (3E)-5-fluoro-3-[4-{6-[(2-{2-[2-(2-hydroxyethoxy)ethoxy]ethoxy}ethyl)amino]pyridin-3-yl}-5,5-dimethylfuran-2(5H)-ylidene]-1,3-dihydro-2H-indol-2-one | 513.5628 |
| 419 | 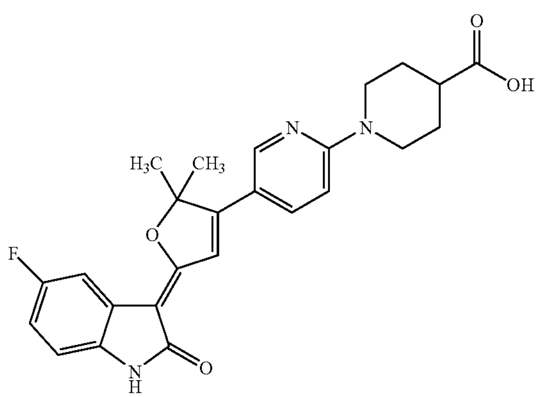 [SMILES: CC1(C)O/C(=C2/C(=O)Nc3ccc(F)cc32)C=C1c1ccc(N2CCC(C(=O)O)CC2)nc1] | 1-{5-[(5E)-5-(5-fluoro-2-oxo-1,2-dihydro-3H-indol-3-ylidene)-2,2-dimethyl-2,5-dihydrofuran-3-yl]pyridin-2-yl}piperidine-4-carboxylic acid | 449.4796 |
| 420 | 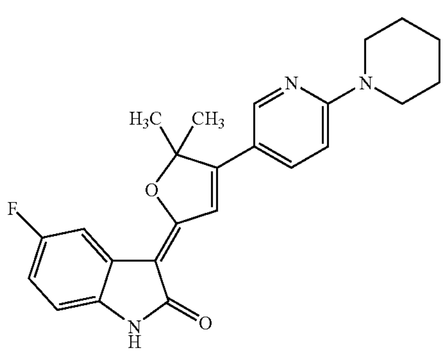 [SMILES: CC1(C)O/C(=C2/C(=O)Nc3ccc(F)cc32)C=C1c1ccc(N2CCCCC2)nc1] | (3E)-3-[5,5-dimethyl-4-(6-piperidin-1-ylpyridin-3-yl)furan-2(5H)-ylidene]-5-fluoro-1,3-dihydro-2H-indol-2-one | 405.4706 |

TABLE 7-continued

[5,5-dimethyl-5H-furan-(2E)-ylidene]-1,3-dihydro-indol-2-one pyridin-3-yl derivatives

| Example # | Chemical Structure | Chemical Name | FW |
|---|---|---|---|
| 421 | 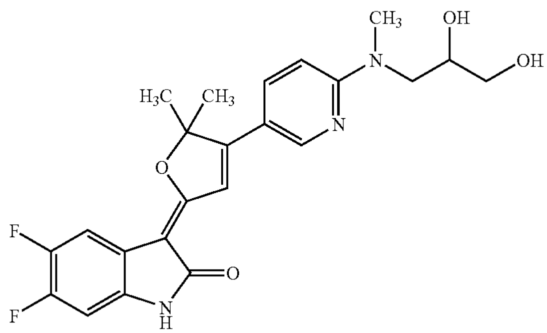 [SMILES: CN(CC(O)CO)c1ccc(C2=C/C(=C3\C(=O)Nc4cc(F)c(F)cc43)OC2(C)C)cn1] | (3E)-3-[4-{6-[(2,3-dihydroxypropyl)(methyl)amino]pyridin-3-yl}-5,5-dimethylfuran-2(5H)-ylidene]-5,6-difluoro-1,3-dihydro-2H-indol-2-one | 443.4477 |

TABLE 8

[5,5-dimethyl-5H-furan-(2E)-ylidene]-1,3-dihydro-indol-2-one pyridin-4-yl derivatives

| Example # | Chemical Structure | Chemical Name | FW |
|---|---|---|---|
| 422 | 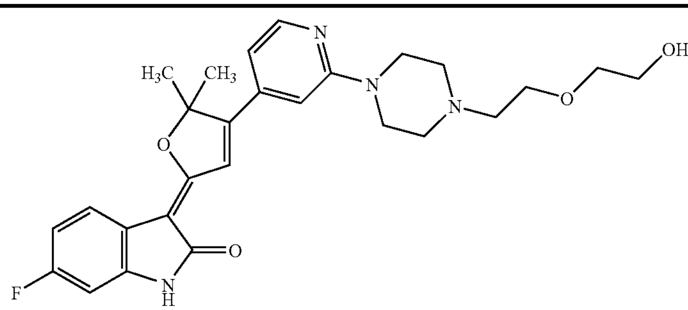 | (3E)-6-fluoro-3-[4-(2-{4-[2-(2-hydroxyethoxy)ethyl]piperazin-1-yl}pyridin-4-yl)-5,5-dimethylfuran-2(5H)-ylidene]-1,3-dihydro-2H-indol-2-one | 494.5639 |
| 423 | 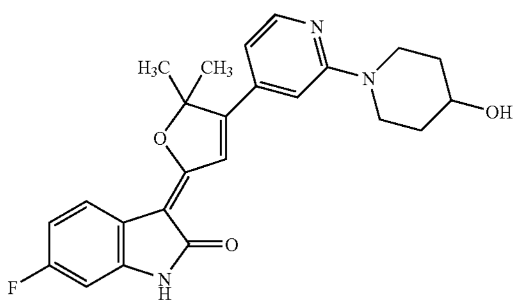 [SMILES: CC1(C)O/C(=C2/C(=O)Nc3cc(F)ccc32)C=C1c1ccnc(N2CCC(O)CC2)c1] | (3E)-6-fluoro-3-{4-[2-(4-hydroxypiperidin-1-yl)pyridin-4-yl]-5,5-dimethylfuran-2(5H)-ylidene}-1,3-dihydro-2H-indol-2-one | 421.4696 |
| 424 | 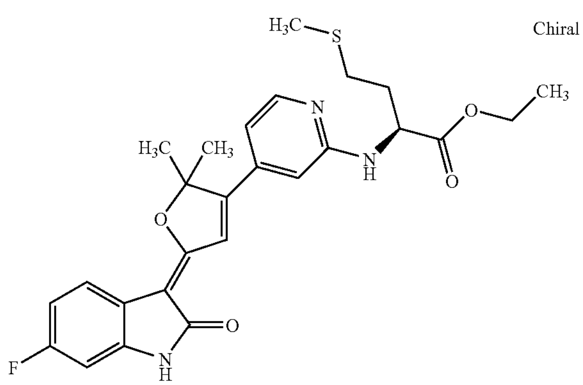 [SMILES: CCOC(=O)[C@H](CCSC)Nc1cc(C2=C/C(=C3\C(=O)Nc4cc(F)ccc43)OC2(C)C)ccn1] | ethyl (2S)-2-({4-[(5E)-5-(6-fluoro-2-oxo-1,2-dihydro-3H-indol-3-ylidene)-2,2-dimethyl-2,5-dihydrofuran-3-yl]pyridin-2-yl}amino)-4-(methylthio)butanoate | 497.5882 |

TABLE 8-continued

[5,5-dimethyl-5H-furan-(2E)-ylidene]-1,3-dihydro-indol-2-one pyridin-4-yl derivatives

| Example # | Chemical Structure | Chemical Name | FW |
|---|---|---|---|
| 425 | 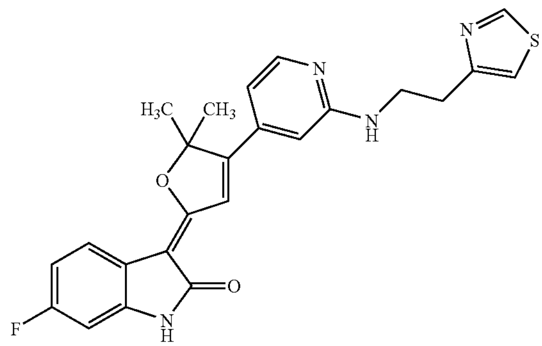 [SMILES: CC1(C)O/C(=C2/C(=O)Nc3cc(F)ccc32)C=C1c1ccnc(NCCc2cscn2)c1] | (3E)-3-[5,5-dimethyl-4-(2-{[2-(1,3-thiazol-4-yl)ethyl]amino}pyridin-4-yl)furan-2(5H)-ylidene]-6-fluoro-1,3-dihydro-2H-indol-2-one | 448.5199 |
| 426 | 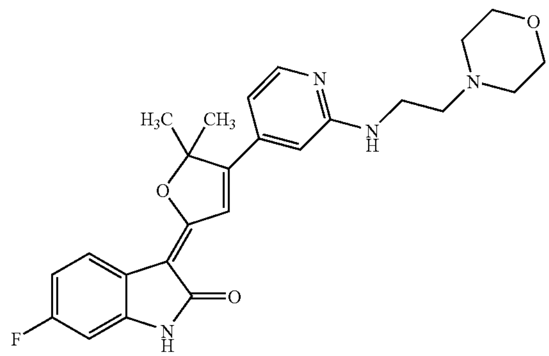 [SMILES: CC1(C)O/C(=C2/C(=O)Nc3cc(F)ccc32)C=C1c1ccnc(NCCN2CCOCC2)c1] | (3E)-3-[5,5-dimethyl-4-{2-[(2-morpholin-4-ylethyl)amino]pyridin-4-yl}furan-2(5H)-ylidene]-6-fluoro-1,3-dihydro-2H-indol-2-one | 450.5113 |
| 427 | 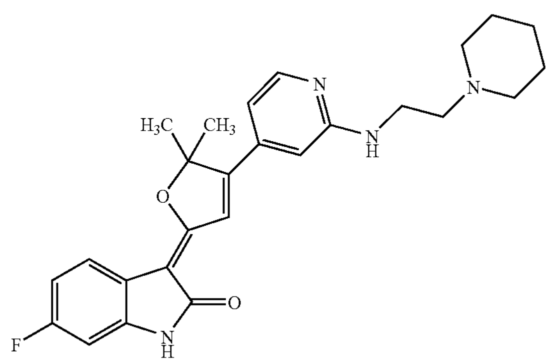 [SMILES: CC1(C)O/C(=C2/C(=O)Nc3cc(F)ccc32)C=C1c1ccnc(NCCN2CCCCC2)c1] | (3E)-3-[5,5-dimethyl-4-{2-[(2-piperidin-1-ylethyl)amino]pyridin-4-yl}furan-2(5H)-ylidene]-6-fluoro-1,3-dihydro-2H-indol-2-one | 448.5391 |
| 428 | 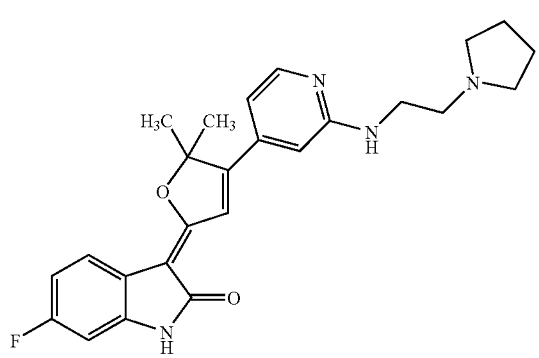 [SMILES: CC1(C)O/C(=C2/C(=O)Nc3cc(F)ccc32)C=C1c1ccnc(NCCN2CCCC2)c1] | (3E)-3-[5,5-dimethyl-4-{2-[(2-pyrrolidin-1-ylethyl)amino]pyridin-4-yl}furan-2(5H)-ylidene]-6-fluoro-1,3-dihydro-2H-indol-2-one | 434.5123 |

TABLE 8-continued

[5,5-dimethyl-5H-furan-(2E)-ylidene]-1,3-dihydro-indol-2-one pyridin-4-yl derivatives

| Example # | Chemical Structure | Chemical Name | FW |
|---|---|---|---|
| 429 | 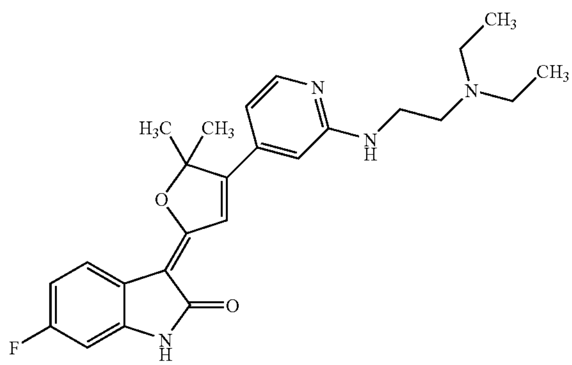 [SMILES: CCN(CC)CCNc1cc(C2=C/C(=C3\C(=O)Nc4cc(F)ccc43)OC2(C)C)ccn1] | (3E)-3-[4-(2-{[2-(diethylamino)ethyl]amino}pyridin-4-yl)-5,5-dimethylfuran-2(5H)-ylidene]-6-fluoro-1,3-dihydro-2H-indol-2-one | 436.5281 |
| 430 | 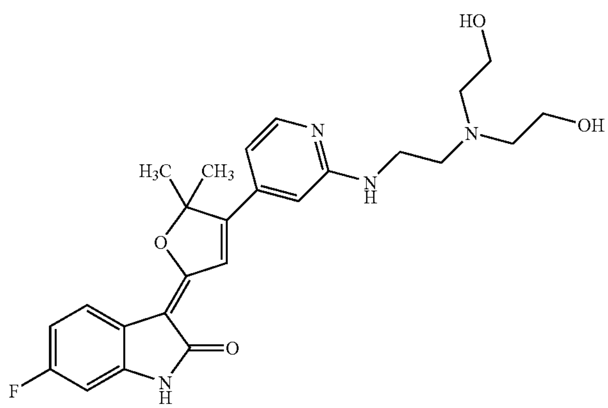 [SMILES: CC1(C)O/C(=C2/C(=O)Nc3cc(F)ccc32)C=C1c1ccnc(NCCN(CCO)CCO)c1] | (3E)-3-{4-[2-({2-[bis(2-hydroxyethyl)amino]ethyl}amino)pyridin-4-yl]-5,5-dimethylfuran-2(5H)-ylidene}-6-fluoro-1,3-dihydro-2H-indol-2-one | 468.5261 |
| 431 | 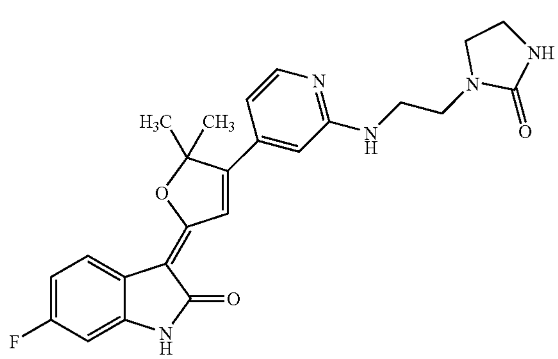 [SMILES: CC1(C)O/C(=C2/C(=O)Nc3cc(F)ccc32)C=C1c1ccnc(NCCN2CCNC2=O)c1] | (3E)-3-[5,5-dimethyl-4-(2-{[2-(2-oxoimidazolidin-1-yl)ethyl]amino}pyridin-4-yl)furan-2(5H)-ylidene]-6-fluoro-1,3-dihydro-2H-indol-2-one | 449.4836 |
| 432 | 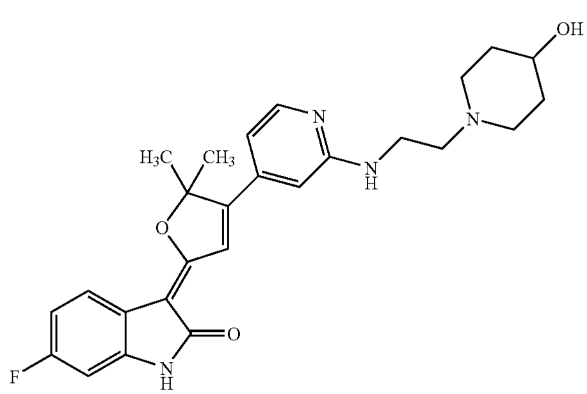 [SMILES: CC1(C)O/C(=C2/C(=O)Nc3cc(F)ccc32)C=C1c1ccnc(NCCN2CCC(O)CC2)c1] | (3E)-6-fluoro-3-[4-(2-{[2-(4-hydroxypiperidin-1-yl)ethyl]amino}pyridin-4-yl)-5,5-dimethylfuran-2(5H)-ylidene]-1,3-dihydro-2H-indol-2-one | 464.5381 |

TABLE 8-continued

[5,5-dimethyl-5H-furan-(2E)-ylidene]-1,3-dihydro-indol-2-one pyridin-4-yl derivatives

| Example # | Chemical Structure | Chemical Name | FW |
|---|---|---|---|
| 433 | 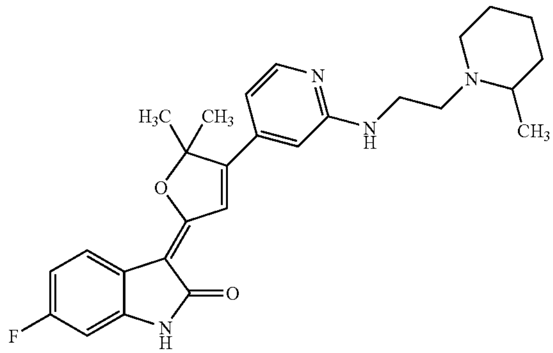 [SMILES: CC1CCCCN1CCNc1cc(C2=C/C(=C3\C(=O)Nc4cc(F)ccc43)OC2(C)C)ccn1] | (3E)-3-[5,5-dimethyl-4-(2-{[2-(2-methylpiperidin-1-yl)ethyl]amino}pyridin-4-yl)furan-2(5H)-ylidene]-6-fluoro-1,3-dihydro-2H-indol-2-one | 462.5659 |
| 434 | 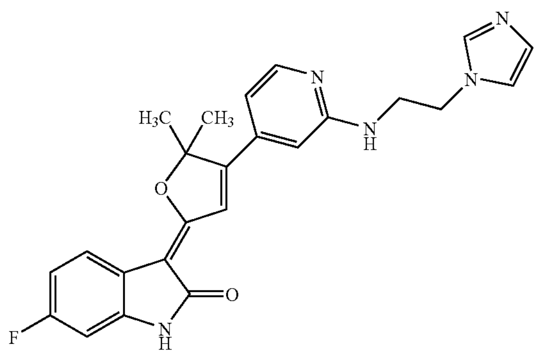 [SMILES: CC1(C)O/C(=C2/C(=O)Nc3cc(F)ccc32)C=C1c1ccnc(NCCn2ccnc2)c1] | (3E)-6-fluoro-3-[4-(2-{[2-(1H-imidazol-1-yl)ethyl]amino}pyridin-4-yl)-5,5-dimethylfuran-2(5H)-ylidene]-1,3-dihydro-2H-indol-2-one | 431.4688 |
| 435 | 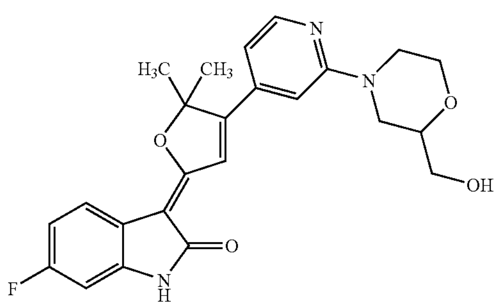 [SMILES: CC1(C)O/C(=C2/C(=O)Nc3cc(F)ccc32)C=C1c1ccnc(N2CCOC(CO)C2)c1] | (3E)-6-fluoro-3-[4-{2-[2-(hydroxymethyl)morpholin-4-yl]pyridin-4-yl}-5,5-dimethylfuran-2(5H)-ylidene]-1,3-dihydro-2H-indol-2-one | 437.4686 |
| 436 | 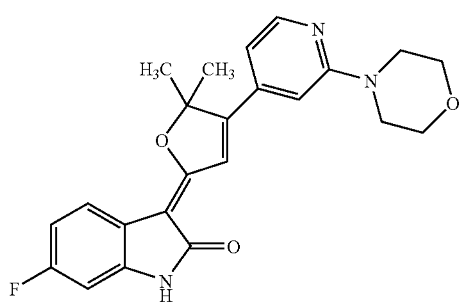 | (3E)-3-[5,5-dimethyl-4-(2-morpholin-4-ylpyridin-4-yl)furan-2(5H)-ylidene]-6-fluoro-1,3-dihydro-2H-indol-2-one | 407.4428 |

TABLE 8-continued

[5,5-dimethyl-5H-furan-(2E)-ylidene]-1,3-dihydro-indol-2-one pyridin-4-yl derivatives

| Example # | Chemical Structure | Chemical Name | FW |
|---|---|---|---|
| 437 | 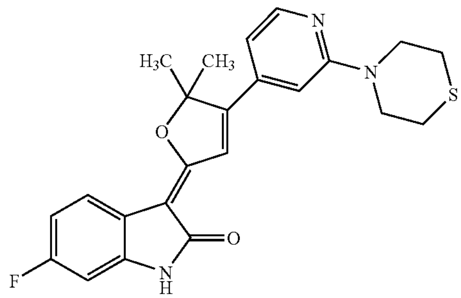 [SMILES: CC1(C)O/C(=C2/C(=O)Nc3cc(F)ccc32)C=C1c1ccnc(N2CCOCC2)c1] | (3E)-3-[5,5-dimethyl-4-(2-thiomorpholin-4-ylpyridin-4-yl)furan-2(5H)-ylidene]-6-fluoro-1,3-dihydro-2H-indol-2-one | 423.5098 |
| 438 | 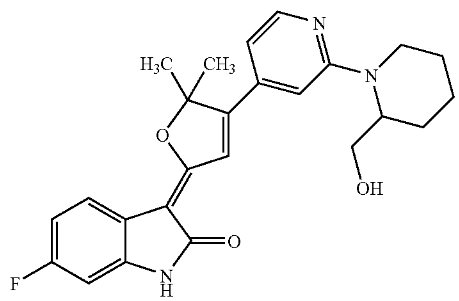 [SMILES: CC1(C)O/C(=C2/C(=O)Nc3cc(F)ccc32)C=C1c1ccnc(N2CCCCC2CO)c1] | (3E)-6-fluoro-3-[4-{2-[2-(hydroxymethyl)piperidin-1-yl]pyridin-4-yl}-5,5-dimethylfuran-2(5H)-ylidene]-1,3-dihydro-2H-indol-2-one | 435.4964 |
| 439 | 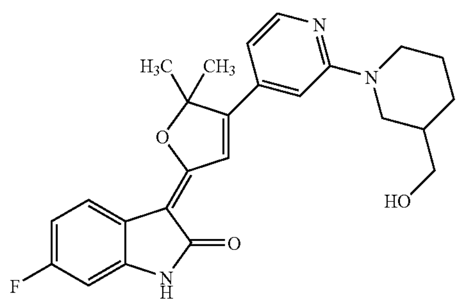 | (3E)-6-fluoro-3-[4-{2-[3-(hydroxymethyl)piperidin-1-yl]pyridin-4-yl}-5,5-dimethylfuran-2(5H)-ylidene]-1,3-dihydro-2H-indol-2-one | 435.4964 |
| 440 | 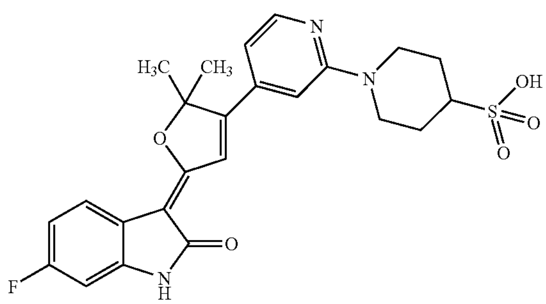 [SMILES: CC1(C)O/C(=C2/C(=O)Nc3cc(F)ccc32)C=C1c1ccnc(N2CCC(S(=O)(=O)O)CC2)c1] | 1-{4-[(5E)-5-(6-fluoro-2-oxo-1,2-dihydro-3H-indol-3-ylidene)-2,2-dimethyl-2,5-dihydrofuran-3-yl]pyridin-2-yl}piperidine-4-sulfonic acid | 485.5336 |
| 441 | 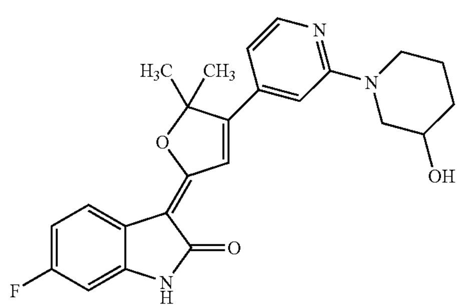 [SMILES: CC1(C)O/C(=C2/C(=O)Nc3cc(F)ccc32)C=C1c1ccnc(N2CCCC(O)C2)c1] | (3E)-6-fluoro-3-{4-[2-(3-hydroxypiperidin-1-yl)pyridin-4-yl]-5,5-dimethylfuran-2(5H)-ylidene}-1,3-dihydro-2H-indol-2-one | 421.4696 |

TABLE 8-continued

[5,5-dimethyl-5H-furan-(2E)-ylidene]-1,3-dihydro-indol-2-one pyridin-4-yl derivatives

| Example # | Chemical Structure | Chemical Name | FW |
|---|---|---|---|
| 442 | 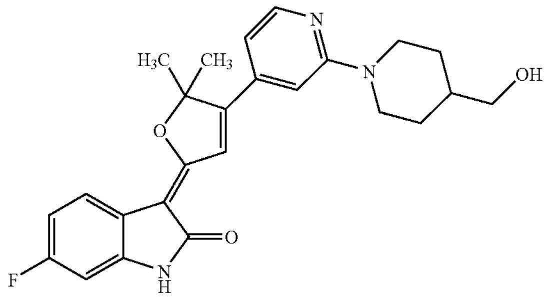 [SMILES: CC1(C)O/C(=C2/C(=O)Nc3cc(F)ccc32)C=C1c1ccnc(N2CCC(CO)CC2)c1] | (3E)-6-fluoro-3-[4-{2-[4-(hydroxymethyl)piperidin-1-yl]pyridin-4-yl}-5,5-dimethylfuran-2(5H)-ylidene]-1,3-dihydro-2H-indol-2-one | 435.4964 |
| 443 | 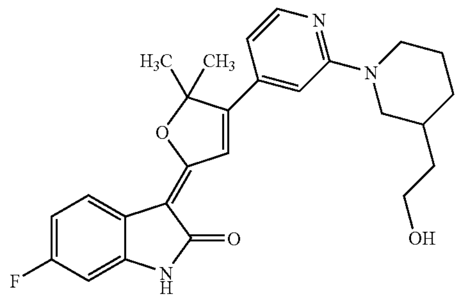 [SMILES: CC1(C)O/C(=C2/C(=O)Nc3cc(F)ccc32)C=C1c1ccnc(N2CCCC(CCO)C2)c1] | (3E)-6-fluoro-3-[4-{2-[3-(2-hydroxyethyl)piperidin-1-yl]pyridin-4-yl}-5,5-dimethylfuran-2(5H)-ylidene]-1,3-dihydro-2H-indol-2-one | 449.5232 |
| 444 | 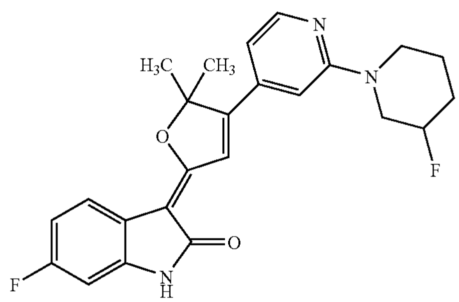 [SMILES: CC1(C)O/C(=C2/C(=O)Nc3cc(F)ccc32)C=C1c1ccnc(N2CCCC(F)C2)c1] | (3E)-6-fluoro-3-{4-[2-(3-fluoropiperidin-1-yl)pyridin-4-yl]-5,5-dimethylfuran-2(5H)-ylidene}-1,3-dihydro-2H-indol-2-one | 423.4607 |
| 445 | 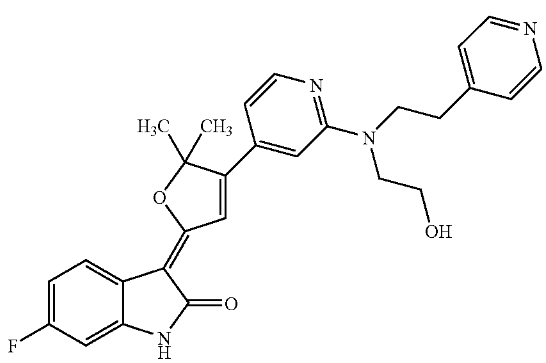 [SMILES: CC1(C)O/C(=C2/C(=O)Nc3cc(F)ccc32)C=C1c1ccnc(N(CCO)CCc2ccncc2)c1] | (3E)-6-fluoro-3-[4-{2-[(2-hydroxyethyl)(2-pyridin-4-ylethyl)amino]pyridin-4-yl}-5,5-dimethylfuran-2(5H)-ylidene]-1,3-dihydro-2H-indol-2-one | 486.5443 |
| 446 | 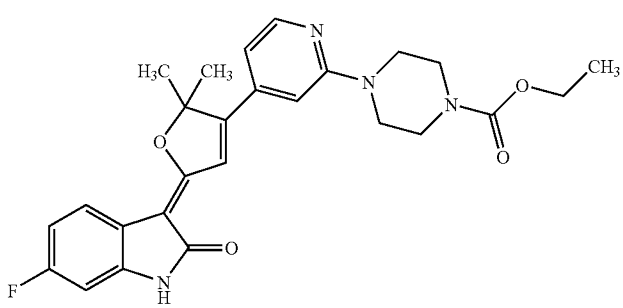 [SMILES: CCOC(=O)N1CCN(c2cc(C3=C/C(=C4\C(=O)Nc5cc(F)ccc54)OC3(C)C)ccn2)CC1] | ethyl 4-{4-[(5E)-5-(6-fluoro-2-oxo-1,2-dihydro-3H-indol-3-ylidene)-2,2-dimethyl-2,5-dihydrofuran-3-yl]pyridin-2-yl}piperazine-1-carboxylate | 478.5213 |

TABLE 8-continued

[5,5-dimethyl-5H-furan-(2E)-ylidene]-1,3-dihydro-indol-2-one pyridin-4-yl derivatives

| Example # | Chemical Structure | Chemical Name | FW |
|---|---|---|---|
| 447 | 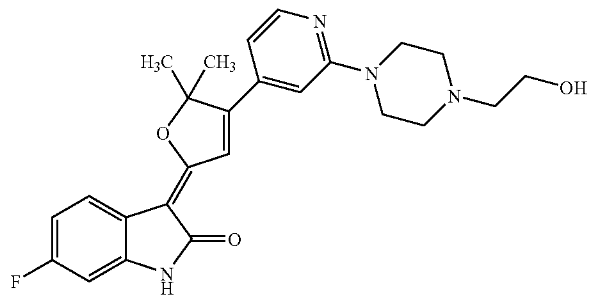 [SMILES: CC1(C)O/C(=C2/C(=O)Nc3cc(F)ccc32)C=C1c1ccnc(N2CCN(CCO)CC2)c1] | (3E)-6-fluoro-3-[4-{2-[4-(2-hydroxyethyl)piperazin-1-yl]pyridin-4-yl}-5,5-dimethylfuran-2(5H)-ylidene]-1,3-dihydro-2H-indol-2-one | 450.5113 |
| 448 | 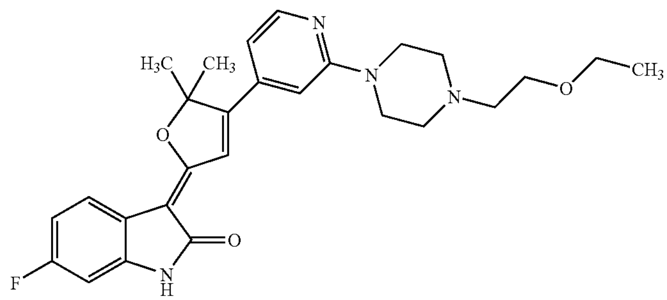 [SMILES: CCOCCN1CCN(c2cc(C3=C/C(=C4\C(=O)Nc5cc(F)ccc54)OC3(C)C)ccn2)CC1] | (3E)-3-[4-{2-[4-(2-ethoxyethyl)piperazin-1-yl]pyridin-4-yl}-5,5-dimethylfuran-2(5H)-ylidene]-6-fluoro-1,3-dihydro-2H-indol-2-one | 478.5649 |
| 449 | 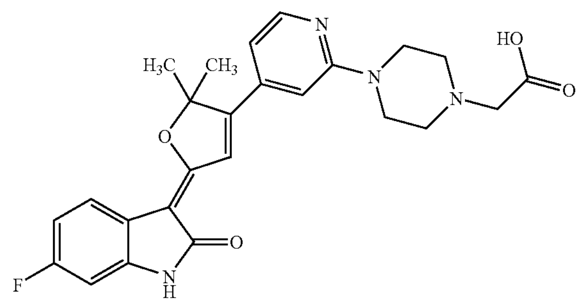 [SMILES: CC1(C)O/C(=C2/C(=O)Nc3cc(F)ccc32)C=C1c1ccnc(N2CCN(CC(=O)O)CC2)c1] | (4-{4-[(5E)-5-(6-fluoro-2-oxo-1,2-dihydro-3H-indol-3-ylidene)-2,2-dimethyl-2,5-dihydrofuran-3-yl]pyridin-2-yl}piperazin-1-yl)acetic acid | 464.4945 |
| 450 | 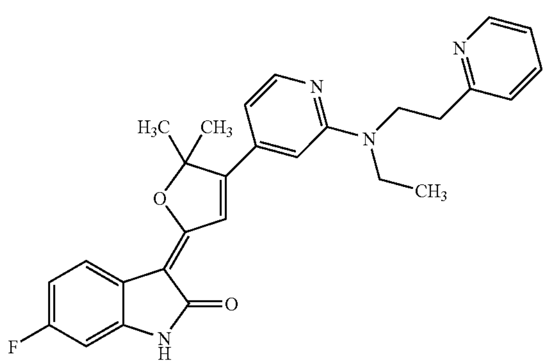 [SMILES: CCN(CCc1ccccn1)c1cc(C2=C/C(=C3\C(=O)Nc4cc(F)ccc43)OC2(C)C)ccn1] | (3E)-3-[4-{2-[ethyl(2-pyridin-2-ylethyl)amino]pyridin-4-yl}-5,5-dimethylfuran-2(5H)-ylidene]-6-fluoro-1,3-dihydro-2H-indol-2-one | 470.5453 |
| 451 | 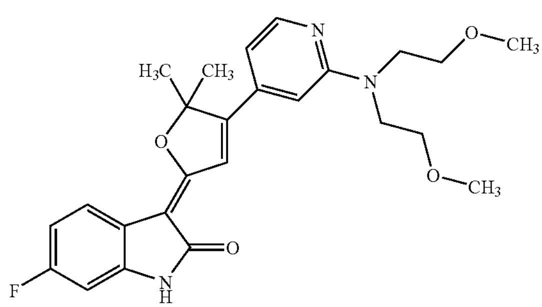 [SMILES: COCCN(CCOC)c1cc(C2=C/C(=C3\C(=O)Nc4cc(F)ccc43)OC2(C)C)ccn1] | (3E)-3-[4-{2-[bis(2-methoxyethyl)amino]pyridin-4-yl}-5,5-dimethylfuran-2(5H)-ylidene]-6-fluoro-1,3-dihydro-2H-indol-2-one | 453.5112 |

TABLE 8-continued

[5,5-dimethyl-5H-furan-(2E)-ylidene]-1,3-dihydro-indol-2-one pyridin-4-yl derivatives

| Example # | Chemical Structure | Chemical Name | FW |
|---|---|---|---|
| 452 | 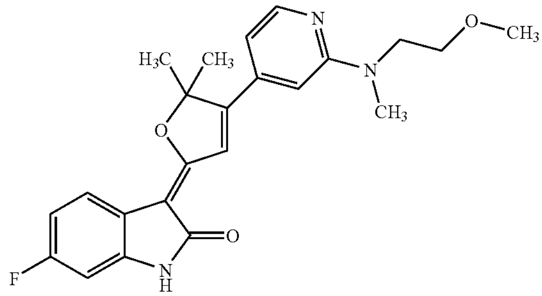 [SMILES: COCCN(C)c1cc(C2=C/C(=C3\C(=O)Nc4cc(F)ccc43)OC2(C)C)ccn1] | (3E)-6-fluoro-3-[4-{2-[(2-methoxyethyl)(methyl)amino]pyridin-4-yl}-5,5-dimethylfuran-2(5H)-ylidene]-1,3-dihydro-2H-indol-2-one | 409.4586 |
| 453 | 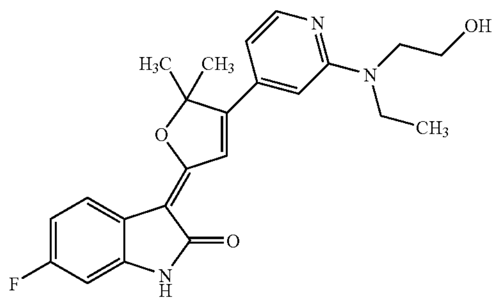 [SMILES: CCN(CCO)c1cc(C2=C/C(=C3\C(=O)Nc4cc(F)ccc43)OC2(C)C)ccn1] | (3E)-3-[4-{2-[ethyl(2-hydroxyethyl)amino]pyridin-4-yl}-5,5-dimethylfuran-2(5H)-ylidene]-6-fluoro-1,3-dihydro-2H-indol-2-one | 409.4586 |
| 454 | 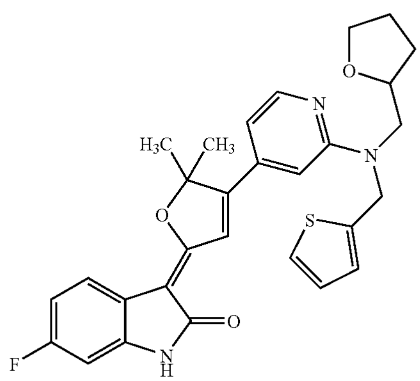 [SMILES: CC1(C)O/C(=C2/C(=O)Nc3cc(F)ccc32)C=C1c1ccnc(N(Cc2cccs2)CC2CCCO2)c1] | (3E)-3-[5,5-dimethyl-4-{2-[(tetrahydrofuran-2-ylmethyl)(2-thienylmethyl)amino]pyridin-4-yl}furan-2(5H)-ylidene]-6-fluoro-1,3-dihydro-2H-indol-2-one | 517.6222 |

TABLE 9

[5,5-dimethyl-5H-furan-(2E)-ylidene]-1,3-dihydro-indol-2-one thienylmethyl derivatives

| Example# | Chemical Structure | Chemical Name | FW |
|---|---|---|---|
| 455 | 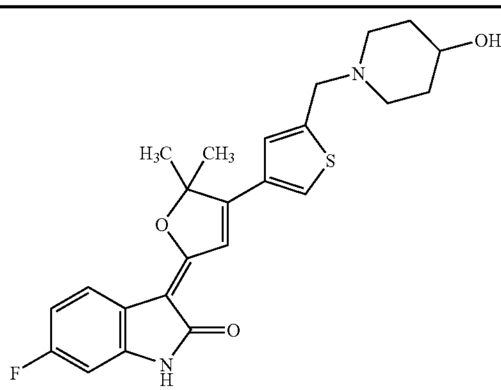 | (3E)-6-fluoro-3-[4-{5-[(4-hydroxypiperidin-1-yl)methyl]-3-thienyl}-5,5-dimethylfuran-2(5H)-ylidene]-1,3-dihydro-2H-indol-2-one | 440.5365 |

TABLE 9-continued

[5,5-dimethyl-5H-furan-(2E)-ylidene]-1,3-dihydro-indol-2-one thienylmethyl derivatives

| Example# | Chemical Structure | Chemical Name | FW |
|---|---|---|---|
| 456 | 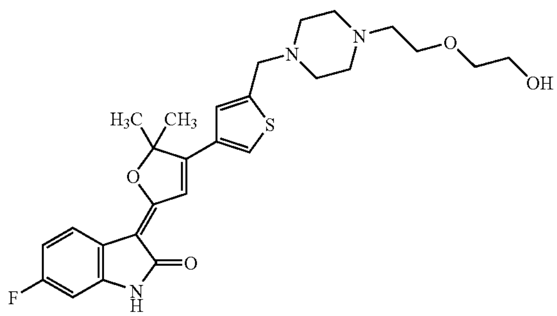 [SMILES: CC1(C)O/C(=C2/C(=O)Nc3cc(F)ccc32)C=C1c1csc(CN2CCN(CCOCCO)CC2)c1] | (3E)-6-fluoro-3-{4-[5-({4-[2-(2-hydroxyethoxy)ethyl]piperazin-1-yl}methyl)-3-thienyl]-5,5-dimethylfuran-2(5H)-ylidene}-1,3-dihydro-2H-indol-2-one | 513.6308 |
| 457 | 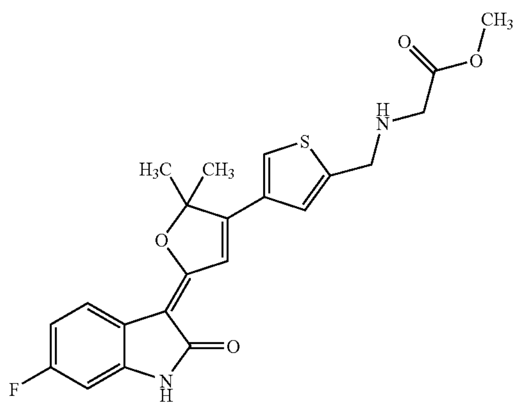 [SMILES: COC(=O)CNCc1cc(C2=C/C(=C3\C(=O)Nc4cc(F)ccc43)OC2(C)C)cs1] | methyl [({4-[(5E)-5-(6-fluoro-2-oxo-1,2-dihydro-3H-indol-3-ylidene)-2,2-dimethyl-2,5-thieny}methyl)amino]acetate | 428.4819 |
| 458 | 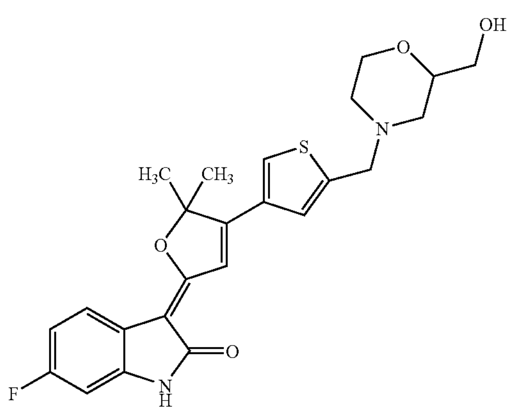 [SMILES: CC1(C)O/C(=C2/C(=O)Nc3cc(F)ccc32)C=C1c1csc(CN2CCOC(CO)C2)c1] | (3E)-6-fluoro-3-[4-(5-{[2-(hydroxymethyl)morpholin-4-yl]methyl}-3-thienyl)-5,5-dimethylfuran-2(5H)-ylidene]-1,3-dihydro-2H-indol-2-one | 456.5355 |
| 459 | 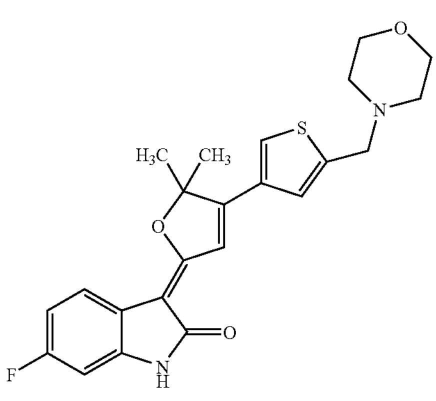 [SMILES: CC1(C)O/C(=C2/C(=O)Nc3cc(F)ccc32)C=C1c1csc(CN2CCOCC2)c1] | (3E)-3-{5,5-dimethyl-4-[5-(morpholin-4-ylmethyl)-3-thienyl]furan-2(5H)-ylidene}-6-fluoro-1,3-dihydro-2H-indol-2-one | 426.5097 |

TABLE 9-continued

[5,5-dimethyl-5H-furan-(2E)-ylidene]-1,3-dihydro-indol-2-one thienylmethyl derivatives

| Example# | Chemical Structure | Chemical Name | FW |
|---|---|---|---|
| 460 | 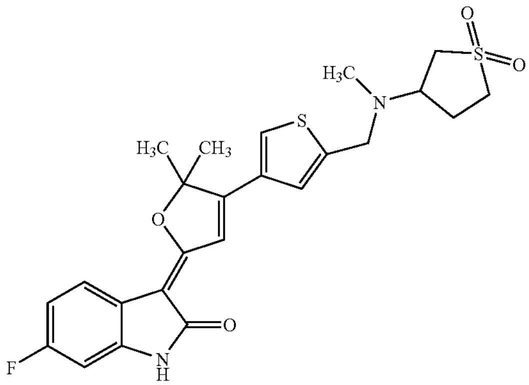 [SMILES: CN(Cc1cc(C2=C/C(=C3\C(=O)Nc4cc(F)ccc43)OC2(C)C)cs1)C1CCS(=O)(=O)C1] | (3E)-3-[4-(5-{[(1,1-dioxidotetrahydro-3-thienyl)(methyl)amino]methyl}-3-thienyl)-5,5-dimethylfuran-2(5H)-ylidene]-6-fluoro-1,3-dihydro-2H-indol-2-one | 488.6015 |
| 461 | 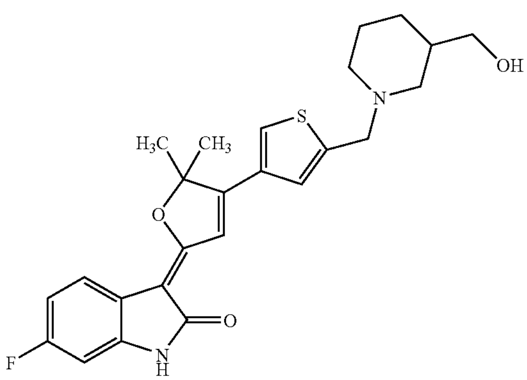 [SMILES: CC1(C)O/C(=C2/C(=O)Nc3cc(F)ccc32)C=C1c1csc(CN2CCCC(CO)C2)c1] | (3E)-6-fluoro-3-[4-(5-{[3-(hydroxymethyl)piperidin-1-yl]methyl}-3-thienyl)-5,5-dimethylfuran-2(5H)-ylidene]-1,3-dihydro-2H-indol-2-one | 454.5633 |
| 462 | 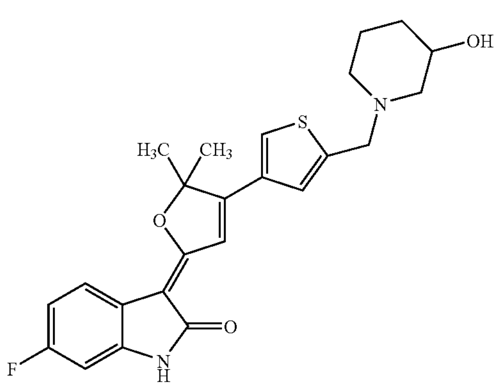 [SMILES: CC1(C)O/C(=C2/C(=O)Nc3cc(F)ccc32)C=C1c1csc(CN2CCCC(O)C2)c1] | (3E)-6-fluoro-3-[4-{5-[(3-hydroxypiperidin-1-yl)methyl]-3-thienyl}-5,5-dimethylfuran-2(5H)-ylidene]-1,3-dihydro-2H-indol-2-one | 440.5365 |

TABLE 9-continued

[5,5-dimethyl-5H-furan-(2E)-ylidene]-1,3-dihydro-indol-2-one thienylmethyl derivatives

| Example# | Chemical Structure | Chemical Name | FW |
|---|---|---|---|
| 463 | 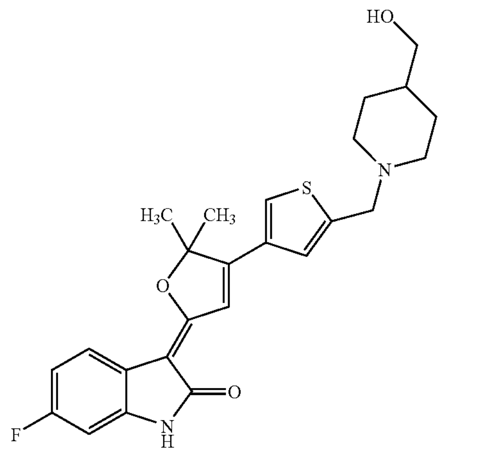 [SMILES: CC1(C)O/C(=C2/C(=O)Nc3cc(F)ccc32)C=C1c1csc(CN2CCC(CO)CC2)c1] | (3E)-6-fluoro-3-[4-(5-{[4-(hydroxymethyl)piperidin-1-yl]methyl}-3-thienyl)-5,5-dimethylfuran-2(5H)-ylidene]-1,3-dihydro-2H-indol-2-one | 454.5633 |
| 464 | 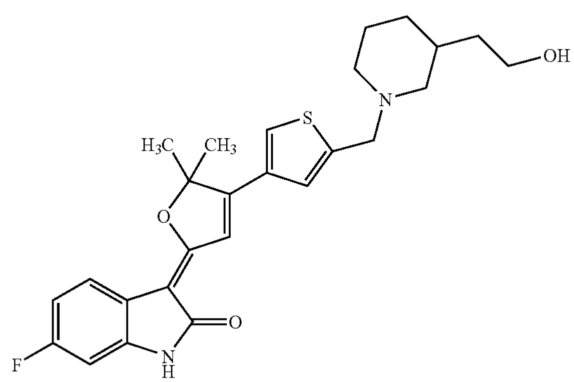 [SMILES: CC1(C)O/C(=C2/C(=O)Nc3cc(F)ccc32)C=C1c1csc(CN2CCCC(CCO)C2)c1] | (3E)-6-fluoro-3-[4-(5-{[3-(2-hydroxyethyl)piperidin-1-yl]methyl}-3-thienyl)-5,5-dimethylfuran-2(5H)-ylidene]-1,3-dihydro-2H-indol-2-one | 468.5901 |
| 465 | 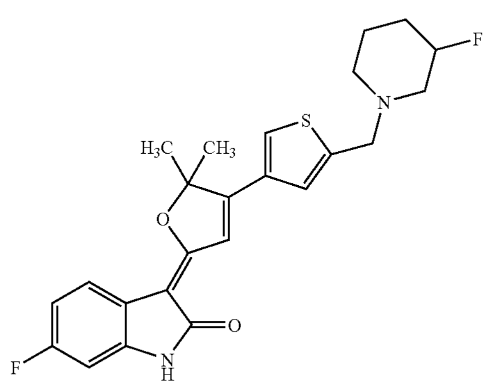 [SMILES: CC1(C)O/C(=C2/C(=O)Nc3cc(F)ccc32)C=C1c1csc(CN2CCCC(F)C2)c1] | (3E)-6-fluoro-3-[4-{5-[(3-fluoropiperidin-1-yl)methyl]-3-thienyl}-5,5-dimethylfuran-2(5H)-ylidene]-1,3-dihydro-2H-indol-2-one | 442.5276 |

TABLE 9-continued

[5,5-dimethyl-5H-furan-(2E)-ylidene]-1,3-dihydro-indol-2-one thienylmethyl derivatives

| Example# | Chemical Structure | Chemical Name | FW |
|---|---|---|---|
| 466 | 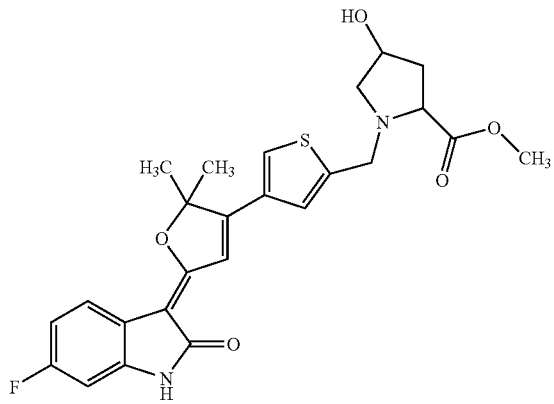 [SMILES: COC(=O)C1CC(O)CN1Cc1cc(C2=C/C(=C3\C(=O)Nc4cc(F)ccc43)OC2(C)C)cs1] | methyl 1-({4-[(5E)-5-(6-fluoro-2-oxo-1,2-dihydro-3H-indol-3-ylidene)-2,2-dimethyl-2,5-dihydrofuran-3-yl]-2-thienyl}methyl)-4-hydroxypyrrolidine-2-carboxylate | 484.5455 |
| 467 | 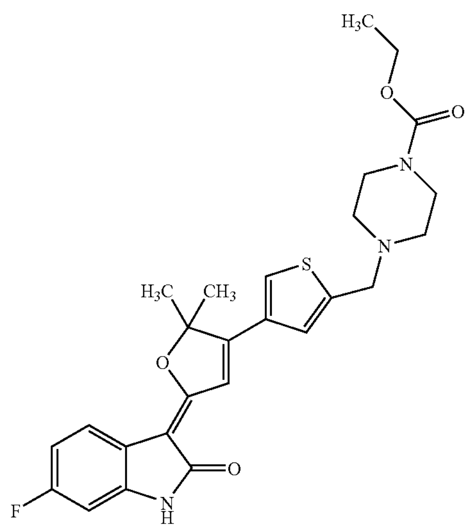 [SMILES: CCOC(=O)N1CCN(Cc2cc(C3=C/C(=C4\C(=O)Nc5cc(F)ccc54)OC3(C)C)cs2)CC1] | ethyl 4-({4-[(5E)-5-(6-fluoro-2-oxo-1,2-dihydro-3H-indol-3-ylidene)-2,2-dimethyl-2,5-dihydrofuran-3-yl]-2-thienyl}methyl)piperazine-1-carboxylate | 497.5882 |
| 468 | 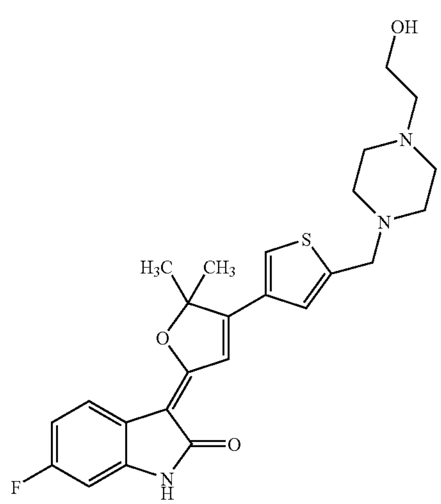 [SMILES: CC1(C)O/C(=C2/C(=O)Nc3cc(F)ccc32)C=C1c1csc(CN2CCN(CCO)CC2)c1] | (3E)-6-fluoro-3-[4-(5-{[4-(2-hydroxyethyl)piperazin-1-yl]methyl}-3-thienyl)-5,5-dimethylfuran-2(5H)-ylidene]-1,3-dihydro-2H-indol-2-one | 469.5782 |

TABLE 9-continued

[5,5-dimethyl-5H-furan-(2E)-ylidene]-1,3-dihydro-indol-2-one thienylmethyl derivatives

| Example# | Chemical Structure | Chemical Name | FW |
|---|---|---|---|
| 469 | 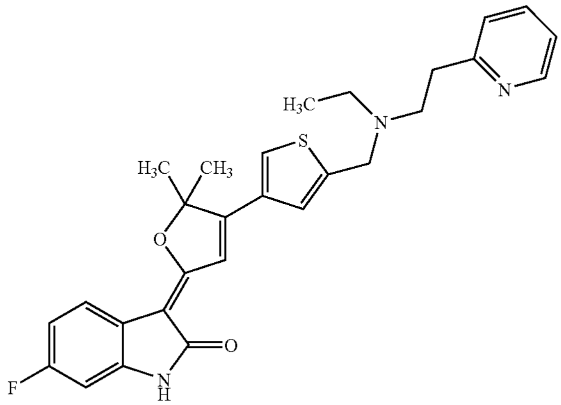 [SMILES: CCN(CCc1ccccn1)Cc1cc(C2=C/C(=C3\C(=O)Nc4cc(F)ccc43)OC2(C)C)cs1] | (3E)-3-[4-(5-{[ethyl(2-pyridin-2-ylethyl)amino]methyl}-3-thienyl)-5,5-dimethylfuran-2(5H)-ylidene]-6-fluoro-1,3-dihydro-2H-indol-2-one | 489.6122 |
| 470 | 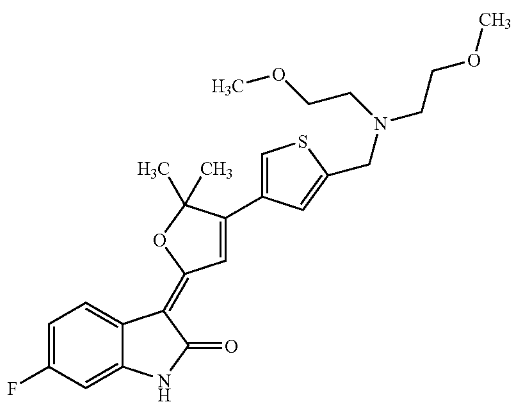 [SMILES: COCCN(CCOC)Cc1cc(C2=C/C(=C3\C(=O)Nc4cc(F)ccc43)OC2(C)C)cs1] | (3E)-3-[4-(5-{[bis(2-methoxyethyl)amino]methyl}-3-thienyl)-5,5-dimethylfuran-2(5H)-ylidene]-6-fluoro-1,3-dihydro-2H-indol-2-one | 472.5781 |
| 471 | 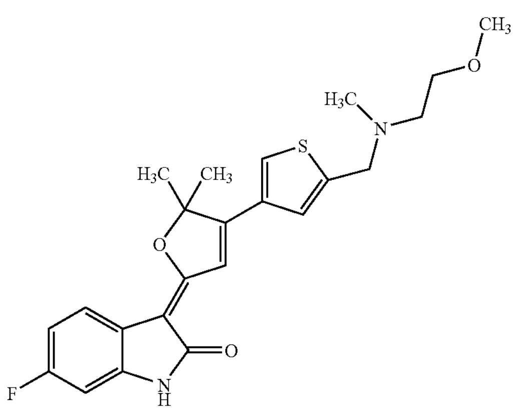 [SMILES: COCCN(C)Cc1cc(C2=C/C(=C3\C(=O)Nc4cc(F)ccc43)OC2(C)C)cs1] | (3E)-6-fluoro-3-[4-(5-{[(2-methoxyethyl)(methyl)amino]methyl}-3-thienyl)-5,5-dimethylfuran-2(5H)-ylidene]-1,3-dihydro-2H-indol-2-one | 428.5255 |
| 472 | 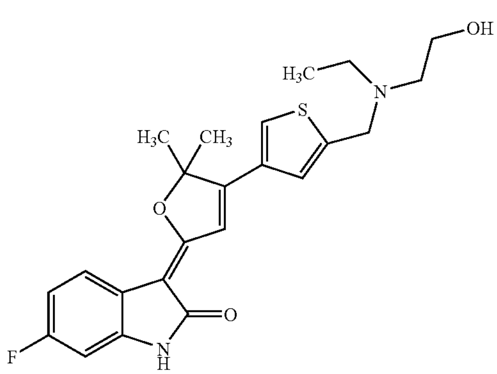 [SMILES: CCN(CCO)Cc1cc(C2=C/C(=C3\C(=O)Nc4cc(F)ccc43)OC2(C)C)cs1] | (3E)-3-[4-(5-{[bis(2-hydroxyethyl)amino]methyl}-3-thienyl)-5,5-dimethylfuran-2(5H)-ylidene]-6-fluoro-1,3-dihydro-2H-indol-2-one | 428.5255 |

TABLE 9-continued

[5,5-dimethyl-5H-furan-(2E)-ylidene]-1,3-dihydro-indol-2-one thienylmethyl derivatives

| Example# | Chemical Structure | Chemical Name | FW |
|---|---|---|---|
| 473 | 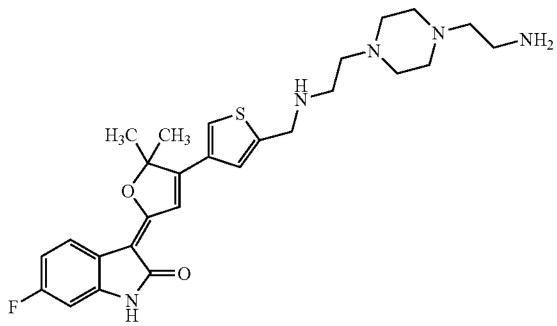 [SMILES: CC1(C)O/C(=C2/C(=O)Nc3cc(F)ccc32)C=C1c1csc(CNCCN2CCN(CCN)CC2)c1] | (3E)-3-[4-{5-[({2-[4-(2-aminoethyl)piperazin-1-yl]ethyl}amino)methyl]-3-thienyl}-5,5-dimethylfuran-2(5H)-ylidene]-6-fluoro-1,3-dihydro-2H-indol-2-one | 511.6626 |
| 474 | 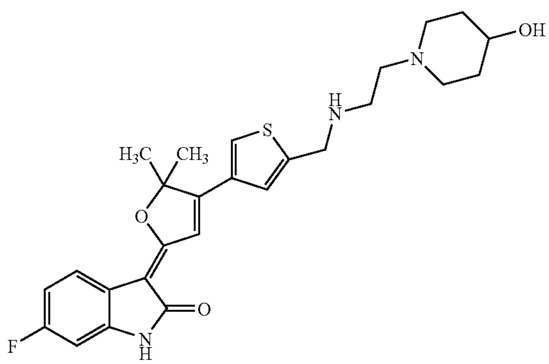 [SMILES: CC1(C)O/C(=C2/C(=O)Nc3cc(F)ccc32)C=C1c1csc(CNCCN2CCC(O)CC2)c1] | (3E)-6-fluoro-3-{4-[5-({[2-(4-hydroxypiperidin-1-yl)ethyl]amino}methyl)-3-thienyl]-5,5-dimethylfuran-2(5H)-ylidene}-1,3-dihydro-2H-indol-2-one | 483.605 |
| 475 | 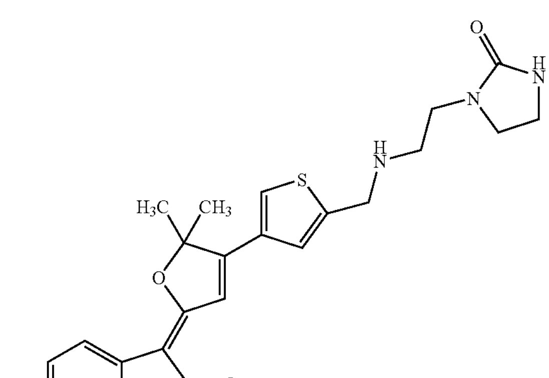 | (3E)-3-{5,5-dimethyl-4-[5-({[2-(2-oxoimidazolidin-1-yl)ethyl]amino}methyl)-3-thienyl]furan-2(5H)-ylidene}-6-fluoro-1,3-dihydro-2H-indol-2-one | 468.5505 |

TABLE 10

[5,5-dimethyl-5H-furan-(2E)-ylidene]-1,3-dihydro-indol-2-one amine derivatives

| Example # | Chemical Name | FW |
|---|---|---|
| 476 | (3E)-6-fluoro-3-{4-[4-(2-hydroxyethyl)piperazin-1-yl]-5,5-dimethylfuran-2(5H)-ylidene}-1,3-dihydro-2H-indol-2-one | 373.4256 |
| 477 | (3E)-3-{4-[(2,4-dimethoxybenzyl)amino]-5,5-dimethylfuran-2(5H)-ylidene}-6-fluoro-1,3-dihydro-2H-indol-2-one | 410.4427 |
| 478 | N-[(5E)-5-(6-fluoro-2-oxo-1,2-dihydro-3H-indol-3-ylidene)-2,2-dimethyl-2,5-dihydrofuran-3-yl]-6-[4-(2-hydroxyethyl)piperazin-1-yl]nicotinamide | 493.5362 |
| 479 | (3E)-6-bromo-3-(5,5-dimethyl-4-morpholin-4-ylfuran-2(5H)-ylidene)-1,3-dihydro-2H-indol-2-one | 391.2631 |
| 480 | (3E)-3-(5,5-dimethyl-4-morpholin-4-ylfuran-2(5H)-ylidene)-6-iodo-1,3-dihydro-2H-indol-2-one | 438.26 |

TABLE 11

[5,5-dimethyl-5H-furan-(2E)-ylidene]-1,3-dihydro-indol-2-one carbonyl derivatives

| Example # | Structure | Chemical Name | FW |
|---|---|---|---|
| 481 | 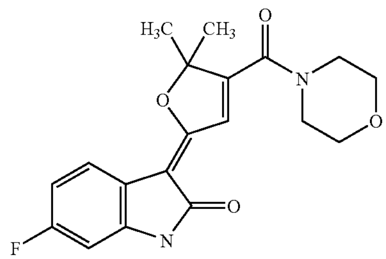 [SMILES: CC1(C)O/C(=C2/C(=O)Nc3cc(F)ccc32)C=C1C(=O)N1CCOCC1] | (3E)-3-[5,5-dimethyl-4-(morpholin-4-ylcarbonyl)furan-2(5H)-ylidene]-6-fluoro-1,3-dihydro-2H-indol-2-one | 358.3671 |
| 482 | 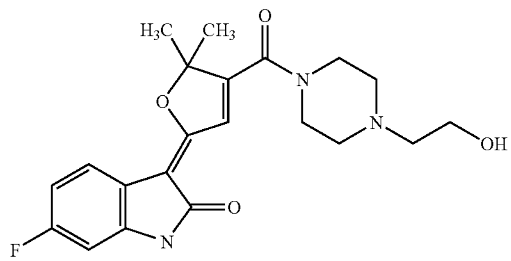 [SMILES: CC1(C)O/C(=C2/C(=O)Nc3cc(F)ccc32)C=C1C(=O)N1CCN(CCO)CC1] | (3E)-6-fluoro-3-[4-{[4-(2-hydroxyethyl)piperazin-1-yl]carbonyl}-5,5-dimethylfuran-2(5H)-ylidene]-1,3-dihydro-2H-indol-2-one | 401.4356 |

TABLE 12

[(3E)-3-(5,5-dimethyl-4-morpholin-4-ylfuran-2(5H)-ylidene)-2-oxo-2,3-dihydro-1H-indol-6-yl]derivatives

| Example # | Chemical Structure | Chemical Name | FW |
|---|---|---|---|
| 483 | 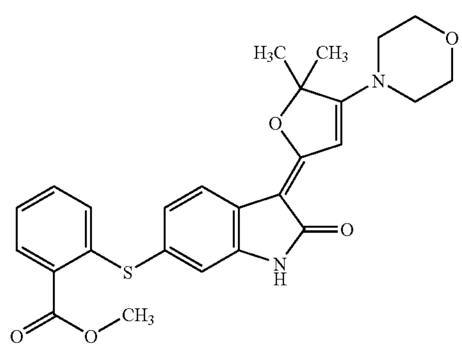 [SMILES: COC(=O)c1ccccc1Sc1ccc2c(c1)NC(=O)/C2=C1\C=C(N2CCOCC2)C(C)(C)O1] | methyl 2-{[(3E)-3-(5,5-dimethyl-4-morpholin-4-ylfuran-2(5H)-ylidene)-2-oxo-2,3-dihydro-1H-indol-6-yl]thio}benzoate | 478.5664 |
| 484 | 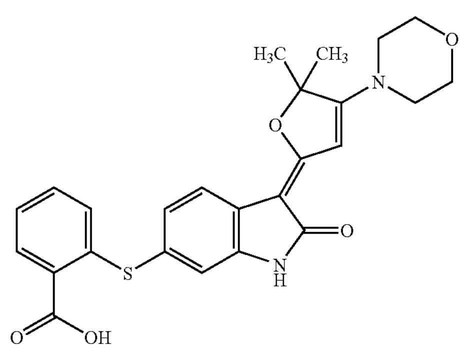 [SMILES: CC1(C)O/C(=C2/C(=O)Nc3cc(Sc4ccccc4C(=O)O)ccc32)C=C1N1CCOCC1] | 2-{[(3E)-3-(5,5-dimethyl-4-morpholin-4-ylfuran-2(5H)-ylidene)-2-oxo-2,3-dihydro-1H-indol-6-yl]thio}benzoic acid | 464.5396 |

TABLE 12-continued

[(3E)-3-(5,5-dimethyl-4-morpholin-4-ylfuran-2(5H)-ylidene)-2-oxo-2,3-dihydro-1H-indol-6-yl]derivatives

| Example # | Chemical Structure | Chemical Name | FW |
|---|---|---|---|
| 485 | 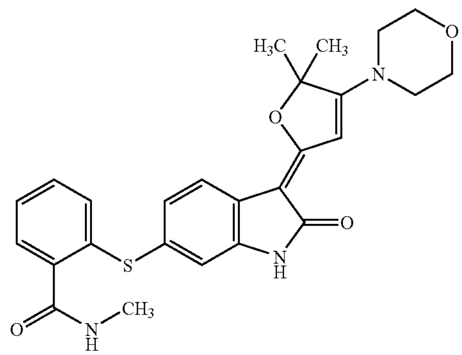 [SMILES: CNC(=O)c1ccccc1Sc1ccc2c(c1)NC(=O)/C2=C1\C=C(N2CCOCC2)C(C)(C)O1] | 2-{[(3E)-3-(5,5-dimethyl-4-morpholin-4-ylfuran-2(5H)-ylidene)-2-oxo-2,3-dihydro-1H-indol-6-yl]thio}-N-methylbenzamide | 477.5823 |
| 486 | 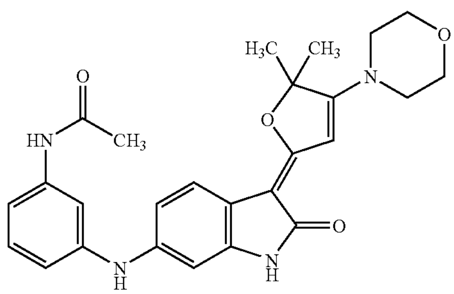 [SMILES: CC(=O)Nc1cccc(Nc2ccc3c(c2)NC(=O)/C3=C2\C=C(N3CCOCC3)C(C)(C)O2)c1] | N-(3-{[(3E)-3-(5,5-dimethyl-4-morpholin-4-ylfuran-2(5H)-ylidene)-2-oxo-2,3-dihydro-1H-indol-6-yl]amino}phenyl)acetamide | 460.5312 |

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"Me" refers to methyl.
"Et" refers to ethyl.
"tBu" refers to t-butyl.
"iPr" refers to i-propyl.
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 2 to 12 carbons. More preferably it is a lower alkenyl of from 2 to 7 carbons, most preferably 2 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 2 to 12 carbons. More preferably it is a lower alkynyl of from 2 to 7 carbons, most preferably 2 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Carbocyclic ring" refers to a cyclic aliphatic ring or an aryl ring wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Heterocyclic ring" refers to an aliphatic ring or heterocyclic aryl wherein one or more of the ring atoms are heteroatoms.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R''' group, wherein R" and R''' are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R'''', where R'''' is aryl, C(CN)=C-aryl, CH$_2$CN, alkyaryl, sulfonamide, NH-alkyl, NH-alkylaryl, or NH-aryl.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

The invention is further illustrated by the following non-limiting examples.

Preparation of 6-Fluoro-3-(4-methoxy-5H-furan-2-ylidene)-1,3-dihydro-indol-2-one

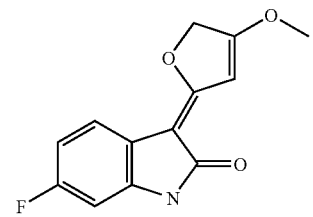 [SMILES: COC1=C/C(=C2\C(=O)Nc3cc(F)ccc32)OC1]

To a stirred solution of 6-fluorooxindole (2.6 g, 17.5 mmol) in anhydrous THF (30 mL) under nitrogen was added 1.0 M LiHMDS/THF solution (35 mL, 35 mmol). The mixture was stirred at room temperature for 10 minutes. Methyl tetronate (1.0 g, 8.8 mmol) was added as one portion. After stirring at room temperature for 1 hour, the reaction was cooled to 0° C., and quenched with 2M HCl until pH=3. The mixture was stirred at room temperature for 2 more hours, and poured into 250 mL of water. The resulting precipitates were filtered, rinsed with water and dried in vacuum to give 6-fluoro-3-(4-methoxy-5H-furan-2-ylidene)-1,3-dihydro-indol-2-one as off-white solid. Yield: 840 mg, 38%.

$^1$H NMR (500 MHz, DMSO-d$_6$) δ ppm 3.99 (s, 3 H) 5.22 (s, 2 H) 6.59 (dd, J=9.52, 2.20 Hz, 1 H) 6.63 (s, 1 H) 6.66-6.72 (m, 1 H) 7.43 (dd, J=8.06, 5.61 Hz, 1 H) 10.32 (s, 1 H)

Preparation of 3-(4-Methoxy-5H-furan-2-ylidene)-1,3-dihydro-indol-2-one

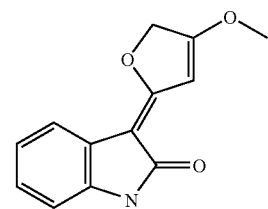 [SMILES: COC1=C/C(=C2\C(=O)Nc3ccccc32)OC1]

$^1$H NMR (500 MHz, DMSO-d$_6$) δ ppm 3.99 (s, 3 H) 5.22 (s, 2 H) 6.67 (s, 1 H) 6.78 (d, J=7.32 Hz, 1 H) 6.88 (t, J=7.32 Hz, 1 H) 6.99 (t, J=7.57 Hz, 1 H) 7.47 (d, J=7.81 Hz, 1 H) 10.17 (s, 1 H)

Example 1

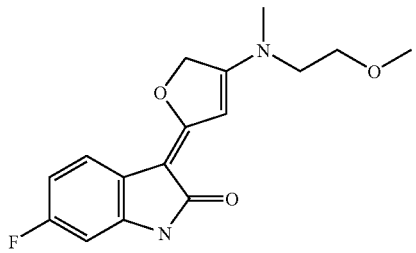 [SMILES: COCCN(C)C1=C/C(=C2\C(=O)Nc3cc(F)ccc32)OC1]

6-Fluoro-3-{4-[(2-methoxy-ethyl)-methyl-amino]-5H-furan-2-ylidene}-1,3-dihydro-indol-2-one

HR MS (ES+): 305.0476 (MH+)
(ES−): 303.1947 (M−H)

Example 2

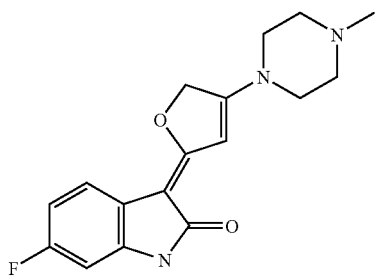 [SMILES: CN1CCN(C2=C/C(=C3\C(=O)Nc4cc(F)ccc43)OC2)CC1]

6-Fluoro-3-[4-(4-methyl-piperazin-1-yl)-5H-furan-2-ylidene]-1,3-dihydro-indol-2-one $^1$H NMR (500 MHz, DMSO-$d_6$) δ ppm 2.22 (s, 3 H) 2.40 (t, J=4.88 Hz, 4 H) 3.32 (br.s., 4 H) 5.33 (s, 2 H) 6.21 (s, 1 H) 6.52 (dd, J=9.76, 2.44 Hz, 1 H) 6.57-6.64 (m, 1 H) 7.33 (dd, J=8.30, 5.86 Hz, 1 H) 10.05 (s, 1 H)
HR MS (ES+): 316.3362 (MH+)

Example 3

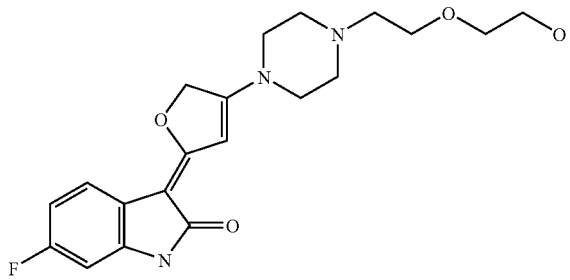 [SMILES: O=C1Nc2cc(F)ccc2/C1=C1/C=C(N2CCN(CCOCCO)CC2)CO1]

6-Fluoro-3-(4-{4-[2-(2-hydroxy-ethoxy)-ethyl]-piperazin-1-yl}-5H-furan-2-ylidene)-1,3-dihydro-indol-2-one $^1$H NMR (500 MHz, DMSO-$d_6$) δ ppm 2.54 (br.s., 6 H) 3.32 (br.s., 4H) 3.41 (t, J=5.37 Hz, 2 H) 3.49 (q, J=4.88 Hz, 2 H) 3.54 (t, J=5.61 Hz, 2 H) 4.59 (t, J=5.13 Hz, 1 H) 5.32 (s, 2 H) 6.20 (s, 1 H) 6.52 (d, J=9.28 Hz, 1 H) 6.60 (t, J=9.52 Hz, 1 H) 7.33 (dd, J=8.06, 6.10 Hz, 1 H) 10.05 (s, 1 H)

Example 4

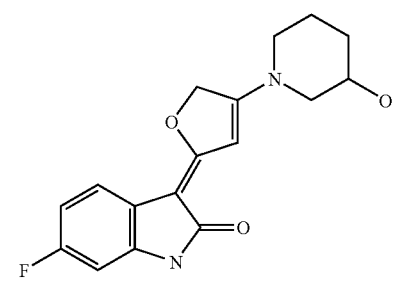 [SMILES: O=C1Nc2cc(F)ccc2/C1=C1/C=C(N2CCCC(O)C2)CO1]

6-Fluoro-3-[4-(3-hydroxy-piperidin-1-yl)-5H-furan-2-ylidene]-1,3-dihydro-indol-2-one $^1$H NMR (500 MHz, DMSO-$d_6$) δ ppm 1.50 (br.s., 2 H) 1.82 (br.s., 2 H) 3.03 (dd, J=12.69, 7.32 Hz, 1 H) 3.10-3.55 (m, 3H) 3.67 (br.s., 1 H) 4.99 (br.s., 1 H) 5.31 (s, 2 H) 6.18 (s, 1 H) 6.52 (dd, J=9.76, 2.44 Hz, 1 H) 6.56-6.64 (m, 1 H) 7.32 (dd, J=8.30, 5.86 Hz, 1 H) 10.03 (s, 1 H)

Example 5

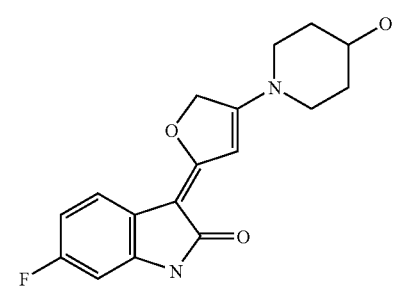 [SMILES: O=C1Nc2cc(F)ccc2/C1=C1/C=C(N2CCC(O)CC2)CO1]

6-Fluoro-3-[4-(4-hydroxy-piperidin-1-yl)-5H-furan-2-ylidene]-1,3-dihydro-indol-2-one $^1$H NMR (500 MHz, DMSO-$d_6$) δ ppm 1.41-1.53 (m, 2 H) 1.77-1.87 (m, 2 H) 3.18 (t, J=7.32 Hz, 2 H) 3.49 (br.s., 2 H) 3.71-3.80 (m, 1 H) 4.84 (d, J=391 Hz, 1 H) 5.32 (s, 2 H) 6.18 (s, 1 H) 6.52 (dd, J=9.76, 2.44 Hz, 1 H) 6.56-6.63 (m, 1 H) 7.32 (dd, J=8.30, 5.86 Hz, 1 H) 10.03 (s, 1 H)
HR MS (ES+): 317.1436 (MH+)

Example 6

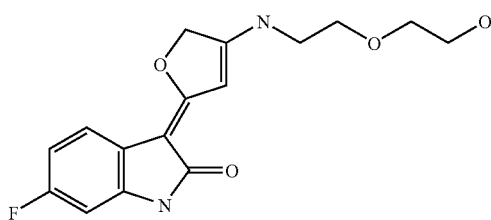 [SMILES: O=C1Nc2cc(F)ccc2/C1=C1/C=C(NCCOCCO)CO1]

6-Fluoro-3-{4-[2-(2-hydroxy-ethoxy)-ethylamino]-5H-furan-2-ylidene}-1,3-dihydro-indol-2-one $^1$H NMR (500 MHz, DMSO-d$_6$) δ ppm 3.34 (br. s, 2 H) 3.46-3.50 (m, 2 H) 3.53 (q, J=5.21 Hz, 2 H) 3.61 (br.s., 2 H) 4.60 (t, J=5.61 Hz, 1 H) 5.13 (s, 2 H) 6.15 (s, 1 H) 6.53 (dd, J=9.52, 2.20 Hz, 1 H) 6.57-6.67 (m, 1 H) 7.34 (dd, J=7.81, 5.86 Hz, 1 H) 7.92 (s, 1 H) 10.05 (s, 1 H)

Example 7

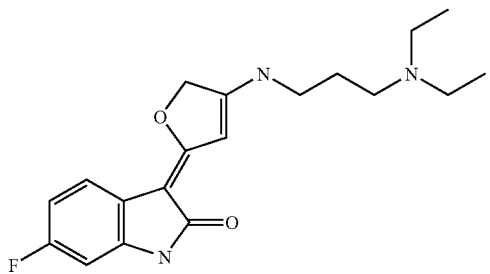 [SMILES: CCN(CC)CCCNC1=C/C(=C2\C(=O)Nc3cc(F)ccc32)OC1]

3-[4-(3-Diethylamino-propylamino)-5H-furan-2-ylidene]-6-fluoro-1,3-dihydro-indol-2-one $^1$H NMR (500 MHz, DMSO-d$_6$) δ ppm 0.96 (t, J=7.08 Hz, 6 H) 1.63-1.73 (m, 2 H) 2.41-2.49 (m, 6 H) 3.19 (br.s., 2 H) 5.13 (s, 2 H) 6.11 (s, 1 H) 6.53 (dd, J=9.52, 2.20 Hz, 1 H) 6.57-6.65 (m, 1 H) 7.34 (dd, J=8.30, 5.86 Hz, 1 H) 7.86 (s, 1 H) 10.04 (s, 1 H).

Example 8

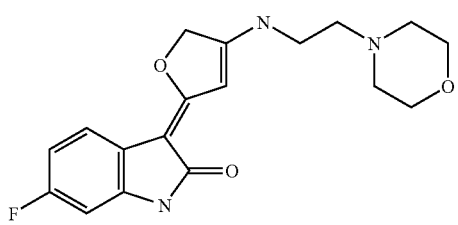 [SMILES: O=C1Nc2cc(F)ccc2/C1=C1/C=C(NCCN2CCOCC2)CO1]

6-Fluoro-3-[4-(2-morpholin-4-yl-ethylamino)-5H-furan-2-ylidene]-1,3-dihydro-indol-2-one $^1$H NMR (500 MHz, DMSO-d$_6$) δ ppm 2.43 (br.s., 4 H) 2.53 (t, J=5.86 Hz, 2H) 3.29 (br.s, 2 H) 3.60 (t, J=4.39 Hz, 4 H) 5.13 (s, 2 H) 6.14 (s, 1 H) 6.53 (dd, J=9.52, 2.20 Hz, 1 H) 6.57-6.64 (m, 1 H) 7.34 (dd, J=8.30, 5.86 Hz, 1 H) 7.80 (s, 1 H) 10.04 (s, 1 H)

Example 9

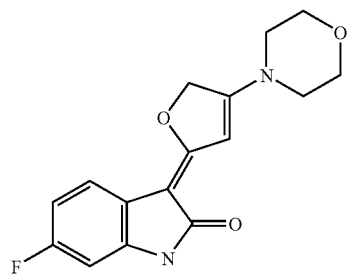

6-Fluoro-3-(4-morpholin-4-yl-5H-furan-2-ylidene)-1,3-dihydro-indol-2-one

A mixture of 6-fluoro-3-(4-methoxy-5H-furan-2-ylidene)-1,3-dihydro-indol-2-one (100 mg, 0.40 mmol) and morpholine (0.5 mL, 5.7 mmol) in 20 mL of EtOH was heated at reflux for 16 hours. The mixture was cooled to room temperature. The precipitates were filtered, rinsed with EtOH and dried in vacuum to give 6-fluoro-3-(4-morpholin-4-yl-5H-furan-2-ylidene)-1,3-dihydro-indol-2-one as a pale yellow powder. Yield: 55 mg, 45%.

$^1$H NMR (500 MHz, DMSO-d$_6$) δ ppm 3.34 (br.s., 4 H) 3.70 (t, J=4.88 Hz, 4 H) 5.35 (s, 2 H) 6.25 (s, 1 H) 6.54 (dd, J=9.28, 2.44 Hz, 1 H) 6.59-6.65 (m, 1 H) 7.35 (dd, J=8.54, 5.61 Hz, 1 H) 10.07 (s, 1 H)

Example 10

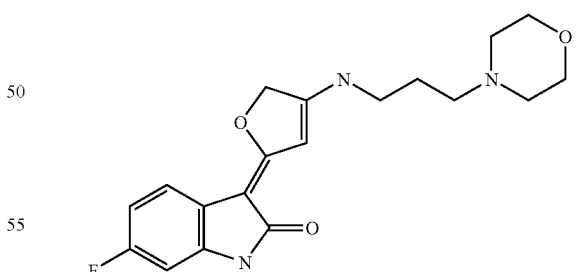

6-Fluoro-3-[4-(3-morpholin-4-yl-propylamino)-5H-furan-2-ylidene]-1,3-dihydro-indol-2-one $^1$H NMR (500 MHz, DMSO-d$_6$) δ ppm 1.68-1.77 (m, 2 H) 2.35 (t, J=6.59 Hz, 6 H) 3.22 (br.s., 2 H) 3.59 (t, J=4.39 Hz, 4 H) 5.13 (s, 2 H) 6.13 (s, 1 H) 6.53 (dd, J=9.52, 1.71 Hz, 1 H) 6.58-6.64 (m, 1 H) 7.34 (dd, J=7.81, 5.86 Hz, 1 H) 7.86 (s, 1 H) 10.04 (s, 1 H).

Example 11

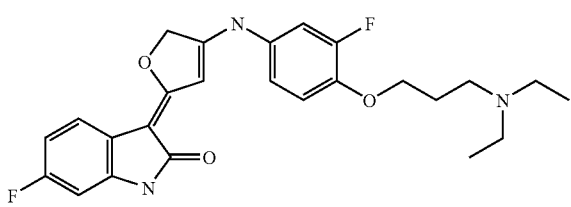 [SMILES: CCN(CC)CCCOc1ccc(NC2=C/C(=C3\C(=O)Nc4cc(F)ccc43)OC2)cc1F]

3-{4-[4-(3-Diethylamino-propoxy)-3-fluoro-phenylamino]-5H-furan-2-ylidene}-6-fluoro-1,3-dihydro-indol-2-one

HR MS (ES+): 456.1934 (MH+)
(ES−): 454.2536 (M−H)

Example 12

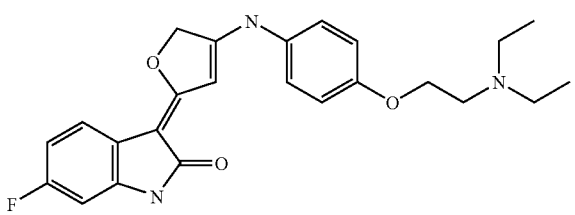 [SMILES: CCN(CC)CCOc1ccc(NC2=C/C(=C3\C(=O)Nc4cc(F)ccc43)OC2)cc1]

3-{4-[4-(2-Diethylamino-ethoxy)-phenylamino]-5H-furan-2-ylidene}-6-fluoro-1,3-dihydro-indol-2-one

HR MS (ES+): 424.2889 (MH+)
(ES−): 422.2836 (M−H)

Preparation of 4-Bromo-5H-furan-2-one

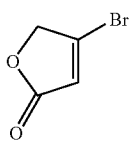

To a stirred suspension of tetronic acid (5.0 g, 50 mmol) in 100 mL of anhydrous $CH_2Cl_2$, was added 5 mL of anhydrous DMF, and cooled with ice bath. Oxalyl bromide (5.6 mL, 60 mmol) was added slowly over 50 minutes. The mixture was stirred at 0° C. for 30 minutes and then room temp for 2 hours. Water (100 mL) was added and the mixture separated into two layers. The aqueous layer was extracted with $Et_2O$ (2×100 mL). All the organic layers were combined, washed with water (100 mL), saturated $NaHCO_3$ (2×100 mL) and brine (100 mL), dried over $Na_2SO_4$, and evaporated to dryness to give 4-bromo-5H-furan-2-one as a light brown solids. Yield: 5.6 g, 69%.

$^1$H NMR (500 MHz, CDCl$_3$) δ ppm 4.87-4.89 (m, 2 H) 6.36-6.38 (m, 1 H)

Preparation of 3-(4-Bromo-5H-furan-2-ylidene)-6-fluoro-1,3-dihydro-indol-2-one

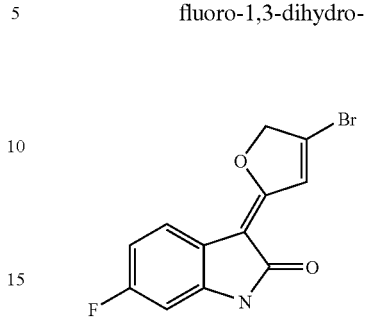

To a 0° C. stirred solution of 6-fluorooxindole (370 mg, 2.45 mmol) in anhydrous THF (10 mL) was added 1M LiHMDS/THF solution (4.9 mL, 4.9 mmol). The mixture was stirred at 0° C. for 10 minutes. 4-Bromo-5H-furan-2-one (200 mg, 1.23) was added as a solution in 2 mL of THF. The resulting mixture was stirred at 0° C. for 30 minutes, then at room temperature for 1 hour and quenched with 10 mL of 2M HCl. Methanol (5 mL) was added and the mixture was stirred at 50° C. for 0.5 hour. The mixture was poured into 150 mL of water and then stirred for 30 minutes. The precipitates were filtered, washed with water, and dried in vacuum to give 3-(4-bromo-5H-furan-2-ylidene)-6-fluoro-1,3-dihydro-indol-2-one as a yellow solid. Yield: 228 mg, 63%.

$^1$H NMR (500 MHz, DMSO-d$_6$) δ ppm 5.44 (s, 2 H) 6.62 (dd, J=9.28, 2.44 Hz, 1 H) 6.70-6.76 (m, 1 H) 7.47 (dd, J=8.30, 5.37 Hz, 1 H) 7.67 (t, J=1.71 Hz, 1 H) 10.48 (s, 1 H)

Example 40

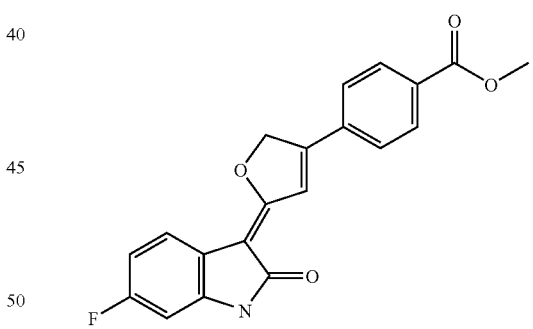

4-[5-(6-Fluoro-2-oxo-1,2-dihydro-indol-3-ylidene)-2,5-dihydro-furan-3-yl]-benzoic acid methyl ester To a 1:1 mixture of toluene/water (10 mL), were added the bromide (40 mg, 0.14 mmol), 4-methoxycarbonylphenylboronic acid (49 mg, 0.27 mmol), PdCl$_2$(PPh$_3$)$_2$ (17 mg, 0.024 mmol), 2 M KF aqueous solution (0.35 mL, 0.7 mmol), benzyltriethylammonium chloride (3 mg, 0.013 mmol). The mixture was heated at 80° C. under N$_2$ for 16 hours, cooled to room temperature and extracted with EtOAc (2×50 mL). The organic layers were combined, washed with saturated NaHCO$_3$ (50 mL) and brine (50 mL), dried over Na$_2$SO$_4$. Purification through silica gel column with 10-25% MeOH/CHCl$_3$ led to the product as a brown solid. Yield: 29 mg, 62%.

¹H NMR (500 MHz, DMSO-d₆) δ ppm 3.88 (s, 3 H) 5.83 (s, 2 H) 6.63 (dd, J=9.28, 2.44 Hz, 1 H) 6.70-6.79 (m, 1 H) 7.55 (dd, J=8.30, 5.86 Hz, 1 H) 7.86 (d, J=8.30 Hz, 2 H) 7.98 (s, 1 H) 8.04 (d, J=8.30 Hz, 2 H) 10.48 (s, 1 H)

The Examples 13 through 46 were prepared using the experiment procedure described in Example 40, but with the appropriate reagent, reaction conditions and reactant substitutions that will be readily realized by those of ordinary skill in this art without the exercise of undue experimentation Example 34

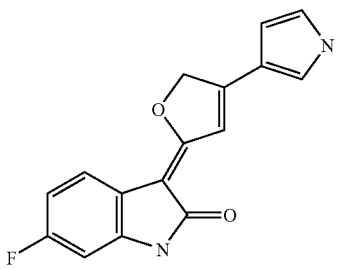 [SMILES: O=C1Nc2cc(F)ccc2/C1=C1/C=C(c2cc[nH]c2)CO1]

(3E)-6-fluoro-3-[4-(1H-pyrrol-3-yl)furan-2(5H)-ylidene]-1,3-dihydro-2H-indol-2-one A solution of (3E)-6-fluoro-3-{4-[1-(triisopropylsilyl)-1H-pyrrol-3-yl]furan-2(5H)-ylidene}-1,3-dihydro-2H-indol-2-one (Example 33; 90 mg) in a mixture of trifluoroacetic acid (7 mL) and CH₂Cl₂ (7 mL) was stirred at room temperature for 3 days. The mixture was evaporated to dryness, and re-dissolved in 1:1 THF/MeOH (6 mL). The solution was slowly added into diluted NaHCO₃ solution (100 mL) with stirring. The precipitates were filtered, washed with water, and dried in vacuum to give (3E)-6-fluoro-3-[4-(1H-pyrrol-3-yl)furan-2(5H)-ylidene]-1,3-dihydro-2H-indol-2-one as brown solid. Yield: 40 mg.

¹H NMR (500 MHz, DMSO-d₆) δ ppm 5.60 (s, 2 H) 6.49 (s, 1 H) 6.59 (dd, J=9.28, 1.95 Hz, 1 H) 6.66-6.74 (m, 1 H) 6.92 (s, 1 H) 7.38 (d, J=5.86 Hz, 2 H) 7.49 (dd, J=7.81, 5.86 Hz, 1 H) 10.32 (s, 1 H) 11.43 (s, 1 H)

Example 35

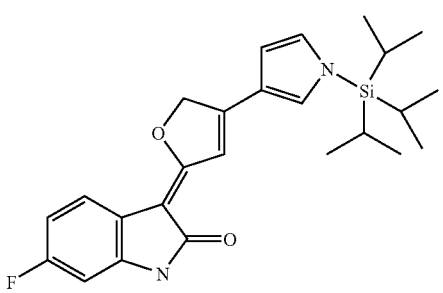 [SMILES: CC(C)[Si](C(C)C)(C(C)C)n1ccc(C2=C/C(=C3\C(=O)Nc4cc(F)ccc43)OC2)c1]

(3E)-6-fluoro-3-{4-[1-(triisopropylsilyl)-1H-pyrrol-3-yl]furan-2(5H)-ylidene}-1,3-dihydro-2H-indol-2-one ¹H NMR (500 MHz, DMSO-d₆) δ ppm 1.06 (d, J=7.81 Hz, 18 H) 1.51-1.61 (m, 3 H) 5.62 (s, 2 H) 6.59 (dd, J=9.28, 2.44 Hz, 1 H) 6.63 (d, J=1.95 Hz, 1 H) 6.67-6.74 (m, 1 H) 6.97 (s, 1 H) 7.44-7.53 (m, 3 H) 10.33 (s, 1 H)

LR MS (EI): 438 (M⁺)

Example 36

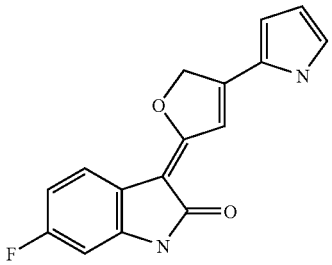 [SMILES: O=C1Nc2cc(F)ccc2/C1=C1/C=C(c2ccc[nH]2)CO1]

(3E)-6-fluoro-3-[4-(1H-pyrrol-2-yl)furan-2(5H)-ylidene]-1,3-dihydro-2H-indol-2-one A solution of tert-butyl 2-[(5E)-5-(6-fluoro-2-oxo-1,2-dihydro-3H-indol-3-ylidene)-2,5-dihydrofuran-3-yl]-1H-pyrrole-1-carboxylate (Example 37; 30 mg) in a mixture of trifluoroacetic acid (2 mL) and CH₂Cl₂ (10 mL) was stirred at room temperature for 16 hours. The mixture was evaporated to dryness, and re-dissolved in 1:1 THF/MeOH (4 mL). The solution was slowly added into diluted NaHCO₃ solution (100 mL) with stirring. The precipitates were filtered, washed with water, and dried in vacuum to give (3E)-6-fluoro-3-[4-(1H-pyrrol-2-yl)furan-2(5H)-ylidene]-1,3-dihydro-2H-indol-2-one as brown solid. Yield: 15 mg.

¹H NMR (500 MHz, DMSO-d₆) δ ppm 5.62 (s, 2 H) 6.21-6.25 (m, 1 H) 6.57-6.62 (m, 2 H) 6.67-6.73 (m, 1 H) 7.13 (s, 1 H) 7.49 (dd, J=8.06, 5.61 Hz, 1 H) 7.61 (s, 1 H) 10.32 (s, 1 H) 11.95 (s, 1 H)

LR MS (EI): 282 (M⁺)

Example 37

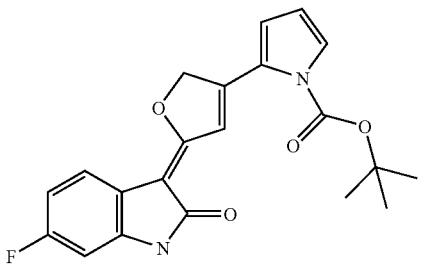 [SMILES: CC(C)(C)OC(=O)n1cccc1C1=C/C(=C2\C(=O)Nc3cc(F)ccc32)OC1]

tert-butyl 2-[(5E)-5-(6-fluoro-2-oxo-1,2-dihydro-3H-indol-3-ylidene)-2,5-dihydrofuran-3-yl]-1H-pyrrole-1-carboxylate ¹H NMR (500 MHz, DMSO-d₆) δ ppm 1.59 (s, 9 H) 5.66 (s, 2 H) 6.40 (t, J=3.42 Hz, 1 H) 6.61 (dd, J=9.76, 2.44 Hz, 1 H) 6.69-6.75 (m, 1 H) 6.82 (dd, J=3.42, 1.46 Hz, 1 H) 7.50 (dd, J=8.30, 5.37 Hz, 1 H) 7.59 (dd, J=3.42, 1.46 Hz, 1 H) 7.70 (s, 1 H) 10.35 (s, 1 H)

LR MS (EI): 382 (M⁺)

Example 38

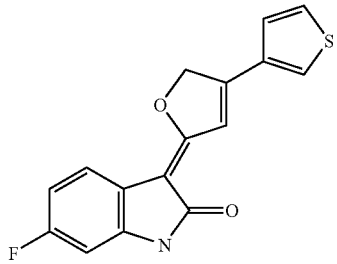

(3E)-6-fluoro-3-[4-(3-thienyl)furan-2(5H)-ylidene]-1,3-dihydro-2H-indol-2-one $^1$H NMR (500 MHz, DMSO-d$_6$) δ ppm 5.71 (s, 2 H) 6.61 (dd, J=9.52, 2.20 Hz, 1 H) 6.70-6.76 (m, 1 H) 7.53 (dd, J=8.30, 5.86 Hz, 1 H) 7.60 (d, J=5.37 Hz, 1 H) 7.68 (s, 1 H) 7.72 (dd, J=5.13, 2.69 Hz, 1 H) 8.06 (d, J=2.44 Hz, 1 H) 10.42 (s, 1 H)

LR MS (EI): 299 (M$^+$)

Example 39

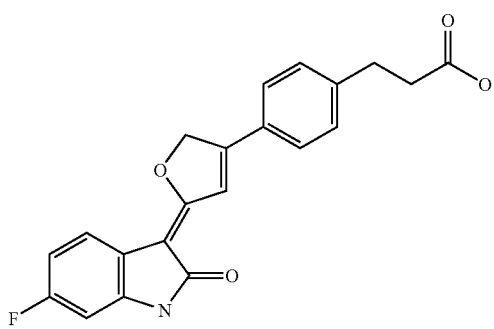 [SMILES: O=C(O)CCc1ccc(C2=C/C(=C3\C(=O)Nc4cc(F)ccc43)OC2)cc1]

3-{4-[5-(6-Fluoro-2-oxo-1,2-dihydro-indol-3-ylidene)-2,5-dihydro-furan-3-yl]-phenyl}-propionic acid

HR MS (ES−): 364.0864 (M−H)

Example 43

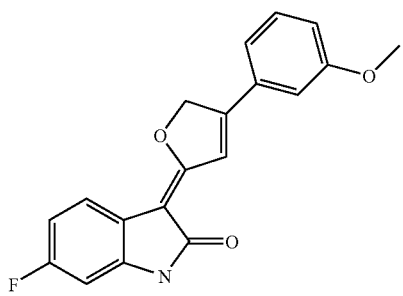 [SMILES: COc1cccc(C2=C/C(=C3\C(=O)Nc4cc(F)ccc43)OC2)c1]

6-Fluoro-3-[4-(3-methoxy-phenyl)-5H-furan-2-ylidene]-1,3-dihydro-indol-2-one

HR MS (ES+): 324.2709 (MH$^+$)

Example 44

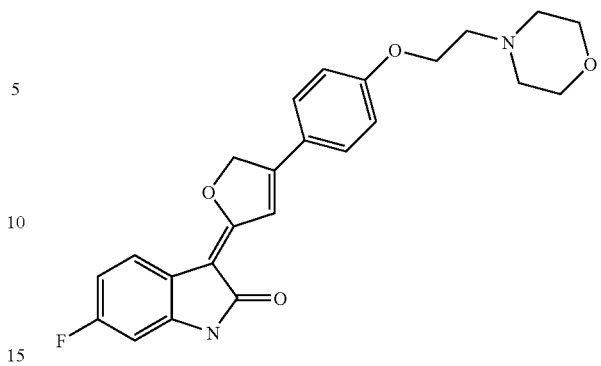

6-Fluoro-3-{4-[4-(2-morpholin-4-yl-ethoxy)-phenyl]-5H-furan-2-ylidene}-1,3-dihydro-indol-2-one $^1$H NMR (500 MHz, DMSO-d$_6$) δ ppm 2.47 (br.s., 4 H) 2.70 (t, J=5.61 Hz, 2 H) 3.57 (t, J=4.88 Hz, 4 H) 4.17 (t, J=5.61 Hz, 2 H) 5.76 (s, 2 H) 6.61 (dd, J=9.28, 2.44 Hz, 1 H) 6.68-6.76 (m, 1 H) 7.07 (d, J=8.79 Hz, 2 H) 7.52 (dd, J=8.30, 5.86 Hz, 1 H) 7.66 (d, J=8.79 Hz, 2 H) 7.72 (s, 1 H) 10.40 (s, 1 H)

Example 45

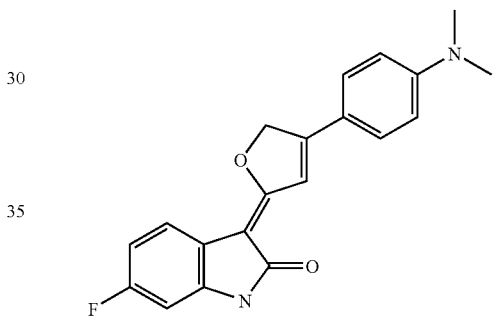

3-[4-(4-Dimethylamino-phenyl)-5H-furan-2-ylidene]-6-fluoro-1,3-dihydro-indol-2-one

HR MS (ES+): 337.1384 (MH$^+$)

Example 46

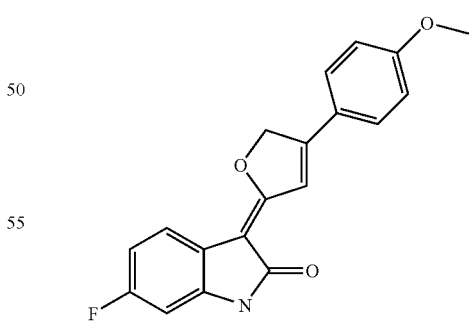

6-Fluoro-3-[4-(4-methoxy-phenyl)-5H-furan-2-ylidene]-1,3-dihydro-indol-2-one $^1$H NMR (500 MHz, DMSO-d$_6$) δ ppm 3.83 (s, 3 H) 5.77 (s, 2 H) 6.61 (dd, J=9.28, 2.44 Hz, 1 H) 6.69-6.77 (m, 1 H) 7.06 (d, J=8.79 Hz, 2 H) 7.52 (dd, J=8.30, 5.86 Hz, 1 H) 7.67 (d, J=8.79 Hz, 2 H) 7.72 (s, 1 H) 10.40 (s, 1 H)

Preparation of 4-pyrrolidin-1-ylfuran-2(5H)-one

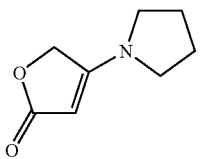 [SMILES: O=C1C=C(N2CCCC2)CO1]

A mixture of methyl tetronate (2.0 g, 17.5 mmol) and pyrrolidine (4.0 mL, 48 mmol) in EtOH (20 mL) was heated at reflux for 2 hours. The mixture was cooled to room temperature, and evaporated to dryness. The resulting solid was recrystallized with benzene/hexanes to give 4-pyrrolidin-1-ylfuran-2(5H)-one as white crystals. Yield: 2.60 g, 96%.

$^1$H NMR (500 MHz, CDCl$_3$) δ ppm 2.01-2.05 (m, 4 H) 3.28 (t, J=6.83 Hz, 4 H) 4.53 (s, 1 H) 4.67 (s, 2 H)

Preparation of 5,5-dimethyl-4-pyrrolidin-1-ylfuran-2(5H)-one

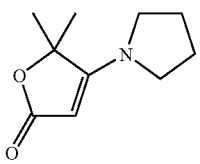

To a −78° C. stirred suspension of 4-pyrrolidin-1-ylfuran-2(5H)-one (1.0 g, 6.5 mmol) in 20 mL of anhydrous THF, was slowly added 1M LiHMDS/THF solution (14.4 mL, 14.4 mmol). The mixture was stirred at −78° C. under nitrogen for 30 minutes, and methyl iodide (3 mL, 24 mmol) was added. The mixture was stirred at −78° C. for 1 hour, then allowed to warm up to room temp. The reaction was quenched with AcOH (3 mL) and water (10 mL), concentrated to about 15 mL, and extracted with CHCl$_3$ (3×50 mL). The organic layers were combined, washed with 0.5M HCl (2×50 mL), brine (50 mL), dried over Na$_2$SO$_4$, and evaporated to give 5,5-dimethyl-4-pyrrolidin-1-ylfuran-2(5H)-one as a brown solid. Yield: 1.08 g, 92%.

$^1$H NMR (500 MHz, CDCl$_3$) δ ppm 1.54 (s, 6 H) 1.89-1.99 (m, 4 H) 3.32 (br.s., 4 H) 4.33 (s, 1 H)

Preparation of 4-Hydroxy-5,5-dimethyl-5H-furan-2-one

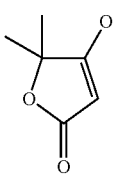

A suspension of 5,5-dimethyl-4-pyrrolidin-1-ylfuran-2(5H)-one (535 mg) in a mixture of MeOH (2 mL) and 5M HCl (8 mL) was heated at 88° C. for 2 hours. The mixture was cooled to room temp., extracted with CHCl$_3$ (10×15 mL), combined, dried over Na$_2$SO$_4$, and evaporated to dryness to give 4-hydroxy-5,5-dimethyl-5H-furan-2-one as light brown solid. Yield: 359 mg, 95%.

$^1$H NMR (500 MHz, DMSO-d$_6$) δ ppm 1.37 (s, 6 H) 4.78 (s, 1 H) 12.64 (s, 1 H)

Preparation of 2,2-dimethyl-5-oxo-2,5-dihydrofuran-3-yl trifluoromethanesulfonate

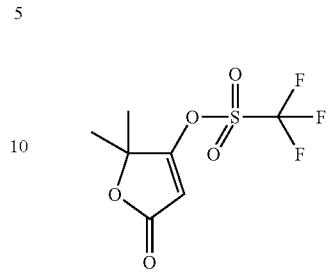

To a −78° C. stirred solution of 4-hydroxy-5,5-dimethyl-5H-furan-2-one (250 mg, 1.95 mmol) in 18 mL of anhydrous CH$_2$Cl$_2$, was added triethylamine (0.40 mL, 2.9 mmol) and Tf$_2$O (0.49 mL, 2.9 mmol). The reaction was stirred at −78° C. for 30 minutes, and quenched with saturated NH$_4$Cl solution (10 mL). The mixture was warmed up to room temperature and separated. The aqueous layer was extracted with CH$_2$Cl$_2$ (2×20 mL). All organic layers were combined, dried over Na$_2$SO$_4$ and evaporated to brown oil, which was purified by plugging through a short pad of silica gel column with EtOAc/hexanes (1/3). Evaporation of solvents gave 2,2-dimethyl-5-oxo-2,5-dihydrofuran-3-yl trifluoromethanesulfonate as a light brown oil (450 mg, 89%).

Preparation of 4-(4-methoxyphenyl)-5,5-dimethylfuran-2(5H)-one

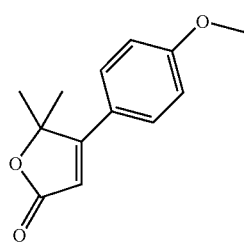 [SMILES: COc1ccc(C2=CC(=O)OC2(C)C)cc1]

To a 1:1 mixture of toluene/water (20 mL), were added 2,2-dimethyl-5-oxo-2,5-dihydrofuran-3-yl trifluoromethanesulfonate (100 mg, 0.38 mmol), 4-methoxyphenylboronic acid (87 mg, 0.57 mmol), PdCl$_2$(PPh$_3$)$_2$ (27 mg, 0.038 mmol), 2M KF aqueous solution (0.95 mL, 1.9 mmol), benzyltriethylammonium chloride (8.7 mg, 0.038 mmol). The mixture was heated at 50° C. under N$_2$ for 30 minutes, cooled to room temperature and extracted with EtOAc (2×50 mL). The organic layers were combined, washed with saturated NaHCO$_3$ (50 mL) and brine (50 mL), dried over Na$_2$SO$_4$. Purification through silica gel column with 10-30% EtOAc/hexanes led to the product as yellow solid. Yield: 33 mg, 40%.

$^1$H NMR (500 MHz, CDCl$_3$) δ ppm 1.70 (s, 6 H) 3.87 (s, 3 H) 6.14 (s, 1 H) 6.97 (d, J=8.79 Hz, 2 H) 7.53 (d, J=8.79 Hz, 2 H)

Example 158

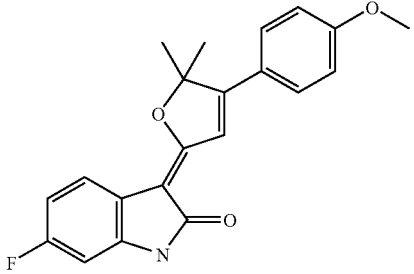 [SMILES: COc1ccc(C2=C/C(=C3\C(=O)Nc4cc(F)ccc43)OC2(C)C)cc1]

(3E)-6-fluoro-3-[4-(4-methoxyphenyl)-5,5-dimethyl-furan-2(5H)-ylidene]-1,3-dihydro-2H-indol-2-one To a 0° C. stirred solution of 6-fluorooxindole (45 mg, 0.3 mmol) in anhydrous THF (5 mL) was added 1M LiHMDS/THF solution (0.6 mL, 0.6 mmol). The mixture was stirred at 0° C. for 10 minutes. 4-(4-methoxyphenyl)-5,5-dimethylfuran-2(5H)-one (33 mg, 0.15 mmol) was added. The resulting mixture was stirred at room temperature for 1 hour and quenched with 2 mL of 2M HCl. The mixture was stirred at room temperature for 16 hours and poured into 100 mL of water. The precipitates were filtered, washed with water, and dried in vacuo to give 3(3E)-6-fluoro-3-[4-(4-methoxyphenyl)-5,5-dimethylfuran-2(5H)-ylidene]-1,3-dihydro-2H-indol-2-one as yellow solids. Yield: 228 mg, 63%.

$^1$H NMR (500 MHz, DMSO-$d_6$) δ ppm 1.76 (s, 6 H) 3.83 (s, 3 H) 6.60 (dd, J=9.28, 2.44 Hz, 1 H) 6.69-6.78 (m, 1 H) 7.05 (d, J=9.28 Hz, 2 H) 7.53 (dd, J=8.30, 5.86 Hz, 1 H) 7.66 (s, 1 H) 7.76 (d, J=8.79 Hz, 2 H) 10.38 (s, 1 H)

Preparation of 4-Bromo-5,5-dimethyl-5H-furan-2-one

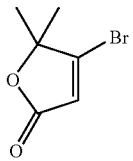

To a solution of 4-hydroxy-5, 5-dimethyl-5H-furan-2-one (2.1 g, 16.4 mmol) in DCE (40 mL) and DMF (1.5 mL) at 0° C. was added dropwise oxalyl bromide (3.0 mL, 32 mmol, 2 equiv). The mixture was stirred at room temperature for 4-5 h, and then put in an ice bath. Ice water (100 mL) was added slowly. The mixture was extracted with $CH_2Cl_2$ (100 mL). The organic phase was washed with 10% $NaHCO_3$ and again with water, dried over sodium sulfate and evaporated to give the title compound 2.7 g (86% yield).

$^1$H NMR (300 MHz, $CDCl_3$) δ 6.17 (s, 1H), 1.54(s, 6H), ESI-MS m/z 251.9 (M+H)$^+$

Preparation of 3-[4-Bromo-5,5-dimethyl-5H-furan-(2E)-ylidene]-6-fluoro-1,3-dihydro-indol-2-one

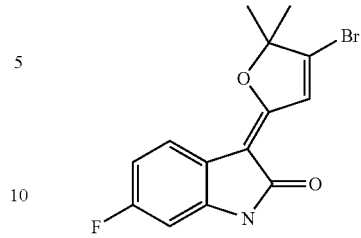

To a solution of 6-fluorooxindole (3 g, 20 mmol) in THF (50 mL) at 0° C., was added 40 mL of 1M LHMDS in THF. The reaction mixture was stirred at 0° C. for 15 minutes. A solution of 4-bromo-5, 5-dimethyl-5H-furan-2-one (5) (1.91 g, 10 mmol) in 5 mL of THF was added to the above reaction mixture. The reaction was stirred at 0° C. for further 30 minutes and then at room temperature for 2.5 hrs. To the reaction, 80 mL of 2M HCl was added. The resulting mixture was stirred at 50-55° C. for one hour, cooled down to room temperature, poured to 1000 mL of water and was stirred at room temperature for one hour. The precipitates formed were collected and washed with water, dried in vacuum to give the title compound as a yellow solid product (2.4 g, yield: 74%).

$^1$H NMR (300 MHz, DMSO-$d_6$) δ 10.46 (s, 1H), 7.54 (s, 1H), 7.49 (dd, J=8.7, 5.4 Hz, 1H), 6.73(ddd, J=10.8, 8.1, 2.4 Hz, 1H), 6.61 (dd, J=9.3, 2.7 Hz, 1H). 1.57 (s, 6H). ESI-MS m/z 324.3 M$^+$

Figure 3:
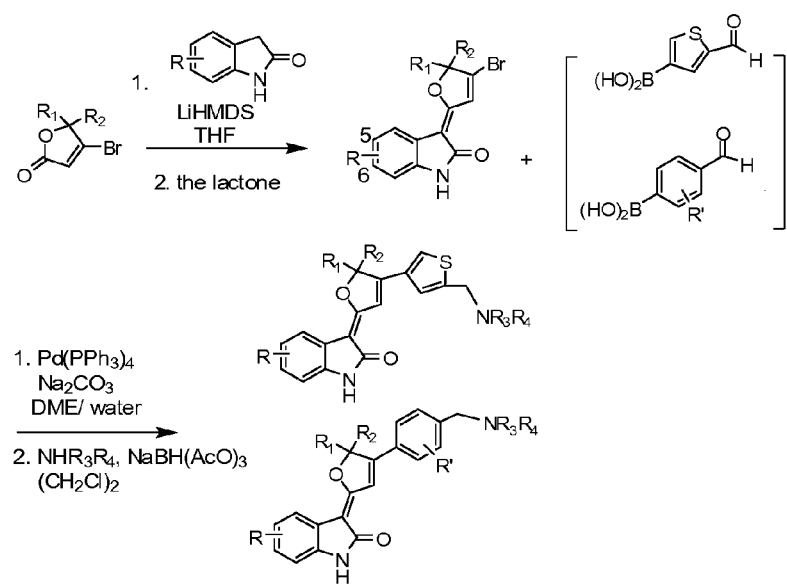
FIG. 3 shows methods for the preparation of compounds of Table 6 and Table 9.
Figure 3:
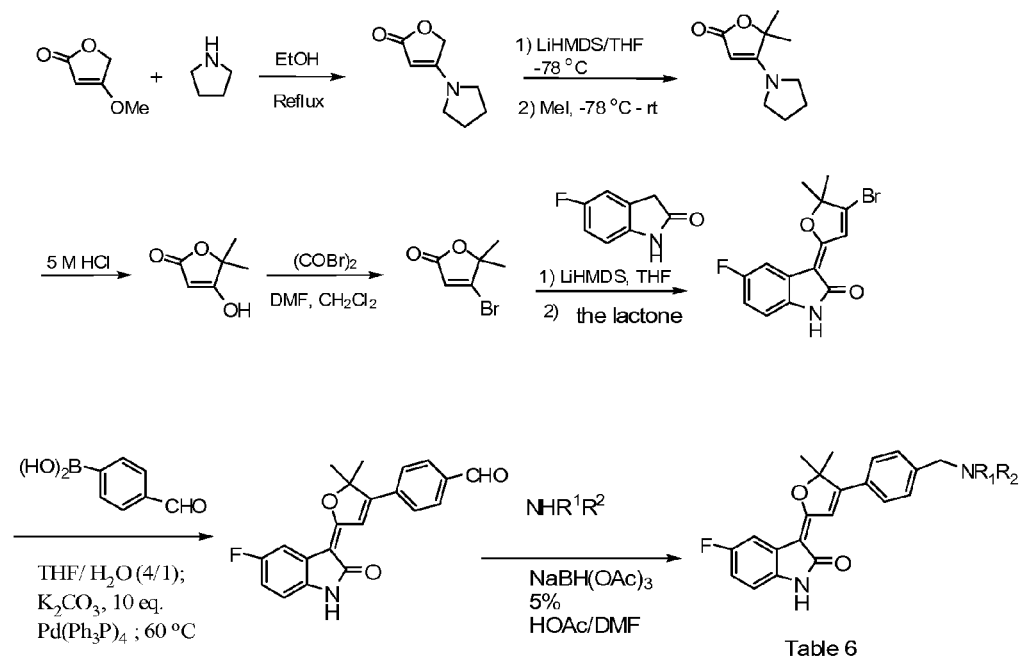

Preparation of Examples 46-158 (FIG. 3)

Each of the examples was synthesized in 40 mL vial. To each reaction vial, 3-[4-Bromo-5,5-dimethyl-5H-furan-(2E)-ylidene]-6-fluoro-1,3-dihydro-indol-2-one(55 mg, 0.17 mmol), boronic acid (0.4 mmol), THF(4 mL), 1M of potassium carbonate water solution (1.5 mL) and tetrakis(triphenylphosphine) palladium(0) (18 mg) were added. The reaction was heated at 60° C. overnight under nitrogen atmosphere. After cooling down to room temperature, 10 mL of ethyl acetate and 8 mL of water were added. The organic layer was evaporated to give the crude product that was subjected to QC and purification. The library compounds were purified by high throughput RP-HPLC. Each compound was re-analyzed by LCMS after purification.

Preparation of methyl 4-[(5E)-5-(6-fluoro-2-oxo-1,2-dihydro-3H-indol-3-ylidene)-2,2-dimethyl-2,5-dihydrofuran-3-yl]benzoate

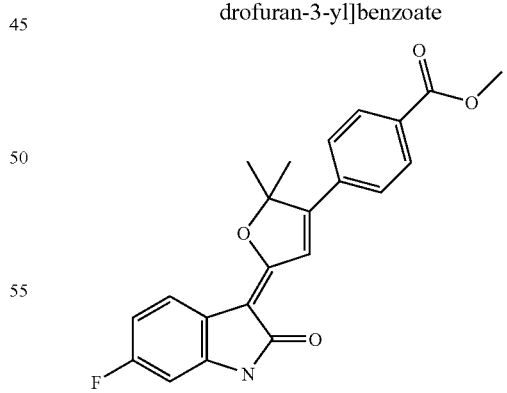

To 30 mL of 1,4-dioxane, was added the following reagents: (3E)-3-(4-bromo-5,5-dimethylfuran-2(5H)-ylidene)-6-fluoro-1,3-dihydro-2H-indol-2-one (500 mg, 1.54 mmol), 4-methoxycarbonylphenylboronic acid (333 mg, 1.85 mmol), $PdCl_2(PPh_3)_2$ (54 mg, 0.077 mmol), 1M $Na_2CO_3$ aqueous solution (6.2 mL, 6.2 mmol). The mixture was heated at 80° C. under $N_2$ for 1 hour, cooled to room temperature and poured into 200 mL of water. The brown precipitates were filtered, washed with water and dried to give the crude product. Purification through silica gel column with 1-5% MeOH/CHCl$_3$ led to methyl 4-[(5E)-5-(6-fluoro-2-oxo-1,2-dihydro-3H-indol-3-ylidene)-2,2-dimethyl-2,5-dihydrofuran-3-yl]benzoate as orange/red solid. Yield: 500 mg, 86%.

$^1$H NMR (500 MHz, d$_6$-DMSO) δ ppm 1.79 (s, 6 H) 3.89 (s, 3 H) 6.63 (d, J=8.79 Hz, 1 H) 6.77 (t, J=8.30 Hz, 1 H) 7.57 (dd, J=7.57, 5.61 Hz, 1 H) 7.89 (s, 1 H) 7.96 (d, J=8.30 Hz, 2 H) 8.05 (d, J=8.30 Hz, 2 H) 10.47 (s, 1 H)

Preparation of 4-[(5E)-5-(6-fluoro-2-oxo-1,2-dihydro-3H-indol-3-ylidene)-2,2-dimethyl-2,5-dihydrofuran-3-yl]benzoic acid

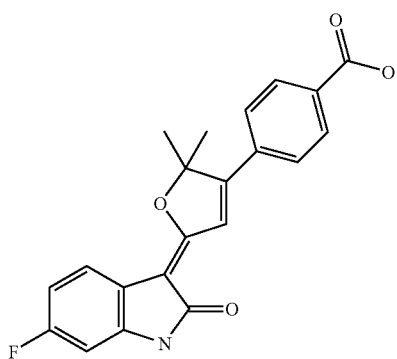 [SMILES: CC1(C)O/C(=C2/C(=O)Nc3cc(F)ccc32)C=C1c1ccc(C(=O)O)cc1]

Methyl 4-[(5E)-5-(6-fluoro-2-oxo-1,2-dihydro-3H-indol-3-ylidene)-2,2-dimethyl-2,5-dihydrofuran-3-yl]benzoate (500 mg, 1.32 mmol) was added to a mixture of 1M NaOH (4 mL, 4 mmol), THF (8 mL) and MeOH (20 mL). The mixture was heated at 58° C. for 5 hours, cooled to room temp., and poured into 200 mL of water. 2M HCl was added to bring pH down to 3. The precipitates were filtered, washed with water and dried in vacuo to give 4-[(5E)-5-(6-fluoro-2-oxo-1,2-dihydro-3H-indol-3-ylidene)-2,2-dimethyl-2,5-dihydrofuran-3-yl]benzoic acid as an orange/red solid. Yield: 480 mg, quantitative.

$^1$H NMR (300 MHz, d$_6$-DMSO) δ ppm 1.77 (s, 6 H) 6.61 (dd, J=9.38, 2.35 Hz, 1 H) 6.71-6.78 (m, 1 H) 7.55 (dd, J=8.50, 5.57 Hz, 1 H) 7.86 (s, 1 H) 7.90 (d, J=8.50 Hz, 2 H) 8.02 (d, J=8.50 Hz, 2 H) 10.44 (s, 1 H) 13.16 (br s, 1 H)

LR MS (ES−): 364 (M−1)

Example 159

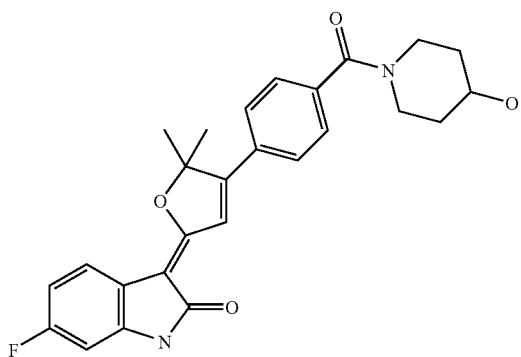 [SMILES: CC1(C)O/C(=C2/C(=O)Nc3cc(F)ccc32)C=C1c1ccc(C(=O)N2CCC(O)CC2)cc1]

(3E)-6-Fluoro-3-[4-{4-[(4-hydroxypiperidin-1-yl)carbonyl]phenyl}-5,5-dimethylfuran-2(5H)-ylidene]-1,3-dihydro-2H-indol-2-one A mixture of 4-[(5E)-5-(6-fluoro-2-oxo-1,2-dihydro-3H-indol-3-ylidene)-2,2-dimethyl-2,5-dihydrofuran-3-yl]benzoic acid (50 mg, 0.137 mmol), 4-hydroxypiperidine (15 mg, 0.15 mmol), O-benzotriazol-1-yl-N,N,N',N'-tetramethyluronium hexafluorophosphate (HBTU) (57 mg, 0.15 mmol) and diisopropylethylamine (39 mg, 0.30 mmol) in 3 mL of anhydrous DMF was stirred at room temperature. The mixture was poured into 75 mL of water. The precipitates were filtered, washed with water, and dried in vacuo to give (3E)-6-fluoro-3-[4-{4-[(4-hydroxypiperidin-1-yl)carbonyl]phenyl}-5,5-dimethylfuran-2(5H)-ylidene]-1,3-dihydro-2H-indol-2-one as orange solid. Yield: 52 mg, 85%.

$^1$H NMR (500 MHz, d$_6$-DMSO) δ ppm 1.30-1.43 (m, 2 H) 1.68-1.83 (m, 2 H) 1.79 (s, 6 H) 3.12-3.28 (m, 2 H) 3.51 (br s, 1 H) 3.72-3.78 (m, 1 H) 4.02 (br s, 1 H) 4.80 (d, J=3.91 Hz, 1 H) 6.63 (dd, J=9.28, 2.44 Hz, 1 H) 6.73-6.79 (m, 1 H) 7.49 (d, J=8.30 Hz, 2 H) 7.56 (dd, J=8.30, 5.86 Hz, 1 H) 7.83 (s, 1 H) 7.86 (d, J=8.30 Hz, 2 H) 10.44 (s, 1 H)

LR MS (ES+): 449 (M+1)

The following examples 160 through 178 were prepared using the experiment procedure described in Example 159, but with the appropriate reagent, reaction conditions and reactant substitutions that will be readily realized by those of ordinary skill in this art without the exercise of undue experimentation.

Example 160

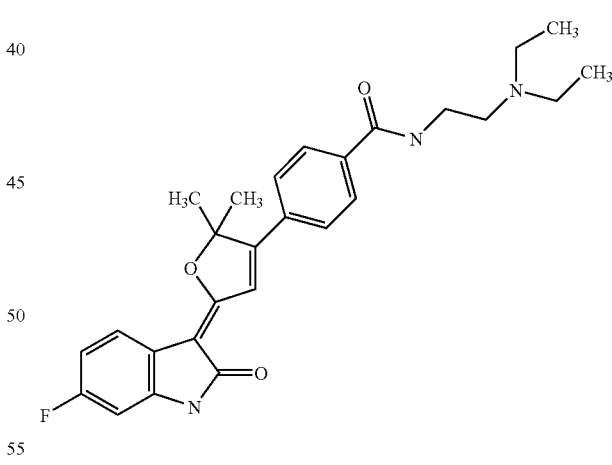

N-[2-(diethylamino)ethyl]-4-[(5E)-5-(6-fluoro-2-oxo-1,2-dihydro-3H-indol-3-ylidene)-2,2-dimethyl-2,5-dihydrofuran-3-yl]benzamide $^1$H NMR (500 MHz, d$_6$-DMSO) δ ppm 0.98 (t, J=7.08 Hz, 6 H) 1.79 (s, 6 H) 2.53 (q, J=7.32 Hz, 4 H) 2.58 (t, J=6.83 Hz, 2 H) 3.28-3.38 (m, 2 H) 6.63 (dd, J=9.28, 2.44 Hz, 1 H) 6.74-6.79 (m, 1 H) 7.57 (dd, J=8.30, 5.86 Hz, 1 H) 7.85 (s, 1 H) 7.89 (d, J=8.79 Hz, 2 H) 7.94 (d, J=8.79 Hz, 2 H) 8.54 (t, J=5.86 Hz, 1 H) 10.46 (s, 1 H)

Example 161

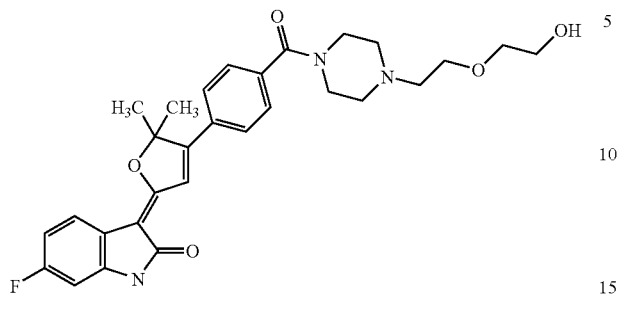

(3E)-6-fluoro-3-{4-[4-({4-[2-(2-hydroxyethoxy)
ethyl]piperazin-1-yl}carbonyl)phenyl]-5,5-dimethyl-
furan-2(5H)-ylidene}-1,3-dihydro-2H-indol-2-one $^1$H NMR (500 MHz, $d_6$-DMSO) δ ppm 1.79 (s, 6 H)
2.40-2.50 (br, 6 H) 3.34-3.37 (m, 2 H) 3.40 (t, J=5.13 Hz, 2 H)
3.48 (q, J=5.21 Hz, 2 H) 3.53 (t, J=5.86 Hz, 2 H) 3.63 (br s, 2
H) 4.61 (t, J=5.61 Hz, 1 H) 6.64 (dd, J=9.76, 2.44 Hz, 1 H)
6.74-6.80 (m, 1 H) 7.51 (d, J=8.30 Hz, 2 H) 7.57 (dd, J=8.30,
5.86 Hz, 1 H) 7.83 (s, 1 H) 7.87 (d, J=8.30 Hz, 2 H) 10.45 (s,
1 H)

LR MS (ES+): 522 (M+1)

Example 162

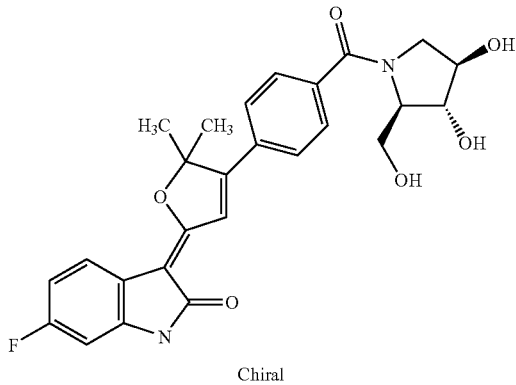 [SMILES: CC1(C)O/C(=C2/C(=O)Nc3cc(F)ccc32)C=C1c1ccc(C(=O)N2C[C@@H](O)[C@H](O)[C@H]2CO)cc1]

Chiral (3E)-3-[4-(4-{[(2R,3R,4R)-3,4-Dihydroxy-2-(hy-
droxymethyl)pyrrolidin-1-yl]carbonyl}phenyl)-5,5-
dimethylfuran-2(5H)-ylidene]-6-fluoro-1,3-dihydro-
2H-indol-2-one $^1$H NMR (500 MHz, $d_6$-DMSO) δ ppm 1.80 (s, 6 H)
3.26-3.30 (m, 1 H) 3.54 (dd, J=10.74, 5.86 Hz, 1 H) 3.64-3.71
(m, 1 H) 3.78-3.83 (m, 1 H) 3.86-3.89 (m, 2 H) 4.04-4.07 (m,
1 H) 4.98 (t, J=5.37 Hz, 1 H) 5.23 (d, J=4.39 Hz, 1 H) 5.30 (d,
J=4.39 Hz, 1 H) 6.63 (dd, J=9.76, 2.44 Hz, 1 H) 6.74-6.79 (m,
1 H) 7.54-7.61 (m, 3 H) 7.84 (s, 1 H) 7.87 (d, J=8.30 Hz, 2 H)
10.45 (s, 1 H)

LR MS (ES+): 481 (M+1)

Example 163

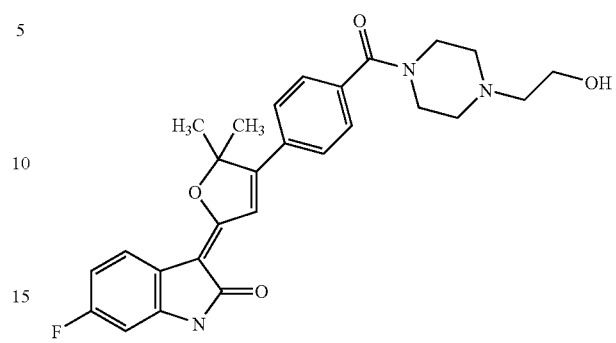

(3E)-6-fluoro-3-[4-(4-{[4-(2-hydroxyethyl)piper-
azin-1-yl]carbonyl}phenyl)-5,5-dimethylfuran-2
(5H)-ylidene]-1,3-dihydro-2H-indol-2-one $^1$H NMR (300 MHz, $d_6$-DMSO) δ ppm 1.77 (s, 6 H)
2.39-2.45 (m, 6 H) 3.34 (br s, 2 H) 3.49 (q, J=5.96 Hz, 2 H)
3.60 (br s, 2 H) 4.41 (t, J=5.28 Hz, 1 H) 6.61 (dd, J=9.53, 2.49
Hz, 1 H) 6.71-6.78 (m, 1 H) 7.48 (d, J=8.21 Hz, 2 H) 7.54 (dd,
J=8.35, 5.72 Hz, 1 H) 7.81 (s, 1 H) 7.84 (d, J=8.50 Hz, 2 H)
10.42 (s, 1 H)

LR MS (ES+): 478 (M+1)

Example 164

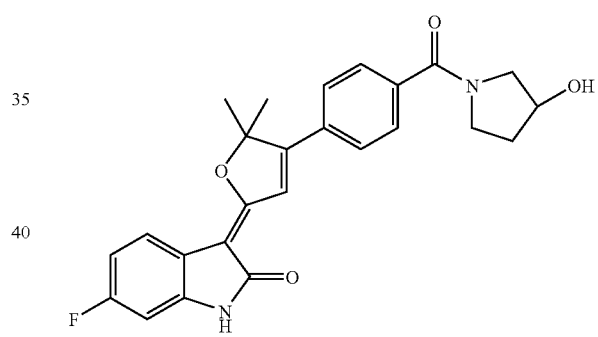

5-Fluoro-3-[4-[4-(3-hydroxy-pyrrolidine-1-carbo-
nyl)-phenyl]-5,5-dimethyl-5H-furan-(2E)-ylidene]-1,
3-dihydro-indol-2-one

LR MS (ES−): 433 (M−1)

Example 165

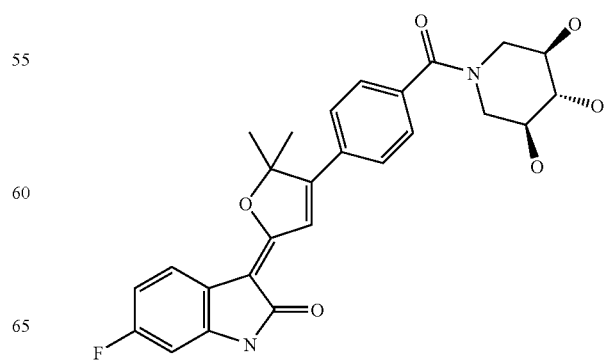

3-[5,5-Dimethyl-4-[4-((3R,4R,5S)-3,4,5-trihydroxy-piperidine-1-carbonyl)-phenyl]-5H-furan-(2E)-ylidene]-6-fluoro-1,3-dihydro-indol-2-one
$^1$H NMR (300 MHz, d$_6$-DMSO) δ ppm 1.78 (s, 6 H) 2.71 (br, 1 H) 2.90 (br, 1 H) 3.09-3.16 (m, 2 H) 3.21 (br, 1 H) 3.49 (br, 1 H) 4.28 (br, 1 H) 5.00 (d, J=3.81 Hz, 2 H) 5.15 (br, 1 H) 6.61 (dd, J=9.38, 2.35 Hz, 1 H) 6.71-6.78 (m, 1 H) 7.49 (d, J=8.50 Hz, 2 H) 7.54 (dd, J=8.21, 5.86 Hz, 1 H) 7.82 (s, 1 H) 7.86 (d, J=8.50 Hz, 2 H) 10.42 (s, 1 H)
LR MS (ES−): 479 (M−1)
Example 166
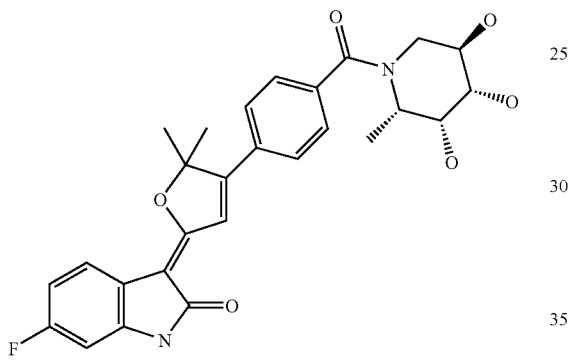
3-[5,5-Dimethyl-4-[4-((2S,3R,4S,5R)-3,4,5-trihydroxy-2-methyl-piperidine-1-carbonyl)-phenyl]-5H-furan-(2E)-ylidene]-6-fluoro-1,3-dihydro-indol-2-one
LR MS (ES−): 493 (M−1)
Example 167
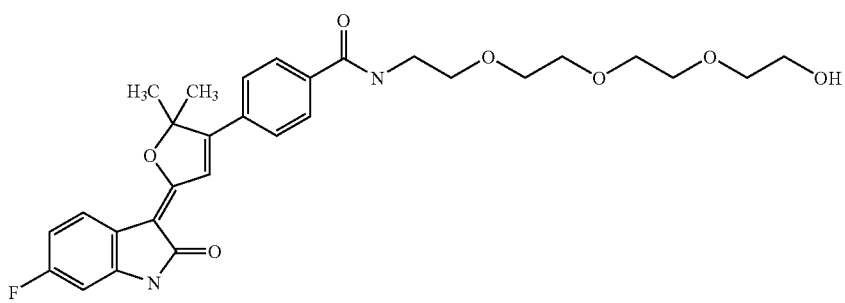 [SMILES: CC1(C)O/C(=C2/C(=O)Nc3cc(F)ccc32)C=C1c1ccc(C(=O)NCCOCCOCCOCCO)cc1]

4-[(5E)-5-(6-Fluoro-2-oxo-1,2-dihydro-3H-indol-3-ylidene)-2,2-dimethyl-2,5-dihydrofuran-3-yl]-N-(2-{2-[2-(2-hydroxyethoxy)ethoxy]ethoxy}ethyl)benzamide ¹H NMR (300 MHz, d₆-DMSO) δ ppm 1.77 (s, 6 H) 3.35-3.55 (m, 16 H) 4.53 (t, J=5.42 Hz, 1 H) 6.61 (dd, J=9.38, 2.35 Hz, 1 H) 6.71-6.78 (m, 1 H) 7.55 (dd, J=8.35, 5.72 Hz, 1 H) 7.83 (s, 1 H) 7.87 (d, J=8.79 Hz, 2 H) 7.94 (d, J=8.50 Hz, 2 H) 8.65 (t, J=5.42 Hz, 1 H) 10.43 (s, 1 H)

LR MS (ES+): 563 (M+Na⁺)

Example 168

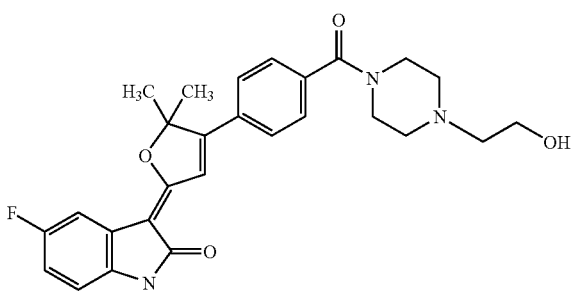

(3E)-5-Fluoro-3-[4-(4-{[4-(2-hydroxyethyl)piperazin-1-yl]carbonyl}phenyl)-5,5-dimethylfuran-2(5H)-ylidene]-1,3-dihydro-2H-indol-2-one ¹H NMR (500 MHz, d₆-DMSO) δ ppm 1.81 (s, 6 H) 2.36-2.48 (m, 6 H) 3.34 (br s, 2 H) 3.49-3.53 (m, 2 H) 3.63 (br s, 2 H) 4.43 (t, J=5.13 Hz, 1 H) 6.78 (dd, J=8.54, 4.64 Hz, 1 H) 6.85-6.92 (m, 1 H) 7.35 (dd, J=8.79, 2.44 Hz, 1 H) 7.51 (d, J=8.30 Hz, 2 H) 7.85 (s, 1 H) 7.88 (d, J=8.30 Hz, 2 H) 10.30 (s, 1 H)

Example 169

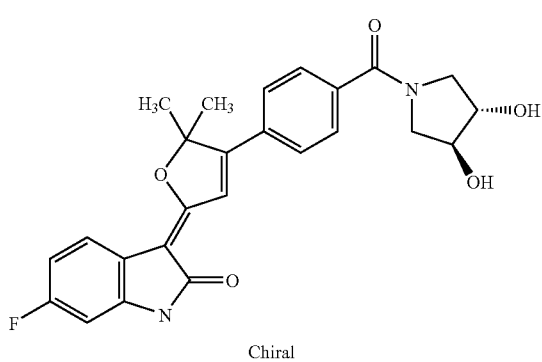 [SMILES: CC1(C)O/C(=C2/C(=O)Nc3cc(F)ccc32)C=C1c1ccc(C(=O)N2C[C@H](O)[C@@H](O)C2)cc1]

(3E)-3-[4-(4-{[(3S,4S)-3,4-Dihydroxypyrrolidin-1-yl]carbonyl}phenyl)-5,5-dimethylfuran-2(5H)-ylidene]-6-fluoro-1,3-dihydro-2H-indol-2-one ¹H NMR (300 MHz, d₆-DMSO) δ ppm 1.78 (s, 6 H) 3.19 (d, J=10.85 Hz, 1 H) 3.34 (d, J=12.90 Hz, 1 H) 3.63-3.73 (m, 2 H) 3.90 (br s, 1 H) 3.97 (br s, 1 H) 5.10 (d, J=3.22 Hz, 1 H) 5.21 (d, J=3.52 Hz, 1 H) 6.61 (dd, J=9.38, 2.35 Hz, 1 H) 6.71-6.78 (m, 1 H) 7.54 (dd, J=8.35, 5.72 Hz, 1 H) 7.61 (d, J=8.50 Hz, 2 H) 7.82 (s, 1 H) 7.84 (d, J=8.50 Hz, 2 H) 10.42 (s, 1 H)

LR MS (ES−): 449 (M−1)

Example 170

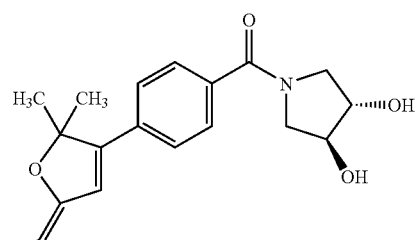

(3E)-3-[4-(4-{[(3S,4S)-3,4-Dihydroxypyrrolidin-1-yl]carbonyl}phenyl)-5,5-dimethylfuran-2(5H)-ylidene]-5-fluoro-1,3-dihydro-2H-indol-2-one ¹H NMR (300 MHz, d₆-DMSO) δ ppm 1.80 (s, 6 H) 3.19 (d, J=10.85 Hz, 1 H) 3.34 (d, J=12.90 Hz, 1 H) 3.63-3.73 (m, 2 H) 3.90 (br s, 1 H) 3.97 (br s, 1 H) 5.10 (d, J=3.22 Hz, 1 H) 5.21 (d, J=3.22 Hz, 1 H) 6.76 (dd, J=8.50, 4.69 Hz, 1 H) 6.84-6.91 (m, 1 H) 7.33 (dd, J=8.79, 2.35 Hz, 1 H) 7.61 (d, J=8.21 Hz, 2 H) 7.84 (s, 1 H) 7.86 (d, J=8.50 Hz, 2 H) 10.28 (s, 1 H)

LR MS (ES−): 449 (M−1)

Example 171

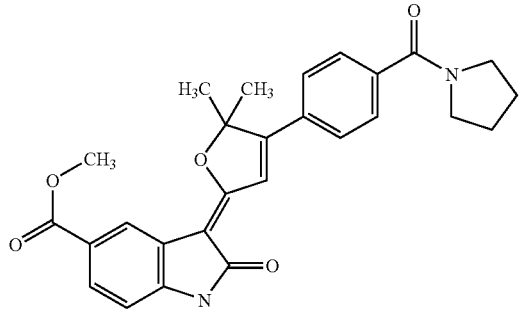 [SMILES: COC(=O)c1ccc2c(c1)/C(=C1/C=C(c3ccc(C(=O)N4CCCC4)cc3)C(C)(C)O1)C(=O)N2]

Methyl (3E)-3-{5,5-dimethyl-4-[4-(pyrrolidin-1-ylcarbonyl)phenyl]furan-2(5H)-ylidene}-2-oxoindoline-5-carboxylate ¹H NMR (300 MHz, d₆-DMSO) δ ppm 1.83 (s, 6 H) 1.79-1.89 (m, 4 H) 3.42 (t, J=6.30 Hz, 2 H) 3.49 (t, J=6.45 Hz, 2 H) 3.84 (s, 3 H) 6.92 (d, J=7.92 Hz, 1 H) 7.65 (d, J=8.21 Hz, 2 H) 7.77 (dd, J=8.06, 1.61 Hz, 1 H) 7.88 (d, J=8.50 Hz, 2 H) 7.90 (s, 1 H) 8.16 (d, J=1.17 Hz, 1 H) 10.73 (s, 1 H)

Example 172

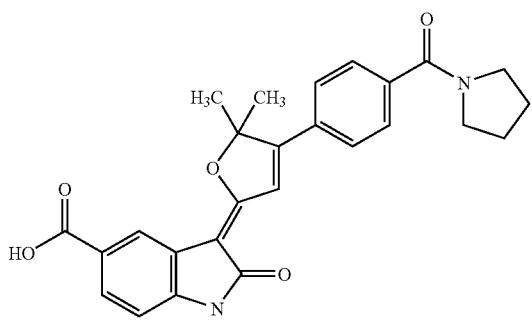 [SMILES: CC1(C)O/C(=C2/C(=O)Nc3ccc(C(=O)O)cc32)C=C1c1ccc(C(=O)N2CCCC2)cc1]

(3E)-3-{5,5-Dimethyl-4-[4-(pyrrolidin-1-ylcarbonyl)phenyl]furan-2(5H)-ylidene}-2-oxoindoline-5-carboxylic acid ¹H NMR (500 MHz, d₆-DMSO) δ ppm 1.83 (s, 6 H) 1.82-1.92 (m, 4 H) 3.42 (t, J=6.35 Hz, 2 H) 3.49 (t, J=6.83 Hz, 2 H) 6.89 (d, J=8.30 Hz, 1 H) 7.64 (d, J=8.30 Hz, 2 H) 7.75 (dd, J=8.06, 1.71 Hz, 1 H) 7.88 (d, J=8.30 Hz, 2 H) 7.91 (s, 1 H) 8.15 (d, J=1.95 Hz, 1 H) 10.70 (s, 1 H) 12.58 (s, 1 H)
LR MS (ES−): 443 (M−1)

Example 173

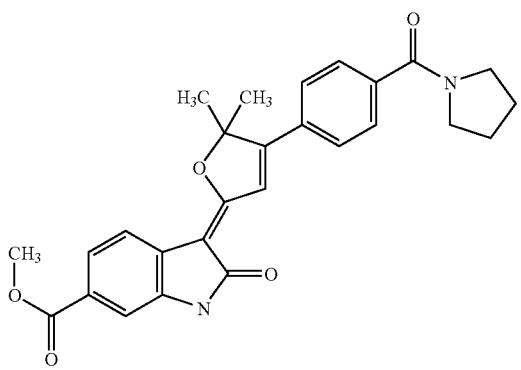

Methyl (3E)-3-{5,5-dimethyl-4-[4-(pyrrolidin-1-ylcarbonyl)phenyl]furan-2(5H)-ylidene}-2-oxoindoline-6-carboxylate ¹H NMR (300 MHz, d₆-DMSO) δ ppm 1.83 (s, 6 H) 1.79-1.91 (m, 4 H) 3.41 (t, J=6.01 Hz, 2 H) 3.49 (t, J=6.74 Hz, 2 H) 3.84 (s, 3 H) 7.37 (s, 1 H) 7.60-7.70 (m, 4 H) 7.88-7.91 (m, 3 H) 10.52 (s, 1 H)

Example 174

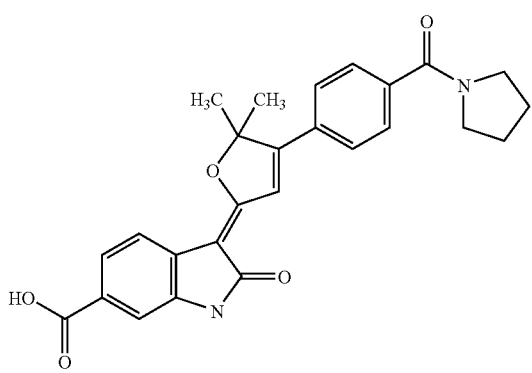 [SMILES: CC1(C)O/C(=C2/C(=O)Nc3cc(C(=O)O)ccc32)C=C1c1ccc(C(=O)N2CCCC2)cc1]

(3E)-3-{5,5-Dimethyl-4-[4-(pyrrolidin-1-ylcarbonyl)phenyl]furan-2(5H)-ylidene}-2-oxoindoline-6-carboxylic acid ¹H NMR (300 MHz, d₆-DMSO) ppm 1.80 (s, 6 H) 1.79-1.86 (m, 4 H) 3.40 (t, J=6.01 Hz, 2 H) 3.47 (t, J=6.74 Hz, 2 H) 7.34 (s, 1 H) 7.56-7.67 (m, 4 H) 7.83-7.92 (m, 3 H) 10.46 (s, 1 H) 12.69 (s, 1 H)
LR MS (ES−): 443 (M−1)

Example 175

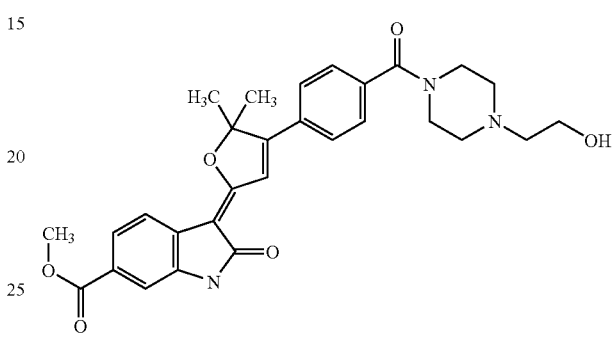

Methyl (3E)-3-[4-(4-{[4-(2-hydroxyethyl)piperazin-1-yl]carbonyl}phenyl)-5,5-dimethylfuran-2(5H)-ylidene]-2-oxoindoline-6-carboxylate ¹H NMR (300 MHz, d₆-DMSO) δ ppm 1.81 (s, 6 H) 2.41 (t, J=5.86 Hz, 6 H) 3.34 (br s, 2 H) 3.49 (q, J=5.28 Hz, 2 H) 3.61 (br s, 2 H) 3.82 (s, 3 H) 4.42 (t, J=5.57 Hz, 1 H) 7.35 (d, J=1.17 Hz, 1 H) 7.50 (d, J=8.21 Hz, 2 H) 7.60 (dd, J=7.62, 1.47 Hz, 1 H) 7.67 (d, J=7.92 Hz, 1 H) 7.88 (d, J=8.21 Hz, 2 H) 7.89 (s, 1 H) 10.50 (s, 1 H)
LR MS (ES+): 539 (M+Na⁺)
LR MS (ES−): 516 (M−1)

Example 176

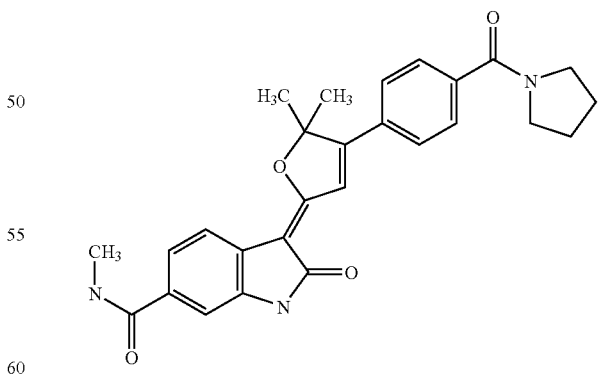

(3E)-3-{5,5-Dimethyl-4-[4-(pyrrolidin-1-ylcarbonyl)phenyl]furan-2(5H)-ylidene}-N-methyl-2-oxoindoline-6-carboxamide

LR MS (ES−): 456 (M−1)

Example 177

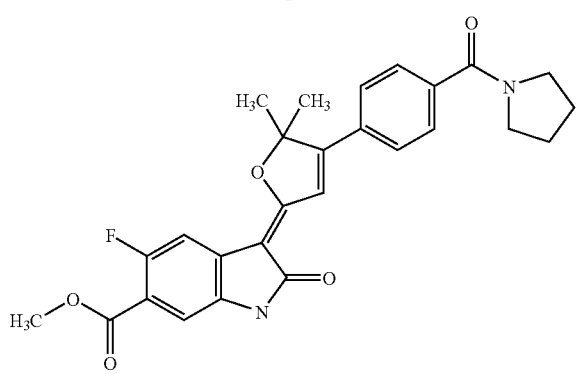 [SMILES: COC(=O)c1cc2c(cc1F)/C(=C1/C=C(c3ccc(C(=O)N4CCCC4)cc3)C(C)(C)O1)C(=O)N2]

Methyl (3E)-3-{5,5-dimethyl-4-[4-(pyrrolidin-1-ylcarbonyl)phenyl]furan-2(5H)-ylidene}-5-fluoro-2-oxoindoline-6-carboxylate LR MS (ES+): 499 (M+Na$^+$)
LR MS (ES−): 475 (M−1)

Example 178

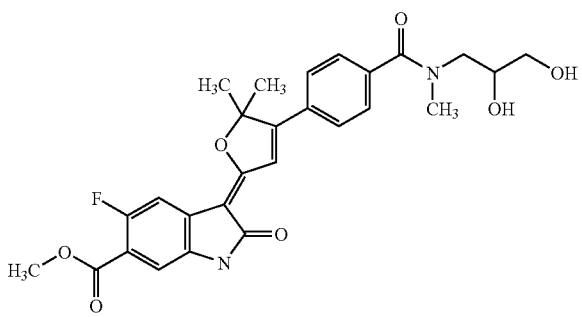 [SMILES: COC(=O)c1cc2c(cc1F)/C(=C1/C=C(c3ccc(C(=O)N(C)CC(O)CO)cc3)C(C)(C)O1)C(=O)N2]

Methyl (3E)-3-[4-(4-{[(2,3-dihydroxypropyl)(methyl)amino]carbonyl}phenyl)-5,5-dimethylfuran-2(5H)-ylidene]-5-fluoro-2-oxoindoline-6-carboxylate

LR MS (ES−): 509 (M−1)

Preparation of (3E)-3-(4-bromo-5,5-dimethylfuran-2(5H)-ylidene)-5,6-difluoro-1,3-dihydro-2H-indol-2-one

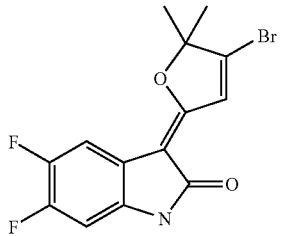

To a solution of 5, 6-difluorooxindole (450 mg, 2.66 mmol) in THF (20 mL) at 0° C., was added 1 M LiHMDS in THF (5.3 mL, 5.3 mmol). The reaction mixture was stirred at 0° C. for 10 minutes. 4-bromo-5, 5-dimethyl-5H-furan-2-one (340 mg, 1.78 mmol) was then added. The reaction mixture was stirred at 0° C. for 30 min., and then at room temperature for an additional 30 min and quenched with 2.5M aqueous H$_2$SO$_4$ (3 mL). The resulting mixture was stirred at room temperature for 16 hours and poured into water (100 mL). The precipitates were filtered, washed with water and dried in vacuo to yield (3E)-3-(4-bromo-5,5-dimethylfuran-2(5H)-ylidene)-5,6-difluoro-1,3-dihydro-2H-indol-2-one as yellow solid. Yield: 547 mg, 90%.

$^1$H NMR (300 MHz, d$_6$-DMSO) δ ppm 1.58 (s, 6 H) 6.81 (dd, J=10.55, 6.74 Hz, 1 H) 7.45 (dd, J=10.55, 8.21 Hz, 1 H) 7.54 (s, 1 H) 10.44 (s, 1 H)

Preparation of methyl 4-[(5E)-5-(5,6-difluoro-2-oxo-1,2-dihydro-3H-indol-3-ylidene)-2,2-dimethyl-2,5-dihydrofuran-3-yl]benzoate

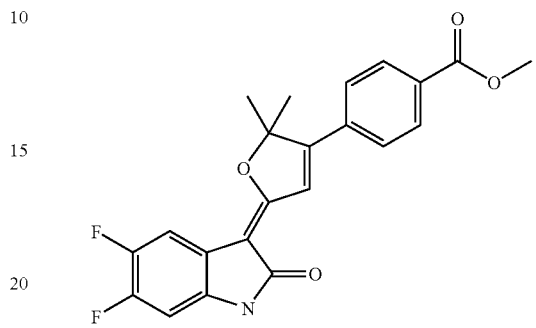

To 10 mL of 1,4-dioxane, was added the following reagents: (3E)-3-(4-bromo-5,5-dimethylfuran-2(5H)-ylidene)-5,6-difluoro-1,3-dihydro-2H-indol-2-one (250 mg, 0.73 mmol), 4-methoxycarbonylphenylboronic acid (158 mg, 0.88 mmol), PdCl$_2$(PPh$_3$)$_2$ (25 mg, 0.036 mmol), 2M Na$_2$CO$_3$ aqueous solution (1.5 mL, 3.0 mmol). The mixture was heated at 86° C. under N$_2$ for 2 hours, cooled to room temperature and poured into 100 mL of water. The brown precipitates were filtered, washed with water and dried to give the crude product. Purification through silica gel column with 1-2% MeOH/CHCl$_3$ led to methyl 4-[(5E)-5-(5,6-difluoro-2-oxo-1,2-dihydro-3H-indol-3-ylidene)-2,2-dimethyl-2,5-dihydrofuran-3-yl]benzoate as orange/red solid. Yield: 112 mg, 39%.

$^1$H NMR (300 MHz, d$_6$-DMSO) δ ppm 1.79 (s, 6 H) 3.87 (s, 3 H) 6.81 (dd, J=10.85, 7.04 Hz, 1 H) 7.50 (dd, J=10.55, 8.21 Hz, 1 H) 7.85 (s, 1 H) 7.95 (d, J=8.50 Hz, 2 H) 8.04 (d, J=8.50 Hz, 2 H) 10.43 (s, 1 H)
LR MS (ES−): 396 (M−1)

Preparation of 4-[(5E)-5-(5,6-difluoro-2-oxo-1,2-dihydro-3H-indol-3-ylidene)-2,2-dimethyl-2,5-dihydrofuran-3-yl]benzoic acid

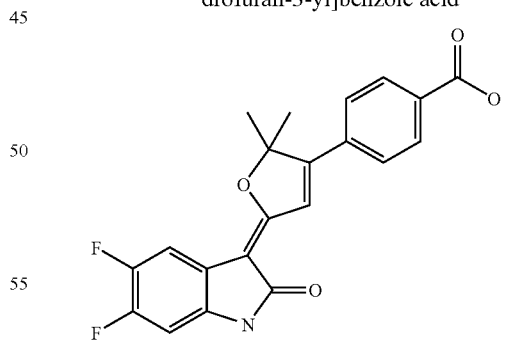

To a solution of methyl 4-[(5E)-5-(5,6-difluoro-2-oxo-1,2-dihydro-3H-indol-3-ylidene)-2,2-dimethyl-2,5-dihydrofuran-3-yl]benzoate (100 mg, 0.25 mmol) in a 1:1 mixture of THF/MeOH (5 mL/5 mL), was added 1M NaOH (2 mL). The mixture was heated in 60° C. bath for 1.5 hours, poured into 100 mL of water and acidified with 2M HCl (2 mL). The precipitates were filtered, washed with water, and dried in vacuum to give 4-[(5E)-5-(5,6-difluoro-2-oxo-1,2-dihydro-3H-indol-3-ylidene)-2,2-dimethyl-2,5-dihydrofuran-3-yl]benzoic acid as yellow solid. Yield: 90 mg, 93%.

¹H NMR (300 MHz, d₆-DMSO) δ ppm 1.79 (s, 6 H) 6.81 (dd, J=10.85, 6.74 Hz, 1 H) 7.49 (dd, J=10.41, 8.35 Hz, 1 H) 7.84 (s, 1 H) 7.92 (d, J=8.50 Hz, 2 H) 8.02 (d, J=8.50 Hz, 2 H) 10.42 (s, 1 H) 13.17 (s, 1 H)

LR MS (ES−): 382 (M−1)

Example 179

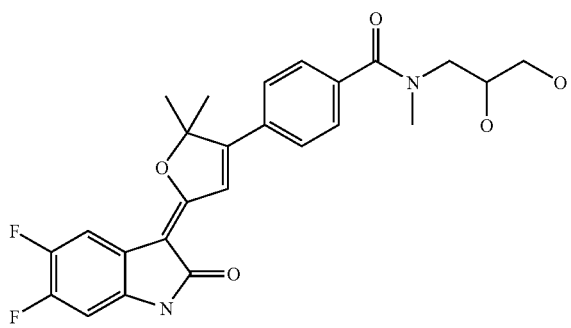 [SMILES: CN(CC(O)CO)C(=O)c1ccc(C2=C/C(=C3\C(=O)Nc4cc(F)c(F)cc43)OC2(C)C)cc1]

4-[(5E)-5-(5,6-difluoro-2-oxo-1,2-dihydro-3H-indol-3-ylidene)-2,2-dimethyl-2,5-dihydrofuran-3-yl]-N-(2,3-dihydroxypropyl)-N-methylbenzamide A mixture of 4-[(5E)-5-(5,6-difluoro-2-oxo-1,2-dihydro-3H-indol-3-ylidene)-2,2-dimethyl-2,5-dihydrofuran-3-yl]benzoic acid (50 mg, 0.13 mmol), 3-methylamino-1,2-propanediol (40 mg, 0.38 mmol), O-benzotriazol-1-yl-N,N,N',N'-tetramethyluronium hexafluorophosphate (HBTU, 61 mg, 0.16 mmol) and diisopropylethylamine (37 mg, 0.29 mmol) in 6 mL of anhydrous DMF was stirred at room temperature for 10 minutes. The mixture was poured into 100 mL of water. The precipitates were filtered, washed with water, and dried in vacuum to give 4-[(5E)-5-(5,6-difluoro-2-oxo-1,2-dihydro-3H-indol-3-ylidene)-2,2-dimethyl-2,5-dihydrofuran-3-yl]-N-(2,3-dihydroxypropyl)-N-methylbenzamide as yellow solid. Yield: 47 mg, 81%.

LR MS (ES−): 469 (M−1)

Example 180

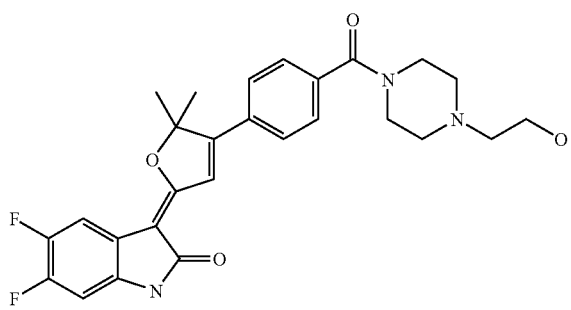 [SMILES: CC1(C)O/C(=C2/C(=O)Nc3cc(F)c(F)cc32)C=C1c1ccc(C(=O)N2CCN(CCO)CC2)cc1]

(3E)-5, 6-Difluoro-3-[4-(4-{[4-(2-hydroxyethyl)piperazin-1-yl]carbonyl}phenyl)-5,5-dimethylfuran-2(5H)-ylidene]-1,3-dihydro-2H-indol-2-one Similar procedure as Example 179.

LR MS (ES−): 494 (M−1)

Figure 4:
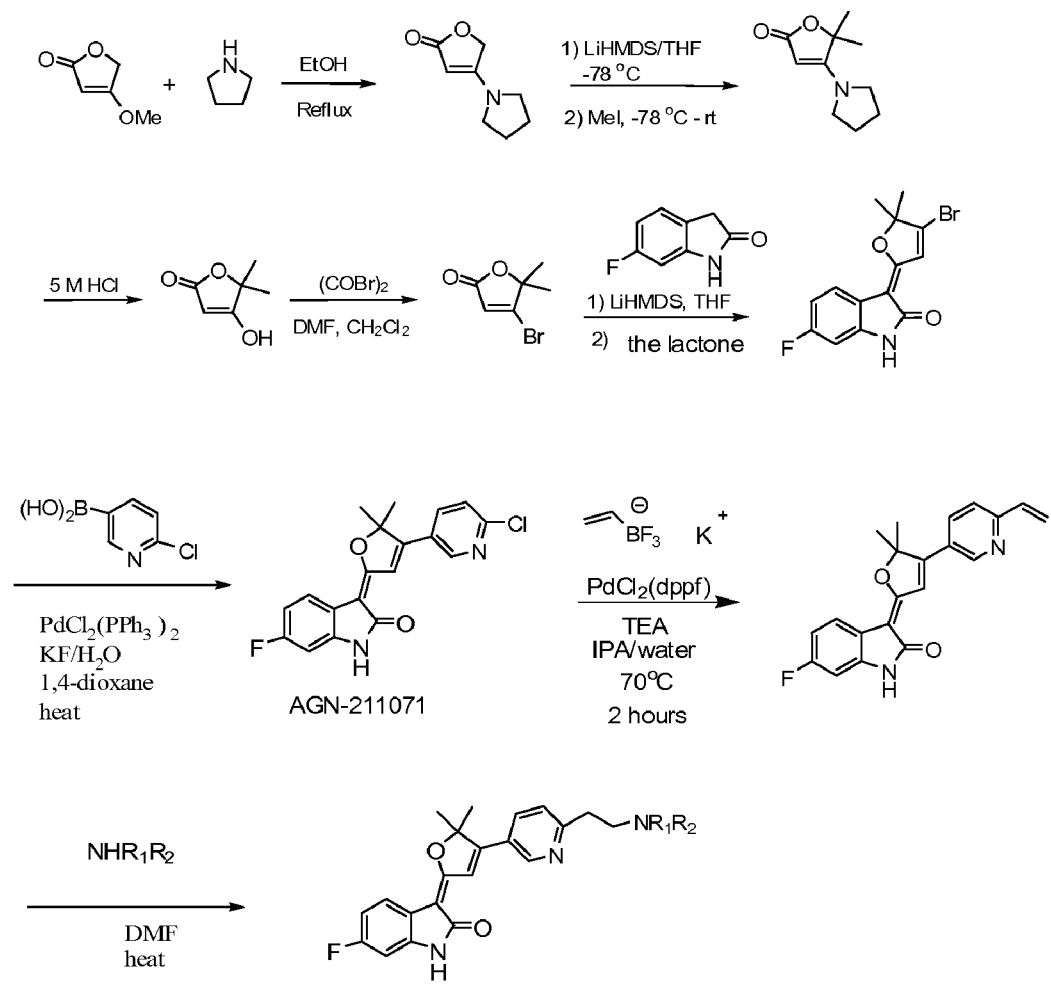
FIG. 4 shows a method for the preparation of the compounds of Table 7.

Preparation of Examples 181-222(FIG. 4)

Each of the examples was prepared through the library synthesis as follows:

To an 8-mL screw cap vial was added 4-[(5E)-5-(6-fluoro-2-oxo-1,2-dihydro-3H-indol-3-ylidene)-2,2-dimethyl-2,5-dihydrofuran-3-yl]benzoic acid (58.5 mg, 0.16 mmol), amine (0.24 mmol, 1.5 eq.), DMF (1 mL), and DIPEA (0.06 mL, 0.35 mmol, 2.2 eq.), and O-benzotriazol-1-yl-N,N,N',N'-tetramethyluronium hexafluorophosphate (HBTU) (91 mg, 0.24 mmol, 1.5 eq). The reaction mixture was shaken at room temperature for 24 hours. The resulting clear reaction mixture was submitted for preparative RP-HPLC purification without workup. The library compounds were purified by high throughput RP-HPLC. Each compound was re-analyzed by LCMS after purification.

Example 97 is the compound example for the library synthesis (FIG. 4).

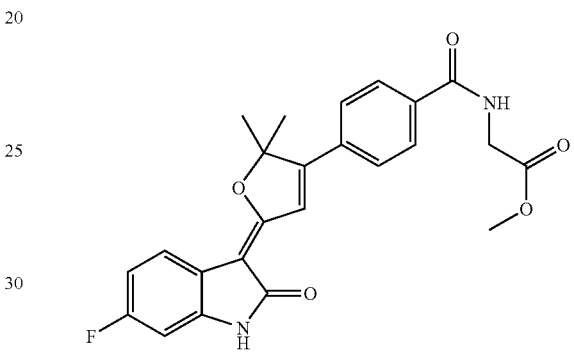

Methyl ({4-[(5E)-5-(6-fluoro-2-oxo-1,2-dihydro-3H-indol-3-ylidene)-2,2-dimethyl-2,5-dihydrofuran-3-yl]benzoyl}amino)acetate ¹H NMR (300 MHz, DMSO-d₆) δ ppm 10.45 (s, 1H), 9.11(t, J=5.7 Hz, 1H), 7.97 (d, J=8.4 Hz, 2H), 7.91(d, J=8.4 Hz, 2H), 7.85 (s, 1H), 7.55 (dd, J=8.4, 5.7 Hz, 1H), 6.75(ddd, J=2.4, 8.4, 10.5 Hz, 1H), 6.62(dd, J=2.4, 9.3 Hz, 1H), 4.03(d, J=5.7 Hz, 2H), 3.66(s, 3H), 1.79 (s, 6H).

ESI-MS m/z 437.4 (M+H)³⁰.

Preparation of 4-[(5E)-5-(6-fluoro-2-oxo-1,2-dihydro-3H-indol-3-ylidene)-2,2-dimethyl-2,5-dihydrofuran-3-yl]benzaldehyde

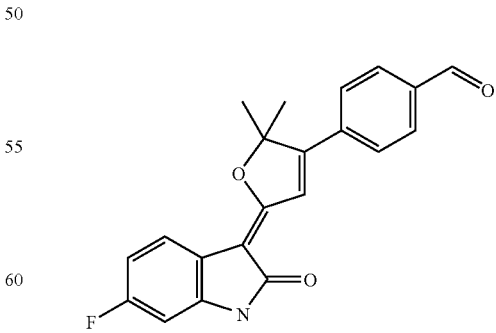

Method A: To 10 mL of 1,4-dioxane was added the following reagents: (3E)-3-(4-bromo-5,5-dimethylfuran-2(5H)-ylidene)-6-fluoro-1,3-dihydro-2H-indol-2-one (100 mg, 0.31 mmol), 4-formylphenylboronic acid (56 mg, 0.37 mmol), PdCl$_2$(PPh$_3$)$_2$ (22 mg, 0.031 mmol), 1M Na$_2$CO$_3$ aqueous solution (1.2 mL, 1.2 mmol). The mixture was heated at 80° C. under N$_2$ for 1 hour, cooled to room temperature and poured into 100 mL of water. The mixture was extracted with EtOAc (3×50 mL). The organic layers were combined, washed with brine (50 mL), dried over Na$_2$SO$_4$, and concentrated to give the crude product, which was purified through silica gel column with 1-5% MeOH/CHCl$_3$ to give 4-[(5E)-5-(6-fluoro-2-oxo-1,2-dihydro-3H-indol-3-ylidene)-2,2-dimethyl-2,5-dihydrofuran-3-yl]benzaldehyde as orange/red solid. Yield: 100 mg, 93%.

Method B: To a mixture of (3E)-3-(4-bromo-5,5-dimethylfuran-2(5H)-ylidene)-6-fluoro-1,3-dihydro-2H-indol-2-one (2.0 g, 6.17 mmol), 4-formyl phenylboronic acid (1.85 g, 12.3 mmol), aqueous potassium carbonate (1 M, 31 mL, 31 mmol) in THF (120 mL) under a nitrogen atmosphere, was added palladium(0) tetrakis(triphenylphosphine) (356 mg, 0.3 mmol, 5 mol %). The mixture was heated at 65° C. overnight (20 h). The reaction was cooled to room temperature and ethyl acetate (500 mL) was added. The organic phase was washed with water (100 mL×2), dried over sodium sulfate, and evaporated. The residue was purified by silica gel column chromatography (5% CH$_3$OH/CH$_2$Cl$_2$ elution). Trituration of the product obtained from the column chromatography with ethyl acetate/hexane (1/1), followed by isolation of the precipitate by filtration, provided 4-[(5E)-5-(6-fluoro-2-oxo-1,2-dihydro-3H-indol-3-ylidene)-2,2-dimethyl-2,5-dihydrofuran-3-yl]benzaldehyde as a red orange solid (1.1 g, yield 51%).

$^1$H NMR (300 MHz, DMSO-d$_6$) δ ppm 10.47 (s, 1H), 10.05 (s, 1H), 8.0 (m, 4H), 7.91 (s, 1H), 7.55 (dd, J=8.4, 6.0 Hz, 1H), 6.75 (ddd, J=10.5, 8.4, 2.4 Hz, 1H), 6.60 (dd, J=9.3, 2.4 Hz, 1H), 1.80 (s, 6H).

ESI-MS m/z 350.1 (M+1)$^+$.

Example 223

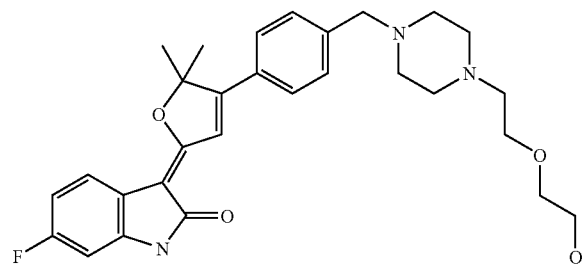 [SMILES: CC1(C)O/C(=C2/C(=O)Nc3cc(F)ccc32)C=C1c1ccc(CN2CCN(CCOCCO)CC2)cc1]

(3E)-6-Fluoro-3-{4-[4-({4-[2-(2-hydroxyethoxy)ethyl]piperazin-1-yl}methyl)phenyl]-5,5-dimethylfuran-2(5H)-ylidene}-1,3-dihydro-2H-indol-2-one A mixture of 4-[(5E)-5-(6-fluoro-2-oxo-1,2-dihydro-3H-indol-3-ylidene)-2,2-dimethyl-2,5-dihydrofuran-3-yl]benzaldehyde (55 mg, 0.16 mmol), 2-(2-(piperazin-1-yl)ethoxy)ethanol (56 mg, 0.32 mmol) and 4 Å molecular sieves (100 mg) in anhydrous DMF (3 mL) was stirred at room temp for 16 hours. To this stirred mixture was added AcOH (10 mg), 1M sodium cyanoborohydride in THF solution (0.32 mL, 0.32 mmol) and 3 mL of anhydrous methanol. The reaction mixture was stirred at room temp for 5 hours and poured into 100 mL of water. Saturated NaHCO$_3$ solution was then added until pH=9. The precipitates were filtered, washed with water, and dried in vacuo to give the crude product, which was purified through silica gel column with 5-10% MeOH/CHCl$_3$ to give (3E)-6-fluoro-3-{4-[4-{4-[2-(2-hydroxyethoxy)ethyl]piperazin-1-yl}methyl)phenyl]-5,5-dimethylfuran-2(5H)-ylidene}-1,3-dihydro-2H-indol-2-one as yellow solid. Yield: 45 mg, 56%.

$^1$H NMR (500 MHz, d$_6$-DMSO) δ ppm 1.78 (s, 6H) 2.36-2.51 (m, 10H) 3.40 (t, J=5.13 Hz, 2H) 3.46-3.52 (m, 6H) 4.61 (s, 1H) 6.62 (dd, J=9.28, 2.44 Hz, 1H) 6.73-6.77 (m, 1H) 7.43 (d, J=8.30 Hz, 2H) 7.55 (dd, J=8.30, 5.86 Hz, 1H) 7.76 (t, J=4.15 Hz, 3H) 10.42 (s, 1H)

LR MS (ES+): 508 (M+1)

The following examples 224-226 were prepared using the experiment procedure described in Example 223, but with the appropriate reagent, reaction conditions and reactant substitutions that will be readily realized by those of ordinary skill in this art without the exercise of undue experimentation.

Example 224

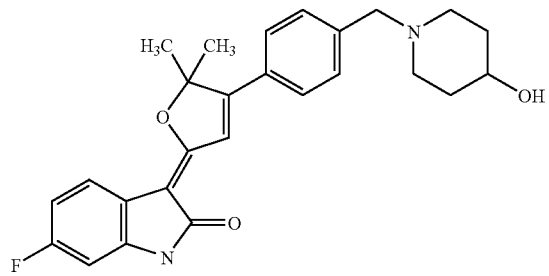 [SMILES: CC1(C)O/C(=C2/C(=O)Nc3cc(F)ccc32)C=C1c1ccc(CN2CCC(O)CC2)cc1]

(3E)-6-Fluoro-3-[4-{4-[(4-hydroxypiperidin-1-yl)methyl]phenyl}-5,5-dimethylfuran-2(5H)-ylidene]-1,3-dihydro-2H-indol-2-one $^1$H NMR (500 MHz, d$_6$-DMSO) δ ppm 1.41 (br s, 2H) 1.71 (br s, 2H) 1.78 (s, 6H) 2.07 (br s, 2H) 2.68 (br s, 2H) 3.49 (br s, 3H) 4.55 (br s, 1H) 6.62 (dd, J=9.28, 1.95 Hz, 1H) 6.73-6.77 (m, 1H) 7.43 (d, J=6.83 Hz, 2H) 7.55 (dd, J=8.30, 5.86 Hz, 1H) 7.76 (br s, 3H) 10.42 (s, 1H)

LR MS (ES+): 435 (M+1)

Example 225

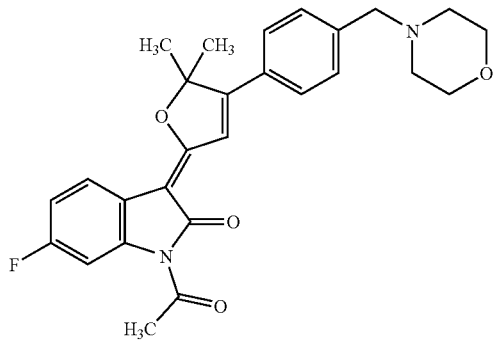 [SMILES: CC(=O)N1C(=O)/C(=C2\C=C(c3ccc(CN4CCOCC4)cc3)C(C)(C)O2)c2ccc(F)cc21]

(3E)-1-Acetyl-3-{5,5-dimethyl-4-[4-(morpholin-4-ylmethyl)phenyl]furan-2(5H)-ylidene}-6-fluoro-1,3-dihydro-2H-indol-2-one $^1$H NMR (500 MHz, d$_6$-DMSO) ppm 1.83 (s, 6 H) 2.39 (br s, 4 H) 2.65 (s, 3 H) 3.54 (br s, 2 H) 3.59 (s, 4 H) 7.07-7.11 (m, 1 H) 7.48 (d, J=7.81 Hz, 2 H) 7.78 (dd, J=8.30, 5.86 Hz, 1 H) 7.84 (s, 1 H) 7.85 (d, J=7.81 Hz, 2 H) 7.92 (dd, J=10.74, 2.44 Hz, 1 H)

LR MS (ES+): 463 (M+1)

Example 226

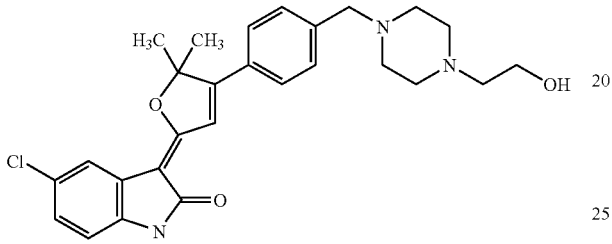

(3E)-5-Chloro-3-[4-(4-{[4-(2-hydroxyethyl)piperazin-1-yl]methyl}phenyl)-5,5-dimethylfuran-2(5H)-ylidene]-1,3-dihydro-2H-indol-2-one $^1$H NMR (300 MHz, d$_6$-DMSO) δ ppm 1.79 (s, 6 H) 2.34-2.44 (m, 10 H) 3.46 (q, J=5.28 Hz, 2 H) 3.49 (s, 2 H) 4.33 (t, J=4.84 Hz, 1 H) 6.78 (d, J=8.21 Hz, 1 H) 7.07 (dd, J=8.35, 2.20 Hz, 1 H) 7.42 (d, J=8.50 Hz, 2 H) 7.50 (d, J=2.05 Hz, 1 H) 7.76 (d, J=8.50 Hz, 2 H) 7.77 (s, 1 H) 10.38 (s, 1 H)

LR MS (ES+): 480 (M+1)

Preparation of methyl (3E)-3-(4-bromo-5,5-dimethylfuran-2(5H)-ylidene)-2-oxoindoline-5-carboxylate

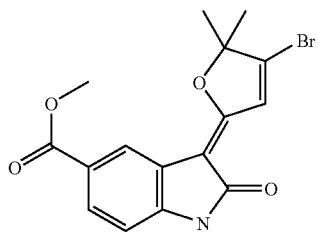 [SMILES: COC(=O)c1ccc2c(c1)/C(=C1/C=C(Br)C(C)(C)O1)C(=O)N2]

To a 0° C. stirred solution of methyl oxindole-5-carboxylate (421 mg, 2.2 mmol) and 4-bromo-5,5-dimethylfuran-2(5H)-one (382 mg, 2.0 mmol) in THF (10 mL), was added 1M LiHMDS/THF solution (4.4 mL, 4.4 mmol) under nitrogen. The mixture was stirred at 0° C. for 80 min, quenched with 2.5M H$_2$SO$_4$ (3 mL), and poured into 100 mL of water. The precipitates were filtered, washed with water, and dried in vacuo to give methyl (3E)-3-(4-bromo-5,5-dimethylfuran-2(5H)-ylidene)-2-oxoindoline-5-carboxylate as yellow solid. Yield: 408 mg, 56%.

$^1$H NMR (300 MHz, d$_6$-DMSO) δ ppm 1.61 (s, 6 H) 3.83 (s, 3 H) 6.91 (d, J=8.21 Hz, 1 H) 7.64 (s, 1 H) 7.78 (dd, J=8.21, 1.76 Hz, 1 H) 8.09 (d, J=1.47 Hz, 1 H) 10.76 (s, 1 H)

Example 227

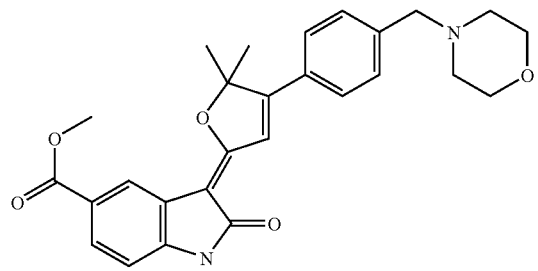 [SMILES: COC(=O)c1ccc2c(c1)/C(=C1/C=C(c3ccc(CN4CCOCC4)cc3)C(C)(C)O1)C(=O)N2]

Methyl (3E)-3-{5,5-dimethyl-4-[4-(morpholin-4-ylmethyl)phenyl]furan-2(5H)-ylidene}-2-oxoindoline-5-carboxylate A mixture of methyl (3E)-3-(4-bromo-5,5-dimethylfuran-2(5H)-ylidene)-2-oxoindoline-5-carboxylate (90 mg, 0.25 mmol), 4-(4-(4,4,5,5-tetramethyl-1,3,2-dioxaborolan-2-yl)benzyl)morpholine hydrochloride (92 mg, 0.27 mol), [1,1'-bis(diphenylphosphino)ferrocene]dichloropalladium(II) (complex with CH$_2$Cl$_2$, 20 mg, 0.027 mmol) and 2M Na$_2$CO$_3$ (0.5 mL, 1.0 mmol) in 8 mL of DMF was heated in 85° C. bath under nitrogen for 90 minutes. The mixture was cooled to room temperature and poured into 100 mL of water. The precipitates were filtered, washed with water and dried to give the crude product, which was purified through silica gel column with 1-5% MeOH/CHCl$_3$ to give methyl (3E)-3-{5,5-dimethyl-4-[4-(morpholin-4-ylmethyl)phenyl]furan-2(5H)-ylidene}-2-oxoindoline-5-carboxylate as yellow solid. Yield: 20 mg, 18%.

$^1$H NMR (300 MHz, d$_6$-DMSO) δ ppm 1.82 (s, 6 H) 2.38 (t, J=4.69 Hz, 4 H) 3.53 (s, 2 H) 3.59 (t, J=4.69, 4 H) 3.84 (s, 3 H) 6.91 (d, J=8.21 Hz, 1 H) 7.47 (d, J=8.21 Hz, 2 H) 7.75 (dd, J=8.21, 1.76 Hz, 1 H) 7.80 (d, J=8.50 Hz, 2 H) 7.84 (s, 1 H) 8.15 (d, J=1.17 Hz, 1 H) 10.71 (s, 1 H)

The following examples 228 through 235 were prepared using the experiment procedure described in Example 227, but with the appropriate reagent, reaction conditions and reactant substitutions that will be readily realized by those of ordinary skill in this art without the exercise of undue experimentation.

Example 228

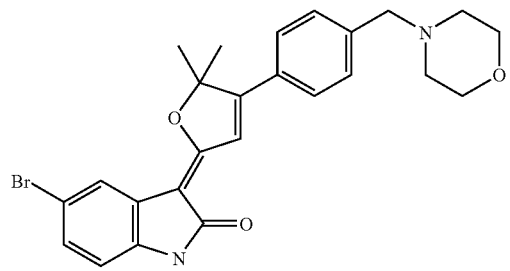 [SMILES: CC1(C)O/C(=C2/C(=O)Nc3ccc(Br)cc32)C=C1c1ccc(CN2CCOCC2)cc1]

(3E)-5-bromo-3-{5,5-dimethyl-4-[4-(morpholin-4-ylmethyl)phenyl]furan-2(5H)-ylidene}-1,3-dihydro-2H-indol-2-one $^1$H NMR (300 MHz, d$_6$-DMSO) δ ppm 1.81 (s, 6 H) 2.38 (br s, 4 H) 3.52 (br s, 2 H) 3.59 (br s, 4 H) 6.77 (d, J=8.21 Hz, 1 H) 7.22 (dd, J=8.21, 2.05 Hz, 1 H) 7.46 (d, J=8.21 Hz, 2 H) 7.64 (d, J=1.76 Hz, 1 H) 7.79 (d, J=8.21 Hz, 2 H) 7.80 (s, 1 H) 10.42 (s, 1 H)

Example 229

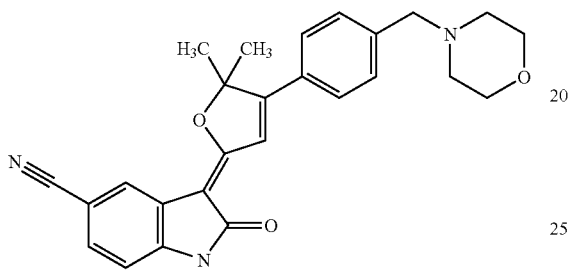

(3E)-3-{5,5-dimethyl-4-[4-(morpholin-4-ylmethyl)phenyl]furan-2(5H)-ylidene}-2-oxoindoline-5-carbonitrile

LR MS (ES+): 428 (M+1)

Example 230

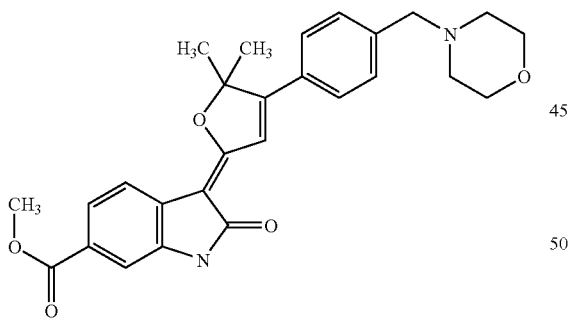

Methyl (3E)-3-{5,5-dimethyl-4-[4-(morpholin-4-ylmethyl)phenyl]furan-2(5H)-ylidene}-2-oxoindoline-6-carboxylate $^1$H NMR (300 MHz, d$_6$-DMSO) δ ppm 1.82 (s, 6 H) 2.38 (br s, 4 H) 3.53 (br s, 2 H) 3.59 (br s, 4 H) 3.84 (s, 3 H) 7.36 (s, 1 H) 7.47 (d, J=8.50 Hz, 2 H) 7.61 (d, J=7.33 Hz, 1 H) 7.68 (d, J=7.92 Hz, 1 H) 7.81 (d, J=8.21 Hz, 2 H) 7.85 (s, 1 H) 10.50 (s, 1 H)

LR MS (ES−): 459 (M−1)

Example 231

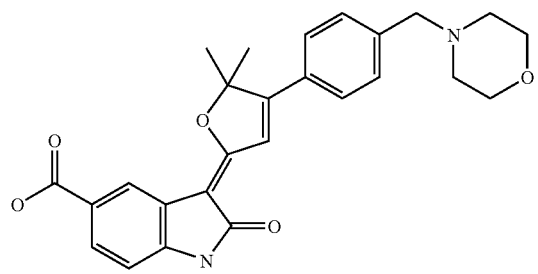 [SMILES: CC1(C)O/C(=C2/C(=O)Nc3ccc(C(=O)O)cc32)C=C1c1ccc(CN2CCOCC2)cc1]

(3E)-3-{5,5-Dimethyl-4-[4-(morpholin-4-ylmethyl)phenyl]furan-2(5H)-ylidene}-2-oxoindoline-5-carboxylic acid To a stirred solution of methyl (3E)-3-{5,5-dimethyl-4-[4-(morpholin-4-ylmethyl)phenyl]furan-2(5H)-ylidene}-2-oxoindoline-5-carboxylate (18 mg, 0.039 mmol) in MeOH (1 mL) was added 1M NaOH solution (1 mL, 1 mmol). The mixture was heated in 50° C. bath under nitrogen for 4 hours, cooled to room temp, and neutralized with 1M HCl to about pH 7. The mixture was extracted with 10% MeOH/CHCl$_3$ solution (3×30 mL). The organic layers were combined, dried over Na$_2$SO$_4$, and evaporated to dryness to give (3E)-3-{5,5-dimethyl-4-[4-(morpholin-4-ylmethyl)phenyl]furan-2(5H)-ylidene}-2-oxoindoline-5-carboxylic acid as yellow solid. Yield: 15 mg, 88%.

LR MS (ES−): 445 (M−1)

The following examples 232 through 233 were prepared using the experiment procedure described in Example 231, but with the appropriate reagent, reaction conditions and reactant substitutions that will be readily realized by those of ordinary skill in this art without the exercise of undue experimentation.

Example 232

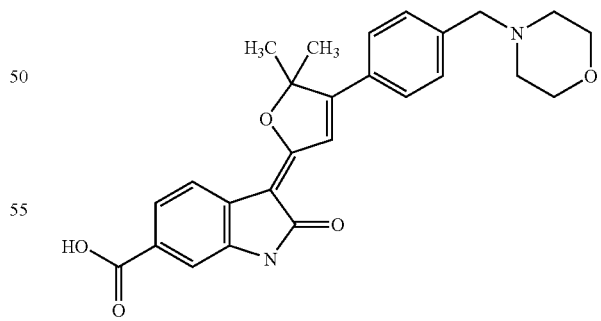

(3E)-3-{5,5-Dimethyl-4-[4-(morpholin-4-ylmethyl)phenyl]furan-2(5H)-ylidene}-2-oxoindoline-6-carboxylic acid

LR MS (ES−): 445 (M−1)

Example 233

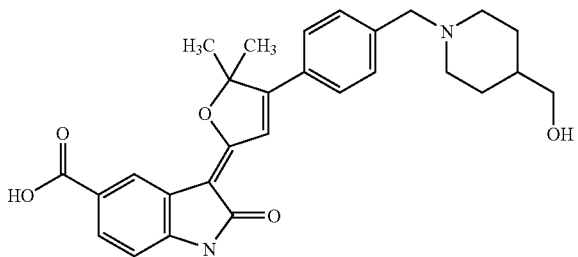 [SMILES: CC1(C)O/C(=C2/C(=O)Nc3ccc(C(=O)O)cc32)C=C1c1ccc(CN2CCC(CO)CC2)cc1]

(3E)-3-[4-(4-{[4-(Hydroxymethyl)piperidin-1-yl]methyl}phenyl)-5,5-dimethylfuran-2(5H)-ylidene]-2-oxoindoline-5-carboxylic acid

LR MS (ES+): 475 (M+1)
LR MS (ES−): 473 (M−1)

Preparation of 4-[(5E)-5-(5,6-difluoro-2-oxo-1,2-dihydro-3H-indol-3-ylidene)-2,2-dimethyl-2,5-dihydrofuran-3-yl]benzaldehyde

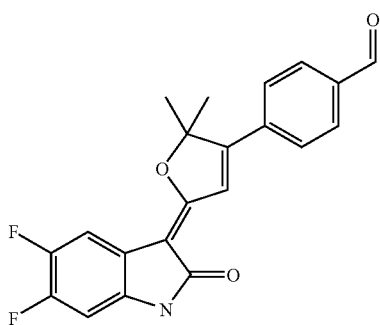 [SMILES: CC1(C)O/C(=C2/C(=O)Nc3cc(F)c(F)cc32)C=C1c1ccc(C=O)cc1]

To 10 mL of 1,4-dioxane was added (3E)-3-(4-bromo-5,5-dimethylfuran-2(5H)-ylidene)-5,6-difluoro-1,3-dihydro-2H-indol-2-one (85 mg, 0.25 mmol), 4-formylphenylboronic acid (45 mg, 0.30 mmol), PdCl$_2$(PPh$_3$)$_2$ (10 mg, 0.014 mmol), 2M Na$_2$CO$_3$ aqueous solution (0.5 mL, 10 mmol). The mixture was heated at 80° C. under N$_2$ for 30 minutes. After cooling to room temperature, the mixture was diluted with EtOAc (80 mL). The EtOAc solution was washed with brine (2×50 mL), dried over Na$_2$SO$_4$, and concentrated to give 4-[(5E)-5-(5,6-difluoro-2-oxo-1,2-dihydro-3H-indol-3-ylidene)-2,2-dimethyl-2,5-dihydrofuran-3-yl]benzaldehyde as the crude product, which was used in the next step without further purification.

Example 234

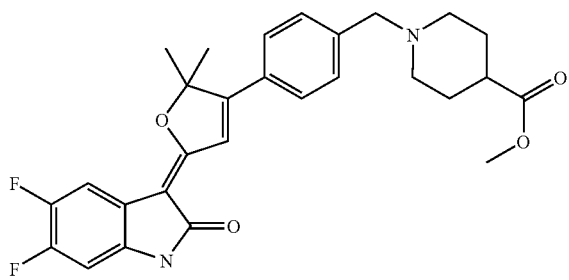 [SMILES: COC(=O)C1CCN(Cc2ccc(C3=C/C(=C4\C(=O)Nc5cc(F)c(F)cc54)OC3(C)C)cc2)CC1]

Methyl 1-{4-[(5E)-5-(5,6-difluoro-2-oxo-1,2-dihydro-3H-indol-3-ylidene)-2,2-dimethyl-2,5-dihydrofuran-3-yl]benzyl}piperidine-4-carboxylate A mixture of 4-[(5E)-5-(5,6-difluoro-2-oxo-1,2-dihydro-3H-indol-3-ylidene)-2,2-dimethyl-2,5-dihydrofuran-3-yl]benzaldehyde (60 mg, 0.16 mmol), methyl isonipecotate (50 mg, 0.35 mmol), and 100 mg of 4 Å molecular sieves in 5 mL of anhydrous DMF was stirred under nitrogen for 16 hours. Acetic acid (20 mg) and 1M sodium cyanoborohydride/THF solution (0.35 mL, 0.35 mmol) were then added. The mixture was diluted with 5 mL of anhydrous methanol, stirred at room temperature for 1 hour, and poured into 100 mL of water with stirring. The resulting precipitates were filtered, washed with water, and dried in vacuo to give the crude product, which was purified through silica gel column with 1-5% MeOH/CHCl$_3$ to give methyl 1-{4-[(5E)-5-(5,6-difluoro-2-oxo-1,2-dihydro-3H-indol-3-ylidene)-2,2-dimethyl-2,5-dihydrofuran-3-yl]benzyl}piperidine-4-carboxylate as yellow solid. Yield: 50 mg, 62%.

LR MS (ES−): 493 (M−1)

Example 235

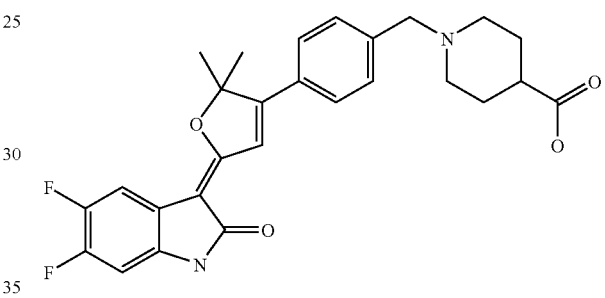

1-{4-[(5E)-5-(5,6-Difluoro-2-oxo-1,2-dihydro-3H-indol-3-ylidene)-2,2-dimethyl-2,5-dihydrofuran-3-yl]benzyl}piperidine-4-carboxylic acid To a suspension of methyl 1-{4-[(5E)-5-(5,6-difluoro-2-oxo-1,2-dihydro-3H-indol-3-ylidene)-2,2-dimethyl-2,5-dihydrofuran-3-yl]benzyl}piperidine-4-carboxylate (50 mg, 0.10 mmol) in MeOH (5 mL), was added 1M NaOH (1 mL). The mixture was heated in 50° C. bath for 1 hour, poured into 50 mL of water and neutralized with 0.5M HCl to pH 7. The precipitates were filtered, washed with water, and dried in vacuo to give 1-{4-[(5E)-5-(5,6-difluoro-2-oxo-1,2-dihydro-3H-indol-3-ylidene)-2,2-dimethyl-2,5-dihydrofuran-3-yl]benzyl}piperidine-4-carboxylic acid as a yellow solid. Yield: 9 mg, 19%.

LR MS (ES−): 479 (M−1)

Figure 5:
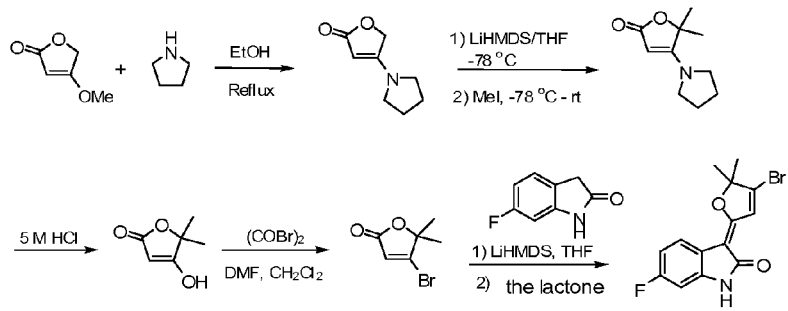
FIG. 5 shows methods for the preparation of compounds of Table 7 and Table 8.
Figure 5:
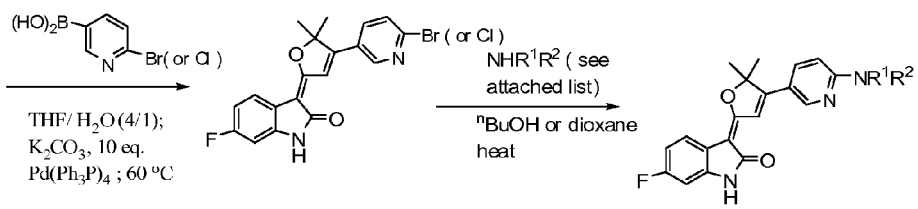
Figure 5:
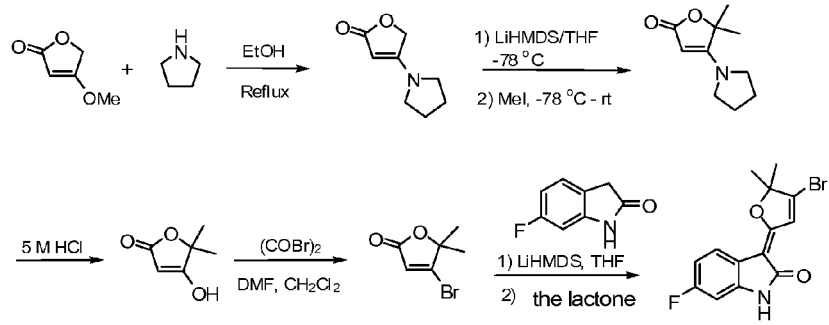
Figure 5:
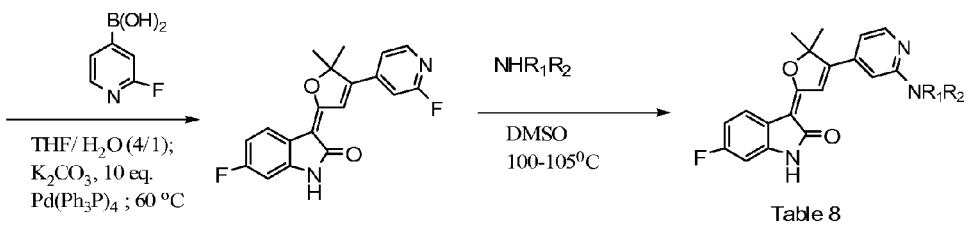

Preparation of Examples 236-260 (FIG. 5)

Each of the examples was prepared through the library synthesis as follows:

To each 8-mL reaction vial was added 4-[(5E)-5-(6-fluoro-2-oxo-1,2-dihydro-3H-indol-3-ylidene)-2,2-dimethyl-2,5-dihydrofuran-3-yl]benzaldehyde (25 mg, 0.07 mmol), amine (0.105 mmol, 1.5 eq), 5% HOAc/DMF (v/v) (1 mL), and NaBH(OAc)$_3$ (45 mg, 0.21 mmol, 3 eq.). The reaction was shaken at room temperature for 20 hours. It was then quenched with water (0.1 mL). The solvents were evaporated in a SpeedVac and the residue was dissolved in DMSO (1 mL). The DMSO solution was submitted for preparative RP-HPLC purification. Each compound was re-analyzed by LCMS after purification.

Preparation of 3-[4-bromo-5,5-dimethyl-5H-furan-(2E)-ylidene]-5-fluoro-1,3-dihydro-indol-2-one

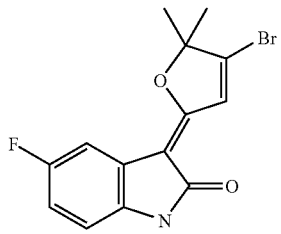 [SMILES: CC1(C)O/C(=C2/C(=O)Nc3ccc(F)cc32)C=C1Br]

To a solution of 5-fluorooxindole (7.5 g, 49 mmol) in THF (80 mL) at 0° C., was added 1 M LHMDS in THF (100 mL, 100 mmol). The reaction mixture was stirred at 0° C. for 20 minutes. A solution of 4-bromo-5,5-dimethyl-5H-furan-2-one(6.4 g, 33 mmol) in THF (20 mL) was added to the reaction mixture. The reaction was stirred at 0° C. for 30 minutes and then allowed to warm to room temperature over 5 hours. To the reaction mixture was added aqueous 2 M HCl (100 mL). The resulting mixture was stirred at 60-65° C. for 1 hour, cooled to room temperature, poured into water (3000 mL) and stirred at room temperature for 2 hours. The precipitates separated and were collected, washed with water, and dried in vacuo to provide 3-[4-bromo-5,5-dimethyl-5H-furan-(2E)-ylidene]-5-fluoro-1,3-dihydro-indol-2-one as a yellow solid (8.7 g, yield 80%), which was used for the next reaction without further purification.

$^1$H NMR (300 MHz, DMSO-$d_6$) δ ppm 0.26 (s, 1H), 7.50 (s, 1H), 7.22 (dd, J=9.0, 2.7 Hz, 1H), 6.84 (ddd, J=11.1, 8.7, 2.7 Hz, 1H), 6.69 (dd, J=8.7, 4.5 Hz, 1H). 1.53 (s, 6H).

ESI-MS m/z 324.0 M$^+$.

Preparation of 4-{5-[5-fluoro-2-oxo-1,2-dihydro-indol-(3E)-ylidene]-2,2-dimethyl-2,5-dihydro-furan-3-yl}-benzaldehyde

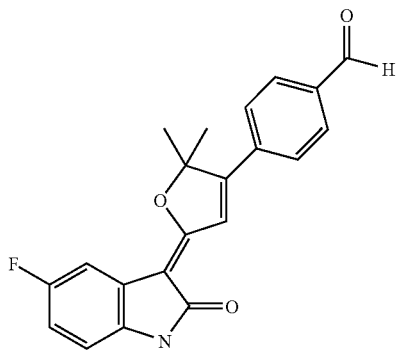 [SMILES: CC1(C)O/C(=C2/C(=O)Nc3ccc(F)cc32)C=C1c1ccc(C=O)cc1]

To a mixture of 3-[4-bromo-5,5-dimethyl-5H-furan-(2E)-ylidene]-5-fluoro-1,3-dihydro-indol-2-one (6.5 g, 20 mmol), 4-formyl phenyl boronic acid (3.6 g, 24 mmol) in THF (250 mL), was added a solution of potassium carbonate (27.6 g, 200 mmol) in water (25 mL). The resulting mixture was deoxygenated with nitrogen, and palladium(0) tetrakis(triphenylphosphine) (1.15 g, 1.0 mmol, 5 mol %) then added. The reaction mixture was heated at 65° C. for 20 hours and then it was allowed to cool to room temperature. Ethyl acetate (800 mL) was added. The organic phase was washed with water (200 mL×2), dried over sodium sulfate and evaporated to give crude product. The purification first by column (SiO$_2$) chromatography (5% CH$_3$OH/CH$_2$Cl$_2$) and then by titration with ethyl acetate led to 4-{5-[5-fluoro-2-oxo-1,2-dihydro-indol-(3E)-ylidene]-2,2-dimethyl-2,5-dihydro-furan-3-yl}-benzaldehyde as a deep red solid (3.6 g, yield 51.5%).

$^1$H NMR (300 MHz, DMSO-$d_6$) δ ppm 10.33 (s, 1H), 10.05 (s, 1H), 8.01 (m, 4H), 7.92 (s, 1H), 7.34 (dd, J=9.0, 2.7 Hz, 1H), 6.90 (ddd, J=9.9, 8.4, 2.7 Hz, 1H), 6.77 (dd, J=8.4, 4.5 Hz, 1H), 1.82 (s, 6H).

ESI-MS m/z 350.1 (M+1)$^+$.

Figure 6:
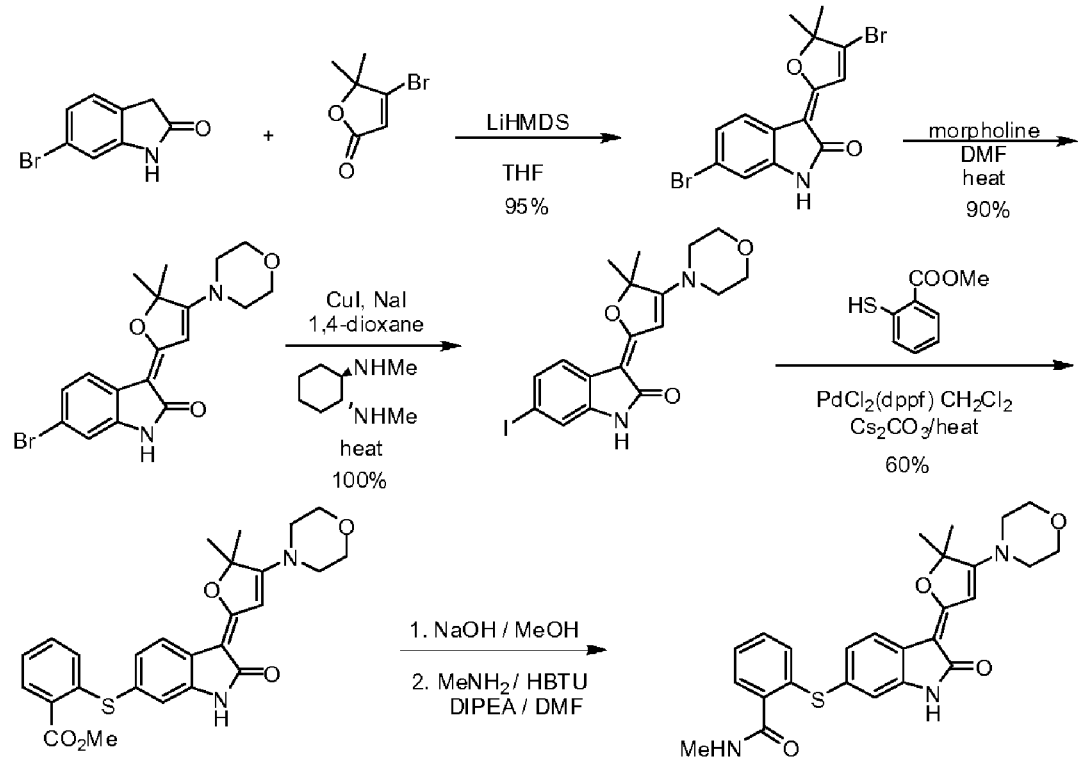
FIG. 6 shows methods for the preparation of compounds of Table 12.
Figure 6:
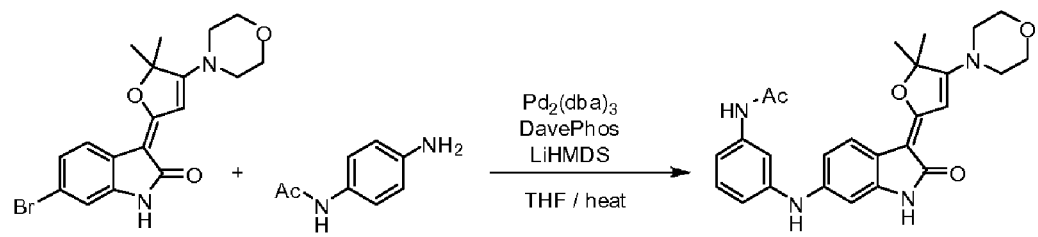

Preparation of Examples 261-310 (FIG. 6)

Each of the examples was prepared through the library synthesis as follows:

To each 8-mL reaction vial was added 4-{5-[5-fluoro-2-oxo-1,2-dihydro-indol-(3E)-ylidene]-2,2-dimethyl-2,5-dihydro-furan-3-yl}-benzaldehyde(55 mg, 0.16 mmol), amine (0.24 mmol, 1.5 eq.), 5% HOAc/DMF (v/v) (1 mL), and NaBH(OAc)$_3$ (62 mg, 0.29 mmol, 1.8 eq.) were added. The reaction was shaken at room temperature overnight. The reaction was quenched with water (0.1 mL), the solvents were evaporated in a SpeedVac, and the residue was dissolved in DMSO (1 mL). The DMSO solution was submitted for preparative RP-HPLC purification. Each compound was re-analyzed by LCMS after purification.

Preparation of 3-[4-(6-chloro-pyridin-3-yl)-5,5-dimethyl-5H-furan-(2E)-ylidene]-6-fluoro-1,3-dihydro-indol-2-one

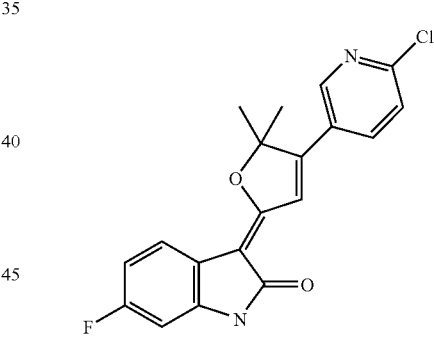

To 240 mL of 1,4-dioxane, were added (3E)-3-(4-bromo-5,5-dimethylfuran-2(5H)-ylidene)-6-fluoro-1,3-dihydro-2H-indol-2-one (3.0 g, 9.3 mmol), [1,1'-bis(diphenylphosphino)ferrocene]dichloropalladium(II) (complex with CH$_2$Cl$_2$, 360 mg, 0.49 mmol), 1M KF aqueous solution (37.5 mL, 37.5 mmol). The resulting mixture was heated at 70° C. under Ar and then 2-chloro-5-pyridineboronic acid (1.57 g, 10.0 mmol) was added in several portions. The reaction was heated at 70° C. under Ar for 22 hours. LC-MS indicated that no starting material molecular peak left; the major peak at 2.59 min with MH$^+$=357.0 was assigned to the product, 3-[4-(6-chloro-pyridin-3-yl)-5,5-dimethyl-5H-furan-(2E)-ylidene]-6-fluoro-1.3-dihydro-indol-2-one (yield>60%).

$^1$H NMR (500 MHz, d$_6$-DMSO) δ ppm 1.76 (s, 6 H) 6.63 (dd, J=9.28, 2.44 Hz, 1 H) 6.73-6.80 (m, 1 H) 7.57 (dd, J=8.54, 5.61 Hz, 1 H) 7.63 (d, J=8.79 Hz, 1 H) 7.88 (s, 1 H) 8.28 (dd, J=8.54, 2.68 Hz, 1 H) 8.83 (d, J=2.44 Hz, 1 H) 10.47 (s, 1 H).

Preparation of (3E)-3-[4-(6'-chloro-2,3'-bipyridin-5-yl)-5,5-dimethylfuran-2(5H)-ylidene]-6-fluoro-1,3-dihydro-2H-indol-2-one

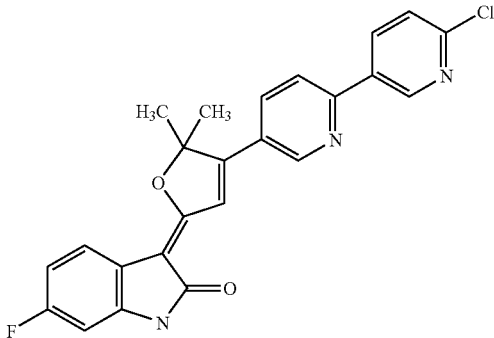 [SMILES: CC1(C)O/C(=C2/C(=O)Nc3cc(F)ccc32)C=C1c1ccc(-c2ccc(Cl)nc2)nc1]

A minor product in a similar procedure as 3-[4-(6-chloropyridin-3-yl)-5,5-dimethyl-5H-furan-(2E)-ylidene]-6-fluoro-1.3-dihydro-indol-2-one.

$^1$H NMR (500 MHz, d$_6$-DMSO) δ ppm 1.82 (s, 6 H) 6.63 (dd, J=9.28, 2.44 Hz, 1 H) 6.74-6.80 (m, 1 H) 7.58 (dd, J=8.30, 5.37 Hz, 1 H) 7.70 (d, J=8.30 Hz, 1 H) 7.94 (s, 1 H) 8.21 (d, J=8.79 Hz, 1 H) 8.37 (dd, J=8.30, 2.44 Hz, 1 H) 8.59 (dd, J=8.30, 2.44 Hz, 1 H) 9.12 (d, J=1.95 Hz, 1 H) 9.19 (d, J=2.44 Hz, 1 H) 10.47 (s, 1 H)

Preparation of (3E)-3-[5,5-Dimethyl-4-(6-vinylpyridin-3-yl)furan-2(5H)-ylidene]-6-fluoro-1,3-dihydro-2H-indol-2-one

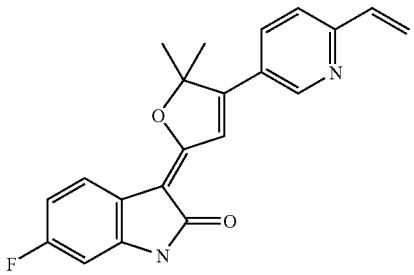 [SMILES: C=Cc1ccc(C2=C/C(=C3\C(=O)Nc4cc(F)ccc43)OC2(C)C)cn1]

Method A: A mixture of 3-[4-(6-chloro-pyridin-3-yl)-5,5-dimethyl-5H-furan-(2E)-ylidene]-6-fluoro-1.3-dihydro-indol-2-one (60 mg, 0.17 mmol), potassium vinyltrifluoroborate (40 mg, 0.30 mmol), [1,1'-bis(diphenylphosphino)ferrocene]dichloropalladium(II) (complex with CH$_2$Cl$_2$, 10 mg, 0.012 mmol) and triethylamine (60 mg, 0.59 mmol) in isopropanol/water (10 mL/5 mL) solution was heated at 76° C. under nitrogen for 2.5 hours. The reaction was cooled to room temperature and poured into 100 mL of water. The resulting precipitates were filtered, washed with water and dried in vacuo to give (3E)-3-[5,5-dimethyl-4-(6-vinylpyridin-3-yl)furan-2(5H)-ylidene]-6-fluoro-1,3-dihydro-2H-indol-2-one as a brown solid. Yield: 50 mg, 85%.

Method B: To a solution of (3E)-3-(4-bromo-5,5-dimethylfuran-2(5H)-ylidene)-6-fluoro-1,3-dihydro-2H-indol-2-one(3.0 g, 9.3 mmol, 1 eq.) in 1,4-dioxane (240 mL) were added Pd(dppf)Cl$_2$ (0.36 g, 0.49 mmol, 0.05 eq.) and 1 M KF aqueous solution (37.5 mL, 37.5 mmol, 4 eq.). The reaction mixture was first heated at 70° C. under Ar and was then added 2-chloro-5-pyridineboronic acid (1.57 g, 10.0 mmol, 1.08 eq.) in several portions in 15 minutes. The reaction mixture was continuously heated at 70° C. under Ar for another 22 hours. LC-MS analysis confirmed that (3E)-3-(4-bromo-5,5-dimethylfuran-2(5H)-ylidene)-6-fluoro-1,3-dihydro-2H-indol-2-one had completely disappeared and 3-[4-(6-chloro-pyridin-3-yl)-5,5-dimethyl-5H-furan-(2E)-ylidene]-6-fluoro-1,3-dihydro-indol-2-one was produced (ESI-MS m/z 357.0 (M+H)$^+$.

To the above reaction mixture under Ar were added Potassium vinyltrifluoroborate (4.98 g, 37.2 mmol, 4 eq.) and extra Pd(dppf)Cl$_2$ (0.36 g, 0.49 mmol, 0.05 eq.). The mixture was heated at 70° C. for 6 hours, cooled to room temperature, and poured into water (300 mL) with stirring. The precipitates were collected by filtration, washed with water (50 mL×2) and dried in vacuo to provide (3E)-3-[5,5-dimethyl-4-(6-vinylpyridin-3-yl)furan-2(5H)-ylidene]-6-fluoro-1,3-dihydro-2H-indol-2-one as a brown solid (1.94 g, 60% yield for two steps; >90% purity by ELS).

ESI-MS m/z 349.2 (M+H$^+$.

Preparation of (3E)-3-[5,5-Dimethyl-4-(6'-vinyl-2,3'-bipyridin-5-yl)furan-2(5H)-ylidene]-6-fluoro-1,3-dihydro-2H-indol-2-one

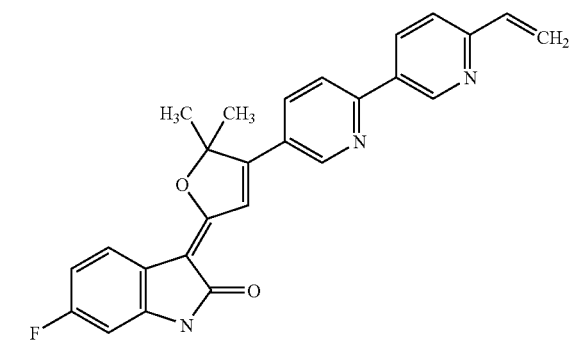 [SMILES: C=Cc1ccc(-c2ccc(C3=C/C(=C4\C(=O)Nc5cc(F)ccc54)OC3(C)C)cn2)cn1]

Similar procedure as (3E)-3-[5,5-dimethyl-4-(6-vinylpyridin-3-yl)furan-2(5H)-ylidene]-6-fluoro-1,3-dihydro-2H-indol-2-one by Method A.

Example 311

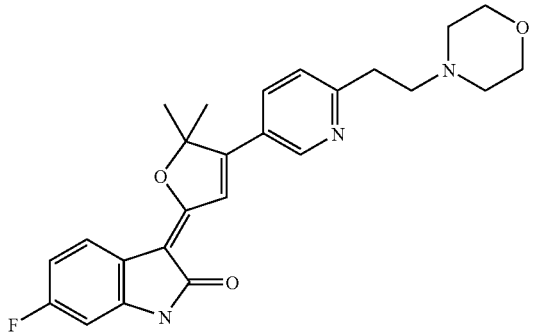 [SMILES: CC1(C)O/C(=C2/C(=O)Nc3cc(F)ccc32)C=C1c1ccc(CCN2CCOCC2)nc1]

(3E)-3-{5,5-Dimethyl-4-[6-(2-morpholin-4-ylethyl)pyridin-3-yl]furan-2(5H)-ylidene}-6-fluoro-1,3-dihydro-2H-indol-2-one A mixture of (3E)-3-[5,5-dimethyl-4-(6-vinylpyridin-3-yl)furan-2(5H)-ylidene]-6-fluoro-1,3-dihydro-2H-indol-2-one (50 mg, 0.14 mmol) and morpholine (0.2 mL, 2.3 mmol) in 5 mL of DMF was heated in 96° C. bath under nitrogen for 3 hours. The mixture was cooled to room temperature and poured into 100 mL of water. The precipitates were filtered, washed with water and dried in vacuo to give (3E)-3-{5,5-dimethyl-4-[6-(2-morpholin-4-ylethyl)pyridin-3-yl]furan-2 (5H)-ylidene}-6-fluoro-1,3-dihydro-2H-indol-2-one as a brown solid. Yield: 40 mg, 64%.

$^1$H NMR (300 MHz, d$_6$-DMSO) δ ppm 1.75 (s, 6 H) 2.50 (br s, 4 H) 2.72 (br s, 2 H) 2.96 (t, J=7.92 Hz, 2 H) 3.56 (br s, 4 H) 6.61 (d, J=9.67 Hz, 1 H) 6.74 (t, J=9.53 Hz, 1 H) 7.42 (d, J=8.21 Hz, 1 H) 7.54 (dd, J=7.77, 6.01 Hz, 1 H) 7.80 (s, 1 H) 8.11 (br s, 1 H) 8.86 (d, J=1.17 Hz, 1 H) 10.42 (s, 1 H)

LR MS (ES+): 436 (M+1)

Example 312

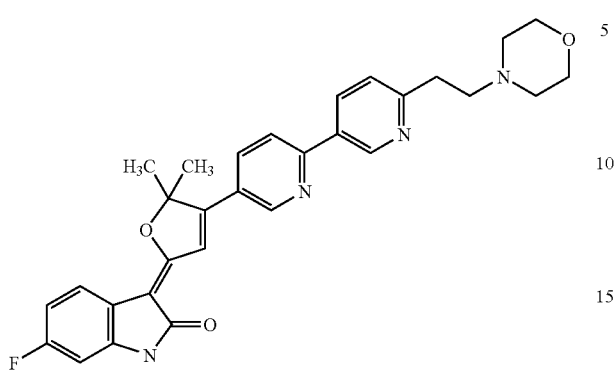

(3E)-3-{5,5-dimethyl-4-[6'-(2-morpholin-4-ylethyl)-2,3'-bipyridin-5-yl]furan-2(5H)-ylidene}-6-fluoro-1,3-dihydro-2H-indol-2-one Similar procedure as Example 311.
LR MS (ES+): 513 (M+1)

Preparation of Examples 314-331(FIG. 7)

Each of the examples was prepared through the library synthesis as follows: To each reaction vial were added (3E)-3-[5,5-dimethyl-4-(6-vinylpyridin-3-yl)furan-2(5H)-ylidene]-6-fluoro-1,3-dihydro-2H-indol-2-one(70 mg, 0.20 mmol, 1 eq.), amine (0.40 mmol, 2 eq.) and DMSO (1 mL). The resulting reaction mixtures were heated at 75° C. for either 20 hours or 45 hours (for the reaction mixtures with the less reactive amine). Representative examples of the reactions were monitored by LCMS. After cooling to room temperature, the DMSO solutions were then submitted for preparative RP-HPLC purification. Each compound was re-analyzed by LCMS after purification.

Example 314 is the compound example for the library synthesis (FIG. 7).

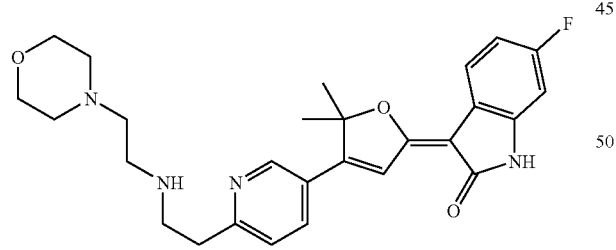

(3E)-3-[5,5-Dimethyl-4-(6-{2-[(2-morpholin-4-yl-ethyl)amino]ethyl}pyridin-3-yl)furan-2(5H)-ylidene]-6-fluoro-1,3-dihydro-2H-indol-2-one To a 8-mL vial were added 3E)-3-[5,5-dimethyl-4-(6-vinylpyridin-3-yl)furan-2(5H)-ylidene]-6-fluoro-1,3-dihydro-2H-indol-2-one (32 mg, 0.095 mmol, 1 eq.), 4-(2-aminoethyl)morpholine (62 mg, 0.48 mmol, 5 eq.) and DMSO (2.5 mL). The reaction was heated at 75° C. for 20 hour. After cooling to room temperature, the DMSO solution was then submitted for preparative RP-HPLC purification to provide (E)-3-(5,5-dimethyl-4-(6-(2-(2-morpholinoethylamino)-ethyl)pyridin-3-yl)furan-2(5H)-ylidene)-6-fluoroindolin-2-one (8.0 mg, 18% yield) as a brown solid.

ESI-MS m/z 479.1 (M+H)$^+$.

Preparation of (3E)-6-fluoro-3-[4-(6-fluoropyridin-3-yl)-5,5-dimethylfuran-2(5H)-ylidene]-1,3-dihydro-2H-indol-2-one

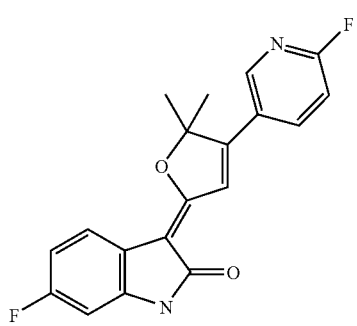 [SMILES: CC1(C)O/C(=C2/C(=O)Nc3cc(F)ccc32)C=C1c1ccc(F)nc1]

To 10 mL of 1,4-dioxane were added (3E)-3-(4-bromo-5,5-dimethylfuran-2(5H)-ylidene)-6-fluoro-1,3-dihydro-2H-indol-2-one (200 mg, 0.62 mmol), 6-fluoropyridin-3-ylboronic acid (104 mg, 0.74 mmol), PdCl$_2$(PPh$_3$)$_2$ (22 mg, 0.031 mmol), 1M Na$_2$CO$_3$ aqueous solution (2.5 mL, 2.5 mmol). The mixture was heated at 88° C. under N$_2$ for 2 hours, cooled to room temperature and poured into 100 mL of water. The precipitates were filtered, washed with water and dried to give the crude product. Purification of the crude product through silica gel column with 1-5% MeOH/CHCl$_3$ afforded (3E)-6-fluoro-3-[4-(6-fluoropyridin-3-yl)-5,5-dimethylfuran-2(5H)-ylidene]-1,3-dihydro-2H-indol-2-one as a yellow solid. Yield: 100 mg, 47%.

$^1$H NMR (300 MHz, d$_6$-DMSO) δ ppm 1.75 (s, 6 H) 6.61 (dd, J=9.38, 2.64 Hz, 1 H) 6.70-6.77 (m, 1 H) 7.30 (dd, J=8.65, 3.08 Hz, 1 H) 7.54 (dd, J=8.35, 5.72 Hz, 1 H) 7.81 (s, 1 H) 8.39-8.45 (m, 1 H) 8.65 (d, J=2.64 Hz, 1 H) 10.43 (s, 1 H)

LR MS (ES−): 339 (M−1)

Example 332

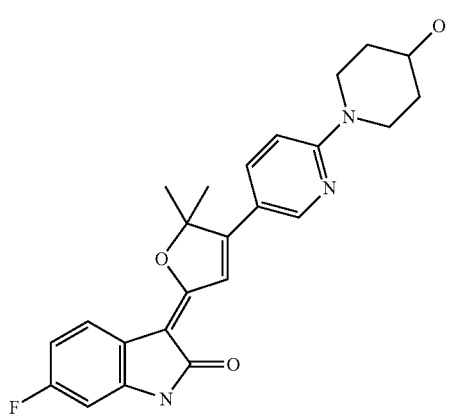 [SMILES: CC1(C)O/C(=C2/C(=O)Nc3cc(F)ccc32)C=C1c1ccc(N2CCC(O)CC2)nc1]

(3E)-6-Fluoro-3-{4-[6-(4-hydroxypiperidin-1-yl)pyridin-3-yl]-5,5-dimethylfuran-2(5H)-ylidene}-1,3-dihydro-2H-indol-2-one A mixture of (3E)-6-fluoro-3-[4-(6-fluoropyridin-3-yl)-5,5-dimethylfuran-2(5H)-ylidene]-1,3-dihydro-2H-indol-2-one (50 mg, 0.15 mmol) and 4-hydroxypiperidine (50 mg, 0.49 mmL) in anhydrous DMSO (3 mL) was heated at 100° C. under nitrogen for 6 hours. The mixture was cooled to room temp and poured into 100 mL of water. The precipitates were filtered, washed with water and dried in vacuo to give (3E)-6-fluoro-3-{4-[6-(4-hydroxypiperidin-1-yl)pyridin-3-yl]-5,5-dimethylfuran-2(5H)-ylidene}-1,3-dihydro-2H-indol-2-one as a yellow solid. Yield: 55 mg, 89%.

$^1$H NMR (500 MHz, d$_6$-DMSO) δ ppm 1.33-1.40 (m, 2 H) 1.76 (s, 6 H) 1.75-1.82 (m,2H) 3.25-3.30 (m,2H) 3.73-3.79 (m, 1 H) 4.08-4.13 (m, 2H) 4.74 (d, J=4.39 Hz, 1 H) 6.60 (dd, J=9.76, 2.44 Hz, 1 H) 6.70-6.75 (m, 1 H) 6.95 (d, J=8.79 Hz, 1 H) 7.53 (dd, J=8.30, 5.86 Hz, 1 H) 7.58 (s, 1 H) 7.93 (dd, J=9.03, 2.68 Hz, 1 H) 8.51 (d, J=2.44 Hz, 1 H) 10.35 (s, 1 H)

LR MS (ES+): 422 (M+1)

Example 333

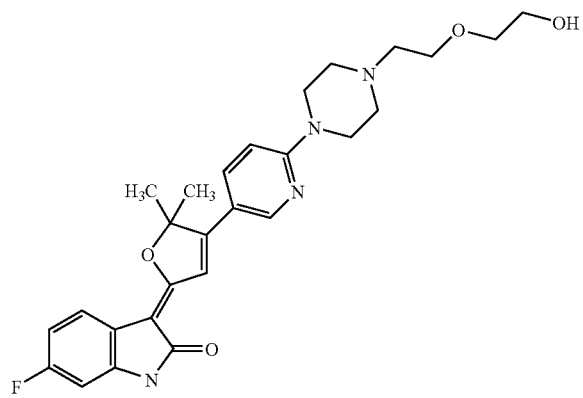 [SMILES: CC1(C)O/C(=C2/C(=O)Nc3cc(F)ccc32)C=C1c1ccc(N2CCN(CCOCCO)CC2)nc1]

(3E)-6-Fluoro-3-[4-(6-{4-[2-(2-hydroxyethoxy)ethyl]piperazin-1-yl}pyridin-3-yl)-5,5-dimethylfuran-2(5H)-ylidene]-1,3-dihydro-2H-indol-2-one Similar procedure as Example 332.

$^1$H NMR (500 MHz, d$_6$-DMSO) δ ppm 1.76 (s, 6 H) 2.50-2.54 (m, 6 H) 3.42 (t, J=5.13 Hz, 2 H) 3.50 (q, J=5.21 Hz, 2 H) 3.56 (t, J=5.86 Hz, 2 H) 3.63 (t, J=5.37 Hz, 4 H) 4.61 (t, J=5.37 Hz, 1 H) 6.60 (dd, J=9.52, 2.20 Hz, 1 H) 6.71-6.75 (m, 1 H) 6.94 (d, J=9.28 Hz, 1 H) 7.53 (dd, J=8.30, 5.86 Hz, 1 H) 7.60 (s, 1 H) 7.95 (dd, J=9.28, 2.44 Hz, 1 H) 8.53 (d, J=2.44 Hz, 1 H) 10.36 (s, 1 H)

LR MS (ES+): 495 (M+1)

Preparation of Examples 334-369 (FIG. 8)

Each of the examples was prepared through the library synthesis as follows: To each 8-mL screw cap reaction vial were added (3E)-6-fluoro-3-[4-(6-fluoropyridin-3-yl)-5,5-dimethylfuran-2(5H)-ylidene]-1,3-dihydro-2H-indol-2-one (40 mg, 0.11 mmol), amine (0.25 mmol, 2.3 eq.), DMSO (1 mL), and DIPEA (0.1 mL, 5 eq.). The vial was flushed with nitrogen, capped, and heated at 115-120° C. for 18 hours. After cooling to room temperature, the reaction mixtures were filtered through a plug of cotton and the resulting DMSO solutions were submitted for preparative RP-HPLC purification. Each compound was re-analyzed by LCMS after purification.

Example 338 is the compound example for the library synthesis (FIG. 8):

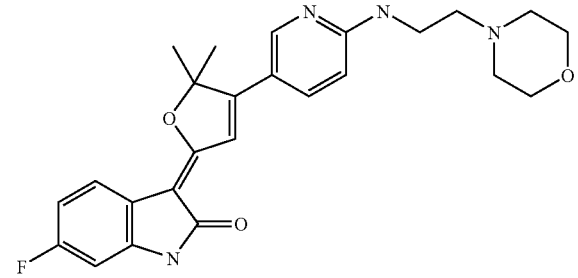 [SMILES: CC1(C)O/C(=C2/C(=O)Nc3cc(F)ccc32)C=C1c1ccc(NCCN2CCOCC2)nc1]

(3E)-3-[5,5-Dimethyl-4-{6-[(2-morpholin-4-ylethyl)amino]pyridin-3-yl}furan-2(5H)-ylidene]-6-fluoro-1,3-dihydro-2H-indol-2-one 32.6 mg, yield 65.7%.

$^1$H NMR (300 MHz, DMSO-d$_6$) δ ppm 10.32 (s, 1H), 8.40 (d, J=2.4 Hz, 1H), 7.80 dd, J=9.0, 2.4 Hz, 1H), 7.52 (s, 1H), 7.50 (dd, J=8.4, 6.3 Hz, 1H), 7.25 (m, 1H), 6.71 (ddd, J=10.5, 8.4, 2.7 Hz, 1H), 6.62 (d, J=8.4 Hz, 1H), 6.60 (dd, J=9.0, 2.4 Hz, 1H), 3.57 (t, J=5.4 Hz, 4 H), 3.45 (m, 2H), 2.45-2.55 (m, 4H), 2.38-2.44 (m, 2H), 1.75 (s, 6H).

ESI-MS m/z 450.6 (M)$^+$.

Preparation of 5-fluoro-3-[4-(6-fluoro-pyridin-3-yl)-5,5-dimethyl-5H-furan-(2E)-ylidene]-1,3-dihydro-indol-2-one

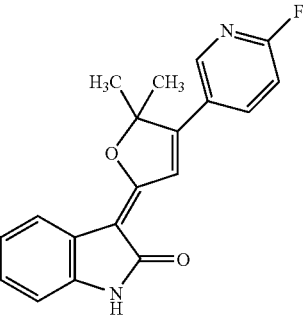

To a mixture of 3-[4-bromo-5,5-dimethyl-5H-furan-(2E)-ylidene]-5-fluoro-1,3-dihydro-indol-2-one (3.24 g, 10.0 mmol), 6-fluoropyridin-3-ylboronic acid (1.8 g, 12 mmol ) in THF (150 mL), was added a solution of potassium carbonate (13.8 g, 100 mmol) in water (20 mL). The resulting mixture was deoxygenated by bubbling nitrogen through the reaction mixture for 3 minutes and palladium(0) tetrakis(triphenylphosphine) (578 mg, 5 mol %) was then added. The reaction mixture was heated at 65° C. for 18 hours. The reaction was cooled to room temperature and ethyl acetate (500 mL) added. The organic phase was washed with water (100 mL×2), dried over sodium sulfate, and evaporated to give the crude product, whci was purified first by silica gel column chromatography (5% CH$_3$OH/CH$_2$Cl$_2$ elution) and then by titration with ethyl acetate. The resulting product was isolated by filtration and dried under vacuum to provide 5-fluoro-3-[4-(6-fluoro-pyridin-3-yl)-5,5-dimethyl-5H-furan-(2E)-ylidene]-1,3-dihydro-indol-2-one as a yellow solid (1.6 g, yield 48%).

$^1$H NMR (300 MHz, DMSO-d$_6$) δ ppm 10.31 (s, 1H), 8.67 (d, J=2.7 Hz, 1H), 8.44 (ddd, J=8.4, 7.5, 2.7 Hz, 1 H), 7.84 (s, 1H), 7.33(m, 2H), 6.89 (ddd, J=9.6, 8.4, 2.7 Hz, 1H), 6.76 (dd, J=8.4, 4.5 Hz, 1H), 1.79(s, 6H).

ESI-MS m/z 341.3 (M+1)$^+$

Preparation of Examples 370-420(FIG. 8)

Each of the examples was prepared through the library synthesis as follows:
To each 8-mL screw cap reaction vial were added 5-fluoro-3-[4-(6-fluoro-pyridin-3-yl)-5,5-dimethyl-5H-furan-(2E)-ylidene]-1,3-dihydro-indol-2-one (55 mg, 0.16 mmol), amine (0.24 mmol, 1.5 eq.), DIPEA (0.1 mL, 0.57 mmol, 3.6 eq.) and DMSO (1.0 mL). The reaction vial was capped and heated at 110° C. for 20 h. After cooling to room temperature, the resulting solution was submitted for preparative RP-HPLC purification. Each compound was re-analyzed by LCMS after purification.

Preparation of (3E)-5,6-difluoro-3-[4-(6-fluoropyridin-3-yl)-5,5-dimethylfuran-2(5H)-ylidene]-1,3-dihydro-2H-indol-2-one

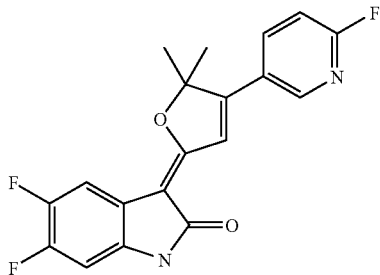 [SMILES: CC1(C)O/C(=C2/C(=O)Nc3cc(F)c(F)cc32)C=C1c1ccc(F)nc1]

To 10 mL of 1,4-dioxane were added (3E)-3-(4-bromo-5,5-dimethylfuran-2(5H)-ylidene)-5,6-difluoro-1,3-dihydro-2H-indol-2-one (150 mg, 0.44 mmol), 6-fluoropyridin-3-ylboronic acid (74 mg, 0.53 mmol), PdCl$_2$(PPh$_3$)$_2$ (22 mg, 0.031 mmol), 2M Na$_2$CO$_3$ aqueous solution (0.6 mL, 1.2 mmol). The mixture was heated at 78° C. under N$_2$ for 3 hours, cooled to room temperature and poured into 100 mL of water. The precipitates were filtered, washed with water and dried to give the crude product. Purification of the crude product through silica gel column with 1-3% MeOH/CHCl$_3$ gave (3E)-5,6-difluoro-3-[4-(6-fluoropyridin-3-yl)-5,5-dimethylfuran-2(5H)-ylidene]-1,3-dihydro-2H-indol-2-one as a yellow solid(yield: 60 mg, 38%).

$^1$H NMR (300 MHz, d$_6$-DMSO) δ ppm 1.77 (s, 6 H) 6.80 (dd, J=10.70, 6.89 Hz, 1 H) 7.31 (dd, J=8.79, 2.93 Hz, 1 H) 7.49 (dd, J=10.55, 8.21 Hz, 1 H) 7.80 (s, 1 H) 8.40-8.47 (m, 1 H) 8.67 (d, J=2.64 Hz, 1 H) 10.41 (s, 1 H)

Example 421

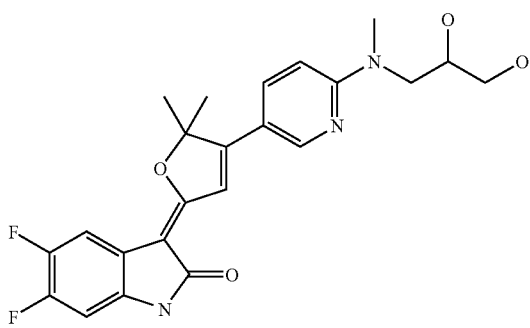 [SMILES: CN(CC(O)CO)c1ccc(C2=C/C(=C3\C(=O)Nc4cc(F)c(F)cc43)OC2(C)C)cn1]

(3E)-3-[4-{6-[(2,3-Dihydroxypropyl)(methyl)amino]pyridin-3-yl}-5,5-dimethylfuran-2(5H)-ylidene]-5,6-difluoro-1,3-dihydro-2H-indol-2-one A mixture of (3E)-5,6-difluoro-3-[4-(6-fluoropyridin-3-yl)-5,5-dimethylfuran-2(5H)-ylidene]-1,3-dihydro-2H-indol-2-one (50 mg, 0.14 mmol) and 3-methylamino-1,2-propanediol (50 mg, 0.48 mmol) in 5 mL of DMF was heated in 100° C. bath under nitrogen for 16 hours. The mixture was cooled to room temp and poured into 100 mL of water. The precipitates were filtered, washed with water and dried in vacuo to give (3E)-3-[4-{6-[(2,3-dihydroxypropyl)(methyl)amino]pyridin-3-yl}-5,5-dimethylfuran-2(5H)-ylidene]-5,6-difluoro-1,3-dihydro-2H-indol-2-one as a brown solid. Yield: 51 mg, 82%.

$^1$H NMR (300 MHz, d$_6$-DMSO) δ ppm 1.76 (s, 6 H) 3.14 (s, 3 H) 3.31-3.37 (m, 2 H) 3.44 (dd, J=13.78, 7.04 Hz, 1 H) 3.67-3.79 (m, 2 H) 4.65 (t, J=5.57 Hz, 1 H) 4.82 (d, J=4.98 Hz, 1 H) 6.71-6.80 (m, 2 H) 7.44 (dd, J=10.70, 8.06 Hz, 1 H) 7.53 (s, 1 H) 7.91 (dd, J=9.09, 2.64 Hz, 1 H) 8.50 (d, J=2.34 Hz, 1 H) 10.29 (s, 1 H)

LR MS (ES−): 442 (M−1)

Preparation of (3E)-6-fluoro-3-[4-(2-fluoropyridin-4-yl)-5,5-dimethylfuran-2(5H)-ylidene]-1,3-dihydro-2H-indol-2-one

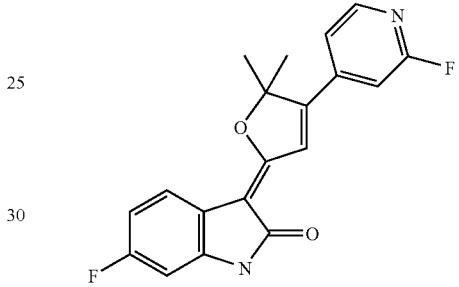

Method A: To 10 mL of 1,4-dioxane were added (3E)-3-(4-bromo-5,5-dimethylfuran-2(5H)-ylidene)-6-fluoro-1,3-dihydro-2H-indol-2-one (200 mg, 0.62 mmol), 2-fluoropyridin-4-ylboronic acid (104 mg, 0.74 mmol), PdCl$_2$(PPh$_3$)$_2$ (22 mg, 0.031 mmol), 1M Na$_2$CO$_3$ aqueous solution (2.5 mL, 2.5 mmol). The mixture was heated at 96° C. under N$_2$ for 4 hours, cooled to room temperature and poured into 150 mL of water. The precipitates were filtered, washed with water and dried to give the crude product. Purification of the crude product through silica gel column with 1-5% MeOH/CHCl$_3$ led to (3E)-6-fluoro-3-[4-(2-fluoropyridin-4-yl)-5,5-dimethylfuran-2(5H)-ylidene]-1,3-dihydro-2H-indol-2-one as a brown solid. Yield: 100 mg, 48%.

Method B: To a mixture of (3E)-3-(4-bromo-5,5-dimethylfuran-2(5H)-ylidene)-6-fluoro-1,3-dihydro-2H-indol-2-one (2.0 g, 6.1 mmol), 2-fluoropyridine-4-boronic acid (1.1 g, 8.0 mmol), potassium fluoride (1.8 g, 5 eq.) in dioxane (50 mL) and water (5 mL) under a nitrogen atmosphere, was added [1,1'-bis(diphenylphosphino)ferrocene]dichloropalladium(II) (250 mg, 5%). The mixture was heated at 80° C. for 20 hour. The reaction was allowed to cool to room temperature and ethyl acetate (350 mL) was added. The organic phase was washed with water (100 mL×2) and evaporated to provide the crude product. The crude product was purified by column chromatography (silica gel, 5% CH$_3$OH/CH$_2$Cl$_2$ elution) and then recrystallized from ethyl acetate/hexanes (80/20) to provide (3E)-6-fluoro-3-[4-(2-fluoropyridin-4-yl)-5,5-dimethylfuran-2(5H)-ylidene]-1,3-dihydro-2H-indol-2-one as a yellow-orange solid (1.2 g, yield 57%).

$^1$H NMR (300 MHz, DMSO-d$_6$) δ 10.50 (s, 1H), 8.34 (d, J=5.4 Hz, 1H), 7.99 (s, 1H), 7.55 (dd, J=8.4, 6.0 Hz, 1H), 7.71 (d, J=5.7 Hz, 1H), 7.50-7.58 (m, 2H), 6.73 (dt, J=10.2, 2.4 Hz, 1H), 6.62 (dd, J=15.6, 5.4 Hz, 1H ), 1.77 (s, 6H).

ESI-MS m/z 341.1 (M+1)$^+$.

Example 422

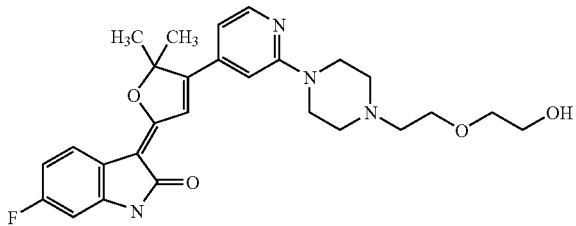 [SMILES: CC1(C)O/C(=C2/C(=O)Nc3cc(F)ccc32)C=C1c1ccnc(N2CCN(CCOCCO)CC2)c1]

(3E)-6-fluoro-3-[4-(2-{4-[2-(2-hydroxyethoxy)ethyl]
piperazin-1-yl}pyridin-4-yl)-5,5-dimethylfuran-2
(5H)-ylidene]-1,3-dihydro-2H-indol-2-one A mixture of (3E)-6-fluoro-3-[4-(2-fluoropyridin-4-yl)-5, 5-dimethylfuran-2(5H)-ylidene]-1,3-dihydro-2H-indol-2-one (50 mg, 0.15 mmol) and 2-(2-(piperazin-1-yl)ethoxy) ethanol (50 mg, 0.29 mmol) in 2 mL of DMSO was heated in 105° C. bath for 6 hours. The mixture was cooled to room temp and poured into 100 mL of water. The precipitates were filtered, washed with water and dried in vacuo to give (3E)-6-fluoro-3-[4-(2-{4-[2-(2-hydroxyethoxy)ethyl]piperazin-1-yl}pyridin-4-yl)-5,5-dimethylfuran-2(5H)-ylidene]-1,3-dihydro-2H-indol-2-one as a brown solid. Yield: 64 mg, 89%.

$^1$H NMR (300 MHz, d$_6$-DMSO) δ ppm 1.72 (s, 6 H) 2.48-2.53 (m, 6 H) 3.38-3.56 (m, 10 H) 4.61 (br s, 1 H) 6.60 (dd, J=9.38, 2.35 Hz, 1 H) 6.70-6.77 (m, 1 H) 6.89 (d, J=5.28 Hz, 1 H) 6.92 (s, 1 H) 7.54 (dd, J=8.35, 5.72 Hz, 1 H) 7.80 (s, 1 H) 8.19 (d, J=5.28 Hz, 1 H) 10.45 (s, 1 H)

LR MS (EI+): 495 (MH$^+$)

Example 423

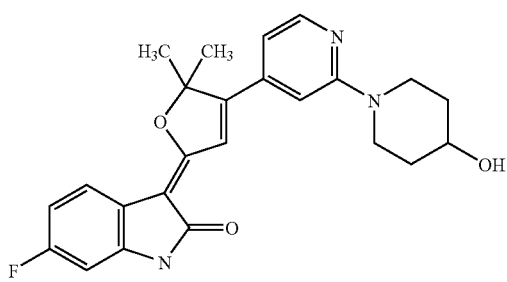 [SMILES: CC1(C)O/C(=C2/C(=O)Nc3cc(F)ccc32)C=C1c1ccnc(N2CCC(O)CC2)c1]

(3E)-6-Fluoro-3-{4-[2-(4-hydroxypiperidin-1-yl)
pyridin-4-yl]-5,5-dimethylfuran-2(5H)-ylidene}-1,3-
dihydro-2H-indol-2-one Similar procedure as Example 422.

$^1$H NMR (300 MHz, d$_6$-DMSO) δ ppm 1.30-1.42 (m, 2 H) 1.72 (s, 6 H) 1.73-1.82 (m, 2 H) 3.08-3.17 (m, 2 H) 3.65-3.74 (m, 1 H) 4.02-4.10 (m, 2 H) 4.67 (d, J=4.10 Hz, 1 H) 6.61 (dd, J=9.38, 2.64 Hz, 1 H) 6.70-6.77 (m, 1 H) 6.83 (dd, J=5.28, 1.17 Hz, 1 H) 6.91 (s, 1 H) 7.54 (dd, J=8.35, 5.72 Hz, 1 H) 7.79 (s, 1 H) 8.18 (d, J=5.28 Hz, 1 H) 10.44 (s, 1 H)

LR MS (EI+): 422 (MH$^+$)

Preparation of Examples 424-454(FIG. 9)

Each of the examples was prepared through the library synthesis as follows:

To each 8-mL screw cap reaction vial were added (3E)-6-fluoro-3-[4-(2-fluoropyridin-4-yl)-5,5-dimethylfuran-2 (5H)-ylidene]-1,3-dihydro-2H-indol-2-one (40 mg, 0.11 mmol), amine (0.25 mmol, 2.3 eq.), DMSO (1 mL), and DIPEA (0.1 mL, 5 eq.). The reaction was heated at 115-120° C. for 1-4 days and monitored by LCMS. After cooling to room temperature, the reaction mixtures were filtered through a plug of cotton and the resulting DMSO solutions were submitted for preparative RP-HPLC purification. Each compound was re-analyzed by LCMS after purification.

Example 426 is the compound example for the library synthesis (FIG. 9).

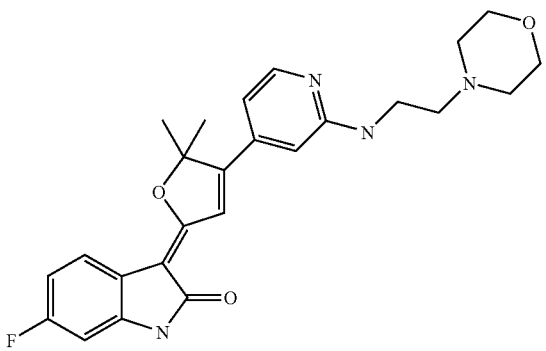 [SMILES: CC1(C)O/C(=C2/C(=O)Nc3cc(F)ccc32)C=C1c1ccnc(NCCN2CCOCC2)c1]

(3E)-3-[5,5-dimethyl-4-{2-[(2-morpholin-4-ylethyl)
amino]pyridin-4-yl}furan-2(5H)-ylidene]-6-fluoro-1,
3-dihydro-2H-indol-2-one 25.2 mg, yield 51%.

$^1$H NMR (300 MHz, DMSO-d$_6$) δ 10.45 (s, 1H), 8.04 (d, J=5.7 Hz, 1H), 7.78 (s, 1H), 7.53 (dd, J=8.4, 5.7 Hz, 1H), 6.86 (s, 1H), 6.70-6.80 (m, 2H), 6.60-6.65 (m, 2H), 3.06 (m, 4 H), 2.38-3.44 (m, 2H), 2.45-2.5 (m, 2H), 2.38-2.44 (m, 4 H), 1.74 (s, 6H).

ESI-MS m/z 450.9 (M+H)$^+$.

Preparation of 4-[(5E)-5-(6-fluoro-2-oxo-1,2-dihy-
dro-3H-indol-3-ylidene)-2,2-dimethyl-2,5-dihydro-
furan-3-yl]thiophene-2-carbaldehyde

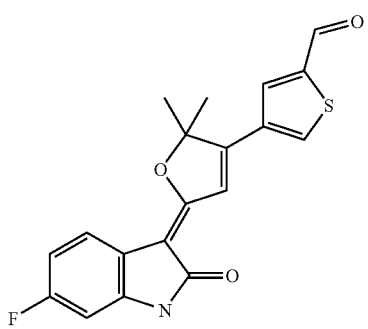 [SMILES: CC1(C)O/C(=C2/C(=O)Nc3cc(F)ccc32)C=C1c1csc(C=O)c1]

To 30 mL of 1,4-dioxane were added (3E)-3-(4-bromo-5,5-dimethylfuran-2(5H)-ylidene)-6-fluoro-1,3-dihydro-2H- indol-2-one (600 mg, 1.85 mmol), 5-formylthiophene-3-boronic acid (348 mg, 2.23 mmol), PdCl₂(PPh₃)₂ (60 mg, 0.085 mmol), 1M Na₂CO₃ aqueous solution (7.4 mL, 7.4 mmol). The mixture was heated at 80° C. under N₂ for 3.5 hours, cooled to room temperature and poured into 200 mL of water. The mixture was extracted with EtOAc (3×80 mL). The organic layers were combined, washed with brine (50 mL), dried over Na₂SO₄, and concentrated to give the crude product, which was purified through silica gel column with 1-5% MeOH/CHCl₃ to give 4-[(5E)-5-(6-fluoro-2-oxo-1,2-dihydro-3H-indol-3-ylidene)-2,2-dimethyl-2,5-dihydrofuran-3-yl]thiophene-2-carbaldehyde as brown solid. Yield: 458 mg, 70%.

¹H NMR (500 MHz, d₆-DMSO) δ ppm 1.78 (s, 6 H) 6.62 (dd, J=9.52, 2.20 Hz, 1 H) 6.74-6.78 (m, 1 H) 7.56 (dd, J=5.37, 2.93 Hz, 1 H) 7.77 (s, 1 H) 8.65 (d, J=1.46 Hz, 1 H) 8.70 (t, J=1.46 Hz, 1 H) 10.02 (s, 1 H) 10.44 (s, 1 H)

Example 455

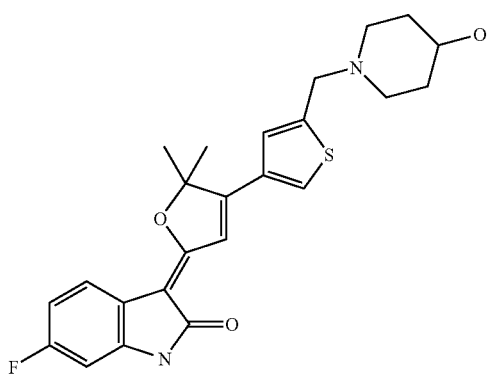 [SMILES: CC1(C)O/C(=C2/C(=O)Nc3cc(F)ccc32)C=C1c1csc(CN2CCC(O)CC2)c1]

(3E)-6-Fluoro-3-[4-{5-[(4-hydroxypiperidin-1-yl)methyl]-3-thienyl}-5,5-dimethylfuran-2(5H)-ylidene]-1,3-dihydro-2H-indol-2-one A mixture of 4-[(5E)-5-(6-fluoro-2-oxo-1,2-dihydro-3H-indol-3-ylidene)-2,2-dimethyl-2,5-dihydrofuran-3-yl]thiophene-2-carbaldehyde (120 mg, 0.34 mmol), 4-hydroxypiperidine (69 mg, 0.68 mmol) and 100 mg of 4 Å molecular sieves in 5 mL of anhydrous DMF was stirred under nitrogen for 16 hours. Acetic acid (20 mg) and 1M sodium cyanoborohydride (0.68 mL, 0.68 mmol) were then added. The mixture was diluted with 5 mL of anhydrous methanol and stirred at room temperature for 3 hours. The mixture was poured into 100 mL of water with stirring, and basified to about pH 8 with saturated NaHCO₃ solution. The resulting precipitates were filtered, washed with water, and dried in vacuo to give the crude product, which was purified through silica gel column with 10-20% MeOH/CHCl₃ to give (3E)-6-fluoro-3-[4-{5-[(4-hydroxypiperidin-1-yl)methyl]-3-thienyl}-5,5-dimethylfuran-2(5H)-ylidene]-1,3-dihydro-2H-indol-2-one as yellow powder. Yield: 38 mg, 26%.

¹H NMR (300 MHz, d₆-DMSO) δ ppm 1.32-1.43 (m, 2 H) 1.66-1.72 (m, 2 H) 1.73 (s, 6 H) 2.09 (t, J=9.67 Hz, 2 H) 2.67-2.74 (m, 2 H) 3.40-3.49 (m, 1 H) 3.66 (s, 2 H) 4.52 (d, J=4.40 Hz, 1 H) 6.59 (dd, J=9.38, 2.35 Hz, 1 H) 6.68-6.75 (m, 1 H) 7.42 (s, 1 H) 7.49-7.53 (m, 2 H) 8.04 (d, J=1.47 Hz, 1 H) 10.37 (s, 1 H)

LR MS (ES−): 439 (M−1)

Example 456

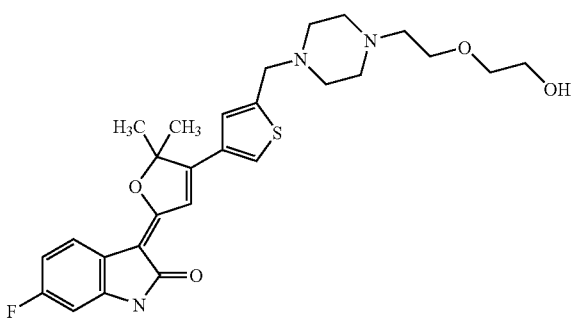 [SMILES: CC1(C)O/C(=C2/C(=O)Nc3cc(F)ccc32)C=C1c1csc(CN2CCN(CCOCCO)CC2)c1]

(3E)-6-Fluoro-3-{4-[5-({4-[2-(2-hydroxyethoxy)ethyl]piperazin-1-yl}methyl)-3-thienyl]-5,5-dimethylfuran-2(5H)-ylidene}-1,3-dihydro-2H-indol-2-one Similar procedure as Example 455.

¹H NMR (300 MHz, d₆-DMSO) δ ppm 1.73 (s, 6 H) 2.38-2.47 (m, J=6.16 Hz, 10 H) 3.37 (t, J=4.98 Hz, 2 H) 3.46 (q, J=6.16 Hz, 4 H) 3.68 (s, 2 H) 6.59 (dd, J=9.38, 2.05 Hz, 1 H) 6.68-6.75 (m, 1 H) 7.44 (s, 1 H) 7.49-7.54 (m, 2 H) 8.05 (d, J=1.17 Hz, 1 H) 10.38 (s, 1 H)

LR MS (ES+): 514 (M+1)

Preparation of Examples 457-475 (FIG. 5)

Each of the examples was prepared through the library synthesis as follows: To each 8-mL reaction vial were added 4-[(5E)-5-(6-fluoro-2-oxo-1,2-dihydro-3H-indol-3-ylidene)-2,2-dimethyl-2,5-dihydrofuran-3-yl]thiophene-2-carbaldehyde (25 mg, 0.07 mmol), amine (0.105 mmol, 1.5 eq), 5% HOAc/DMF (v/v) (1 mL), and NaBH(OAc)₃ (45 mg, 0.21 mmol, 3 eq.). The resulting reaction mixture was shaken at room temperature for 20 hours. It was then quenched by the addition of water (0.1 mL). The solvents were evaporated in a SpeedVac and the residue was dissolved in DMSO (1 mL). The DMSO solutions were submitted for preparative RP-HPLC purification. Each compound was re-analyzed by LCMS after purification.

Example 476

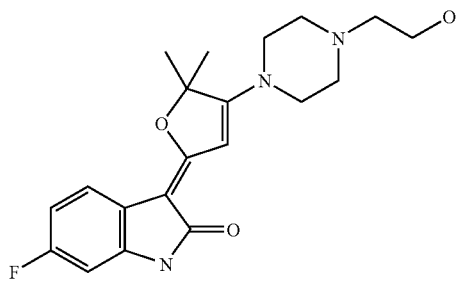 [SMILES: CC1(C)O/C(=C2/C(=O)Nc3cc(F)ccc32)C=C1N1CCN(CCO)CC1]

(3E)-6-Fluoro-3-{4-[4-(2-hydroxyethyl)piperazin-1-yl]-5,5-dimethylfuran-2(5H)-ylidene}-1,3-dihydro-2H-indol-2-one A mixture of (3E)-3-(4-bromo-5,5-dimethylfuran-2(5H)-ylidene)-6-fluoro-1,3-dihydro-2H-indol-2-one (95 mg, 0.29 mmol) and 1-(2-hydroxyethyl)piperazine (0.40 mL, 3.3 mmol) in 6 mL of DMF was heated in 100° C. bath for 2 hours. The mixture was cooled, diluted with ethyl acetate (60 mL), washed with brine (3×50 mL), and concentrated to give the crude product, which was purified by silica gel chromatography with 5-20% methanol in chloroform to give (3E)-6-fluoro-3-{4-[4-(2-hydroxyethyl)piperazin-1-yl]-5,5-dimethylfuran-2(5H)-ylidene}-1,3-dihydro-2H-indol-2-one as a grey solid. Yield: 73 mg, 67%.

$^1$H NMR (300 MHz, d$_6$-DMSO) δ ppm 1.64 (s, 6 H) 2.42 (t, J=6.16 Hz, 2 H) 2.51 (br s, 4 H) 3.41 (br s, 4 H) 3.51 (q, J=5.96 Hz, 2 H) 4.44 (t, J=5.28 Hz, 1 H) 6.10 (s, 1 H) 6.50 (dd, J=9.53, 2.49 Hz, 1 H) 6.56-6.63 (m, 1 H) 7.33 (dd, J=8.35, 5.72 Hz, 1 H) 10.02 (s, 1 H)

LR MS (ES−): 372 (M−1)

Example 477

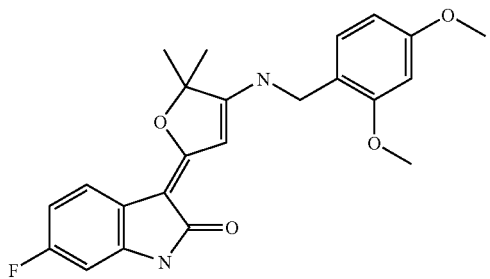 [SMILES: COc1ccc(CNC2=C/C(=C3\C(=O)Nc4cc(F)ccc43)OC2(C)C)c(OC)c1]

(3E)-3-{4-[(2,4-Dimethoxybenzyl)amino]-5,5-dimethylfuran-2(5H)-ylidene}-6-fluoro-1,3-dihydro-2H-indol-2-one Similar procedure as Example 476.

$^1$H NMR (500 MHz, d$_6$-DMSO) δ ppm 1.56 (s, 6 H) 3.75 (s, 3 H) 3.83 (s, 3 H) 4.25 (d, J=5.37 Hz, 2 H) 5.96 (s, 1 H) 6.49-6.54 (m, 2 H) 6.58-6.62 (m, 2 H) 7.11 (d, J=8.30 Hz, 1 H) 7.34 (dd, J=8.30, 5.86 Hz, 1 H) 8.00 (t, J=5.61 Hz, 1 H) 9.98 (s, 1 H)

LR MS (ES+): 411 (M+1)
LR MS (ES−): 409 (M−1)

Preparation of 6-fluoro-N-[(5E)-5-(6-fluoro-2-oxo-1,2-dihydro-3H-indol-3-ylidene)-2,2-dimethyl-2,5-dihydrofuran-3-yl]nicotinamide

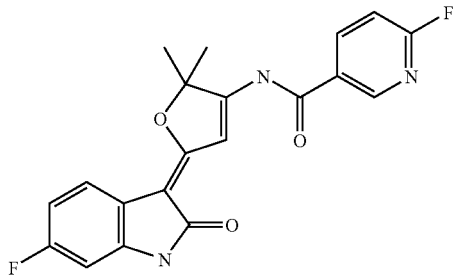 [SMILES: CC1(C)O/C(=C2/C(=O)Nc3cc(F)ccc32)C=C1NC(=O)c1ccc(F)nc1]

To a stirred solution of (3E)-3-{4-[(2,4-dimethoxybenzyl)amino]-5,5-dimethylfuran-2(5H)-ylidene}-6-fluoro-1,3-dihydro-2H-indol-2-one (370 mg, 0.90 mmol) in 5 mL of methylene chloride was added 5 mL of TFA. The mixture was stirred at room temperature for 1 hour and evaporated to dryness. The residue was re-dissolved in ethyl acetate (80 mL), washed with saturated NaHCO$_3$ solution (2×30 mL) and brine (30 mL), dried over Na$_2$SO$_4$, and evaporated to dryness to afford the enamine intermediate as a light yellow solid. The enamine was dissolved in 10 mL of dry THF, and then cooled to 0° C. Pyridine (0.5 mL, 6.2 mmol) and 6-fluoronicotinoyl chloride (180 mg, 1.13 mmol) were then added. The mixture was allowed to warm up to room temperature and stirred for 1 hour. The mixture was diluted with ethyl acetate (80 mL), washed with 0.1M HCl (2×30 mL), saturated NaHCO$_3$ (30 mL) and brine (30 mL), concentrated, and purified by silica gel chromatography to give 6-fluoro-N-[(5E)-5-(6-fluoro-2-oxo-1,2-dihydro-3H-indol-3-ylidene)-2,2-dimethyl-2,5-dihydrofuran-3-yl]nicotinamide as a yellow solid. Yield: 150 mg, 43%.

$^1$H NMR (300 MHz, d$_6$-DMSO) δ ppm 1.51 (s, 6 H) 6.02 (s, 1 H) 6.49 (dd, J=9.53, 2.49 Hz, 1 H) 6.53-6.61 (m, 1 H) 7.29-7.36 (m, 2 H) 7.38 (br s, 1 H) 8.42-8.49 (m, 1 H) 8.78 (d, J=1.76 Hz, 1 H) 9.90 (s, 1 H)

LR MS (ES−): 382 (M−1)

Example 478

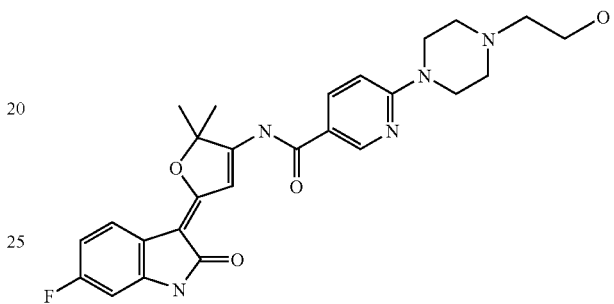

N-[(5E)-5-(6-Fluoro-2-oxo-1,2-dihydro-3H-indol-3-ylidene)-2,2-dimethyl-2,5-dihydrofuran-3-yl]-6-[4-(2-hydroxyethyl)piperazin-1-yl]nicotinamide To a stirred solution of 6-fluoro-N-[(5E)-5-(6-fluoro-2-oxo-1,2-dihydro-3H-indol-3-ylidene)-2,2-dimethyl-2,5-dihydrofuran-3-yl]nicotinamide (75 mg, 0.20 mmol) in DMF (3 mL) was added 1-(2-hydroxyethyl)piperazine (70 mg, 0.54 mmol). The reaction mixture was heated in 66° C. bath for 30 minutes, cooled to room temperature, and diluted with ethyl acetate (80 mL). The ethyl acetate solution was washed with brine (4×20 mL), dried over Na$_2$SO$_4$, and concentrated to give the crude product. Purification of the crude product by silica gel chromatography with a gradient of methanol in chloroform (5-20%) gave N-[(5E)-5-(6-fluoro-2-oxo-1,2-dihydro-3H-indol-3-ylidene)-2,2-dimethyl-2,5-dihydrofuran-3-yl]-6-[4-(2-hydroxyethyl)piperazin-1-yl]nicotinamide as a yellow solid. Yield: 42 mg, 43%.

LR MS (ES+): 494 (M+1)
LR MS (ES−): 492 (M−1)

Example 479

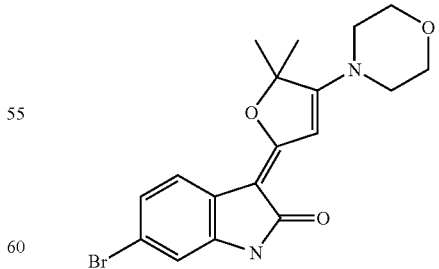

(3E)-6-Bromo-3-(5,5-dimethyl-4-morpholin-4-ylfuran-2(5H)-ylidene)-1,3-dihydro-2H-indol-2-one A mixture of (3E)-6-bromo-3-(4-bromo-5,5-dimethylfuran-2(5H)-ylidene)-1,3-dihydro-2H-indol-2-one (2.3 g, 6.0 mmol) and morpholine (1.0 mL, 11.4 mmol) in 10 mL of DMF was heated in 96 C bath for 3 hours. The mixture was cooled to room temperature and poured into 200 mL of water. The precipitates were filtered, washed with water, and dried in vacuo to give (3E)-6-bromo-3-(5,5-dimethyl-4-morpholin-4-ylfuran-2(5H)-ylidene)-1,3-dihydro-2H-indol-2-one as a brown solid. Yield: 2.1 g, 89%.

$^{1}$H NMR (500 MHz, d$_6$-DMSO) δ ppm 1.68 (s, 6 H) 3.45 (br s, 4 H) 3.70 (br s, 4 H) 6.18 (s, 1 H) 6.85 (s, 1 H) 6.98 (d, J=7.81 Hz, 1 H) 7.32 (d, J=7.32 Hz, 1 H) 10.05 (s, 1 H)

Example 480

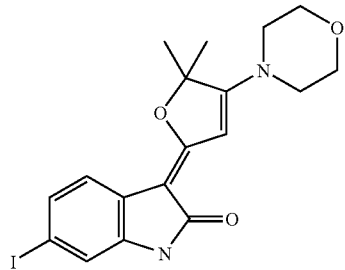 [SMILES: CC1(C)O/C(=C2/C(=O)Nc3cc(I)ccc32)C=C1N1CCOCC1]

(3E)-3-(5,5-Dimethyl-4-morpholin-4-ylfuran-2(5H)-ylidene)-6-iodo-1,3-dihydro-2H-indol-2-one To a heavy-wall pressure tube were added (3E)-6-bromo-3-(5,5-dimethyl-4-morpholin-4-ylfuran-2(5H)-ylidene)-1,3-dihydro-2H-indol-2-one (1.6 g, 4.09 mmol), copper (I) iodide (39 mg, 0.20 mmol), sodium iodide (1.23 g, 8.18 mmol), rac-trans-N,N'-dimethylcyclohexane-1,2-diamine (58 mg, 0.41 mmol), and 20 mL of anhydrous 1,4-dioxane. The mixture was purged with nitrogen, sealed and heated in 110° C. bath for 3 days. The mixture was poured into 200 mL of water. The precipitates were filtered, washed with water and dried in vacuo to give the crude product, (3E)-3-(5,5-dimethyl-4-morpholin-4-ylfuran-2(5H)-ylidene)-6-iodo-1,3-dihydro-2H-indol-2-one, as a brown solid. Yield: 2.1 g. This crude material was used in the next step without further purification.

$^{1}$H NMR (500 MHz, d$_6$-DMSO) δ ppm 1.67 (s, 6 H) 3.45 (t, J=4.88 Hz, 4 H) 3.69 (t, J=4.88 Hz, 4 H) 6.18 (s, 1 H) 7.01 (d, J=1.46 Hz, 1 H) 7.14 (dd, J=7.81, 1.46 Hz, 1 H) 7.21 (d, J=7.81 Hz, 1 H) 10.01 (s, 1 H)

LR MS (ES+): 439 (M+1)

Example 481

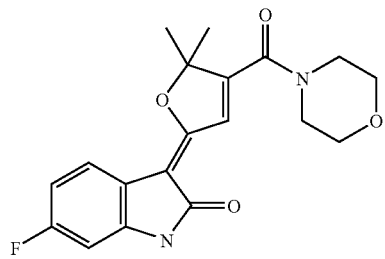 [SMILES: CC1(C)O/C(=C2/C(=O)Nc3cc(F)ccc32)C=C1C(=O)N1CCOCC1]

(3E)-3-[5,5-Dimethyl-4-(morpholin-4-ylcarbonyl)furan-2(5H)-ylidene]-6-fluoro-1,3-dihydro-2H-indol-2-one A pressure tube was charged with (3E)-3-(4-bromo-5,5-dimethylfuran-2(5H)-ylidene)-6-fluoro-1,3-dihydro-2H-indol-2-one (60 mg, 0.19 mmol), morpholine (48 mg, 0.56 mmol), Mo(CO)$_6$ (49 mg, 0.19 mmol), palladium(II) acetate (4.0 mg, 0.018 mmol), DBU (85 mg, 0.56 mmol) and anhydrous THF (3 mL). The tube was immediately capped under nitrogen and heated in 108° C. bath for 1 hour. After cooling, the reaction mixture was filtered through a short celite pad. The filtrate was concentrated and purified by silica gel flash chromatography (5-10% MeOH in CHCl$_3$) to give (3E)-3-[5,5-dimethyl-4-(morpholin-4-ylcarbonyl)furan-2(5H)-ylidene]-6-fluoro-1,3-dihydro-2H-indol-2-one as a yellow solid. Yield: 39 mg, 55%.

1H NMR (500 MHz, d$_6$-DMSO) δ ppm 1.61 (s, 6 H) 3.53-3.65 (m, 8 H) 6.62 (dd, J=9.28, 2.44 Hz, 1 H) 6.74-6.78 (m, 1 H) 7.36 (s, 1 H) 7.52 (dd, J=8.30, 5.86 Hz, 1 H) 10.46 (s, 1 H)

LR MS (ES−): 357 (M−1)

Example 482

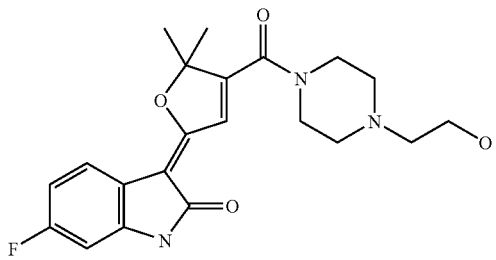 [SMILES: CC1(C)O/C(=C2/C(=O)Nc3cc(F)ccc32)C=C1C(=O)N1CCN(CCO)CC1]

(3E)-6-Fluoro-3-[4-{[4-(2-hydroxyethyl)piperazin-1-yl]carbonyl}-5,5-dimethylfuran-2(5H)-ylidene]-1,3-dihydro-2H-indol-2-one Similar procedure as Example 481.

$^{1}$H NMR (500 MHz, d$_6$-DMSO) δ ppm 1.67 (s, 6 H) 2.44 (t, J=6.10 Hz, 2 H) 2.53 (t, J=4.88 Hz, 4 H) 3.43 (t, J=4.88 Hz, 4 H) 3.53 (q, J=5.37 Hz, 2 H) 4.46 (t, J=5.37 Hz, 1 H) 6.12 (s, 1 H) 6.52 (dd, J=9.28, 2.44 Hz, 1 H) 6.60-6.64 (m, 1 H) 7.35 (dd, J=8.30, 5.37 Hz, 1 H) 10.04 (s, 1 H)

LR MS (ES+): 402 (M+1)

Example 483

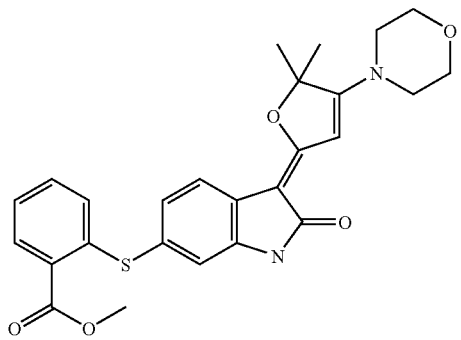 [SMILES: COC(=O)c1ccccc1Sc1ccc2c(c1)NC(=O)/C2=C1\C=C(N2CCOCC2)C(C)(C)O1]

Methyl 2-{[(3E)-3-(5,5-dimethyl-4-morpholin-4-ylfuran-2(5H)-ylidene)-2-oxo-2,3-dihydro-1H-indol-6-yl]thio}benzoate A 25 mL reaction vessel was charged with (3E)-3-(5,5-dimethyl-4-morpholin-4-ylfuran-2(5H)-ylidene)-6-iodo-1,3-dihydro-2H-indol-2-one (100 mg, 0.23 mmol), methyl thiosalicylate (77 mg, 0.46 mmol), PdCl$_2$(dppf).CH$_2$Cl$_2$ (19 mg, 0.023 mmol), cesium carbonate (225 mg, 0.69 mmol) and 8 mL of anhydrous DMF. The mixture was purged with nitrogen and heated in 90° C. bath for 2.5 hours. The mixture was cooled to room temperature, diluted with 50 mL of water and extracted with EtOAc (3×50 mL). The organic layers were combined, washed with saturated NaHCO₃ (50 mL), brine (2×50 mL), dried over Na₂SO₄, and concentrated to give a brown oil. Purification of the oily mixture by silica gel chromatography eluted with 1-10% MeOH/CHCl₃ provided methyl 2-{[(3E)-3-(5,5-dimethyl-4-morpholin-4-ylfuran-2(5H)-ylidene)-2-oxo-2,3-dihydro-1 H-indol-6-yl]thio}benzoate as a brown solid. Yield: 60 mg, 55%.

¹H NMR (500 MHz, d₆-DMSO) δ ppm 1.70 (s, 6 H) 3.48 (br s, 4 H) 3.71 (br s, 4 H) 3.87 (s, 3 H) 6.23 (s, 1 H) 6.77 (d, J=8.30 Hz, 1 H) 6.83 (d, J=1.46 Hz, 1 H) 7.03 (dd, J=7.81, 1.46 Hz, 1 H) 7.16-7.19 (m, 1 H) 7.35-7.38 (m, 1 H) 7.52 (d, J=7.81 Hz, 1 H) 7.89 (d, J=7.81 Hz, 1 H) 10.08 (s, 1 H)

LR MS (ES+): 479 (M+1)

Example 484

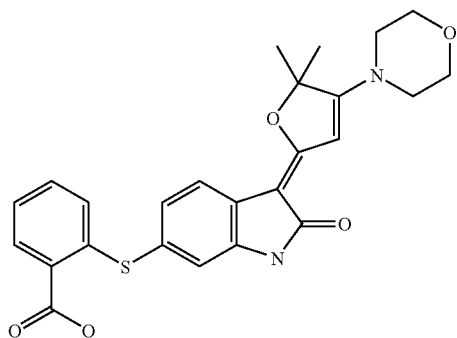 [SMILES: CC1(C)O/C(=C2/C(=O)Nc3cc(Sc4ccccc4C(=O)O)ccc32)C=C1N1CCOCC1]

2-{[(3E)-3-(5,5-Dimethyl-4-morpholin-4-ylfuran-2(5H)-ylidene)-2-oxo-2,3-dihydro-1H-indol-6-yl]thio}benzoic acid A mixture of methyl 2-{[(3E)-3-(5,5-dimethyl-4-morpholin-4-ylfuran-2(5H)-ylidene)-2-oxo-2,3-dihydro-1 H-indol-6-yl]thio}benzoate (50 mg) and 1 M NaOH (3 mL) in 20 mL of MeOH was heated in 66° C. bath for 2 hours. The mixture was cooled to room temp, poured into 100 mL of water, and acidified to about pH 3. The precipitates were filtered, washed with water and dried in vacuo to give 2-{[(3E)-3-(5,5-dimethyl-4-morpholin-4-ylfuran-2(5H)-ylidene)-2-oxo-2,3-dihydro-1H-indol-6-yl]thio}benzoic acid as a brown solid. Yield: 50 mg, 97%.

LR MS (ES−): 463 (M−1)

Example 485

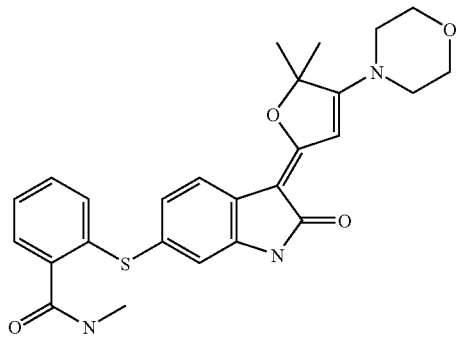

2-{[(3E)-3-(5,5-Dimethyl-4-morpholin-4-ylfuran-2(5H)-ylidene)-2-oxo-2,3-dihydro-1H-indol-6-yl]thio}-N-methylbenzamide To a stirred solution of 2-{[(3E)-3-(5,5-dimethyl-4-morpholin-4-ylfuran-2(5H)-ylidene)-2-oxo-2,3-dihydro-1H-indol-6-yl]thio}benzoic acid in 5 mL of anhydrous DMF, were added 2M methylamine in THF solution (0.066 mL, 0.13 mmol), HBTU (49 mg, 0.13 mmol) and DIPEA (31 mg, 0.24 mmol). The reaction mixture was stirred at room temperature for 15 minutes and poured into 100 mL of water. The precipitates were filtered, washed with water and dried to give the crude product as a brown solid. Purification of the crude product by silica gel chromatography eluted with a gradient of 5-15% MeOH in CHCl₃ afforded 2-{[(3E)-3-(5,5-dimethyl-4-morpholin-4-ylfuran-2(5H)-ylidene)-2-oxo-2,3-dihydro-1 H-indol-6-yl]thio}-N-methylbenzamide as brown solid. Yield: 6 mg, 12%.

¹H NMR (300 MHz, d₆-DMSO) δ ppm 1.70 (s, 6 H) 2.78 (d, J=4.69 Hz, 3 H) 3.47 (br s, 4 H) 3.71 (br s, 4 H) 6.22 (s, 1 H) 6.79-6.84 (m, 2 H) 6.99 (dd, J=7.92, 1.47 Hz, 1 H) 7.11-7.16 (m, 1 H) 7.20-7.27 (m, 1 H) 7.41 (dd, J=7.33, 1.47 Hz, 1 H) 7.48 (d, J=7.92 Hz, 1 H) 8.32 (br s, 1 H) 10.05 (s, 1 H)

LR MS (ES−): 476 (M−1)

Example 486

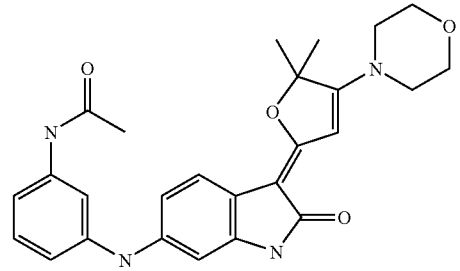 [SMILES: CC(=O)Nc1cccc(Nc2ccc3c(c2)NC(=O)/C3=C2\C=C(N3CCOCC3)C(C)(C)O2)c1]

N-(3-{[(3E)-3-(5,5-Dimethyl-4-morpholin-4-ylfuran-2(5H)-ylidene)-2-oxo-2,3-dihydro-1H-indol-6-yl]amino}phenyl)acetamide A 25 mL reaction flask was charged with (3E)-6-bromo-3-(5,5-dimethyl-4-morpholin-4-ylfuran-2(5H)-ylidene)-1,3-dihydro-2H-indol-2-one (100 mg, 0.26 mmol), N-(4-aminophenyl)acetamide (46 mg, 0.31 mmol), dicyclohexylphosphino-2'-(N,N-dimethylamino)biphenyl (4.9 mg, 0.012 mmol), Pd₂(dba)₃ (4.8 mg, 0.0052 mmol), 1M LiHMDS in THF (0.83 mL, 0.83 mmol) and dry THF (10 mL). The mixture was purged with nitrogen and heated in 62° C. bath under nitrogen for 2 hours. After cooling to room temperature, the reaction mixture was quenched with 0.5 mL of 2M HCl, and diluted with ethyl acetate (100 mL). The solution was washed with saturated NaHCO₃ (2×50 mL), brine (50 mL), and concentrated to give the crude product. Purification of the crude prduct by silica gel chromatography with a gradient of methanol in chloroform (5-10%) led to N-(3-{[(3E)-3-(5,5-dimethyl-4-morpholin-4-ylfuran-2(5H)-ylidene)-2-oxo-2,3-dihydro-1H-indol-6-yl]amino}phenyl)acetamide as a yellow solid. Yield: 20 mg, 17%.

¹H NMR (500 MHz, d₆-DMSO) δ ppm 1.66 (s, 6 H) 2.00 (s, 3 H) 3.39 (t, J=4.39 Hz, 4 H) 3.69 (t, J=4.39 Hz, 4 H) 6.15 (s, 1 H) 6.53 (s, 1 H) 6.63 (t, J=7.57 Hz, 2 H) 6.94 (d, J=8.30

Hz, 1 H) 7.05 (t, J=8.06 Hz, 1 H) 7.29 (d, J=7.81 Hz, 1 H) 7.34 (s, 1 H) 7.91 (s, 1 H) 9.73 (s, 1 H) 9.81 (s, 1 H)

LR MS (ES−): 459 (M−1)

The present invention is not to be limited in scope by the exemplified embodiments which are intended as illustrations of single aspects of the invention only. Indeed, various modifications of the invention in addition to those described herein will become apparent to those skilled in the art from the foregoing description. For example novel compounds of formula VIII, below may be utilized in the method of treating diseases described above.

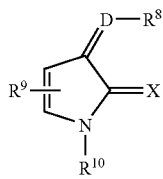

VIII wherein D is a 5-membered unsaturated heterocyclic group, $R^8$, $R^9$ and $R^{10}$ are independently selected from the group consisting of hydrogen, halogen, nitro, hydroxy, hydrocarbyl, substituted hydrocarbyl, amide, thioamide, amine, thioether and sulfonyl.

Such modifications are intended to fall within the scope of the appended claims.

All references cited herein are hereby incorporated by reference in their entirety.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:
1. A compound represented by the following formula:

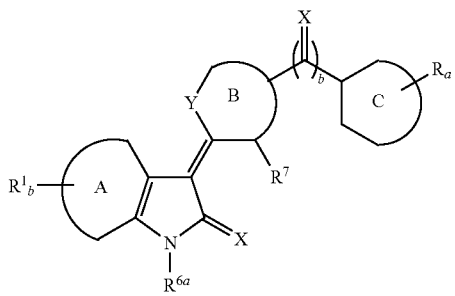

II or a pharmaceutically acceptable salt thereof;
wherein
X is O or S;
Y is selected from the group consisting of O, S, $NR^3$ and $CR^3R^4$;

and wherein the ring system represented by A in formula V, below, is a 6 membered aryl group,

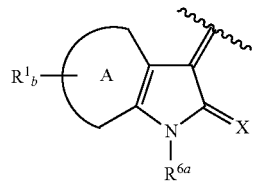

V wherein said aryl group is:

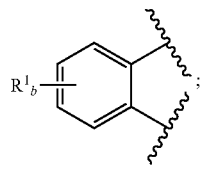

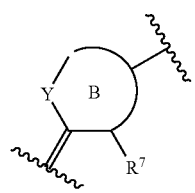

VI and wherein the ring system represented by B in formula VI, above, is a five membered unsaturated heterocyclic ring wherein said unsaturated heterocyclic ring is selected from the group consisting of:

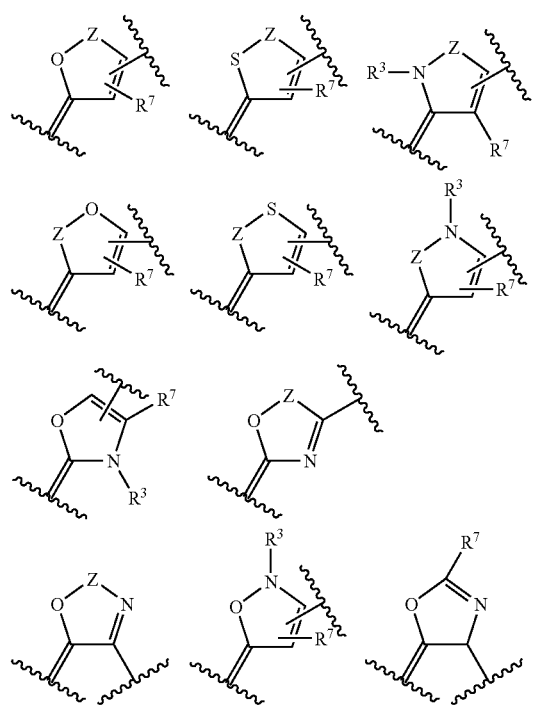

321
-continued

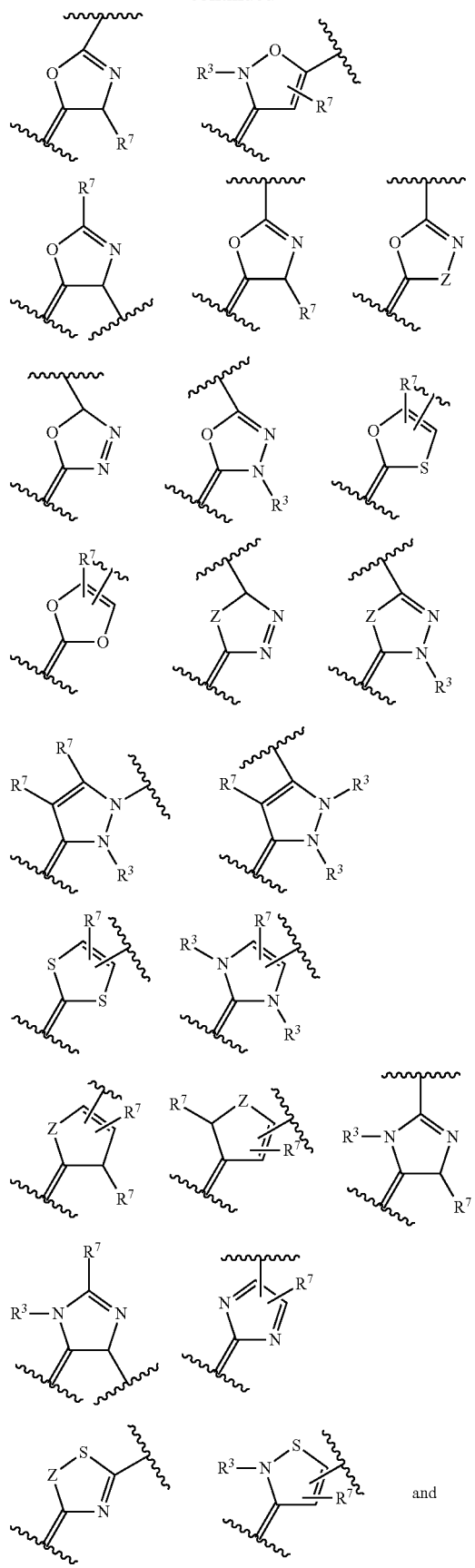

322
-continued

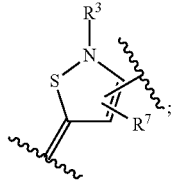

wherein Z is selected from the group consisting of [C(R²)₂]$_c$, O, NR³ and S;

VII

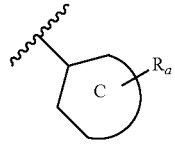

and wherein the ring system represented by C in formula VII, above, is a 6 membered aryl group, wherein said aryl group is:

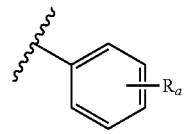

wherein R¹ is selected from the group consisting of halogen, aryl, C₁ to C₈ alkyl, C₂ to C₈ alkenyl; CF₃, OCF₃, OCF₂H, S(O)$_f$R², (CR³R⁴)$_d$C(O)OR², O(CR³R⁴)$_e$C(O)OR², NR²(CR³R⁴)$_d$C(O)R², NR²(CR³R⁴)$_d$C(O)OR², OP(O)(OR²)₂, OC(O)OR², NR²(CH₂)$_e$N(R²)₂, O(CH₂)$_e$N(R²)₂, (CR³R⁴)$_d$CN, O(CR³R⁴)$_e$CN, (CR³R⁴)$_g$Ar, NR²(CR³R⁴)$_e$Ar, O(CR³R⁴)$_e$Ar, S(O)$_f$(CR³R⁴)$_e$Ar, (CR³R⁴)$_e$SO₂R², (CR³R⁴)$_e$C(O)N(R²)₂, NR²(CR³R⁴)$_e$C(O)N(R²)₂, O(CR³R⁴)$_d$C(O)N(R²)₂, C(O)(CR²CR³)$_e$Ar, S(O)$_f$(CR³R⁴)$_e$C(O)N(R²)₂, (CR³R⁴)$_d$OR², NR²(CR³R⁴)$_e$OR², O(CR³R⁴)$_e$OR², S(O)$_f$(CR³R⁴)$_d$OR², C(O)(CR³R⁴)$_d$R³, NR²C(O)(CR³R⁴)$_e$R³, OC(O)(CR³R⁴)$_d$N(R²)₂, C(O)(CR³R⁴)$_e$N(R²)₂, NR²C(O)(CR³R⁴)$_d$N(R²)₂, OC(O)(CR³R⁴)$_d$N(R²)₂, (CR³R⁴)$_d$R³, NR²(CR³R⁴)$_d$R³, O(CR³R⁴)$_d$R³, S(O)$_f$(CR³R⁴)$_d$R³, (CR³R⁴)$_e$N(R²)₂, NR²(CR³R⁴)$_e$N(R²)₂, O(CR³R⁴)$_e$N(R²)₂, S(O)$_f$(CR³R⁴)$_d$N(R²)₂;

each R² is independently selected from the group consisting of hydrogen, C₁ to C₈ alkyl, C₂ to C₈ alkenyl, C₂ to C₈ alkynyl, C₁ to C₄ alkylol, lower alkylphenyl, phenyl, (CR³R⁴)$_d$Ar, (CR³R⁴)$_d$C(O)OR⁶, (CR³R⁴)$_d$SO₂R⁶, (CR³R⁴)$_d$OR⁶, (CR³R⁴)$_d$OSO₂R⁶, (CR³R⁴)$_d$P(O)(OR⁶)₂, (CR³R⁴)$_d$R⁶, (CR³R⁴)$_e$N(R⁶)₂ and (CR³R⁴)$_e$NR⁶C(O)N(R⁶)₂;

wherein each R⁶ is independently selected from the group consisting of hydrogen, C₁-C₈ alkyl, hydroxylmethyl and phenyl, or wherein N(R⁶)₂ may form a 3-7 membered heterocyclic ring, and wherein said heterocyclic ring may be substituted with one or more of R³; and [C(R²)₂]$_c$ may form a 3-7 membered carbocyclic or heterocyclic ring;

each R is independently selected from the group consisting of halogen, C₁ to C₈ alkyl, C₂ to C₈ conjugated alkenyl, (CR²=CR²)$_d$CON(R²)₂, CF₃, OCF₃, OCF₂H, (CR³

R⁴)_dCN, NR²(CR³R⁴)_eCN, O(CR³R⁴)_eCN, S(O)_fR², (CR³R⁴)_cC(O)OR², NR²(CR³R⁴)_dC(O)OR², O(CR³R⁴)_dC(O)OR², S(O)_f(CR³R⁴)_dC(O)OR², (CR³R⁴)_dAr, NR²(CR³R⁴)_dAr, O(CR³R⁴)_dAr, S(O)_f (CR³R⁴)_dAr, (CR³R⁴)_dSO₂R², NR²(CR³R⁴)_dS(O)_fR², O(CR³R⁴)_d S(O)_fR², S(O)_f(CR³R⁴)_eS(O)_fR², (CR³ R⁴)_dC(O)N(R²)₂, NR²(CR³R⁴)_dC(O)N(R²)₂, O(CR³R⁴)_dC(O)N(R²)₂, S(O)_f(CR³R⁴)_eC(O)N(R²)₂, (CR³ R⁴)_dOR², NR² (CR³ R⁴)_dOR², O(CR³ R⁴)_eOR², S(O)_f(CR³ R⁴)_dOR², (CR³ R⁴)_dOSO₂R², NR² (CR³ R⁴)_eOSO₂R², O(CR³ R⁴)_eOSO₂R², S(O)_f(CR³ R⁴)_eOSO₂R²(CR³ R⁴)_dP(O)(OR²)₂, NR² (CR³ R⁴)_dP (O)(OR²)₂, O(CR³ R⁴)_dP(O)(OR²)₂, S(O)_f(CR₃ R⁴)_eP (O)(OR²)₂, C(O)(CR³R⁴)_dR³, NR² C(O)(CR³R⁴)_dR³, OC(O)(CR³R⁴)_dN(R²)₂, C(O)(CR³R⁴)_dN(R²)₂, NR² C(O)(CR³R⁴)_dN(R²)₂, OC(O)(CR³R⁴)_dN(R²)₂, (CR³R⁴)_dR³, NR²(CR³R⁴)_dR³, O(CR³R⁴)_dR³, S(O)_f (CR³R⁴)_dR³, HNC(O)R², HN—C(O)OR², (CR³R⁴)_dN (R²)₂, NR²(CR³R⁴)_eN(R²)₂, O(CR³R⁴)_eN(R²)₂, S(O)_f (CR³R⁴)_dN(R²)₂, OP(O)(OR²)₂, OC(O)OR², (CR³ R⁴)_dC=C(CR³R⁴)_dR², (CR³R⁴)_dC=C(CR³R⁴)_dOR², (CR³R⁴)_dC=C(CR³R⁴)_dN(R²)₂, (CR³R⁴)_dCC(CR³ R⁴)_dR², (CR³R⁴)_dCC(CR³R⁴)_eOR², (CR³R⁴)_dCC (CR³R⁴)_eN(R²)₂, (CR³R⁴)_dC(O)(CR³R⁴)_dR², (CR³ R⁴)_dC(O)(CR³R⁴)_dOR² and (CR³R⁴)_dC(O)(CR³R⁴)_dN (R²)₂;

R³ and R⁴ are selected from the group consisting of H, F, hydroxy, and C₁-C₄ alkyl or CR³R⁴ may represent a carbocyclic or heterocyclic ring of from 3 to 6 carbons or alternatively, (CR³R⁴)_d and (CR³R⁴)_e may form a 3-7 membered carbocyclic or heterocyclic ring;

R⁶ᵃ is selected from the group consisting of hydrogen, C₁-C₈ alkyl, hydroxylmethyl and phenyl;

R⁷ is selected from the group consisting of hydrogen, C₁-C₈ alkyl, C₂-C₈ alkenyl, C₂-C₈ alkynyl, (R²CCR²) aCN and aryl;

a is 0 or an integer of from 1 to 3;
b is 0;
c is an integer of from 1 to 2;
d is 0 or an integer of from 1 to 5;
e is an integer of from 1 to 4;
f is 0 or an integer of from 1 to 2;
g is an integer of from 2 to 5, and further provided said alkyl or aryl radicals may be substituted with one or two halo, hydroxy, lower alkyloxy, lower alkyl amino or cycloalkylamino radicals wherein the cycloalkyl ring can include an enchained oxygen, sulfur or additional nitrogen atom and may be substituted with one or two halo or lower alkyl radicals.

2. The compound of claim 1 wherein R¹ is a carbocyclic aryl group.

3. The compound of claim 1 wherein R¹ is a heterocyclic aryl group.

4. The compound of claim 1 wherein N(R⁶)₂ is selected from the group consisting of pyrrolidine, 3-fluoropyrrolidine, piperidine, 4-fluoropiperidine, N-methylpiperazine, morpholine, 2,6-dimethylmorpholine and thiomorpholine each of which is independently unsubstituted or substituted with one or more of R³.

5. A compound selected from the group consisting of
(3E)-6-fluoro-3-{4-[4-({4-[2-(2-hydroxyethoxy)ethyl] piperazin-1-yl}carbonyl)phenyl]-5,5-dimethylfuran-2 (5H)-ylidene}-1,3-dihydro-2H-indol-2-one, (3E)-6-fluoro-3-[4-(4-{[4-(2-hydroxyethyl)piperazin-1-yl] carbonyl}phenyl)-5,5-dimethylfuran-2(5H)-ylidene]-1, 3-dihydro-2H-indol-2-one,
6-Fluoro-3-[4-[4-(3-hydroxy-pyrrolidine-1-carbonyl)-phenyl]-5,5-dimethyl-5H-furan-(2E)-ylidene]-1,3-dihydro-indol-2-one,
4-[(5E)-5-(6-fluoro-2-oxo-1,2-dihydro-3H-indol-3-ylidene)-2,2-dimethyl-2,5-dihydrofuran-3-yl]-N-(2-{2-[2-(2-hydroxyethoxy)ethoxy]ethoxy}ethyl)benzamide methyl (3E)-3-{5,5-dimethyl-4-[4-(pyrrolidin-1-ylcarbonyl)phenyl]furan-2(5H)-ylidene}-2-oxoindoline-5-carboxylate,
methyl (3E)-3-{5,5-dimethyl-4-[4-(pyrrolidin-1-ylcarbonyl)phenyl]furan-2(5H)-ylidene}-2-oxoindoline-6-carboxylate,
(3E)-3-{5,5-dimethyl-4-[4-(pyrrolidin-1-ylcarbonyl)phenyl]furan-2(5H)-ylidene}-N-methyl-2-oxoindoline-6-carboxamide,
methyl (3E)-3-{5,5-dimethyl-4-[4-(pyrrolidin-1-ylcarbonyl)phenyl]furan-2(5H)-ylidene}-5-fluoro-2-oxoindoline-6-carboxylate,
methyl (3E)-3-[4-(4-{[(2,3-dihydroxypropyl)(methyl) amino]carbonyl}phenyl)-5,5-dimethylfuran-2(5H)-ylidene]-5-fluoro-2-oxoindoline-6-carboxylate,
4-[(5E)-5-(5,6-difluoro-2-oxo-1,2-dihydro-3H-indol-3-ylidene)-2,2-dimethyl-2,5-dihydrofuran-3-yl]-N-(2,3-dihydroxypropyl)-N-methylbenzamide,
ethyl (2S)-2-({4-[(5E)-5-(6-fluoro-2-oxo-1,2-dihydro-3H-indol-3-ylidene)-2,2-dimethyl-2,5-dihydrofuran-3-yl]benzoyl}amino)-4-(methylthio)butanoate,
(3E)-6-fluoro-3-[4-(4-{[3-(hydroxymethyl)piperidin-1-yl]carbonyl}phenyl)-5,5-dimethylfuran-2(5H)-ylidene]-1,3-dihydro-2H-indol-2-one,
ethyl 3-({4-[(5E)-5-(6-fluoro-2-oxo-1,2-dihydro-3H-indol-3-ylidene)-2,2-dimethyl-2,5-dihydrofuran-3-yl] benzoyl}amino)propanoate,
methyl (2S)-2-({4-[(5E)-5-(6-fluoro-2-oxo-1,2-dihydro-3H-indol-3-ylidene)-2,2-dimethyl-2,5-dihydrofuran-3-yl]benzoyl}amino)-3-hydroxypropanoate,
N-(2,3-dihydroxypropyl)-4-[(5E)-5-(6-fluoro-2-oxo-1,2-dihydro-3H-indol-3-ylidene)-2,2-dimethyl-2,5-dihydrofuran-3-yl]-N-methylbenzamide,
methyl 1-{4-[(5E)-5-(6-fluoro-2-oxo-1,2-dihydro-3H-indol-3-ylidene)-2,2-dimethyl-2,5-dihydrofuran-3-yl] benzoyl}piperidine-4-carboxylate,
methyl (3E)-3-{5,5-dimethyl-4-[4-(morpholin-4-ylmethyl)phenyl]furan-2(5H)-ylidene}-2-oxoindoline-6-carboxylate,
(3E)-3-{5,5-dimethyl-4-[4-(morpholin-4-ylmethyl)phenyl]furan-2(5H)-ylidene}-2-oxoindoline-5-carboxylic acid,
(3E)-3-[4-(4-{[4-(hydroxymethyl)piperidin-1-yl] methyl}phenyl)-5,5-dimethylfuran-2(5H)-ylidene]-2-oxoindoline-5-carboxylic acid,
methyl 1-{4-[(5E)-5-(5,6-difluoro-2-oxo-1,2-dihydro-3H-indol-3-ylidene)-2,2-dimethyl-2,5-dihydrofuran-3-yl]benzyl}piperidine-4-carboxylate,
1-{4-[(5E)-5-(5,6-difluoro-2-oxo-1,2-dihydro-3H-indol-3-ylidene)-2,2-dimethyl-2,5-dihydrofuran-3-yl] benzyl}piperidine-4-carboxylic acid,
(3E)-6-fluoro-3-[4-{4-[(3-hydroxypiperidin-1-yl)methyl] phenyl}-5,5-dimethylfuran-2(5H)-ylidene]-1,3-dihydro-2H-indol-2-one,
(3E)-6-fluoro-3-[4-(4-{[3-(2-hydroxyethyl)piperidin-1-yl]methyl}phenyl)-5,5-dimethylfuran-2(5H)-ylidene]-1,3-dihydro-2H-indol-2-one,
methyl 1-{4-[(5E)-5-(6-fluoro-2-oxo-1,2-dihydro-3H-indol-3-ylidene)-2,2-dimethyl-2,5-dihydrofuran-3-yl] benzyl}-4-hydroxypyrrolidine-2-carboxylate (3E)-3-[5,5-dimethyl-4-{4-[(4-methylpiperazin-1-yl)methyl]phenyl}furan-2(5H)-ylidene]-6-fluoro-1,3-dihydro-2H-indol-2-one, (3E)-6-fluoro-3-[4-(4-{[4-(2-hydroxyethyl)piperazin-1-yl]methyl}phenyl)-5,5-dimethylfuran-2(5H)-ylidene]-1,3-dihydro-2H-indol-2-one, (3E)-5-fluoro-3-[4-(4-{[3-(hydroxymethyl)piperidin-1-yl]methyl}phenyl)-5,5-dimethylfuran-2(5H)-ylidene]-1,3-dihydro-2H-indol-2-one, (3E)-5-fluoro-3-{4-[4-({4-[2-(2-hydroxyethoxy)ethyl]piperazin-1-yl}methyl)phenyl]-5,5-dimethylfuran-2(5H)-ylidene}-1,3-dihydro-2H-indol-2-one, (3E)-3-[4-(4-{[(2,3-dihydroxypropyl)(methyl)amino]methyl}phenyl)-5,5-dimethylfuran-2(5H)-ylidene]-5-fluoro-1,3-dihydro-2H-indol-2-one, (3E)-3-[5,5-dimethyl-4-(4-{[(2S,3R,4S,5R)-3,4,5-trihydroxy-2-methylpiperidin-1-yl]methyl}phenyl)furan-2(5H)-ylidene]-5-fluoro-1,3-dihydro-2H-indol-2-one, 1-{4-[(5E)-5-(5-fluoro-2-oxo-1,2-dihydro-3H-indol-3-ylidene)-2,2-dimethyl-2,5-dihydrofuran-3-yl]benzyl}piperidine-4-carboxylic acid, (3E)-6-(4-methoxyphenyl)-3-[4-(4-methoxyphenyl)-5,5-dimethylfuran-2(5H)-ylidene]-1,3-dihydro-2H-indol-2-one, 3-{4-[5-(6-Fluoro-2-oxo-1,2-dihydro-indol-3-ylidene)-2,5-dihydro-furan-3-yl]-phenyl}-propionic acid, 6-Fluoro-3-{4-[4-(2-morpholin-4-yl-ethoxy)-phenyl]-5H-furan-2-ylidene}-1,3-dihydro-indol-2-one, (3E)-6-fluoro-3-{4-[4-(3-hydroxypropyl)phenyl]-5,5-dimethylfuran-2(5H)-ylidene}-1,3-dihydro-2H-indol-2-one, methyl ({4-[(5E)-5-(6-fluoro-2-oxo-1,2-dihydro-3H-indol-3-ylidene)-2,2-dimethyl-2,5-dihydrofuran-3-yl]benzoyl}amino)acetate, ethyl 3-{4-[(5E)-5-(6-fluoro-2-oxo-1,2-dihydro-3H-indol-3-ylidene)-2,2-dimethyl-2,5-dihydrofuran-3-yl]phenyl}propanoate, and N-{3-[(5E)-5-(6-fluoro-2-oxo-1,2-dihydro-3H-indol-3-ylidene)-2,2-dimethyl-2,5-dihydrofuran-3-yl]phenyl}acetamide; or a pharmaceutically acceptable salt thereof.

6. A compound represented by formula II

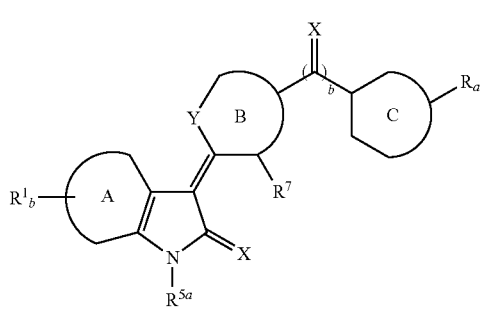

wherein
X is O;
Y is O;
and wherein the ring system represented by A in formula V, below, is a 6 membered aryl group,

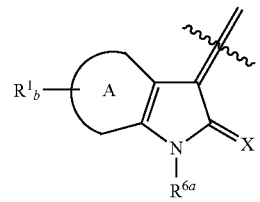

wherein said aryl group is:

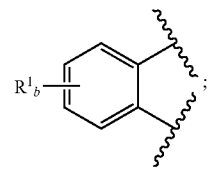

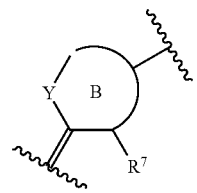

and wherein the ring system represented by B in formula VI, above, is a five membered unsaturated heterocyclic ring of the formula:

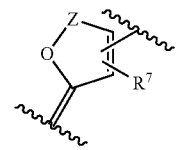

wherein Z is $[C(R^2)_2]_c$;

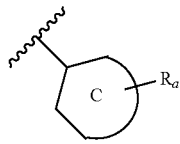

and wherein the ring system represented by C in formula VII, above, is a 6 membered aryl group, wherein said aryl group is:

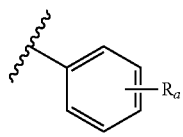

wherein:
$R^1$ is selected from the group consisting of halogen, aryl, $C_1$ to $C_8$ alkyl, $(CR^3R^4)_d C(O)OR^2$, and $(CR^3R^4)_e C(O)N(R^2)_2$;

each $R^2$ is independently selected from the group consisting of hydrogen, $C_1$ to $C_8$ alkyl, $C_2$ to $C_8$ alkenyl, $C_1$ to $C_4$ alkylol, lower alkylphenyl, phenyl, $(CR^3R^4)_dC(O)OR^6$, $(CR^3R^4)_dSO_2R^6$, $(CR^3R^4)_dOR^6$, $(CR^3R^4)_dOSO_2R^6$, $(CR^3R^4)_dR^6$, $(CR^3R^4)_eN(R^6)_2$ and $(CR^3R^4)_eNR^6C(O)N(R^6)_2$;

each $R^6$ is independently selected from the group consisting of hydrogen, $C_1$-$C_8$ alkyl, hydroxylmethyl and phenyl, or wherein $N(R^6)_2$ may form a 3-7 membered heterocyclic ring, and wherein said heterocyclic ring may be substituted with one or more of $R^3$;

each R is independently selected from the group consisting of halogen, $C_1$ to $C_8$ alkyl, $(CR^3R^4)_dC(O)N(R^2)_2$, $(CR^3R^4)_dOR^2$, $C(O)(CR^3R^4)_dR^3$, $NR^2C(O)(CR^3R^4)_dR^3$, $C(O)(CR^3R^4)_dN(R^2)_2$, $NR^2C(O)(CR^3R^4)_dN(R^2)_2$, $(CR^3R^4)_dR^3$, $NR^2(CR^3R^4)_dR^3$, $O(CR^3R^4)_dR^3$, $HNC(O)R^2$, $HN-C(O)OR^2$, $(CR^3R^4)_dN(R^2)_2$, $(CR^3R^4)_dC=C(CR^3R^4)_dR^2$, $(CR^3R^4)_dC(O)(CR^3R^4)_dR^2$, $(CR^3R^4)_dC(O)(CR^3R^4)_dOR^2$ and $(CR^3R^4)_dC(O)(CR^3R^4)_dN(R^2)_2$;

$R^3$ and $R^4$ are independently be selected from the group consisting of H, F, hydroxy, and $C_1$-$C_4$ alkyl or $CR^3R^4$ may represent a carbocyclic or heterocyclic ring of from 3 to 6 carbons or alternatively, $(CR^3R^4)_d$ and $(CR^3R^4)_e$ may form a 3-7 membered carbocyclic or heterocyclic ring;

$R^{6a}$ is selected from the group consisting of hydrogen, $C_1$-$C_8$ alkyl, hydroxylmethyl and phenyl;

$R^7$ is selected from the group consisting of hydrogen and $C_1$-$C_8$ alkyl;

a is 0 or an integer of from 1 to 3;

b is 0;

c is an integer of from 1 to 2;

d is 0 or an integer of from 1 to 5;

e is an integer of from 1 to 4;

and further provided said alkyl or aryl radicals may be substituted with one or two halo, hydroxy, lower alkyloxy, lower alkyl amino or cycloalkylamino radicals wherein the cycloalkyl ring can include an enchained oxygen, sulfur or additional nitrogen atom and may be substituted with one or two halo or lower alkyl radicals; or a pharmaceutically acceptable salt thereof.

7. A pharmaceutical composition comprising at least one compound of claim 1 or a pharmaceutically acceptable salt thereof and a pharmaceutically acceptable carrier.

8. A pharmaceutical composition comprising at least one compound of claim 5 or a pharmaceutically acceptable salt thereof and a pharmaceutically acceptable carrier.

9. A pharmaceutical composition comprising at least one compound of claim 6 or a pharmaceutically acceptable salt thereof and a pharmaceutically acceptable carrier.

10. A method for treating age-related macular degeneration, the method comprising the step of administering to a subject in need thereof a therapeutically effective amount of a compound of claim 1.

11. A method for treating age-related macular degeneration, the method comprising the step of administering to a subject in need thereof a therapeutically effective amount of a compound of claim 5.

* * * * *